United States Patent
Kim et al.

(10) Patent No.: US 11,832,515 B2
(45) Date of Patent: Nov. 28, 2023

(54) ORGANIC ELECTROLUMINESCENT COMPOUND, ORGANIC ELECTROLUMINESCENT MATERIAL COMPRISING THE SAME, AND ORGANIC ELECTROLUMINESCENT DEVICE

(71) Applicant: ROHM AND HAAS ELECTRONIC MATERIALS KOREA LTD., Chungcheongnam-do (KR)

(72) Inventors: Chi-Sik Kim, Gyeonggi-do (KR); Hyun Kim, Gyeonggi-do (KR); Kyoung-Jin Park, Gyeonggi-do (KR); Jin-Man Kim, Gyeonggi-do (KR); Hyun-Woo Kang, Gyeonggi-do (KR); So-Young Jung, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 490 days.

(21) Appl. No.: 17/118,120

(22) Filed: Dec. 10, 2020

(65) Prior Publication Data
US 2021/0193932 A1    Jun. 24, 2021

(30) Foreign Application Priority Data

Dec. 24, 2019  (KR) .................. 10-2019-0173733
Oct. 27, 2020  (KR) .................. 10-2020-0140470

(51) Int. Cl.
| | |
|---|---|
| *H10K 85/60* | (2023.01) |
| *C07D 405/14* | (2006.01) |
| *H10K 50/11* | (2023.01) |
| *H10K 50/18* | (2023.01) |
| *H10K 101/10* | (2023.01) |
| *H10K 101/00* | (2023.01) |
| *C09K 11/02* | (2006.01) |

(52) U.S. Cl.
CPC ........ *H10K 85/654* (2023.02); *C07D 405/14* (2013.01); *C09K 11/025* (2013.01); *H10K 85/6572* (2023.02); *H10K 85/6574* (2023.02); *H10K 50/11* (2023.02); *H10K 50/18* (2023.02); *H10K 2101/10* (2023.02); *H10K 2101/90* (2023.02)

(58) Field of Classification Search
CPC .. C07D 405/14; C07D 409/14; C07D 251/24; C07D 209/82; H10K 85/654; H10K 85/6572; H10K 85/6574; H10K 85/6576
See application file for complete search history.

(56) References Cited

FOREIGN PATENT DOCUMENTS

| | | | |
|---|---|---|---|
| JP | 2017222623 A | 12/2017 | |
| KR | 101447961 B | 10/2014 | |
| KR | 101850245 B | 4/2018 | |
| KR | 20200086233 A | * 7/2020 | ........... C07D 405/14 |
| WO | 2012150826 A1 | 11/2012 | |

OTHER PUBLICATIONS

Computer-generated English-language translation of KR-20200086233-A.*

* cited by examiner

*Primary Examiner* — Vu A Nguyen
(74) *Attorney, Agent, or Firm* — G. Creston Campbell

(57) ABSTRACT

The present disclosure relates to an organic electroluminescent compound, an organic electroluminescent material comprising the same, and an organic electroluminescent device. By comprising the organic electroluminescent compound according to the present disclosure, an organic electroluminescent device having improved driving voltage and/or luminous efficiency and/or lifespan characteristics can be provided, compared with the organic electroluminescent device comprising a conventional organic electroluminescent compound.

11 Claims, No Drawings

ORGANIC ELECTROLUMINESCENT COMPOUND, ORGANIC ELECTROLUMINESCENT MATERIAL COMPRISING THE SAME, AND ORGANIC ELECTROLUMINESCENT DEVICE

TECHNICAL FIELD

The present disclosure relates to an organic electroluminescent compound, an organic electroluminescent material comprising the same, and an organic electroluminescent device.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an organic electroluminescent device is light-emitting materials. Until now, fluorescent materials have been widely used as light-emitting materials. However, in view of electroluminescent mechanisms, since phosphorescent light-emitting materials theoretically enhance luminous efficiency by four (4) times compared to fluorescent light-emitting materials, phosphorescent light-emitting materials have been widely researched. Iridium(III) complexes have been widely known as phosphorescent light-emitting materials, including bis(2-(2'-benzothienyl)-pyrdinato-N,C-3') iridium(acetylacetonate) [(acac)Ir(btp)$_2$], tris(2-phenylpyridine)irdium [Ir(ppy)s] and bis(4,6-difluorophenylpyridinato-N,C2)picolinato iridium (Firpic) as red-, green-, and blue-emitting materials, respectively.

In the prior art, 4,4'-N,N'-dicarbazol-biphenyl (CBP) is the most widely known phosphorescent host material. Recently, Pioneer (Japan) et al., developed a high performance organic electroluminescent device using bathocuproine (BCP) and aluminum(III) bis(2-methyl-8-quinolinate)(4-phenylphenolate) (BAlq), etc., as host materials, which were known as hole blocking materials.

However, although the conventional materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the organic electroluminescent device is determined by [(π/voltage)×current efficiency], and the power efficiency is inversely proportional to the voltage. Although the organic electroluminescent device comprising phosphorescent host materials provides higher current efficiency (cd/A) than one comprising fluorescent materials, a significantly high driving voltage is necessary. Thus, there is no merit in terms of power efficiency (lm/V). (3) Also, the operational lifespan of the organic electroluminescent device is short, and luminous efficiency is still necessary to improve.

In order to improve luminous efficiency, driving voltage and/or lifetime, various materials or concepts for an organic layer of an organic electroluminescent device have been proposed, but they have not been satisfactory in practical use.

DISCLOSURE OF INVENTION

Technical Problem

The object of the present disclosure is firstly, to provide an organic electroluminescent compound and an organic electroluminescent material comprising the same which is effective to produce an organic electroluminescent device having low driving voltage and/or high luminous efficiency, and/or long lifespan, and secondly, to provide an organic electroluminescent device comprising the organic electroluminescent compound.

Solution to Problems

Specifically, the present inventors found that the aforementioned objective can be achieved by an organic electroluminescent compound represented by the following formula 1, so that the present invention was completed.

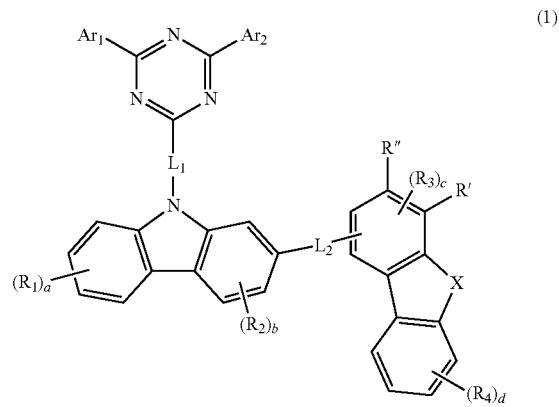

wherein,

X represents O or S:

Ar$_1$ and Ar$_2$ each independently represent a substituted or unsubstituted phenyl, a substituted or unsubstituted biphenyl, a substituted or unsubstituted naphthyl, a substituted or unsubstituted terphenyl, a substituted or unsubstituted 9,9-dimethylfluorenyl, a substituted or unsubstituted 9,9-diphenylfluorenyl, a substituted or unsubstituted 9,9'-spirobifluorenyl, a substituted or unsubstituted dibenzofuranyl, a substituted or unsubstituted dibenzothiophenyl, a substituted or unsubstituted 9-phenyl-carbazolyl, a substituted or unsubstituted 2-phenylbenzoxazolyl, or a substituted or unsubstituted 2-phenylbenzothiazolyl;

L$_1$ and L$_2$ each independently represent a single bond, a substituted or unsubstituted phenylene, a substituted or unsubstituted biphenylene, a substituted or unsubstituted naphthylene, a substituted or unsubstituted terphenylene, a substituted or unsubstituted dibenzofuranylene, a substituted or unsubstituted dibenzothiophenylene, a substituted or unsubstituted 9-phenyl-carbazolylene, a substituted or unsubstituted 9,9-dimethylfluorenylene, a substituted or unsubstituted 9,9-diphenylfluorenylene, or a substituted or unsubstituted 9,9'-spirobifluorenylene;

$R_1$ to $R_4$, R', and R" each independently represent hydrogen or deuterium;

a and d each independently represent an integer of 1 to 4, b represents an integer of 1 to 3, c represents an integer of 1; and when a, b, and d are an integer of 2 or more, each of $R_1$, $R_2$, and $R_4$ may be the same or different.

Advantageous Effects of Invention

By comprising an organic electroluminescent compound and an organic electroluminescent material comprising the same according to the present disclosure, an organic electroluminescent device having low driving voltage and/or high luminous efficiency and/or long lifespan can be prepared.

EMBODIMENTS OF THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

Herein, "organic electroluminescent material" means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material, etc.

Herein, "a plurality of host materials" means an organic electroluminescent material comprising a combination of at least two host materials. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The two or more compounds comprised in the plurality of host materials of the present disclosure may be included in one light-emitting layer or may be respectively included in different light-emitting layers. When the at least two host materials are comprised in one layer, the at least two host materials may be mixture-evaporated to form a layer, or simultaneously may be co-evaporated individually to form a layer.

The term "an electron transport zone" in the present disclosure means a zone where electrons move between the cathode and the light-emitting layer. For example, the electron transport zone may include at least one of an electron buffer layer, a hole blocking layer, an electron transport layer, and an electron injection layer, preferably, at least one of a hole blocking layer, an electron transport layer, and an electron injection layer. The hole blocking layer serves to prevent holes from entering the cathode through the light-emitting layer in driving the organic electroluminescent device.

Herein, "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. Herein, the term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. Herein, the term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. Herein, the term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. Herein, "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 25, more preferably 6 to 18, and may be partially saturated. Examples of the aryl specifically include phenyl, biphenyl, terphenyl, quaterphenyl, naphthyl, binaphthyl, phenylnaphthyl, naphthylphenyl, fluorenyl, phenylfluorenyl, dimethylfluorenyl, diphenytfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, tetramethyl-dihydrophenanthrenyl, etc. More specifically, the aryl may be o-tolyl, m-toyl, p-toyl, 2,3-xylyl, 3,4-xyyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]

fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc. Herein, "(3- to 30-membered) heteroaryl" is an aryl having 3 to 30 ring backbone atoms including at least one, preferably 1 to 4 heteroatoms selected from the group consisting of B, N, O, S, Si, P, Se, and Ge. The above heteroaryl may be a monocyclic ring, or a fused ring condensed with at least one benzene ring; and may be partially saturated. Also, the above heteroaryl herein may be one formed by linking at least one heteroaryl or aryl group to a heteroaryl group via a single bond(s) and may comprise a spiro structure. Examples of the heteroaryl specifically may include a monocyclic ring-type heteroaryl including furyl, thiophenyl, pyrrolyl, imidazoyl, pyrazolyl, thiazoyl, thiadiazolyl, isothiazolyl, isoxazolyl, oxazolyl, oxadiazolyl, triazinyl, tetrazinyl, triazolyl, tetrazoyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, dibenzoselenophenyl, benzofuroquinolinyl, benzofuroquinazolinyl, benzofuronaphthiridinyl, benzofuropyrimidinyl, naphthofuropyrimidinyl, benzothienoquinolinyl, benzothienoquinazolinyl, benzothienonaphthiridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzoimidazolyl, benzothiazolyl, benzoisothiazolyl, benzoisoxazoyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazoyl, benzocarbazolyl, dibenzocarbazolyl, phenoxazinyl, phenanthridinyl, benzodioxoyl, indolizidinyl, acridinyl, silafluorenyl, germafluorenyl, benzotriazolyl, phenazinyl, imidazopyridinyl, chromenoquinazolinyl, thiochromenoquinazolinyl, dimethylbenzoperimidinyl, indolocarbazolyl, indenocarbazolyl, etc. More specifically, the heteroaryl may be 1-pyrrolyl, 2-pyrrolyl, 3-pyrrolyl, 2-pyridinyl, 3-pyrdinyl, 4-pyridinyl, 2-pyrimidinyl, 4-pyrimidinyl, 5-pyrmidinyl, 6-pyrimidinyl, 1,2,3-triazin-4-yl, 1,2,4-triazin-3-yl, 1,3,5-trazin-2-yl, 1-imidazoyl, 2-imidazolyl, 1-pyrazoyl, 1-indolizidinyl, 2-indolizidinyl, 3-indolizidinyl, 5-indolizidinyl, 6-indolizidinyl, 7-indolizidinyl, 8-indolizidinyl, 2-imidazopyrdinyl, 3-imidazopyridinyl, 5-imidazopyridinyl, 6-imidazopyridinyl, 7-imidazopyridinyl, 8-imidazopyrdinyl, 1-indolyl, 2-indolyl, 3-indolyl, 4-indolyl, 5-indolyl, 6-indolyl, 7-indoyl, 1-isoindoyl, 2-isoindoyl, 3-isoindoyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinoyl, 6-isoquinoyl, 7-isoquinoyl, 8-isoquinoyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazol-1-yl, azacarbazol-2-yl, azacarbazol-3-yl, azacarbazol-4-yl, azacarbazol-5-yl, azacarbazol-6-yl, azacarbazol-7-yl, azacarbazol-8-yl, azacarbazol-9-yl, 1-phenanthridinyl, 2-phenanthridinyl, 3-phenanthridinyl, 4-phenanthridinyl, 6-phenanthrdinyl, 7-phenanthrdinyl, 8-phenanthridinyl, 9-phenanthrdinyl, 10-phenanthridinyl, 1-acridinyl, 2-acridinyl, 3-acridinyl, 4-acrdinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indoyl, 2-methyl-3-indoyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Herein, "Halogen" includes F, Cl, Br, and I.

In addition, "ortho (o)." "meta (m)," and "para (p)" are meant to signify the substitution position of all substituents. Ortho position is a compound with substituents, which are adjacent to each other, e.g., at the 1 and 2 positions on benzene. Meta position is the next substitution position of the immediately adjacent substitution position, e.g., a compound with substituents at the 1 and 3 positions on benzene. Para position is the next substitution position of the meta position, e.g., a compound with substituents at the 1 and 4 positions on benzene.

Herein, "a ring formed in linking to an adjacent substituent" means a substituted or unsubstituted (3- to 30-membered) mono- or polycyclic, alicyclic, aromatic ring, or a combination thereof, formed by linking or fusing two or more adjacent substituents, preferably may be a substituted or unsubstituted (3- to 26-membered) mono- or polycyclic, alicyclic, aromatic ring, or a combination thereof. Further, the formed ring may be included at least one heteroatom selected from the group consisting of B, N, O, S, Si and P, preferably, N, O and S. According to one embodiment of the present disclosure, the number of atoms in the ring skeleton is 5 to 20; according to another embodiment of the present disclosure, the number of atoms in the ring skeleton is 5 to 15. In one embodiment, the fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, a substituted or unsubstituted carbazole ring, a substituted or unsubstituted benzocarbazole ring, etc.

In addition, "substituted" in the expression "substituted or unsubstituted" means that a hydrogen atom in a certain functional group is replaced with another atom or functional group, i.e., a substituent, and substituted with a group to which two or more substituents are connected among the substituents. For example, "a substituent to which two or more substituents are connected" may be pyridine-triazine. That is, pyridine-triazine may be heteroaryl or may be interpreted as a substituent in which two heteroaryls are connected. Preferably, the substituent of the substituted (C1-C30)alkyl, the substituted (C2-C30)alkenyl, the substituted (C2-C30)alkynyl, the substituted (C3-C30)cycloalkyl, the substituted (C6-C30)aryl(ene), the substituted (3- to 30-membered)heteroaryl, the substituted tri(C1-C30)alkylsilyl, the substituted tri(C6-C30)arylsilyl, the substituted di(C1-C30)alkyl(C6-C30)arylsilyl, the substituted (C1-C30)alkyldi(C6-C30)arylsilyl the substituted mono- or di-(C1-C30)alkylamino, and the substituted mono- or di-(C6-C30)arylamino, in the formulas of the present disclosure, each is independently at least one selected from the group consisting of deuterium, halogen, cyano, carboxyl, nitro, hydroxy, phosphinoxide, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (C6-C30)aryl-substituted or unsubstituted (5- to 30-membered)heteroaryl, (5- to 30-membered)heteroaryl-substituted or unsubstituted (C6-C30)aryl, tri(C1-C30)alkylsilyl, tri(C6-C30)arylsilyl, di(C1-C30)alkyl(C6-C30)arylsilyl, (C1-C30)alkyldi(C6-C30)arylsiyl, amino, mono- or di(C1-C30)alkylamino, (C1-C30)alkyl-substituted or unsubstituted mono- or di(C6-C30)arylamino, (C1-C30)alkyl(C6-C30)arylamino, (C1-C30)alkylcarbonyl, (C1-C30)alkoxycarbonyl, (C6-C30)arylcarbonyl, (C6-C30)arylphosphinyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30)aryl. More preferably, the substituent may be at least one selected from the group consisting of deuterium, cyano, (C1-C5)alkyl, (C6-C12)aryl, (5- to 15-membered)heteroaryl, and tri(C6-C12)arylsilyl. For example, the substituent may be deuterium, cyano, methyl, tert-butyl, phenyl, biphenyl, naphthyl, pyridyl unsubstituted or substituted with phenyl, carbazolyl, or triphenylsilyl, etc.

Hereinafter, the organic electroluminescent compound according to one embodiment will be described.

The organic electroluminescent compound according to one embodiment is represented by the following formula 1.

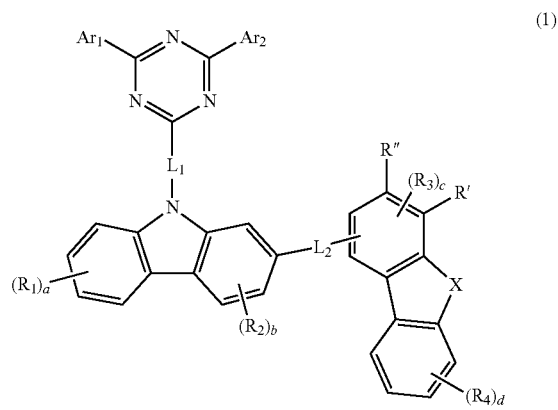

(1)

In formula 1,

X represents O or S:

Ar$_1$ and Ar$_2$ each independently represent a substituted or unsubstituted phenyl, a substituted or unsubstituted biphenyl, a substituted or unsubstituted naphthyl, a substituted or unsubstituted terphenyl, a substituted or unsubstituted 9,9-dimethylfluorenyl, a substituted or unsubstituted 9,9-diphenylfluorenyl, a substituted or unsubstituted 9,9'-spirobifluorenyl, a substituted or unsubstituted dibenzofuranyl, a substituted or unsubstituted dibenzothiophenyl, a substituted or unsubstituted 9-phenyl-carbazolyl, a substituted or unsubstituted 2-phenylbenzoxazolyl, or a substituted or unsubstituted 2-phenylbenzothiazolyl;

$L_1$ and $L_2$ each independently represent a single bond, a substituted or unsubstituted phenylene, a substituted or unsubstituted biphenylene, a substituted or unsubstituted naphthylene, a substituted or unsubstituted terphenylene, a substituted or unsubstituted dibenzofuranylene, a substituted or unsubstituted dibenzothiophenylene, a substituted or unsubstituted 9-phenyl-carbazolylene, a substituted or unsubstituted 9,9-dimethylfluorenylene, a substituted or unsubstituted 9,9-diphenylfluorenylene, or a substituted or unsubstituted 9,9'-spirobifluorenylene;

$R_1$ to $R_4$, R', and R" each independently represent hydrogen or deuterium;

a and d each independently represent an integer of 1 to 4, b represents an integer of 1 to 3, and c represents an integer of 1; and when a, b, and d are an integer of 2 or more, each of $R_1$, $R_2$, and $R_4$ may be the same or different.

According to one embodiment, the organic electroluminescent compound represented by formula 1 may be represented by the following formula 1-1 or 1-2.

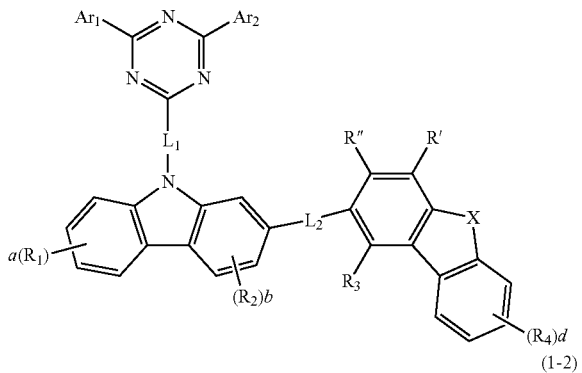

(1-1)

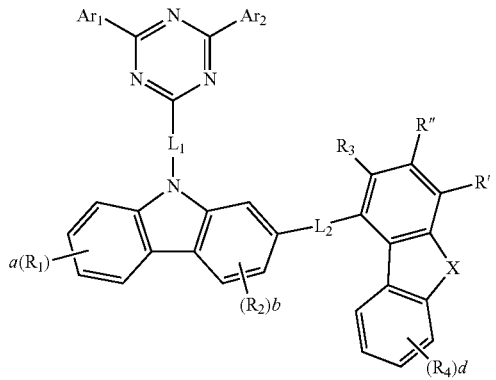

(1-2)

In formulas 1-1 and 1-2,

X, $Ar_1$, $Ar_2$, $L_1$, $L_2$, $R_1$ to $R_4$, R', R", a, b, and d are as defined in formula 1.

In one embodiment, $Ar_1$ and $Ar_2$ each independently represent a substituted or unsubstituted phenyl, a substituted or unsubstituted biphenyl, a substituted or unsubstituted naphthyl, a substituted or unsubstituted terphenyl, a substituted or unsubstituted 99-dimethylfluorenyl, a substituted or unsubstituted 9,9-diphenylfluorenyl, a substituted or unsubstituted 9,9'-spirobifluorenyl, a substituted or unsubstituted dibenzofuranyl, a substituted or unsubstituted dibenzothiophenyl, a substituted or unsubstituted 9-phenyl-carbazolyl, a substituted or unsubstituted 2-phenylbenzoxazolyl, or a substituted or unsubstituted 2-phenylbenzothiazolyl, preferably, a substituted or unsubstituted phenyl, a substituted or unsubstituted p-biphenyl, a substituted or unsubstituted m-biphenyl, a substituted or unsubstituted naphthyl, a substituted or unsubstituted m-terphenyl, a substituted or unsubstituted 9,9-dimethylfluorenyl, a substituted or unsubstituted 9,9'-spirobifluorenyl, a substituted or unsubstituted dibenzofuranyl, a substituted or unsubstituted dibenzothiophenyl, or a substituted or unsubstituted 9-phenyl-carbazolyl, more preferably, phenyl unsubstituted or substituted with one or more selected from the group consisting of deuterium, cyano, (C1-C5)alkyl, (C6-C12)aryl, and (5- to 15-membered)heteroaryl, a substituted or unsubstituted p-biphenyl, m-biphenyl unsubstituted or substituted with (C6-C12)aryl, a substituted or unsubstituted naphthyl, a substituted or unsubstituted m-terphenyl, a substituted or unsubstituted 9,9-dimethylfluorenyl, a substituted or unsubstituted 9,9'-spirobifluorenyl, a substituted or unsubstituted dibenzofuranyl, a substituted or unsubstituted dibenzothiophenyl, or a substituted or unsubstituted 9-phenyl-carbazolyl. For example, $Ar_1$ and $Ar_2$ each independently may be phenyl unsubstituted or substituted with one or more selected from the group consisting of cyano, tert-butyl, phenyl, naphthyl, and carbazolyl, an unsubstituted p-biphenyl, m-biphenyl unsubstituted or substituted with phenyl, an unsubstituted naphthyl, an unsubstituted m-terphenyl, an unsubstituted 9,9-dimethylfluorenyl, an unsubstituted 9,9'-spirobifluorenyl, an unsubstituted dibenzofuranyl, an unsubstituted dibenzothiophenyl, or an unsubstituted 9-phenyl-carbazolyl.

In one embodiment, $L_1$ and $L_2$ each independently represent a single bond, a substituted or unsubstituted phenylene, a substituted or unsubstituted biphenylene, a substituted or unsubstituted naphthylene, a substituted or unsubstituted terphenylene, a substituted or unsubstituted dibenzofuranylene, a substituted or unsubstituted dibenzothiophenylene, a substituted or unsubstituted 9-phenyl-carbazolylene, a substituted or unsubstituted 9,9-dimethylfluorenylene, a substituted or unsubstituted 9,9-diphenylfluorenylene, or a substituted or unsubstituted 9,9'-spirobifluorenylene, preferably, $L_1$ and $L_2$ each independently may be a single bond, a substituted or unsubstituted phenylene, a substituted or unsubstituted p-biphenylene, a substituted or unsubstituted m-biphenylene, a substituted or unsubstituted o-biphenylene, a substituted or unsubstituted naphthylene, or a substituted or unsubstituted dibenzofuranylene, more preferably, a single bond, phenylene unsubstituted or substituted with one or more selected from the group consisting of deuterium, cyano, (C1-C5)alkyl, (C6-C12)aryl, and (5- to 15-membered)heteroaryl, a substituted or unsubstituted p-biphenylene, a substituted or unsubstituted m-biphenylene, a substituted or unsubstituted o-biphenylene, a substituted or unsubstituted naphthylene, or a substituted or unsubstituted dibenzofuranylene. For example, $L_1$ and $L_2$ each independently may be a single bond or phenylene unsubstituted or substituted with phenyl, an unsubstituted p-biphenylenen, an unsubstituted m-biphenylene, an unsubstituted o-biphenylene, an unsubstituted naphthylene, or an unsubstituted dibenzofuranylene.

According to one embodiment, the organic electroluminescent compound represented by formula 1 above may be more specifically illustrated by the following compounds, but is not limited thereto.

H1-1
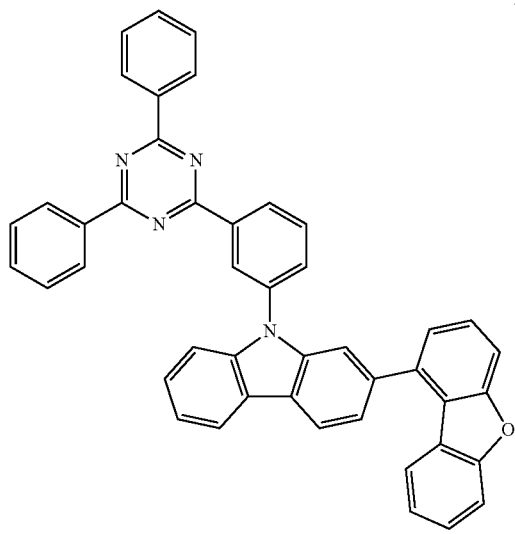
H1-2
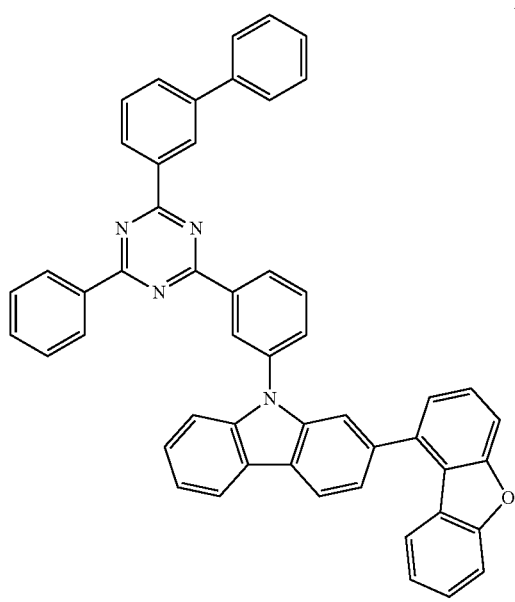
H1-3
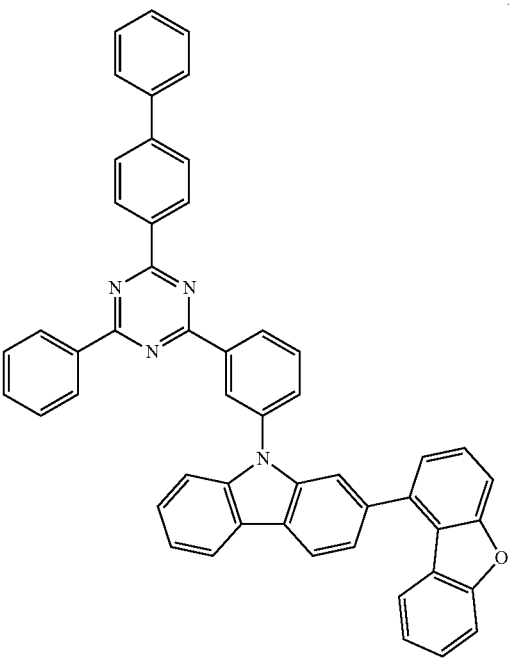
H1-4
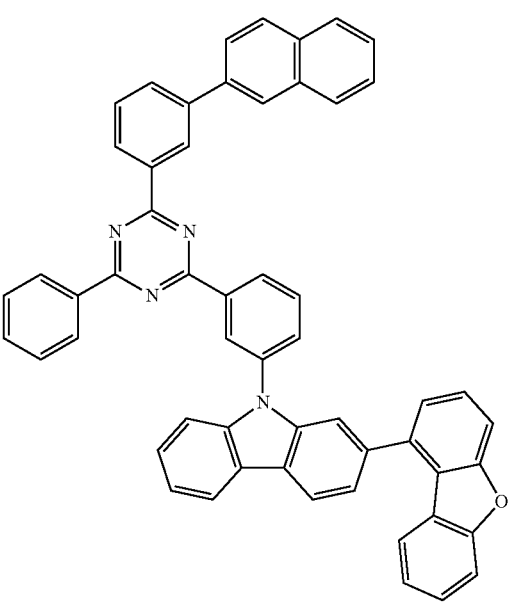

H1-5
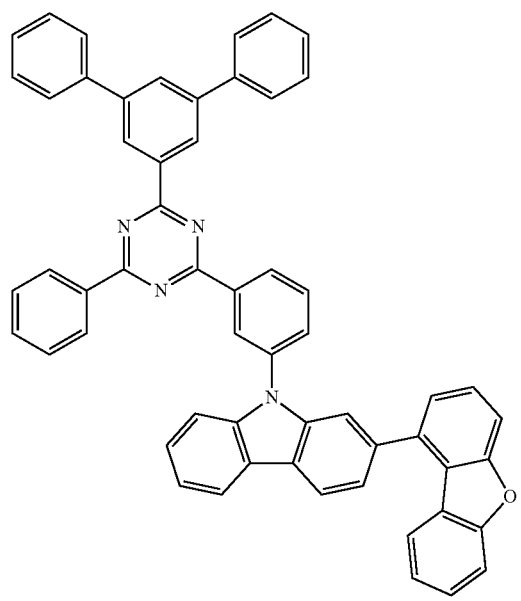
H1-6
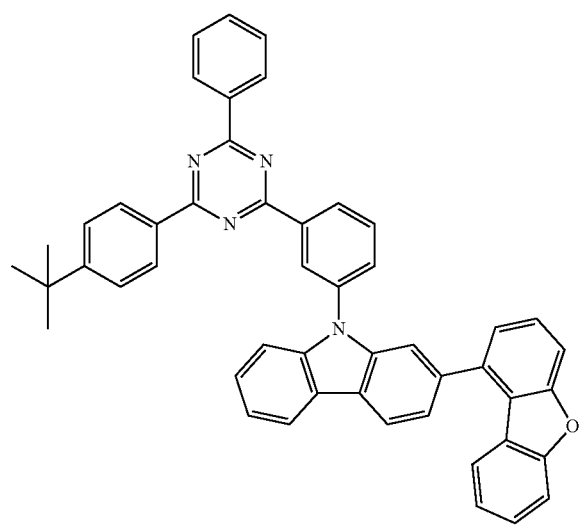
H1-7
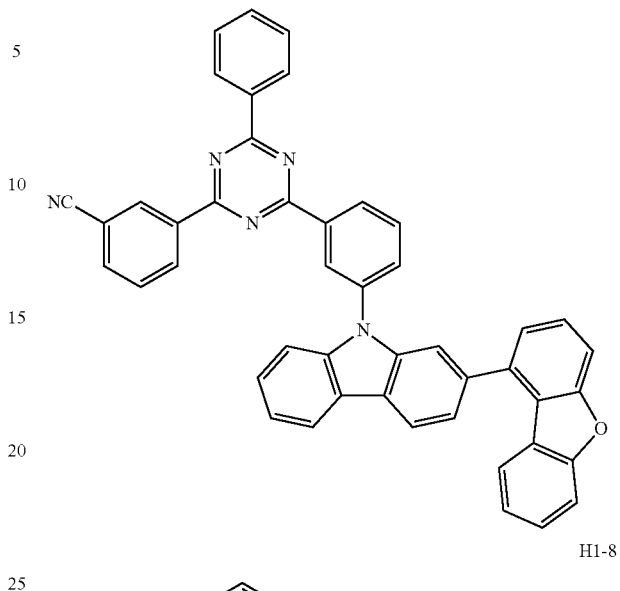
H1-8
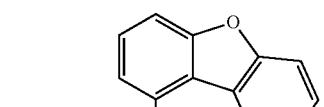
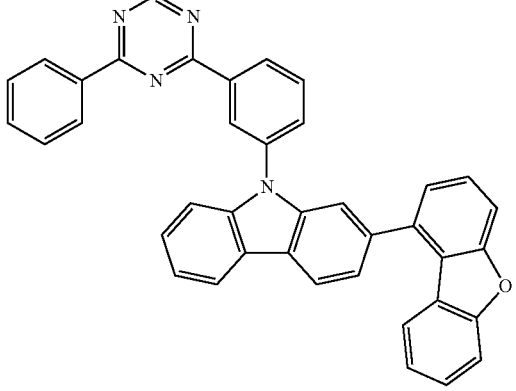
H1-9

H1-10
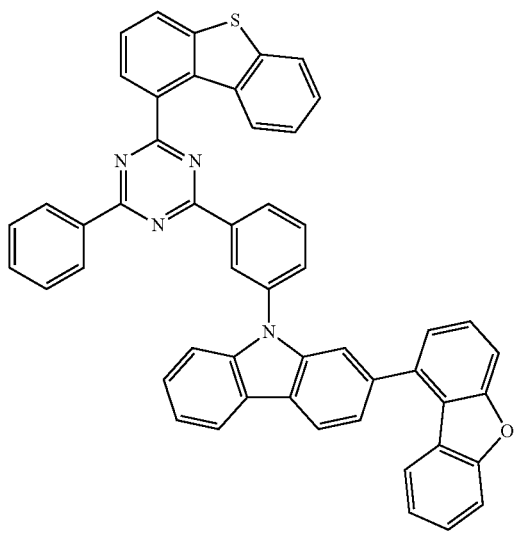
H1-11
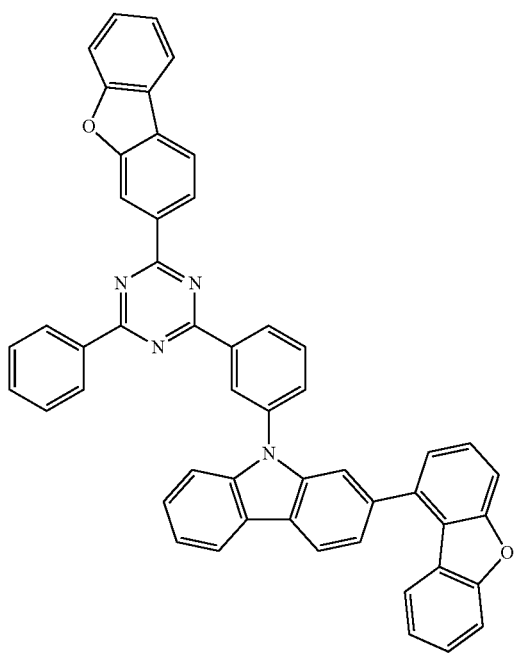
H1-12
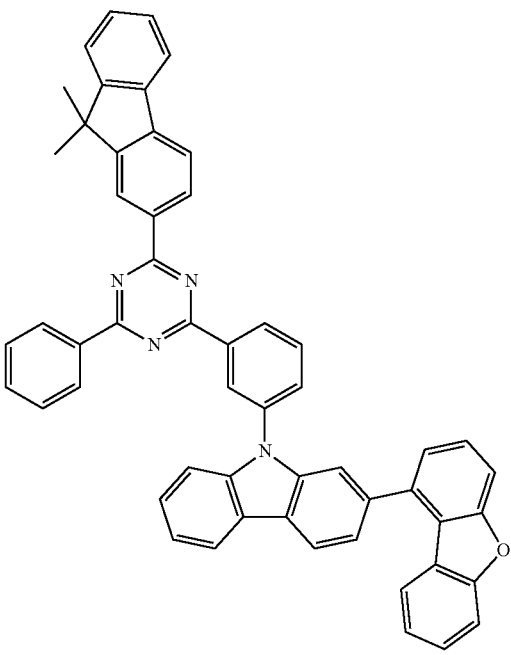
H1-13
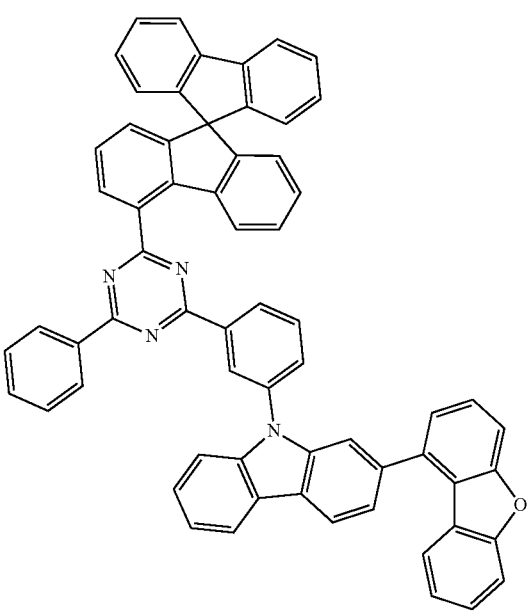

H1-14
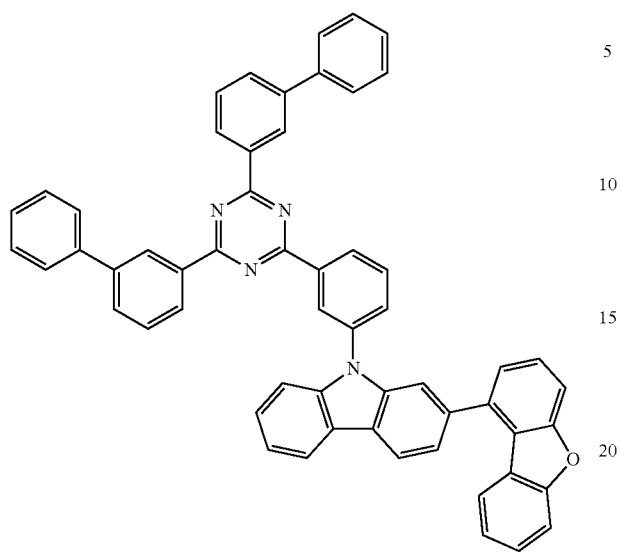
H1-15
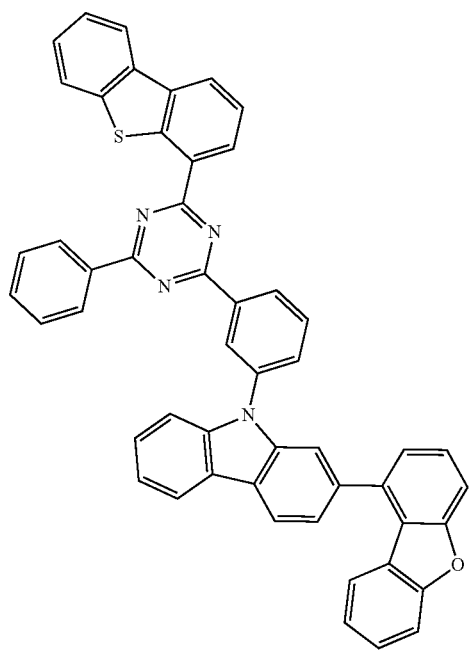
H1-16
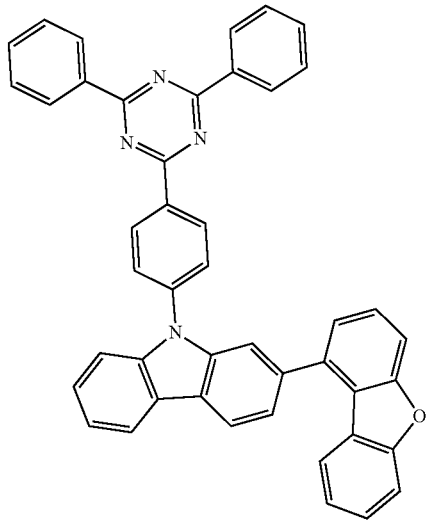
H1-17
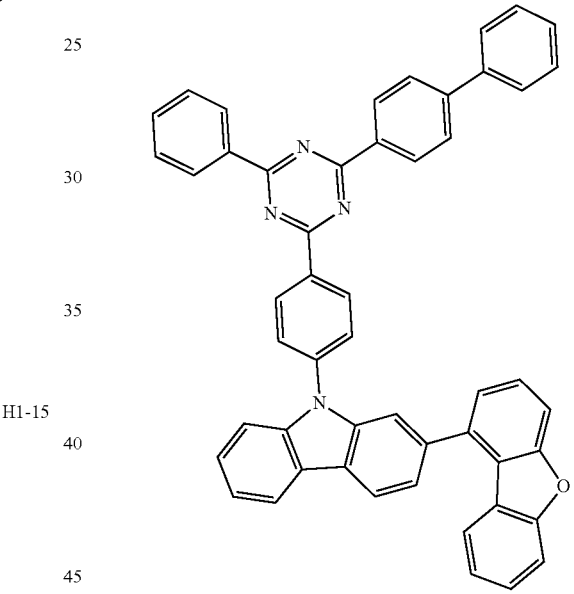
H1-18
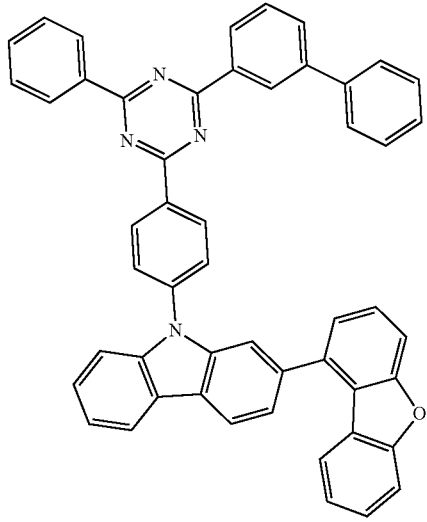

H1-19
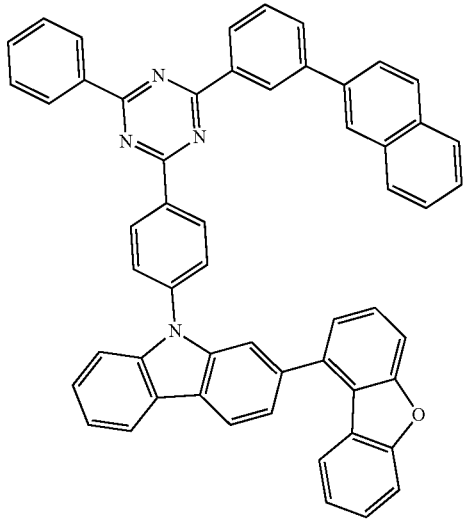
H1-20
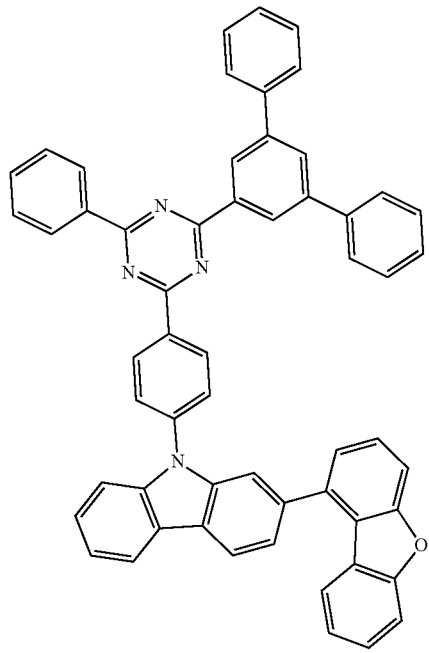
H1-21
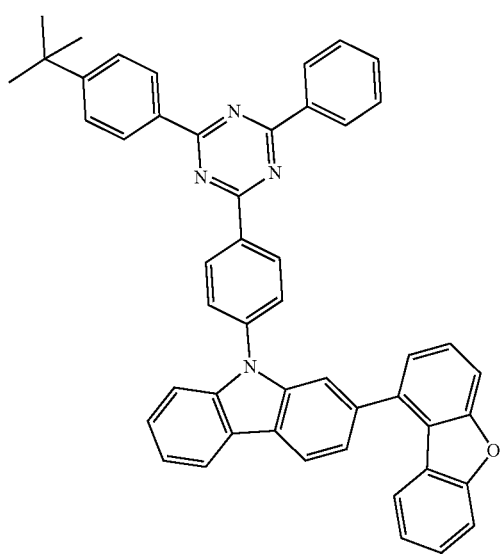
H1-22
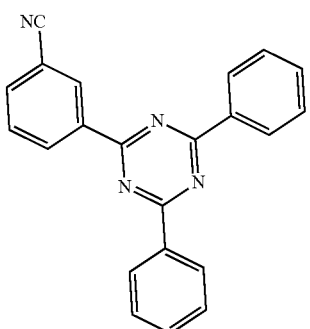
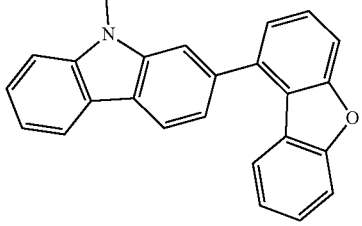
H1-23
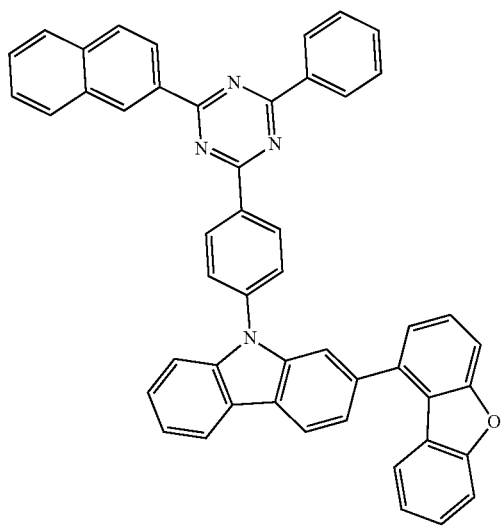

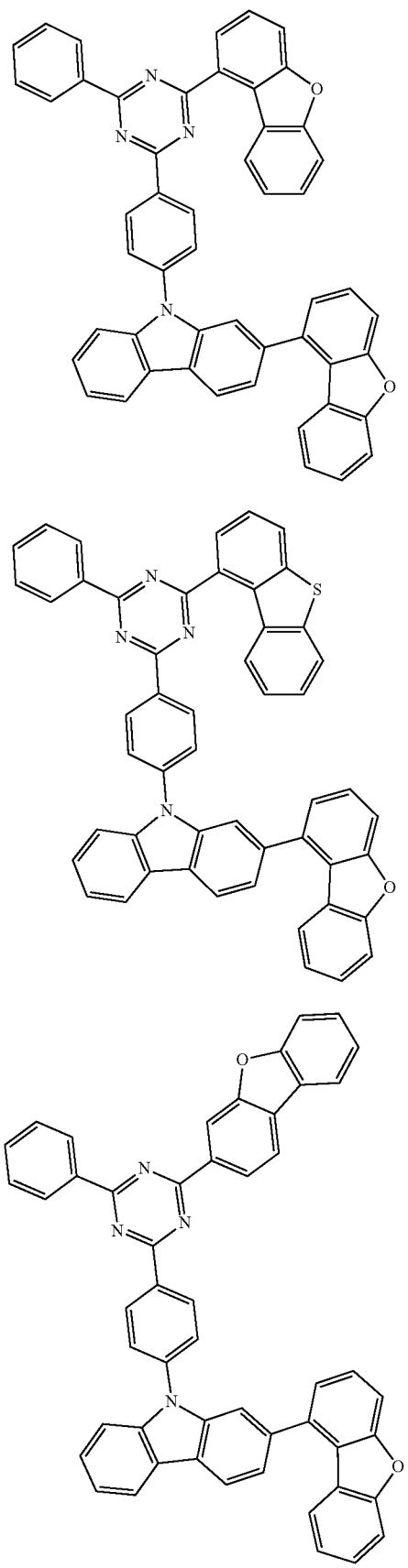
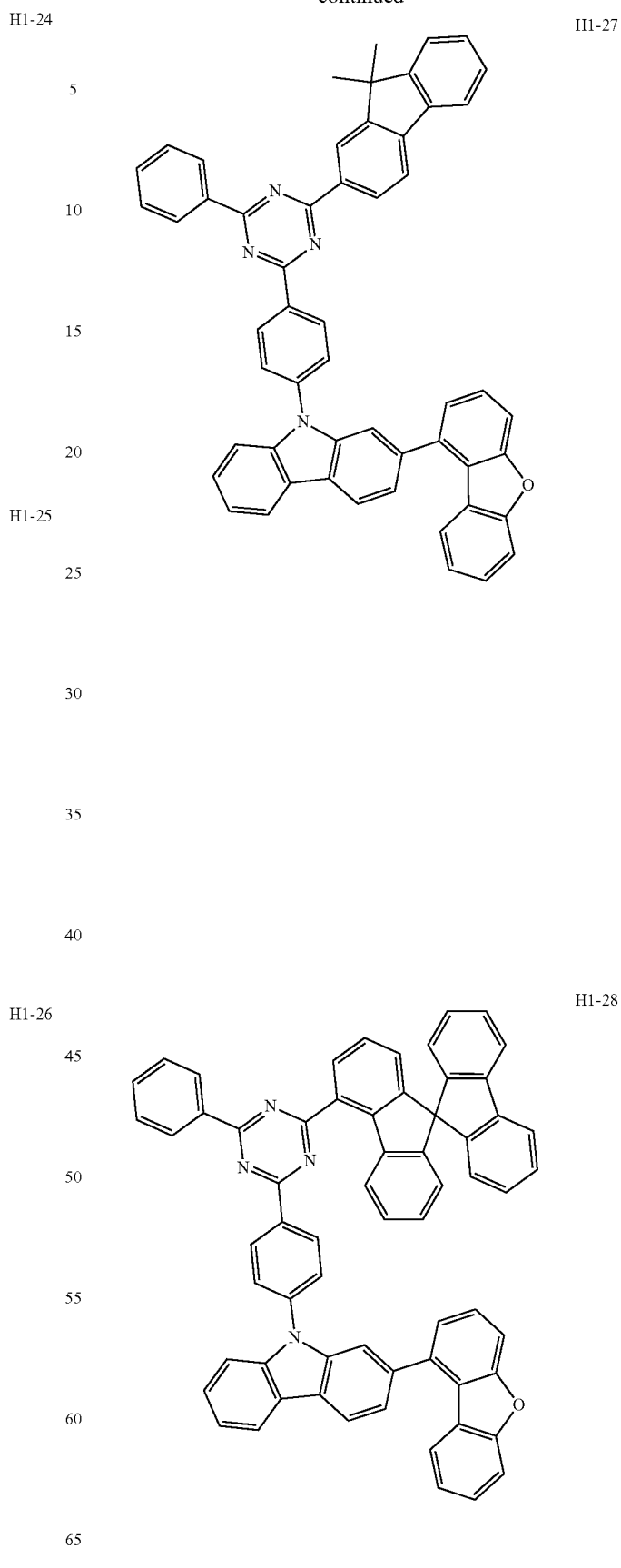

H1-29
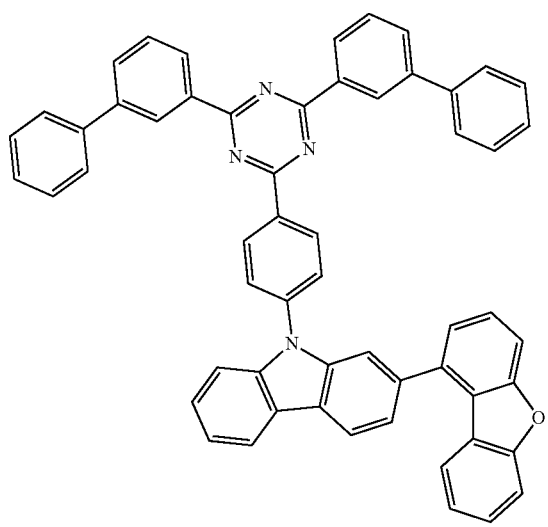
H1-30
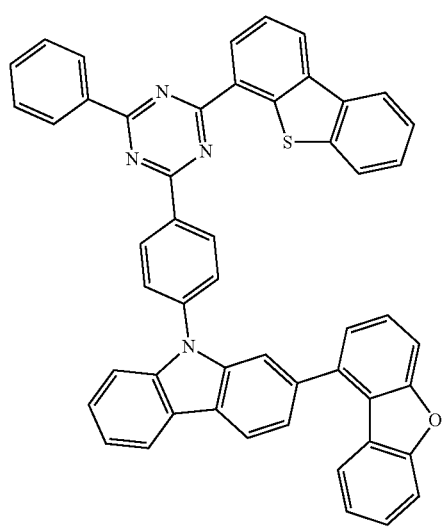
H1-31
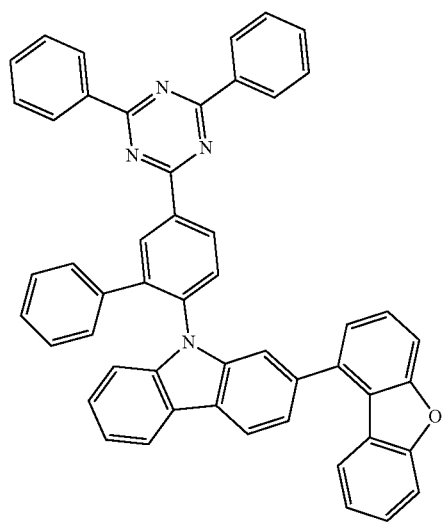
H1-32
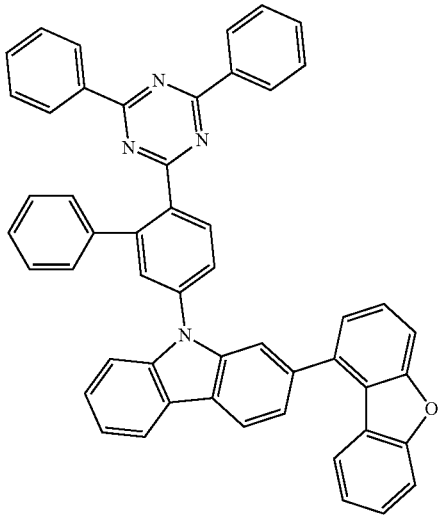
H1-33
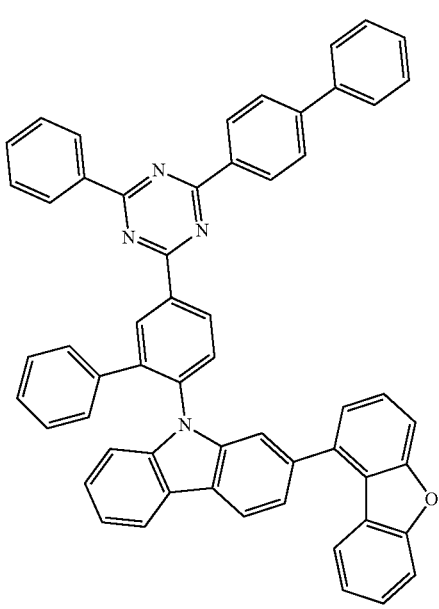
H1-34
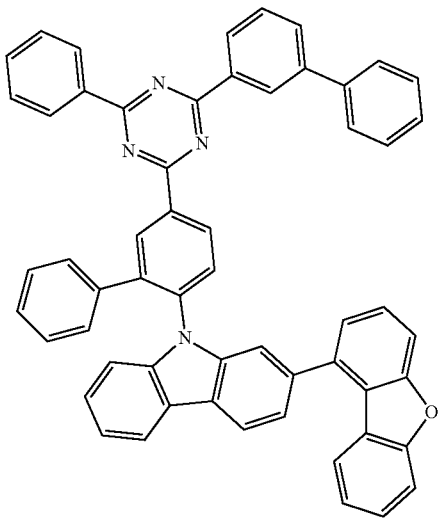

H1-35
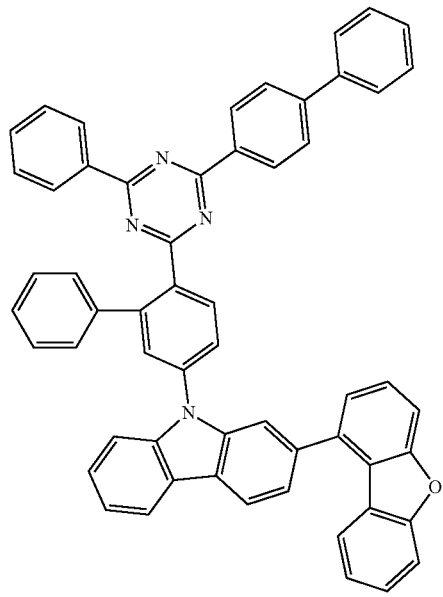
H1-36
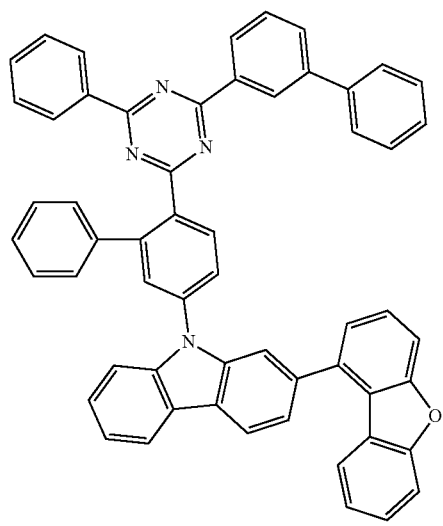
H1-37
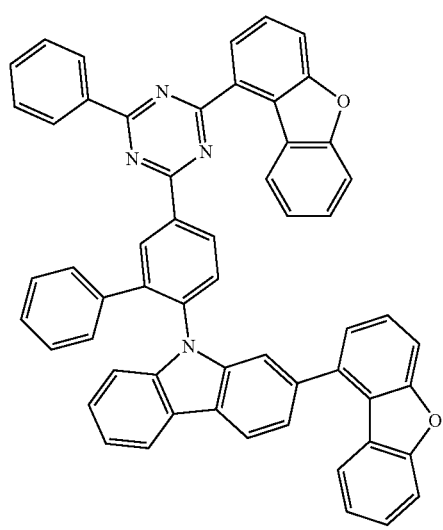
H1-38
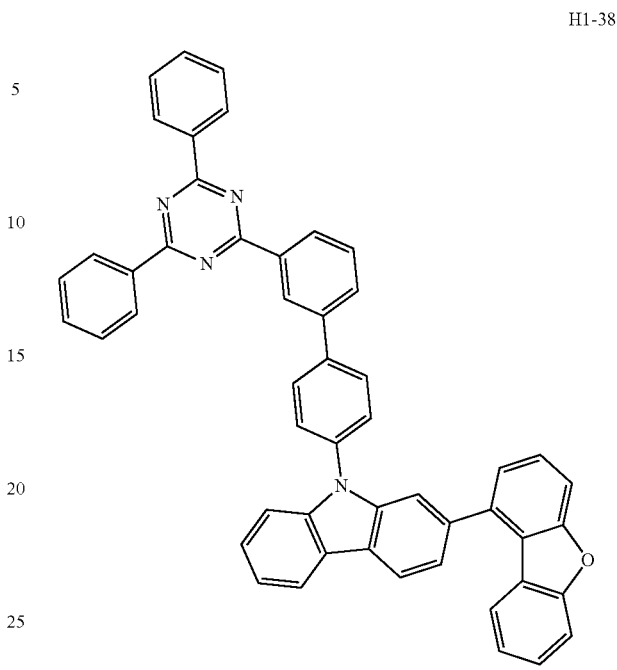
H1-39
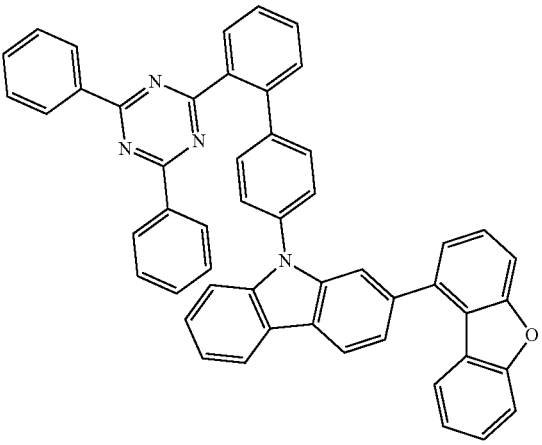

H1-40
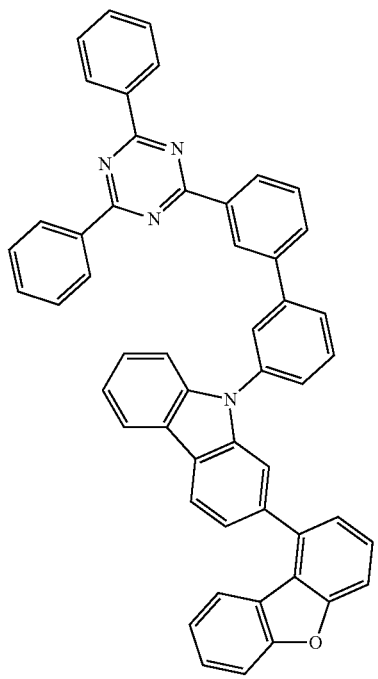
H1-41
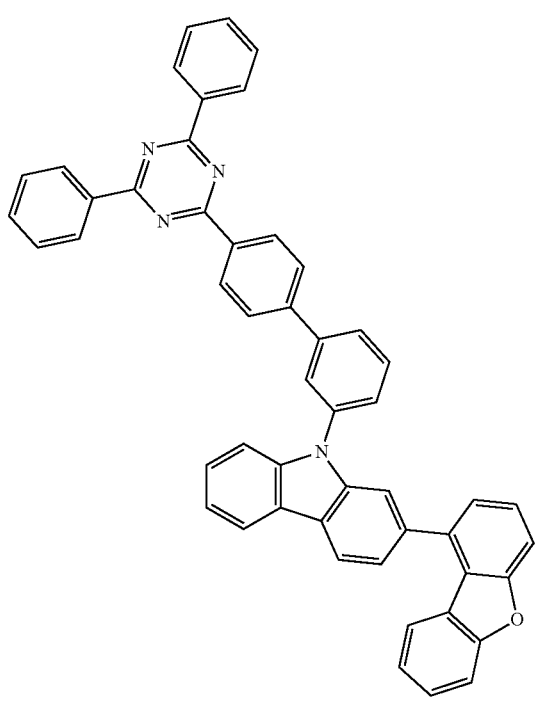
H1-42
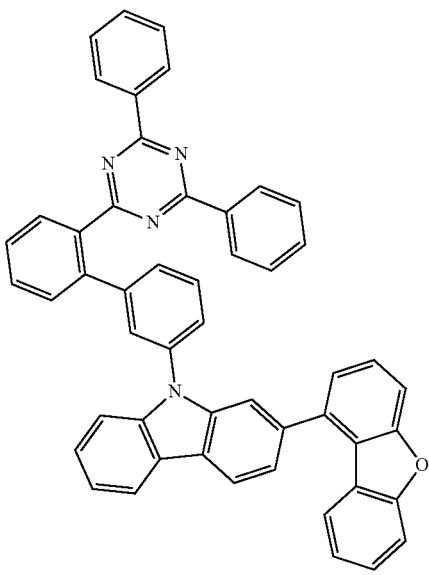
H1-43
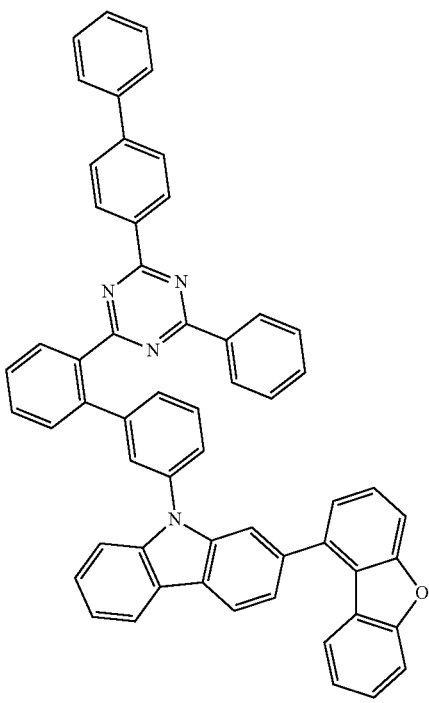

H1-44
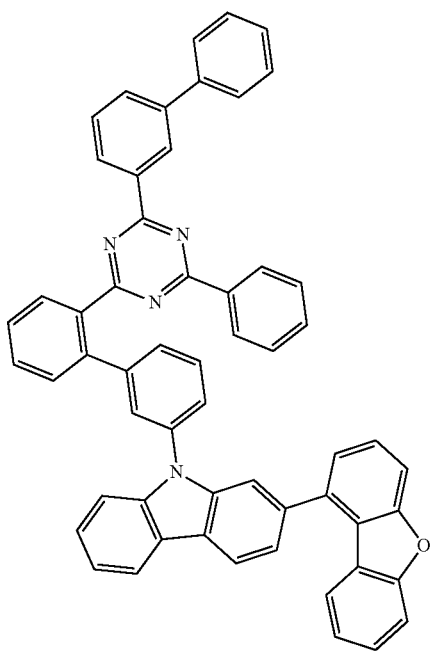
H1-45
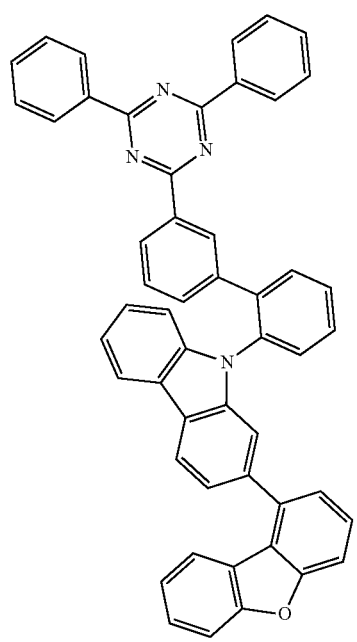
H1-46
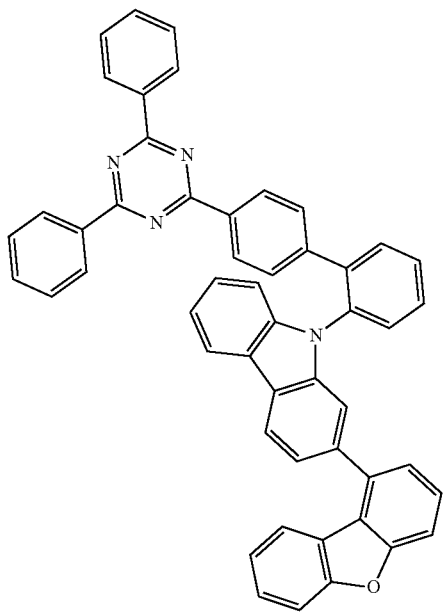
H1-47
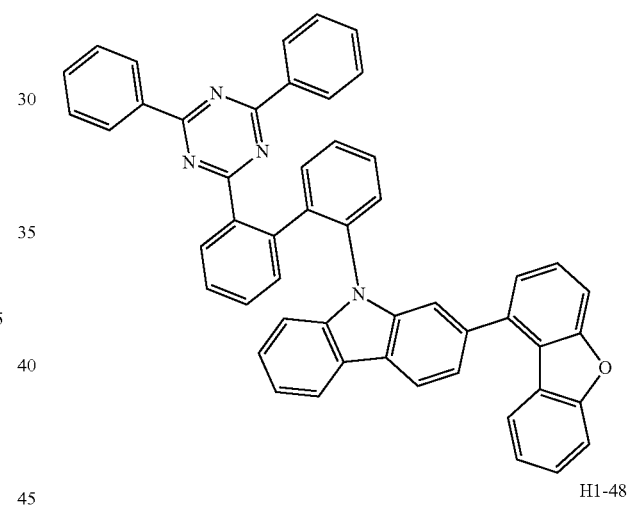
H1-48
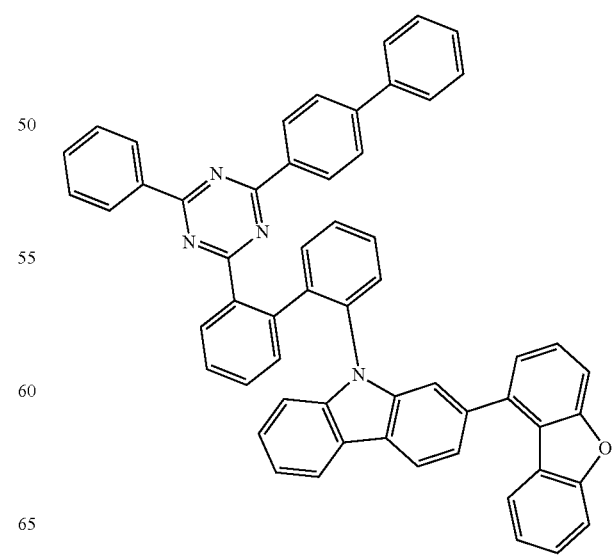

H1-49
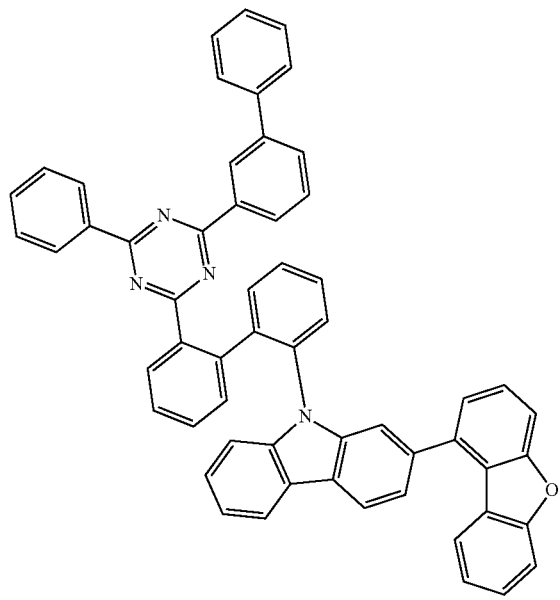
H1-50
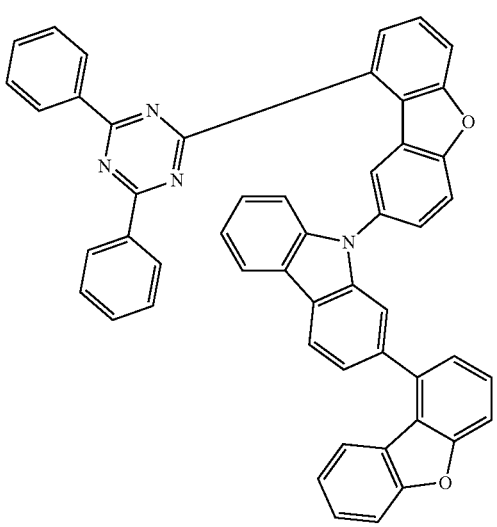
H1-51
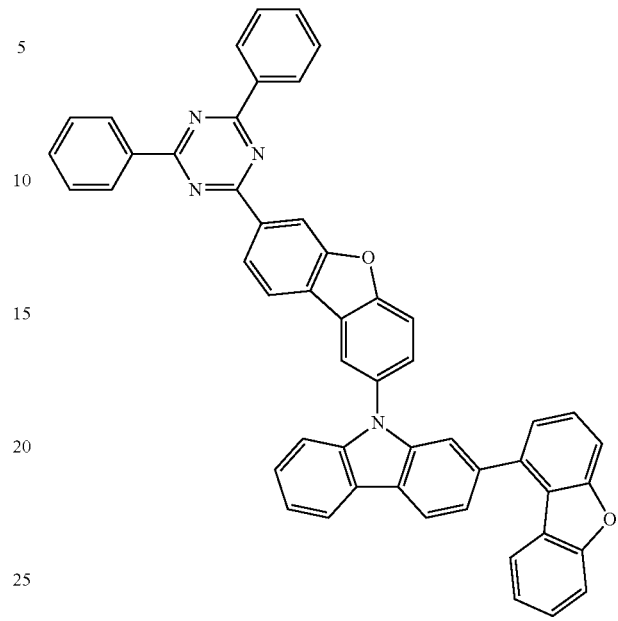
H1-52
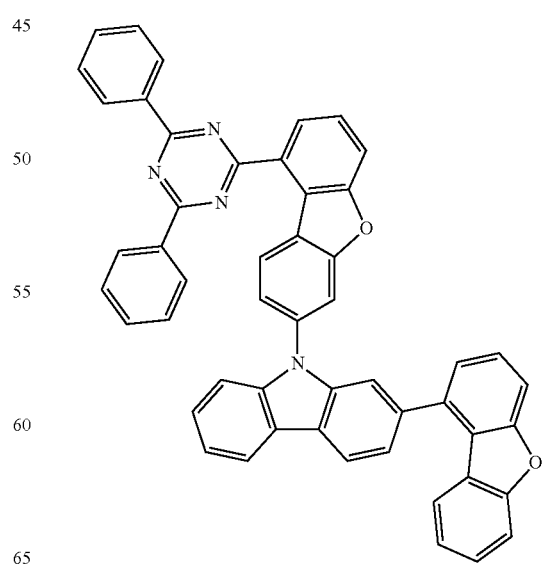

H1-53
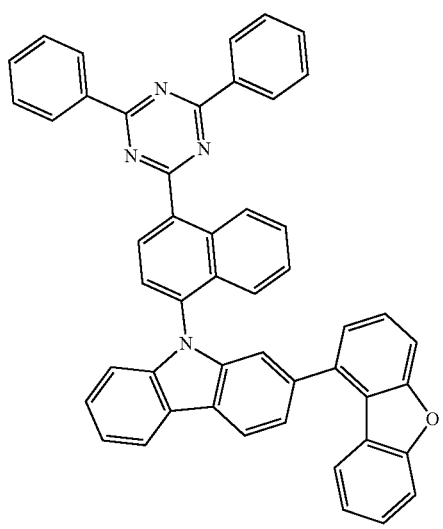
H1-54
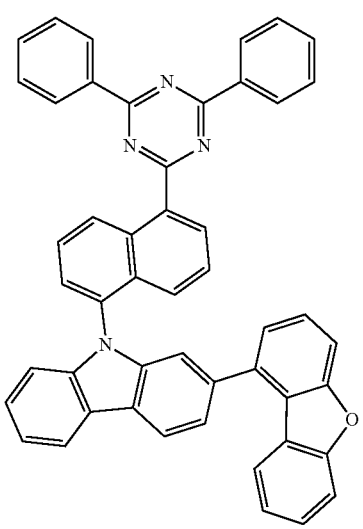
H1-55
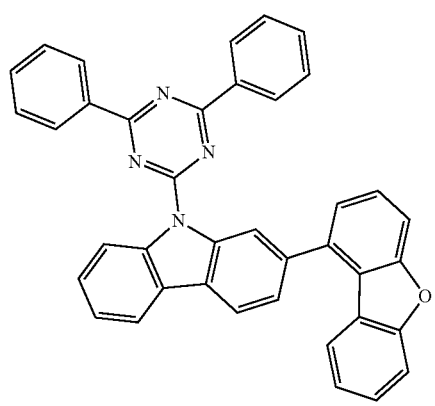
H1-56
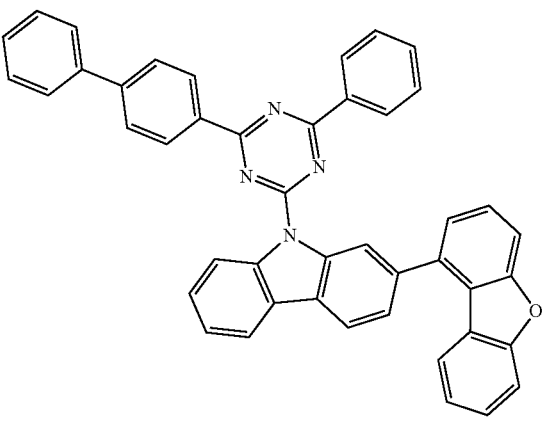
H1-57
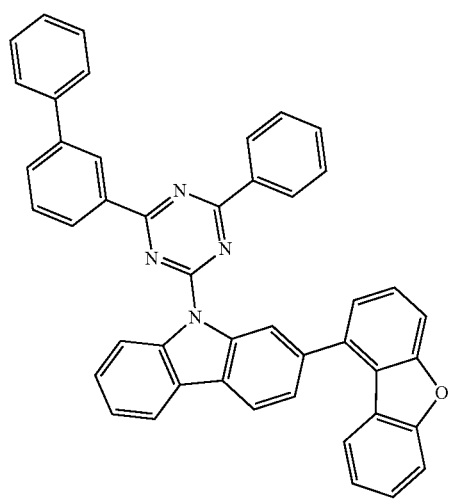
H1-58
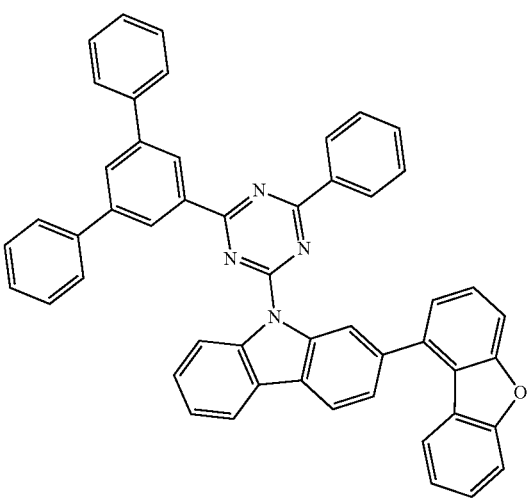

H1-59
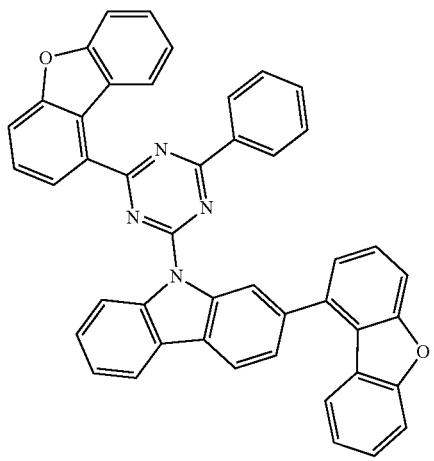
H1-60
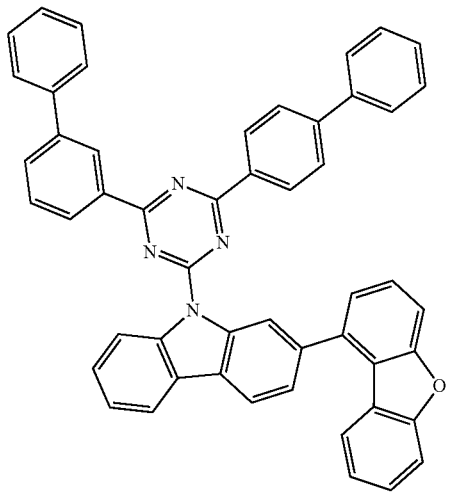
H1-61
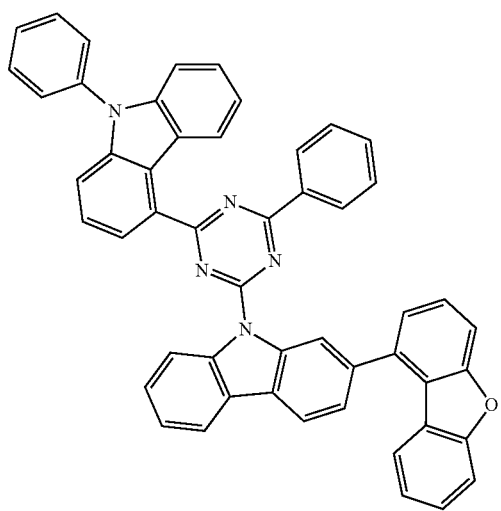
H1-62
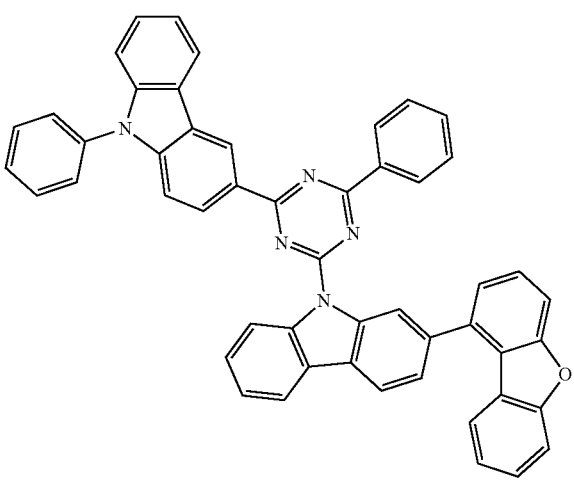
H1-63
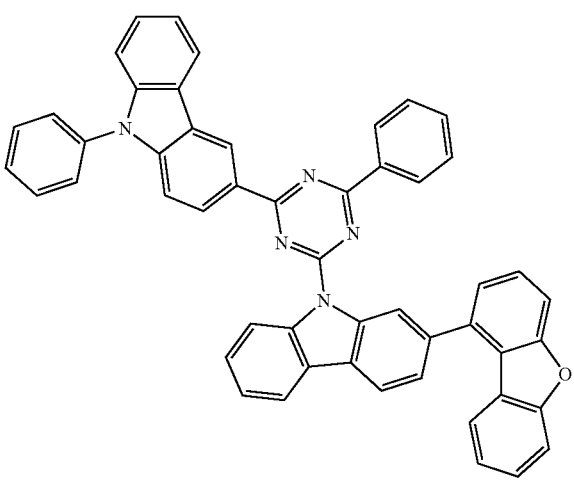
H1-64
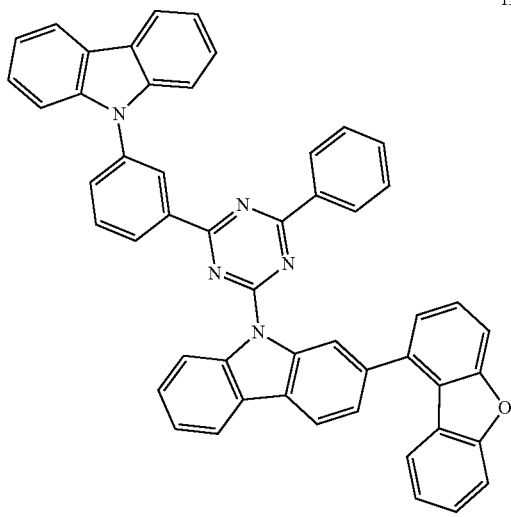

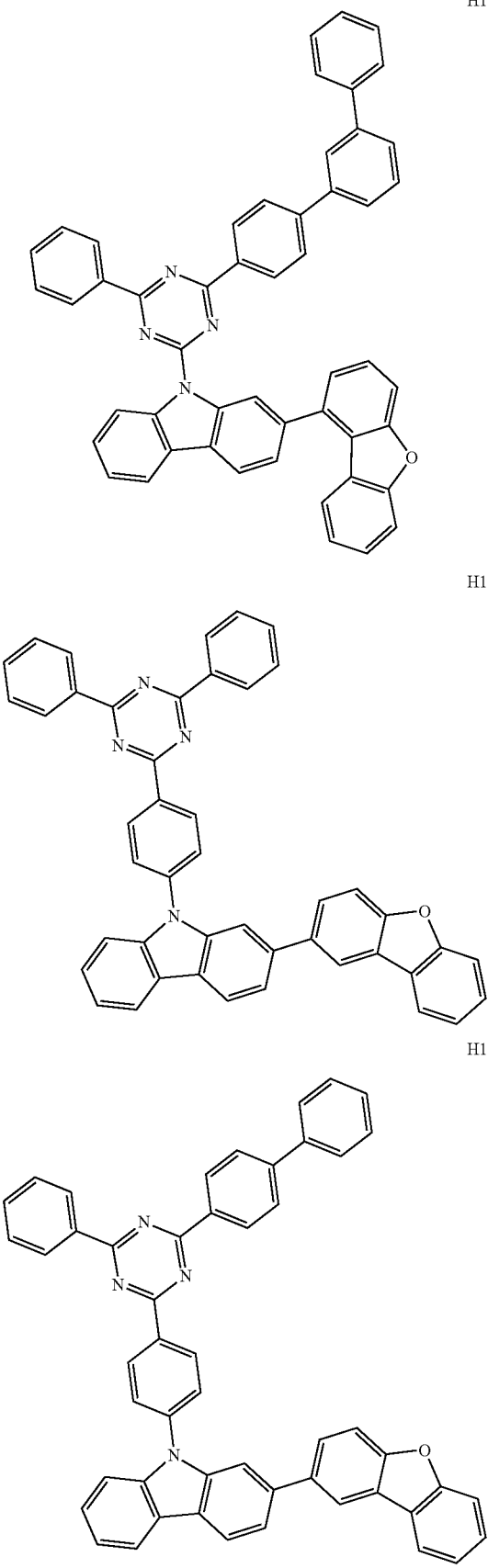
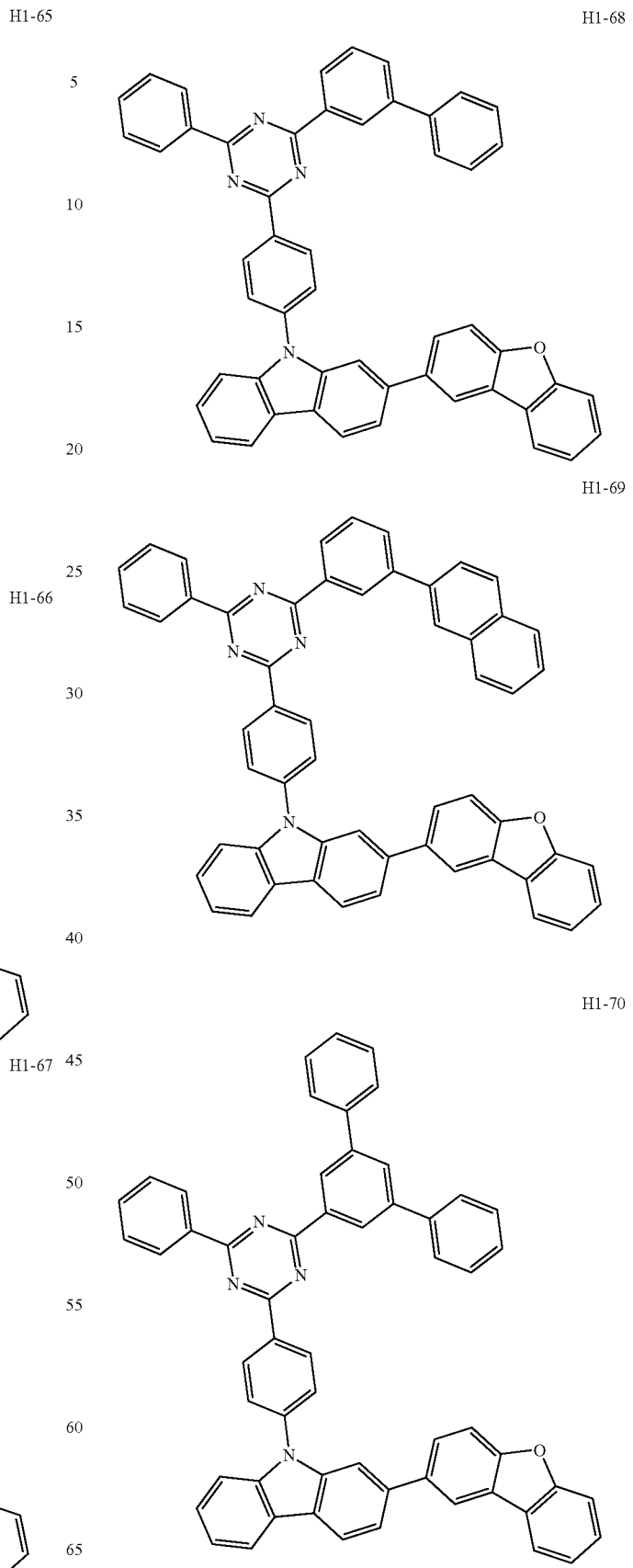

-continued
H1-71
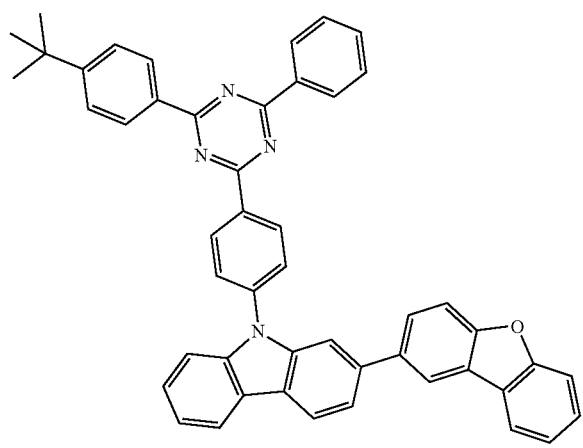
H1-72
H1-73
H1-74
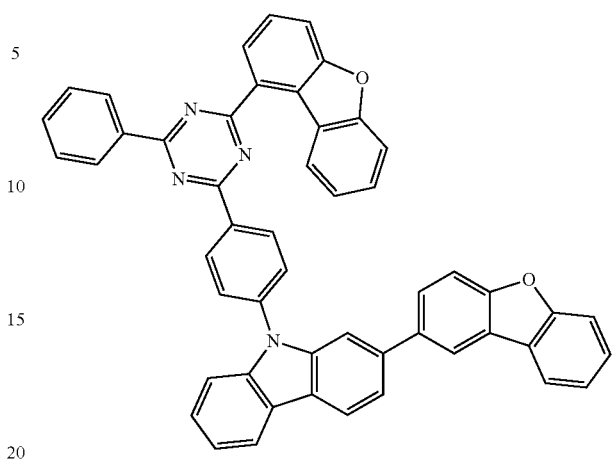
H1-75
H1-76

H1-77
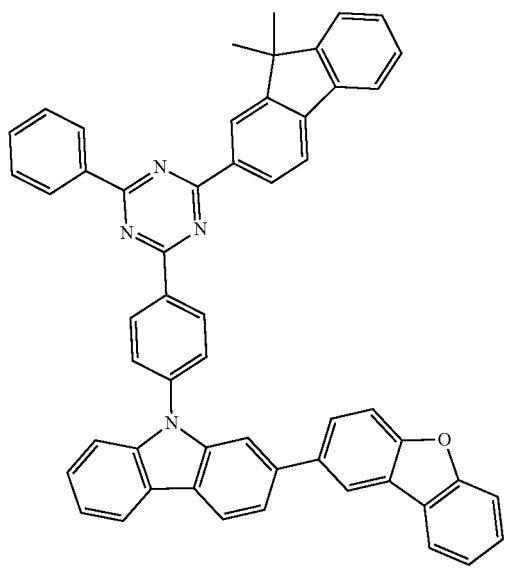
H1-78
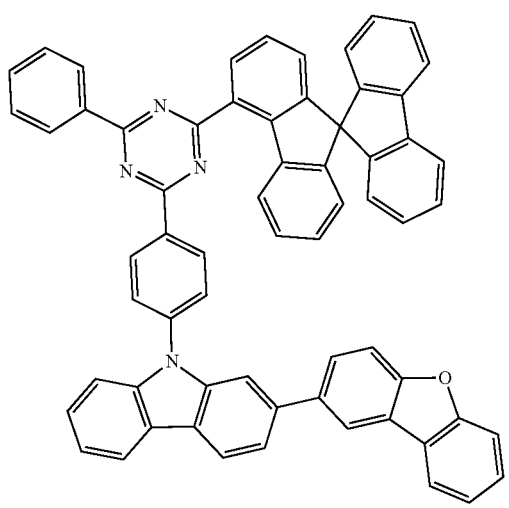
H1-79
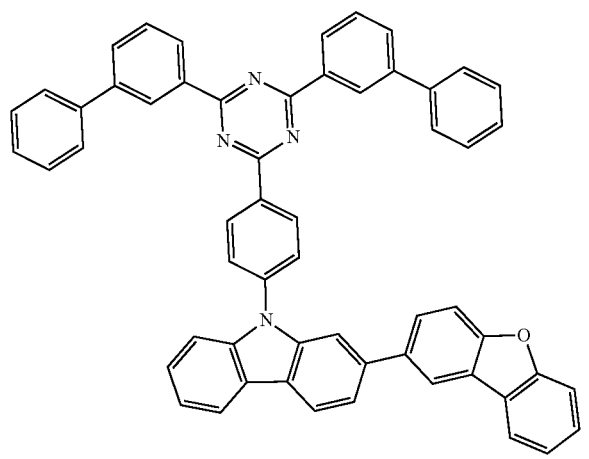
H1-80
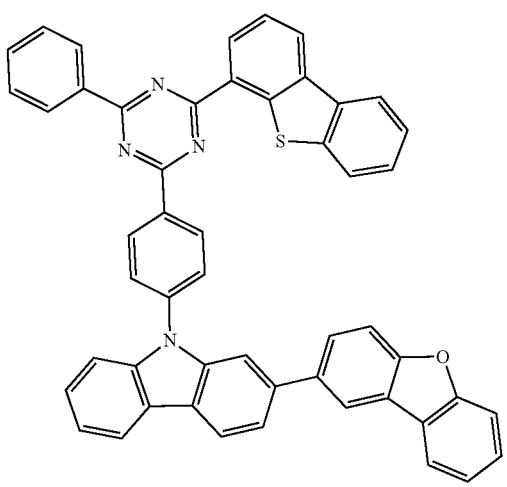
H1-81
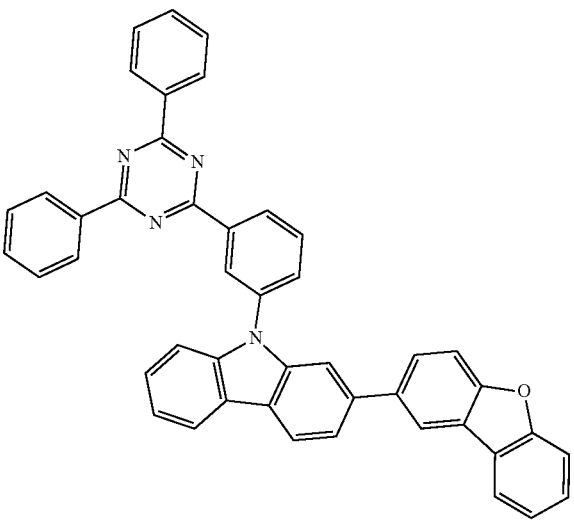

H1-82
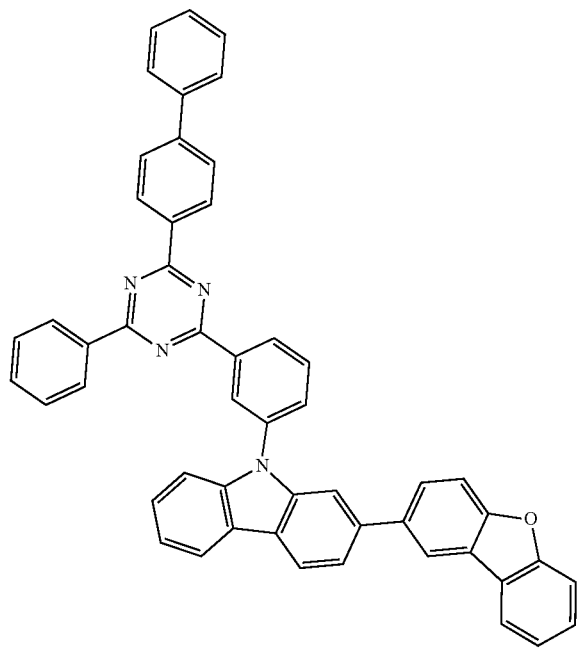
H1-83
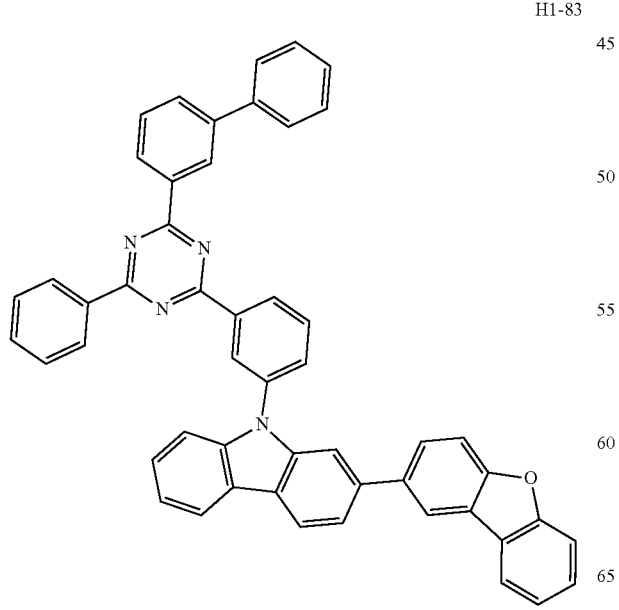
H1-84
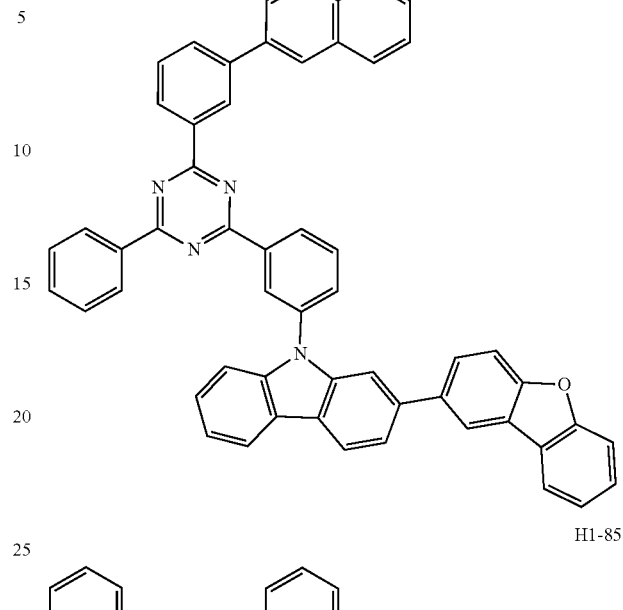
H1-85
H1-86
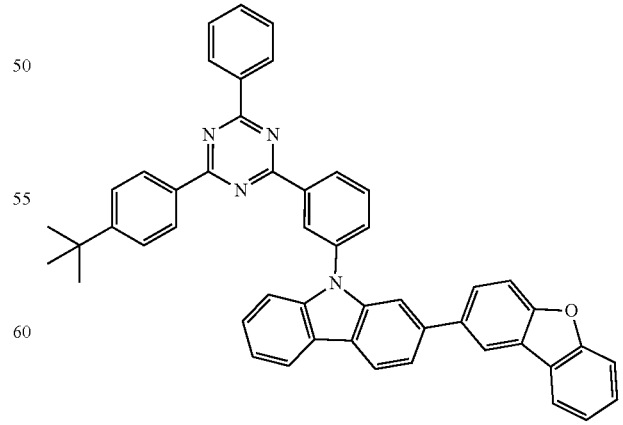

H1-87
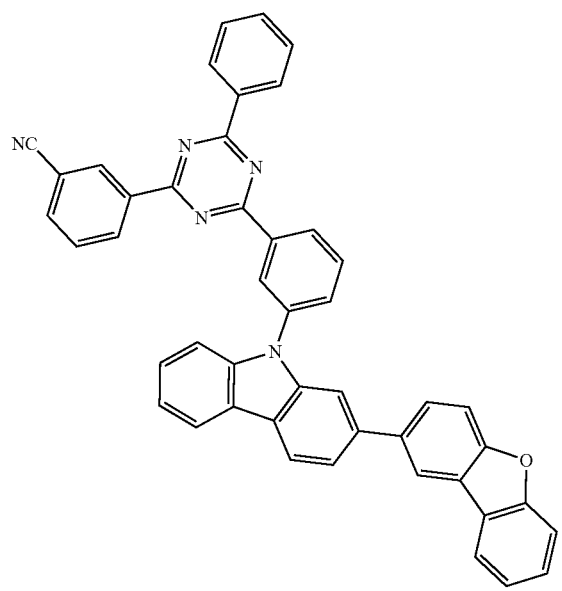
H1-89
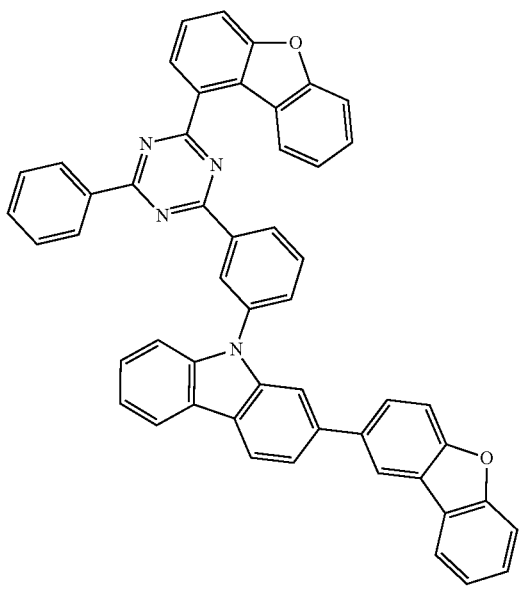
H1-88
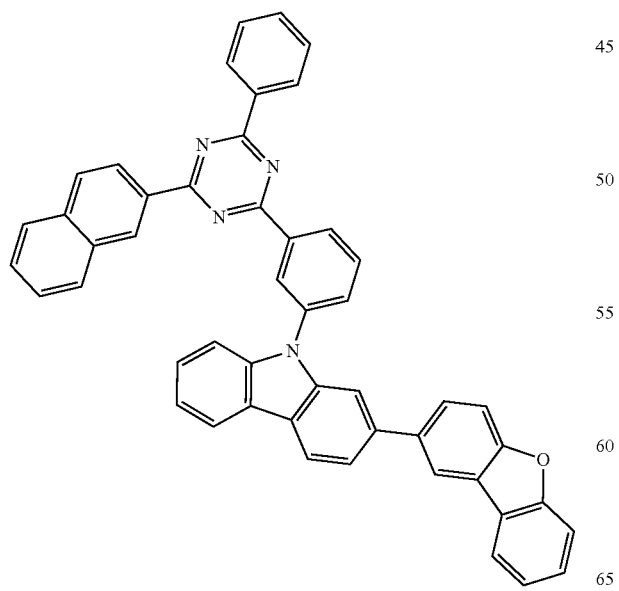
H1-90
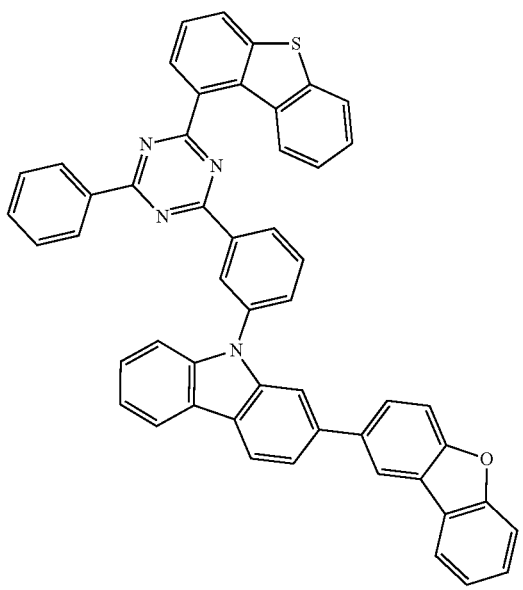

H1-91
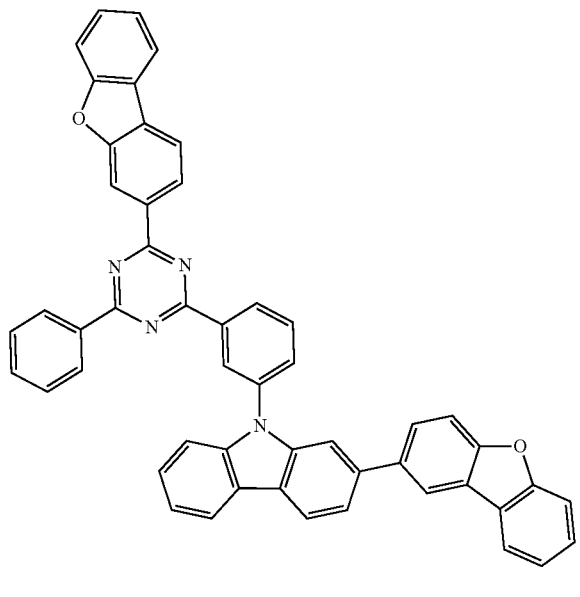
H1-92
H1-93
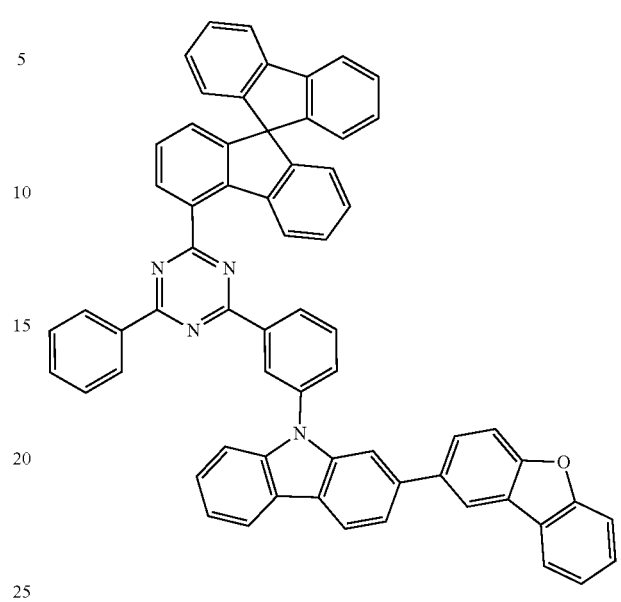
C-94
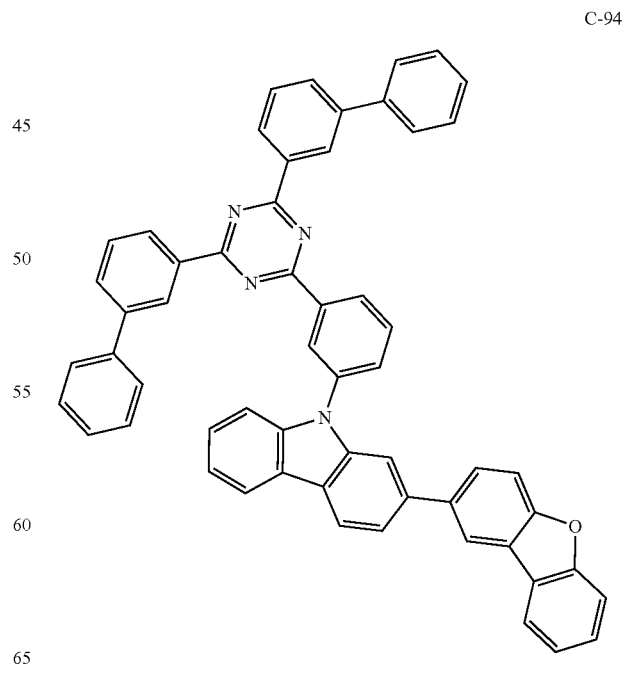

C-95
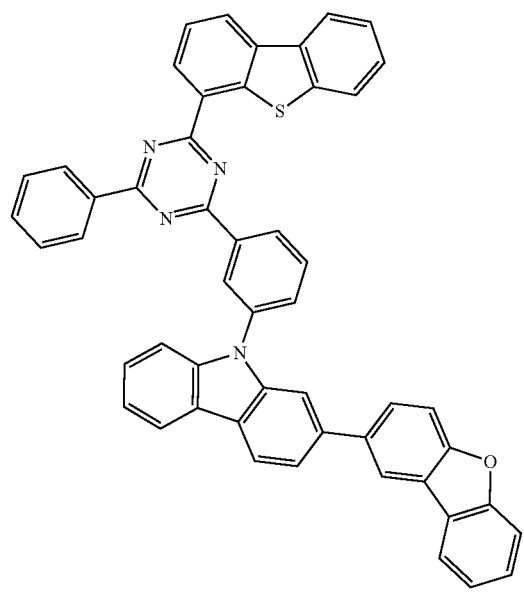
H1-96
H1-97
H1-98
H1-99
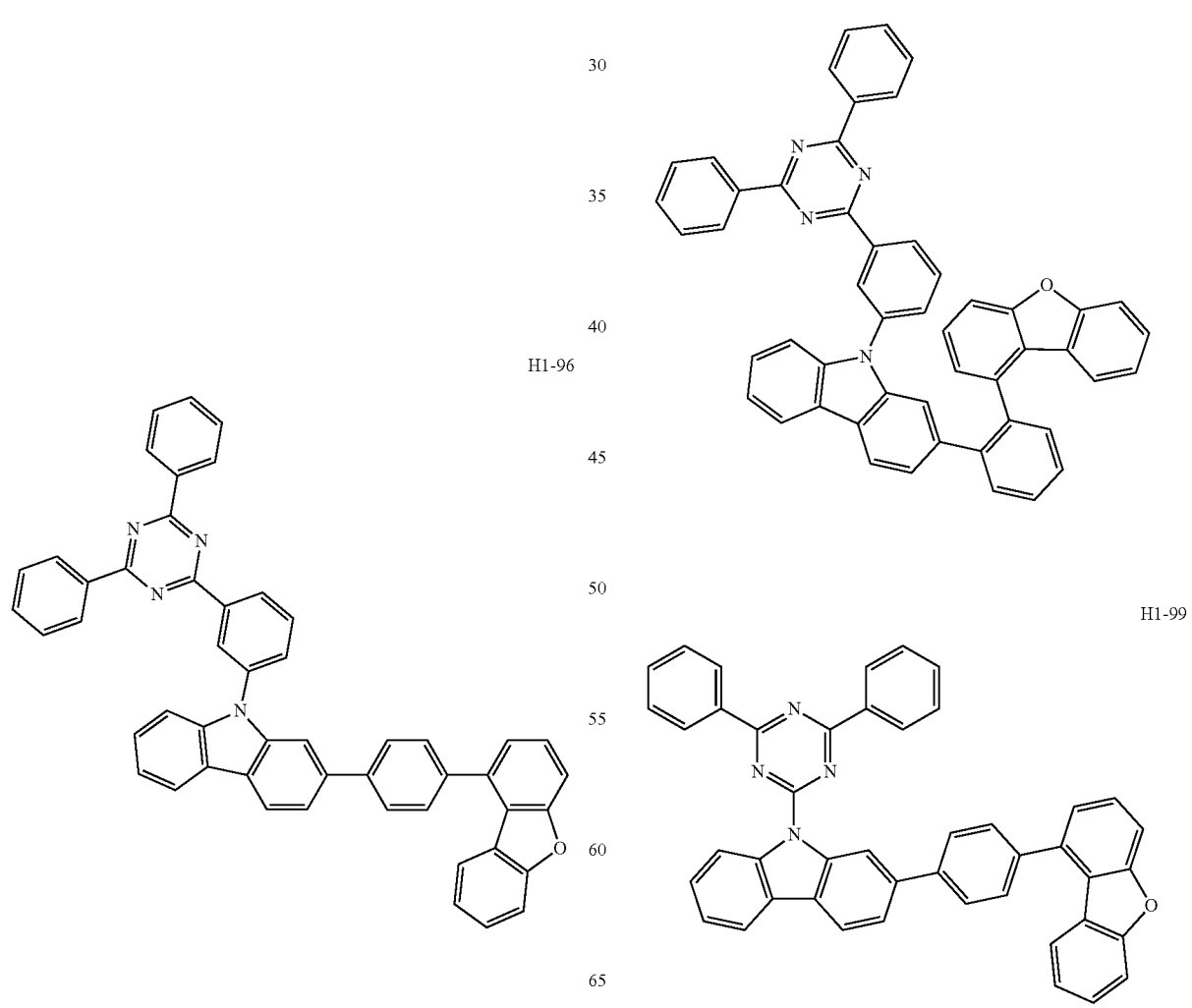

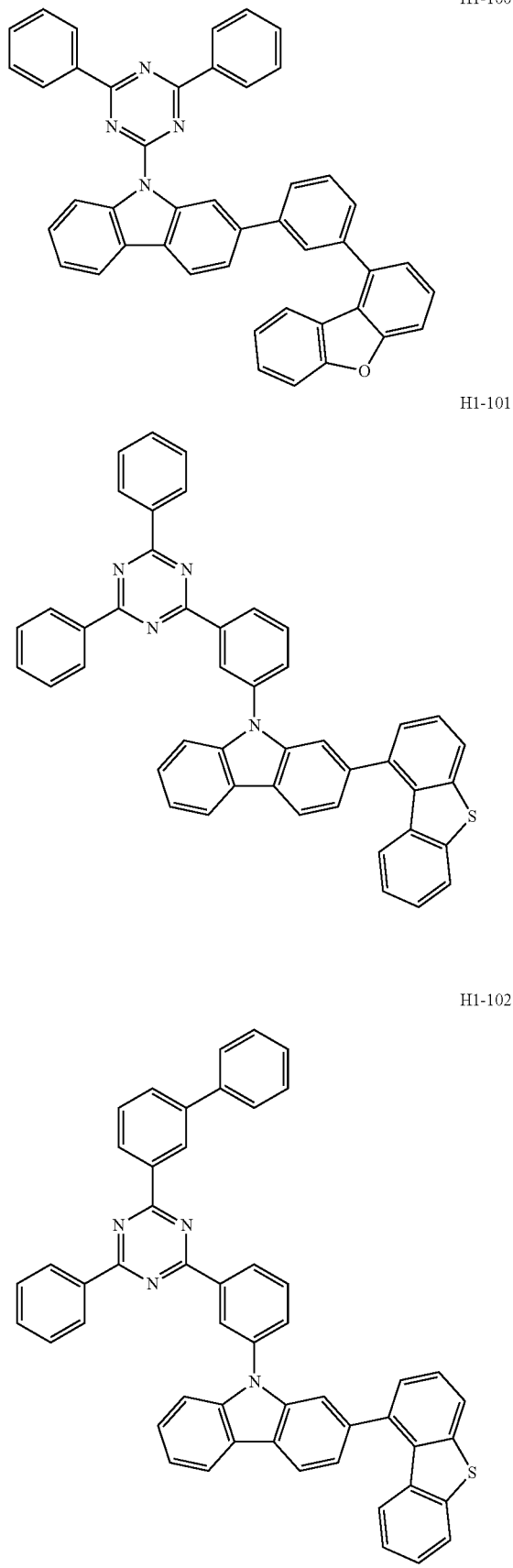
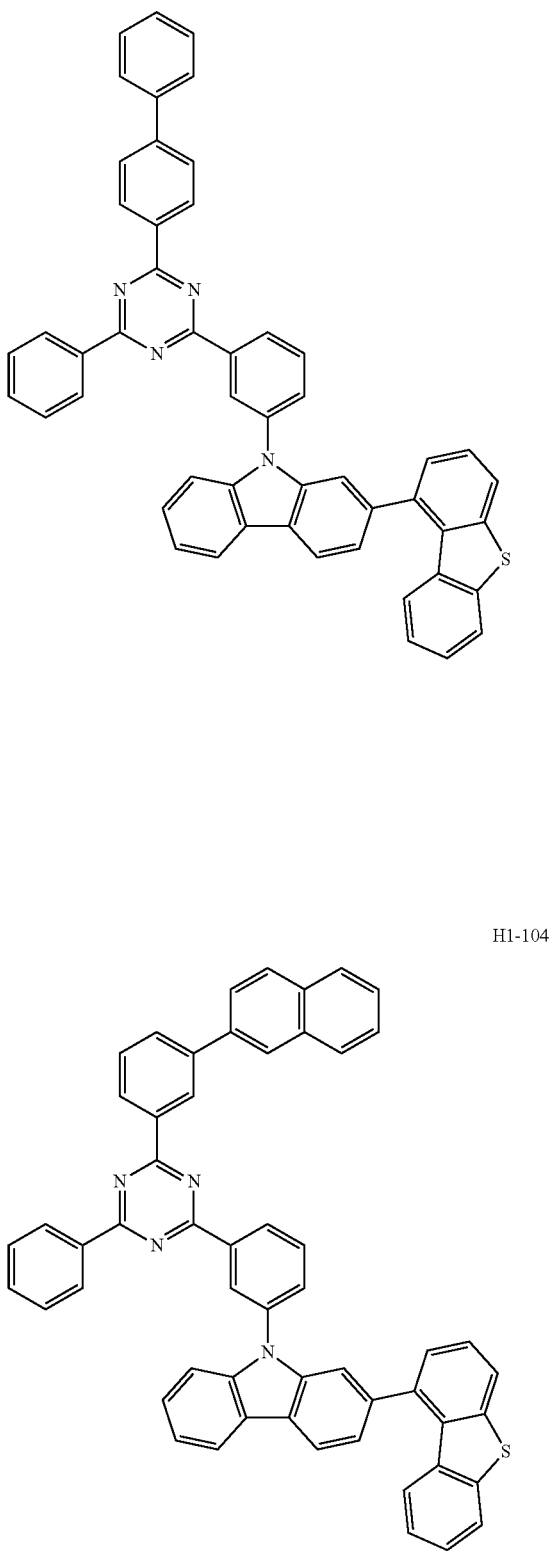

H1-105
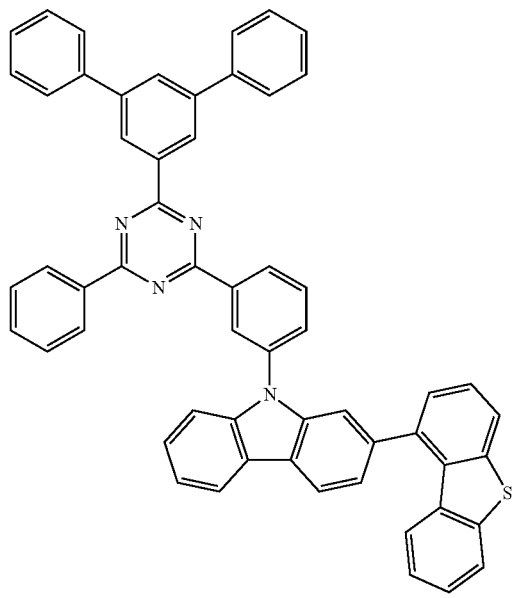
H1-107
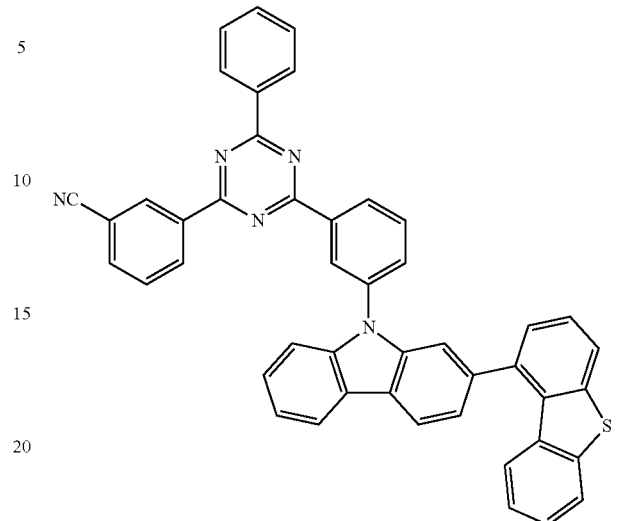
H1-108
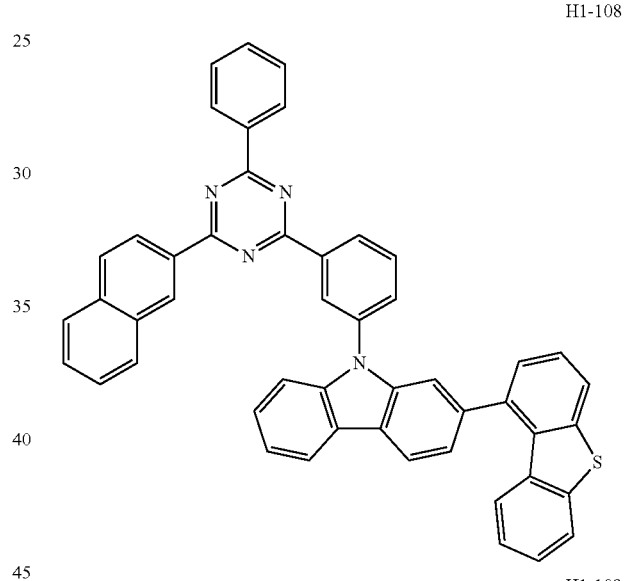
H1-106
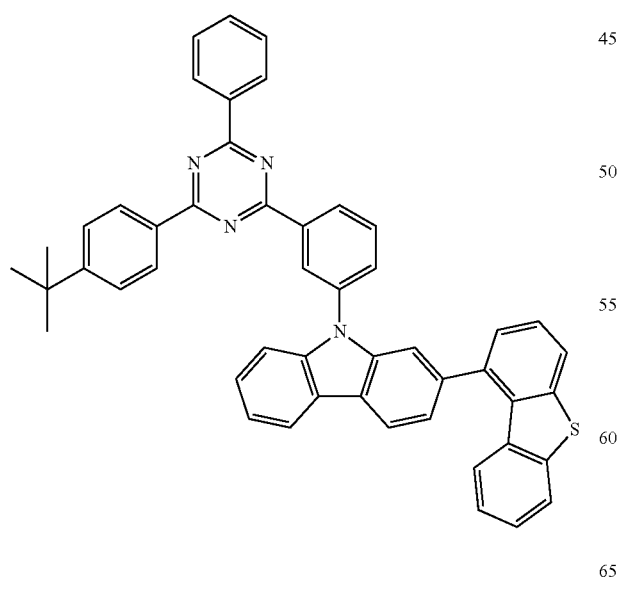
H1-109
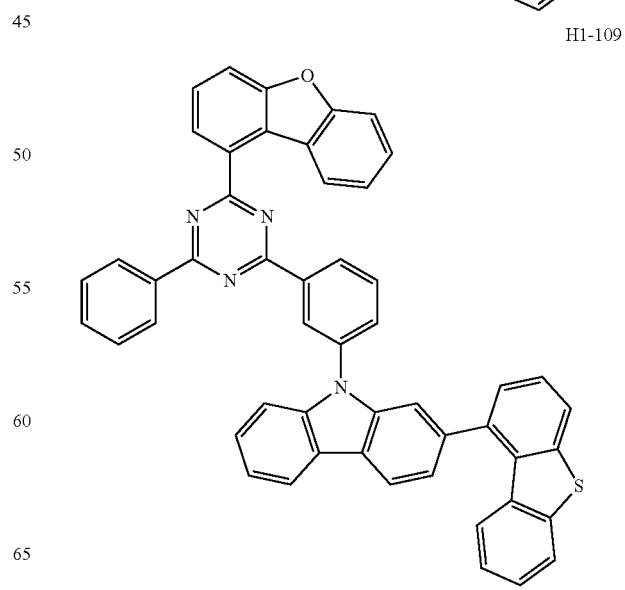

H1-110
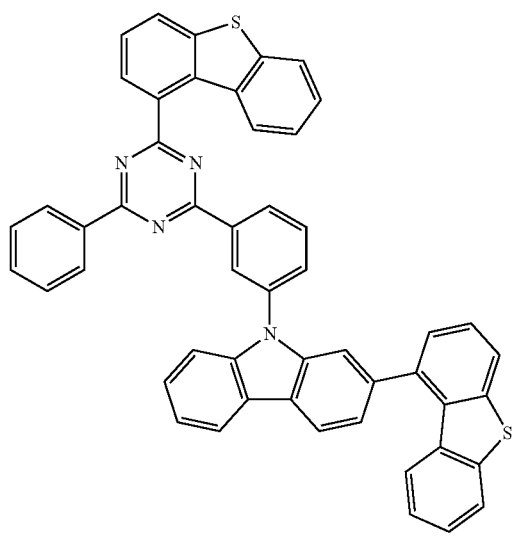
H1-111
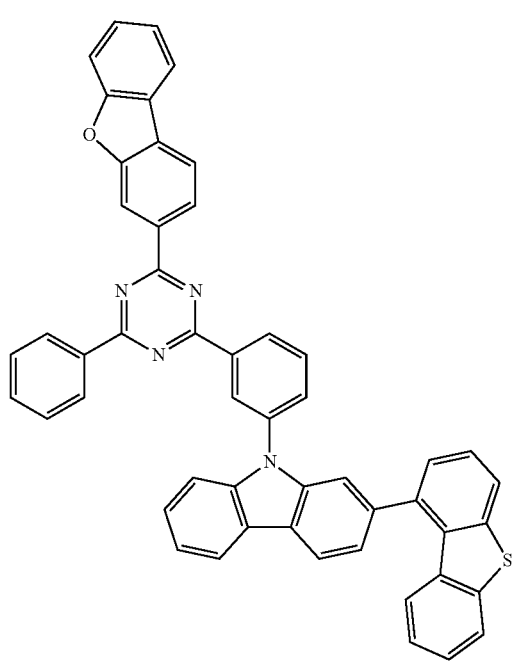
H1-112
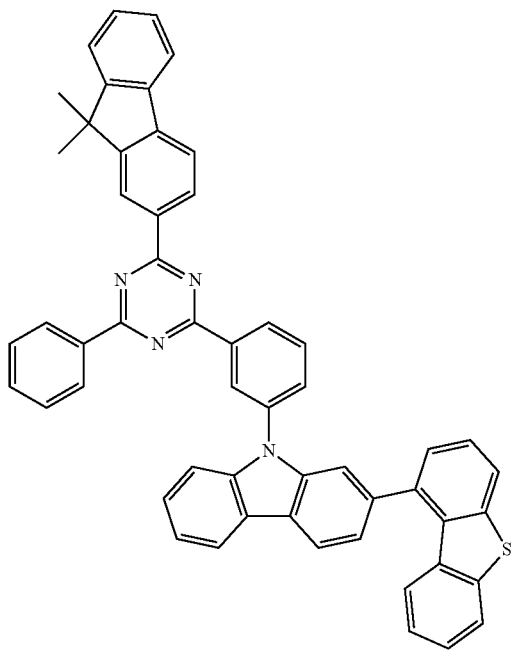
H1-113
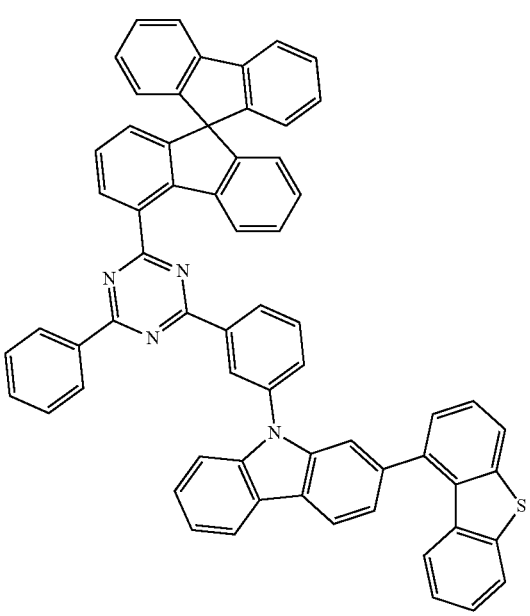

H1-114
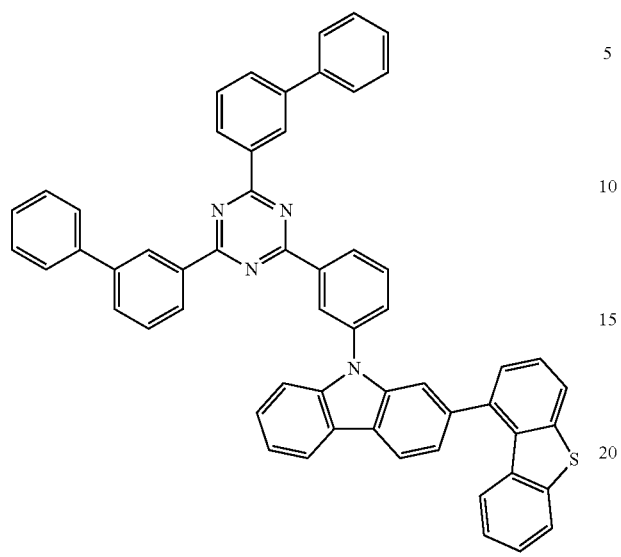
H1-115
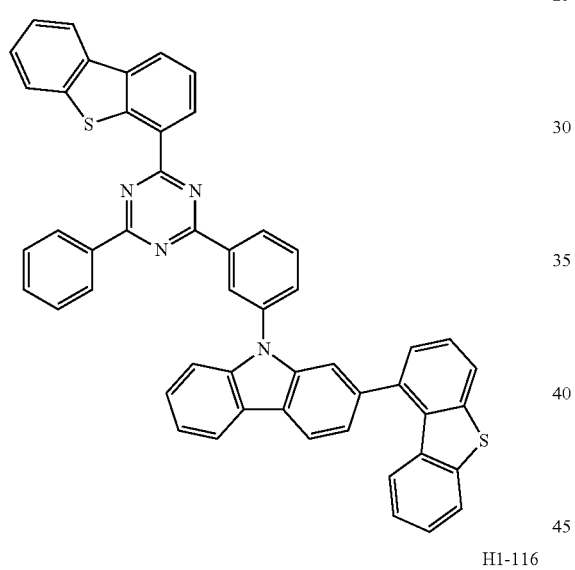
H1-116
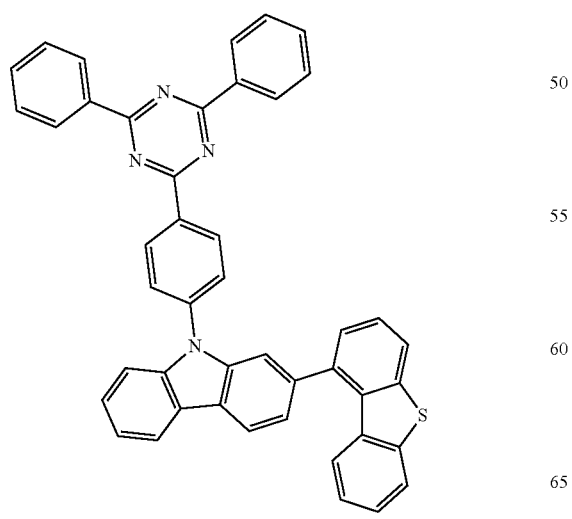
H1-117
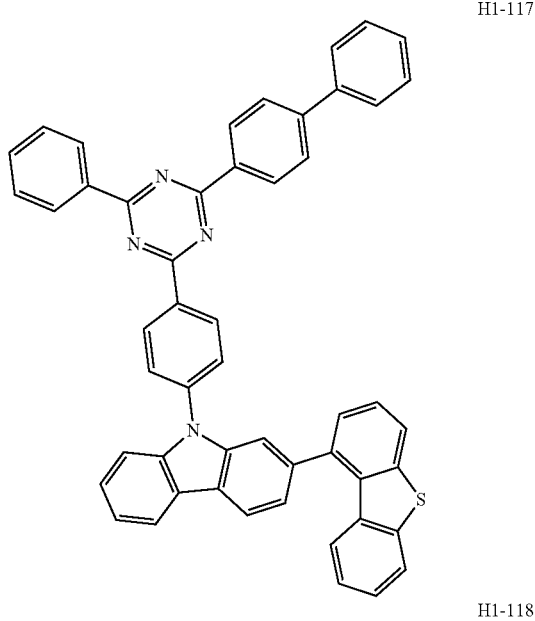
H1-118
H1-119

H1-120
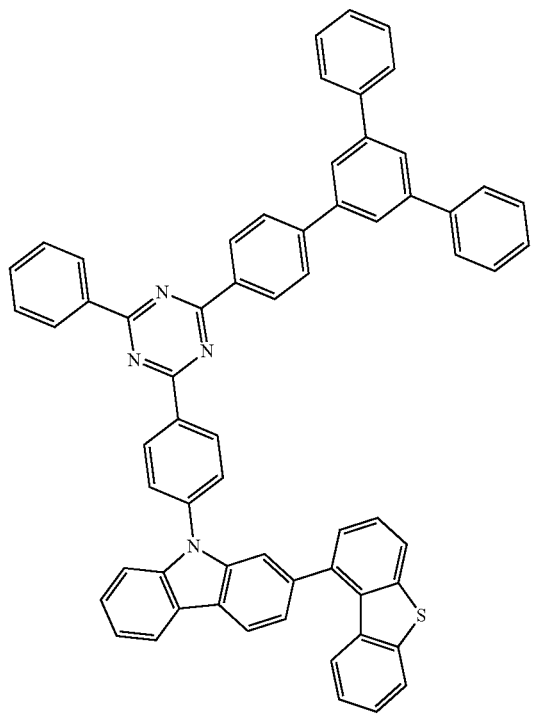
H1-121
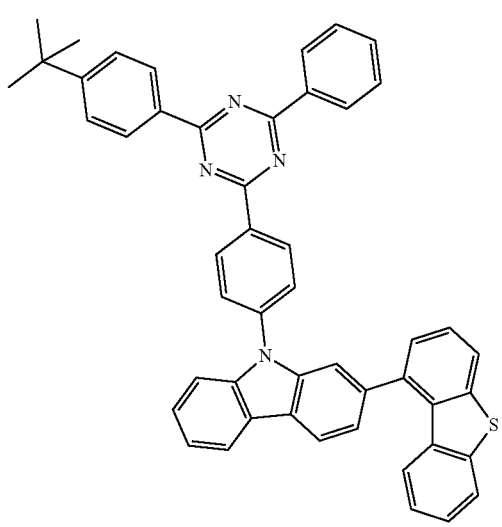
H1-122
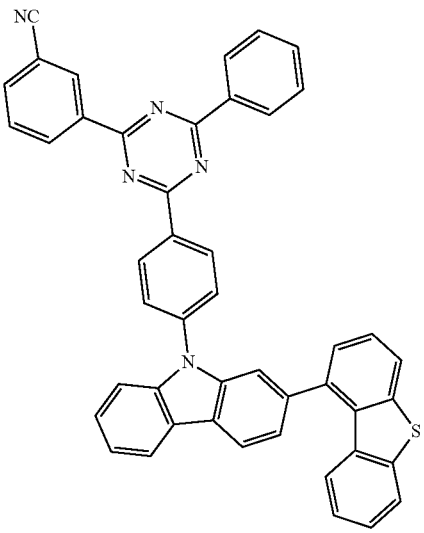
H1-123
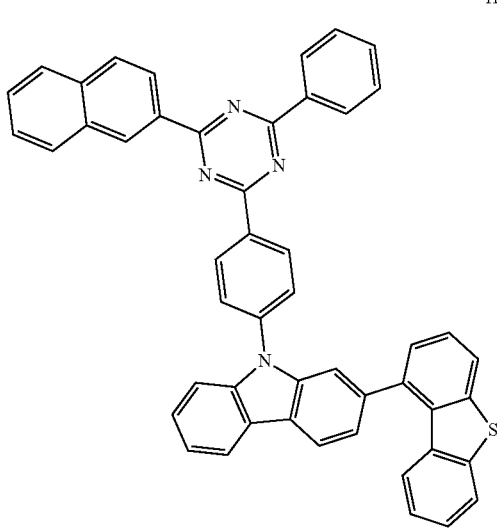
H1-124
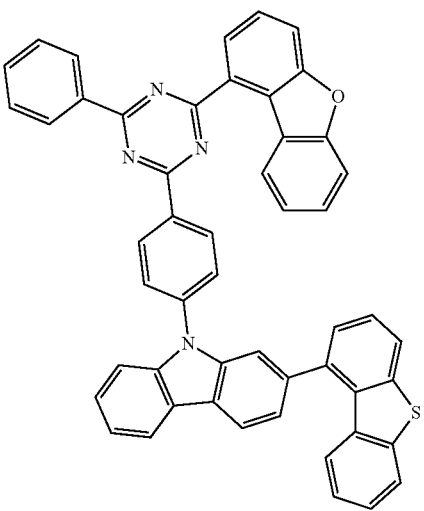

H1-125
H1-126
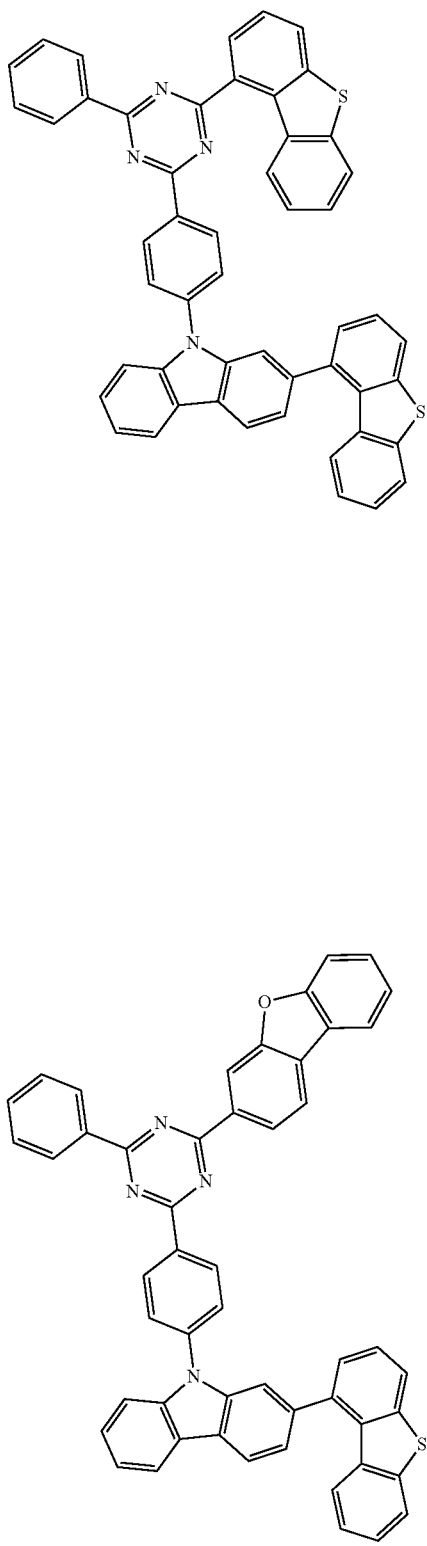
H1-127
H1-128
H1-129
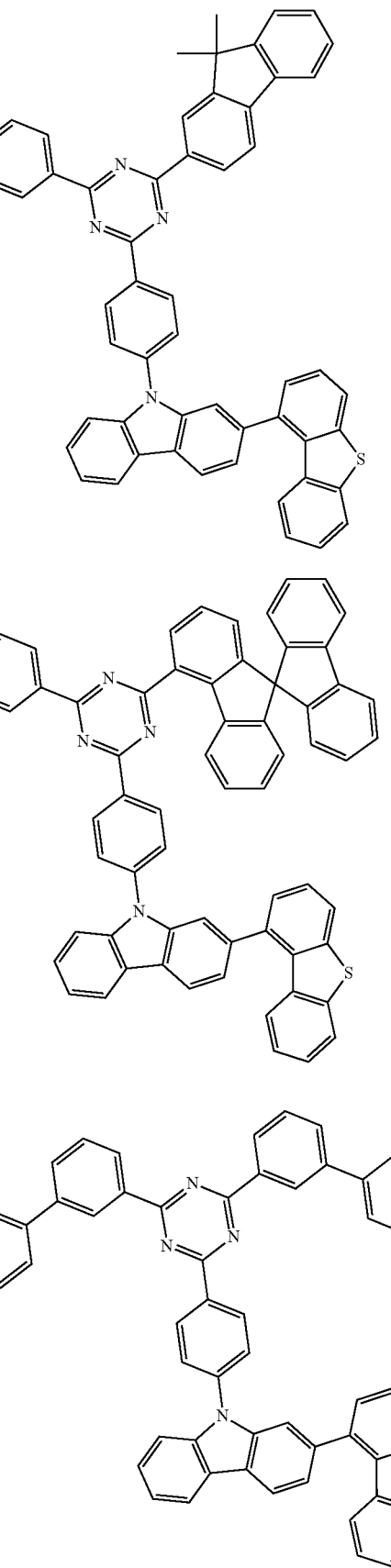

H1-130
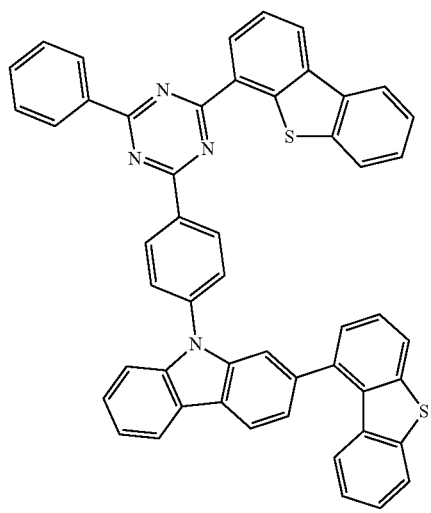
H1-133
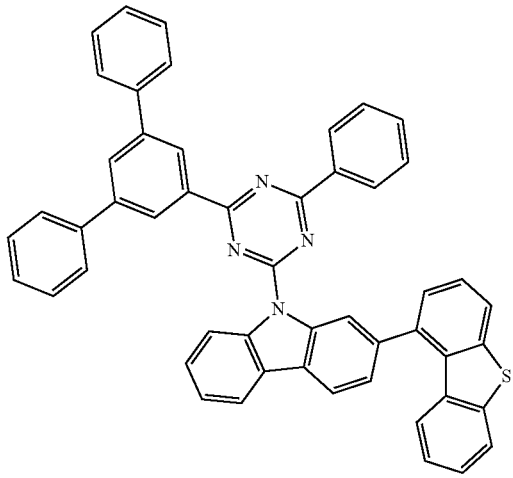
H1-131
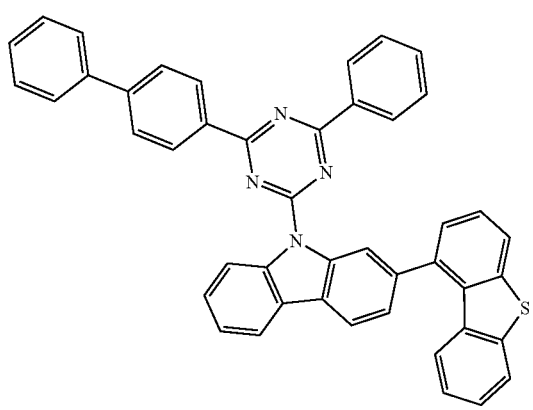
H1-134
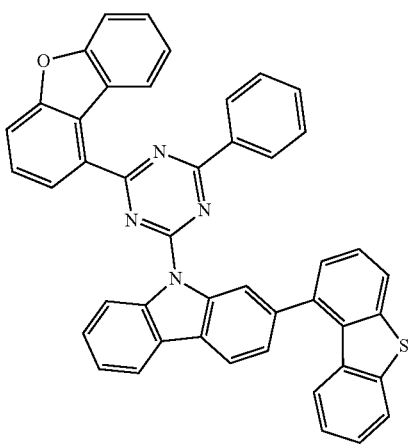
H1-132
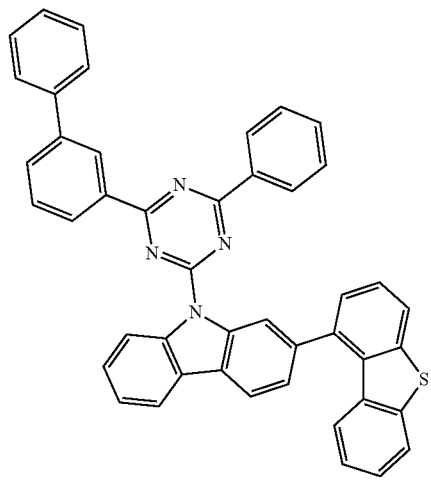
H1-135
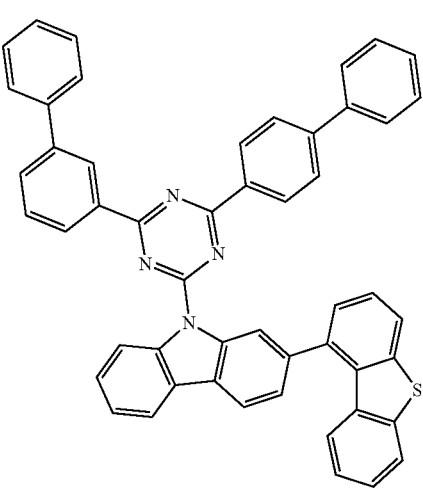

-continued
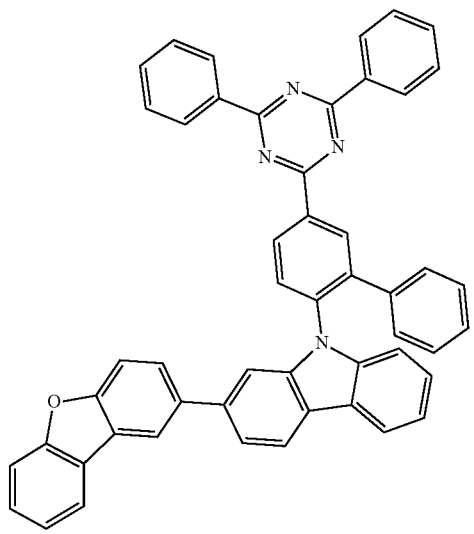
H1-136
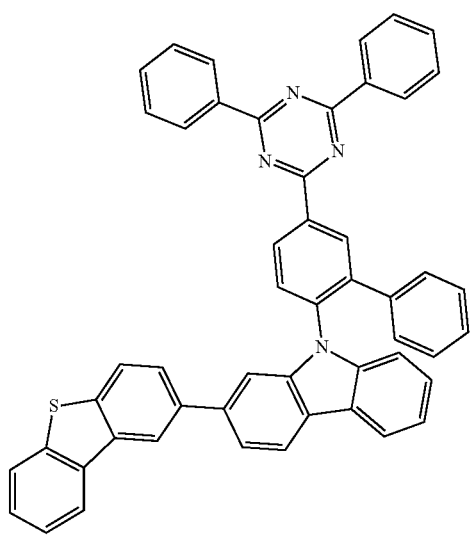
H1-137
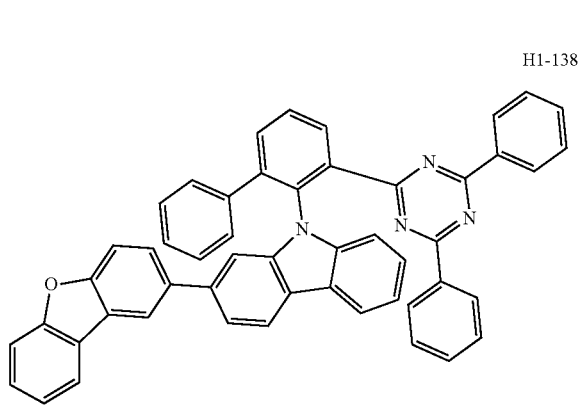
H1-138
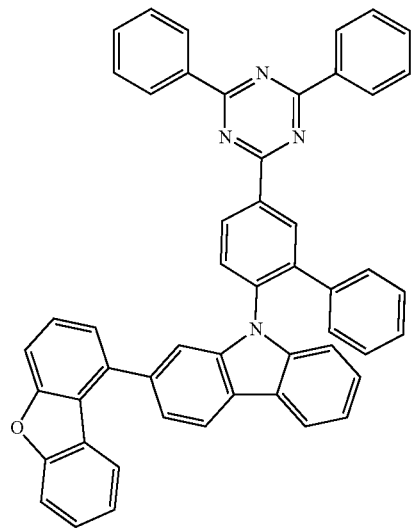
H1-139
H1-140
H1-141
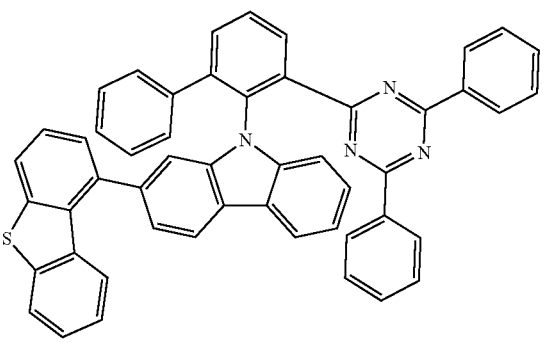

H1-142
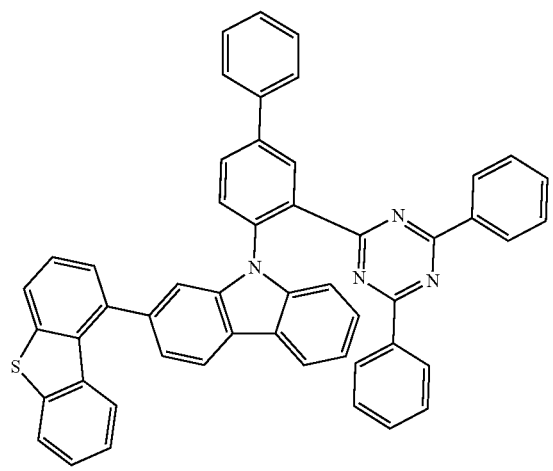
H-143
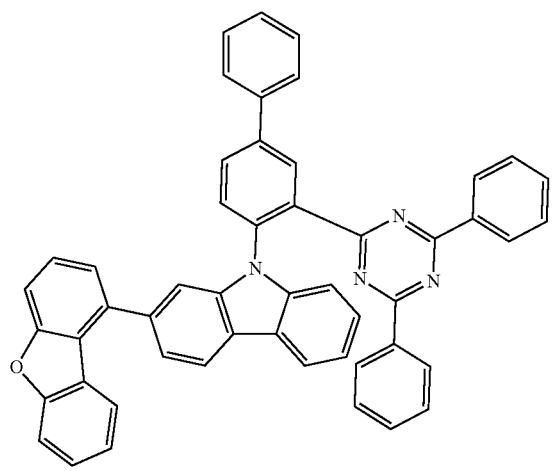
H1-144
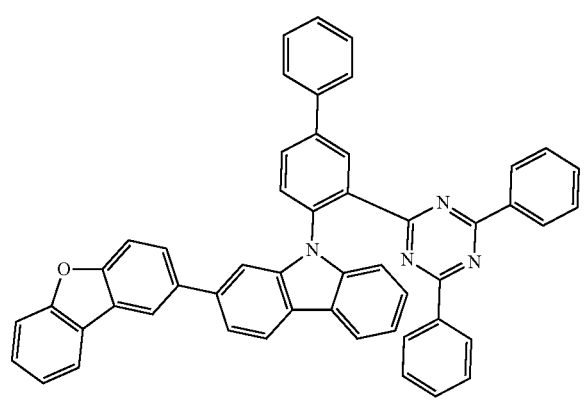
[Reation Scheme 1]
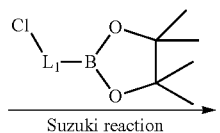
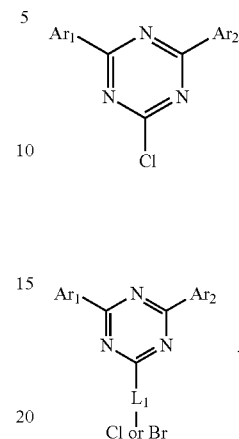
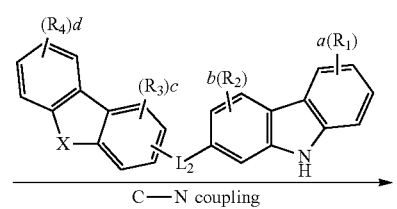
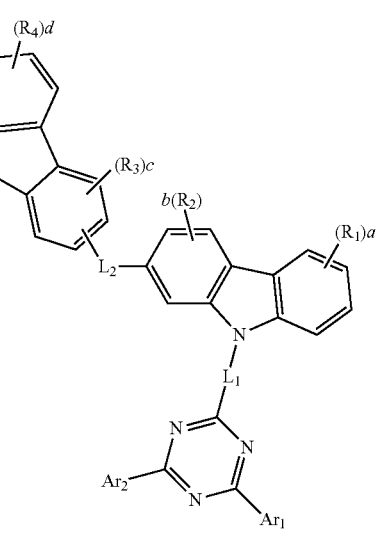
[Reaction Scheme 2]
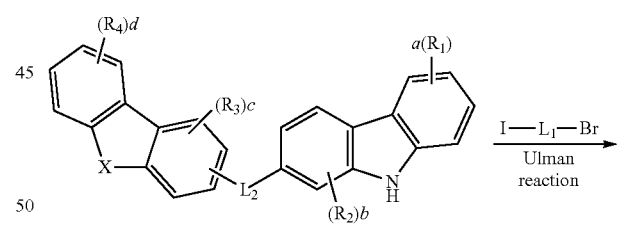
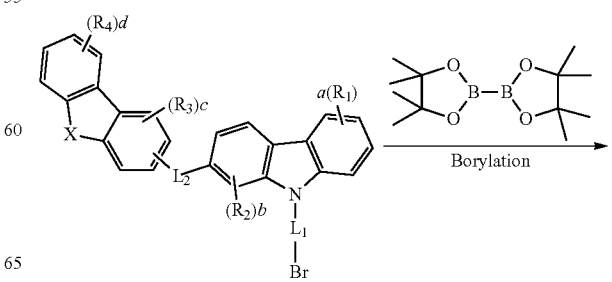
The compound of formula 1 according to the present disclosure may be produced by a synthetic method known to a person skilled in the art. For example it may be prepared as represented by the following reaction scheme 1 or 2.

-continued

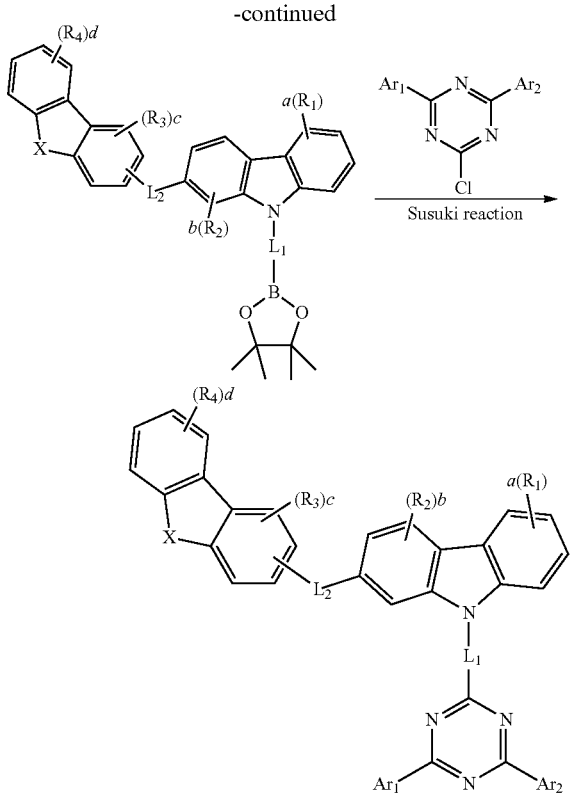

In reaction schemes 1 and 2 above, the definition of the respective substituents is as defined in formula 1.

As described above, exemplary synthesis examples of the compounds represented by formula 1 according to the present disclosure are described, but they are based on Ullmann reaction, Miyaura borylation reaction, Suzuki cross-coupling reaction, Buchwald-Hartwig cross coupling reaction, N-arylation reaction, H-mont-mediated etherification reaction, Intramolecular acid-induced cyclization reaction, Pd(II)-catalyzed oxidative cyclization reaction, Grignard reaction, Heck reaction, Cyclic Dehydration reaction, $SN_1$ substitution reaction, $SN_2$ substitution reaction, and Phosphine-mediated reductive cyclization reaction, etc. It will be understood by one skilled in the art that the above reaction proceeds even if other substituents defined in formula 1, other than the substituents described in the specific synthesis examples, are bonded.

According to one embodiment, the present disclosure provides an organic electroluminescent material comprising an organic electroluminescent compound of formula 1, and an organic electroluminescent device comprising the organic electroluminescent material.

According to one embodiment of the present disclosure, the organic electroluminescent material of the present disclosure may be comprised solely of the organic electroluminescent compound of formula 1, or may further comprise conventional materials included in the organic electroluminescent material. Specifically, the organic electroluminescent material of the present disclosure may comprise at least one compound represented by formula 1 above. For example, the compound of formula 1 may be included in a light-emitting layer, and when the compound of formula 1 is included in the light-emitting layer, the compound of formula 1 may be included as a host, more specifically as a phosphorescent green host.

According to another embodiment of the present disclosure, the organic electroluminescent material of the present disclosure may further comprises an organic electroluminescent compound which is different from the organic electroluminescent compound of formula 1 (a first host material), as a second host material. That is, the organic electroluminescent material according to one embodiment of the present disclosure may comprise a plurality of host materials. Specifically, the plurality of host materials according to one embodiment may comprise at least one compound of formula 1 as a first host material and at least one second host material which is different from the first host material. The weight ratio between the first host material and the second host material is in a ratio of 1:99 to 99:1, preferably in a ratio of 10:90 to 90:10, and more preferably in a ratio of 30:70 to 70:30.

The second host material according to one embodiment includes a compound represented by the following formula 11.

(11)

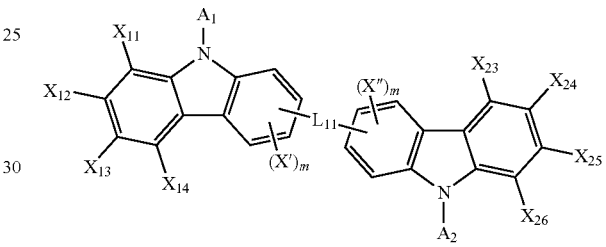

In formula 11, $A_1$ and $A_2$ each independently represent a substituted or unsubstituted (C6-C30)aryl;

L represents a single bond or a substituted or unsubstituted (C6-C30)arylene;

X', X", $X_{11}$ to $X_{14}$, and $X_{23}$ to $X_{26}$ each independently represent hydrogen, deuterium, halogen, cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30) cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsiyl, a substituted or unsubstituted (C1-C30)alkyldi(C6-C30)arylsiyl, a substituted or unsubstituted mono- or di-(C1-C30)alkylamino, or a substituted or unsubstituted mono- or di-(C6-C30)arylamino; or adjacent substituent(s) may be linked to each other to form a ring(s);

m and n each independently represent an integer of 1 to 3; and when m and n are an integer of 2 or more, each of X' and X" may be the same or different.

The second host material represented by formula 11 according to one embodiment may be represented by any one of the following formulas 12 to 14.

(12)

(13)

(14)

In formulas 12 to 14, $A_1$, $A_2$, $X_{11}$ to $X_{14}$, and $X_{23}$ to $X_{26}$ are as defined in formula 11; and $X_{15}$ to $X_{22}$ each independently are the same as the definition of X' in formula 11.

In one embodiment, $A_1$ and $A_2$ preferably each independently represent a substituted or unsubstituted (C6-C18)aryl, more preferably each independently, (C6-C18)aryl unsubstituted or substituted with one or more selected from the group consisting of (C1-C6)alkyl, (C6-C18)aryl, (5- to 20-membered)heteroaryl, and tri(C6-C12)arylsilyl. Specifically, $A_1$ and $A_2$ each independently may be phenyl unsubstituted or substituted with one or more selected from the group consisting of methyl, phenyl, naphthyl, triphenylsilyl, and pyridyl unsubstituted or substituted with phenyl, a substituted or unsubstituted p-biphenyl, a substituted or unsubstituted m-biphenyl, a substituted or unsubstituted terphenyl, a substituted or unsubstituted naphthyl, fluorenyl unsubstituted or substituted with at least one of methyl and phenyl, benzofluorenyl unsubstituted or substituted with at least one of methyl and phenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted phenylnaphthyl, a substituted or unsubstituted naphthylphenyl, or a substituted or unsubstituted fluoranthenyl.

In one embodiment, $L_{11}$ represents preferably a single bond, or a substituted or unsubstituted (C6-C18)arylene, more preferably a single bond, or an unsubstituted (C6-C18) arylene. Specifically, L may be a single bond, a substituted or unsubstituted phenylene, a substituted or unsubstituted naphthylene, or a substituted or unsubstituted biphenylene.

In one embodiment, $X_{11}$ to $X_{26}$ preferably each independently represent hydrogen or a substituted or unsubstituted (5- to 20-membered)heteroaryl; or adjacent substituent(s) may be linked to each other to form a substituted or unsubstituted (C6-C12) mono- or polycyclic alicyclic or aromatic ring(s), more preferably each independently represent hydrogen or unsubstituted (5- to 20-membered)heteroaryl; or adjacent substituent(s) may be linked to each other to form unsubstituted (C6-C12) mono- or polycyclic aromatic ring(s). Specifically, $X_{11}$ to $X_{26}$ each independently represent hydrogen, a substituted or unsubstituted dibenzothiophenyl, or a substituted or unsubstituted dibenzofuranyl; or adjacent ones of $X_{11}$ to $X_{14}$ or adjacent ones of $X_{23}$ to $X_{26}$ may be linked to each other to form a benzene ring(s).

According to one embodiment, the compound represented by formula 11 may be more specifically exemplified by the following compounds, but is not limited thereto.

H2-1

H2-2

H2-3
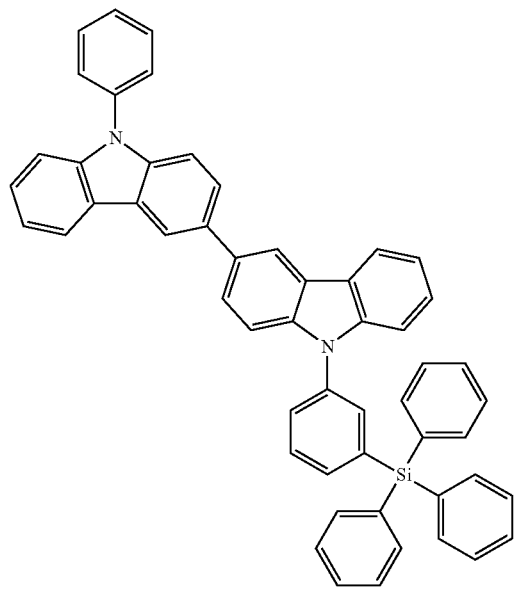
H2-5
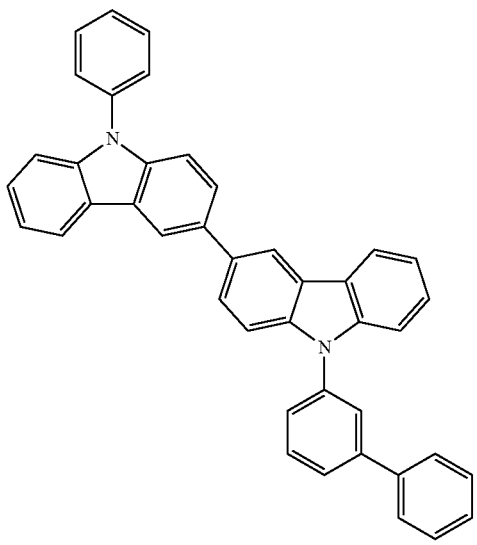
H2-4
H2-6
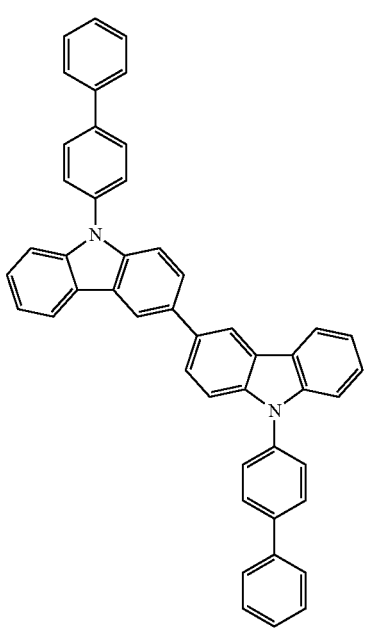

H2-7
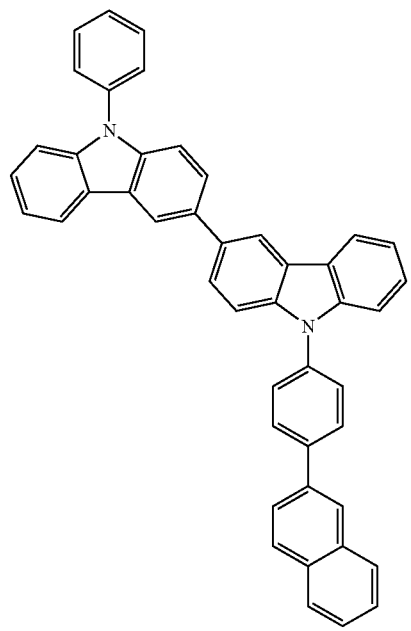
H2-8
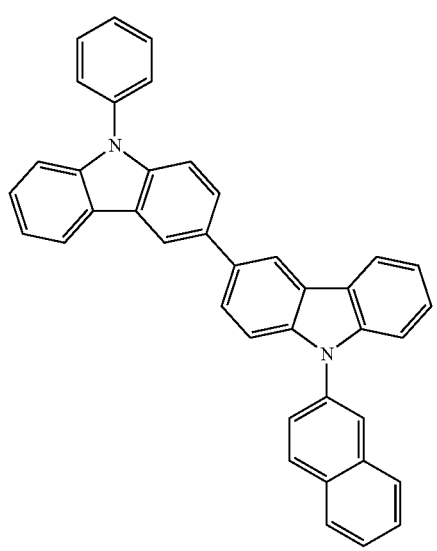
H2-9
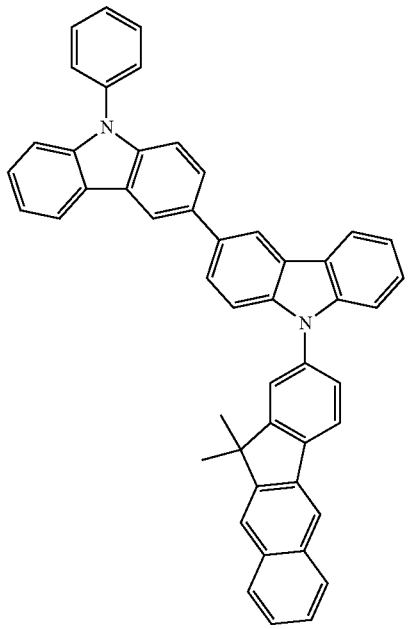
H2-10
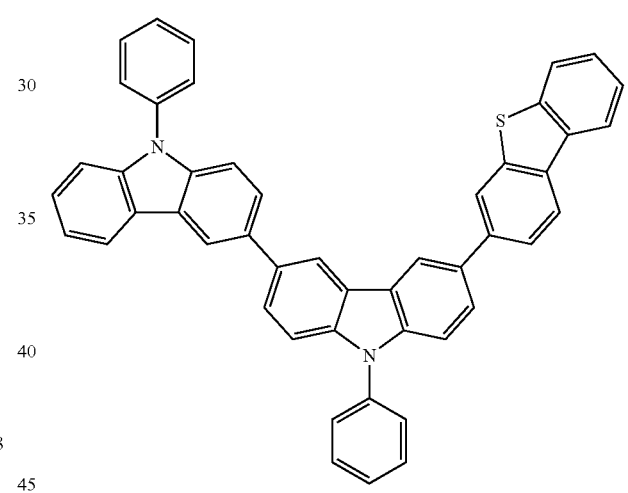
H2-11
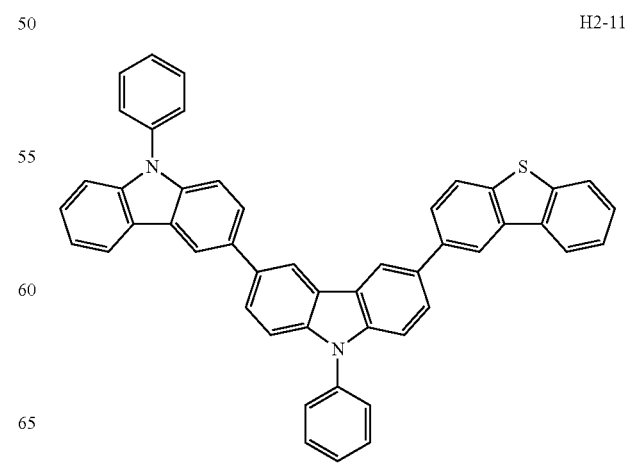

H2-12
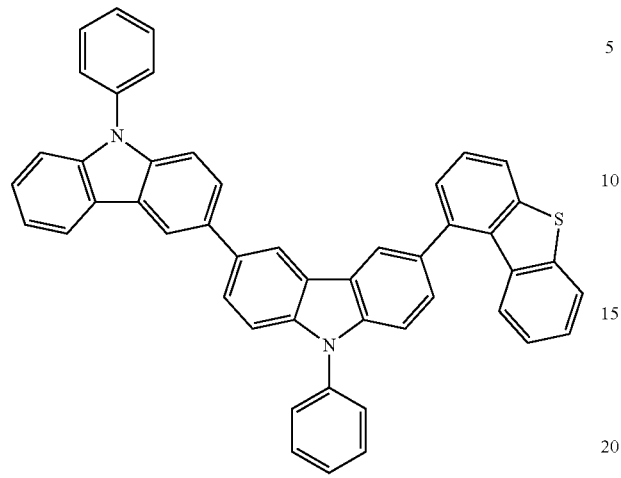
H2-13
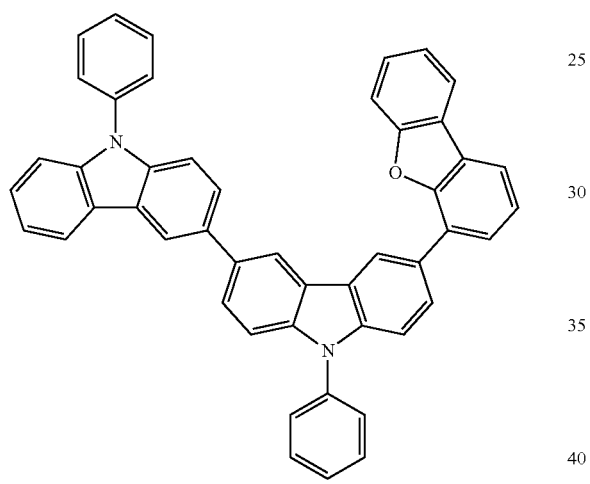
H2-14
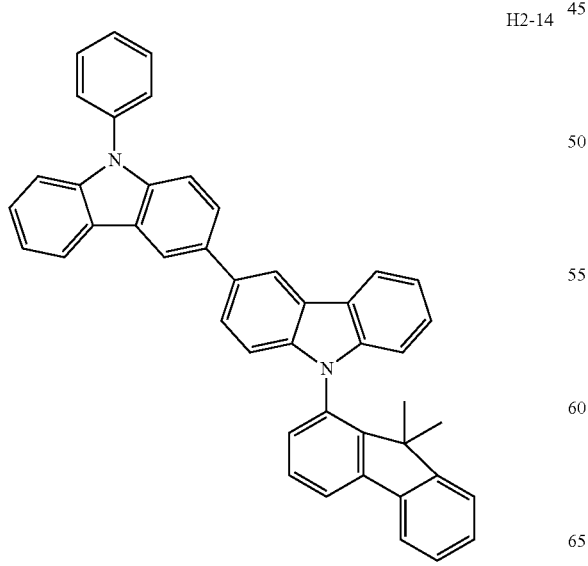
H2-15
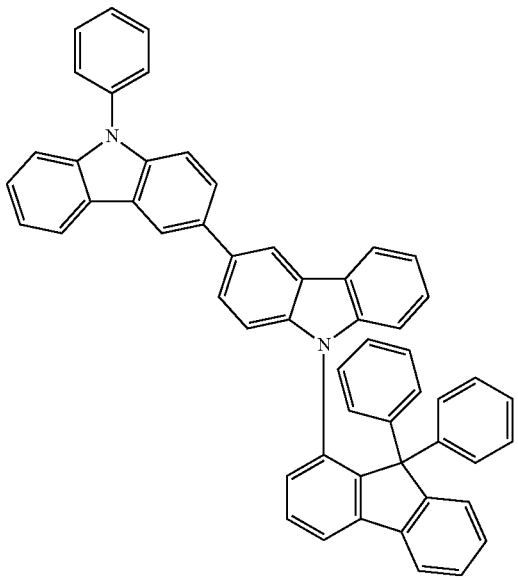
H2-16
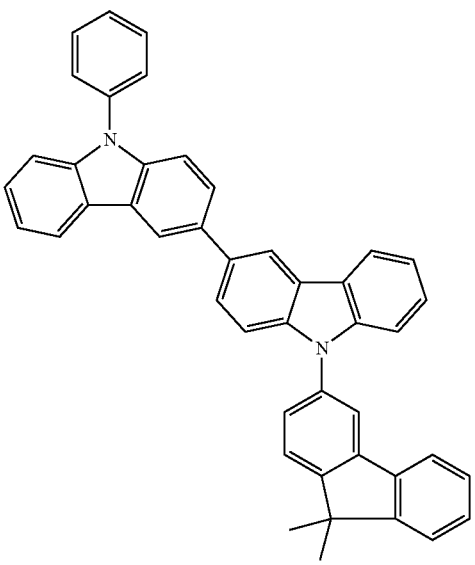

H2-17
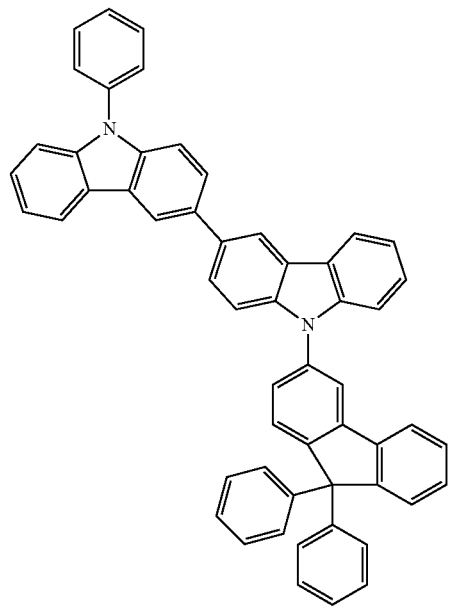
H2-19
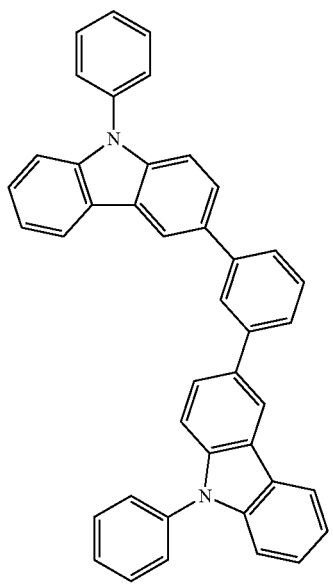
H2-18
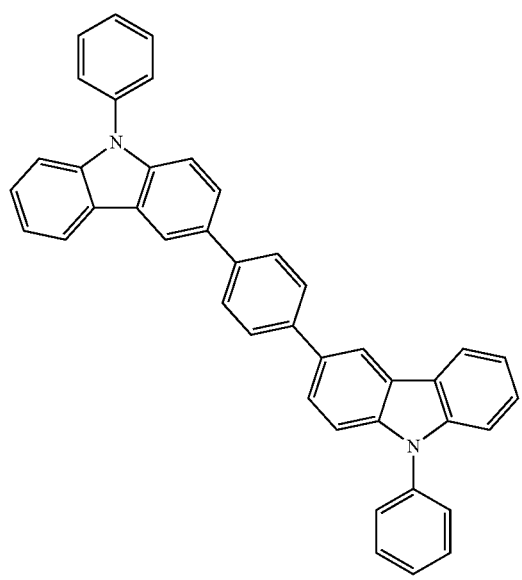
H2-20
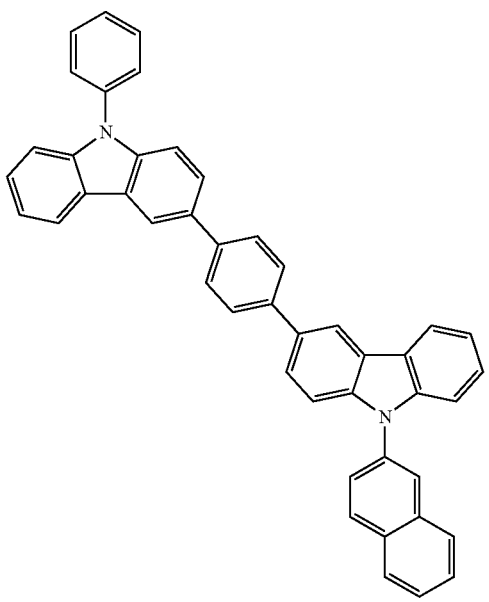

H2-21
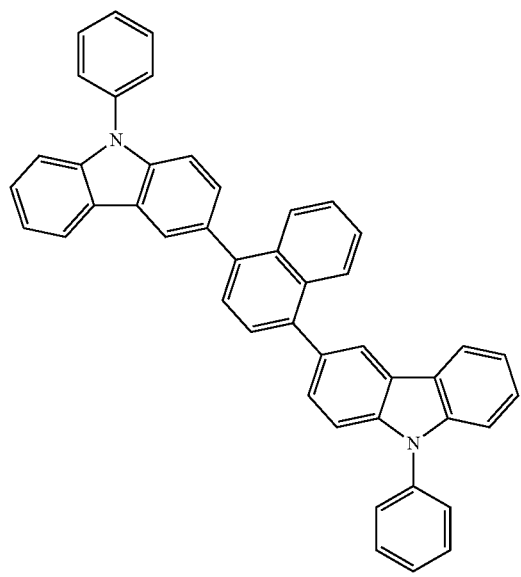
H2-23
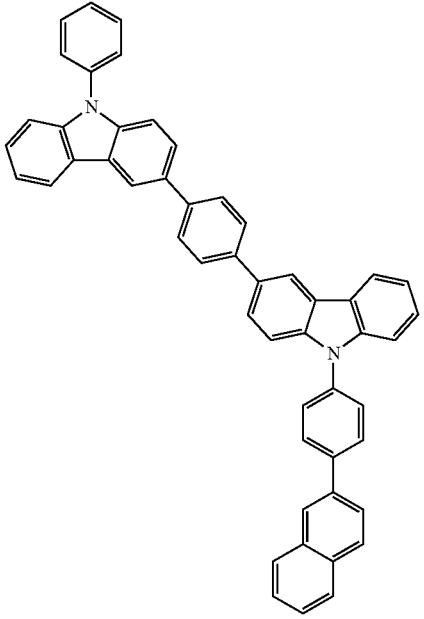
H2-22
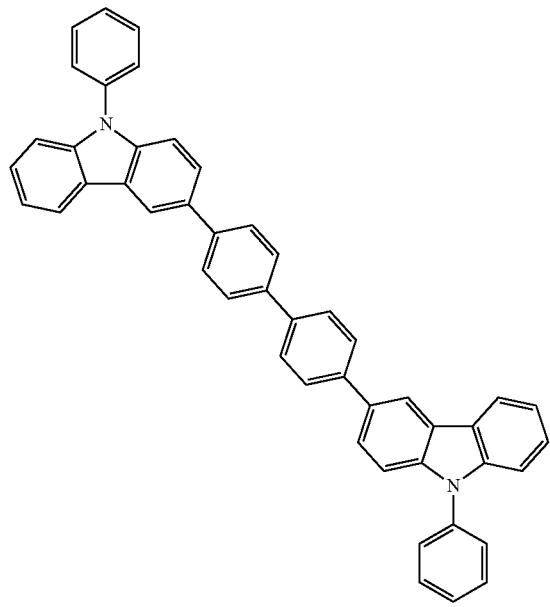
H2-24
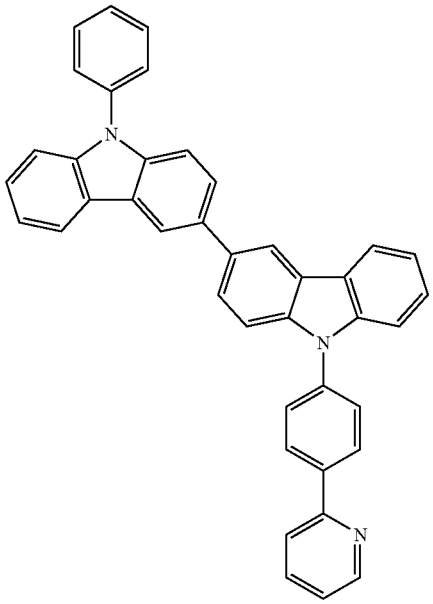

H2-25
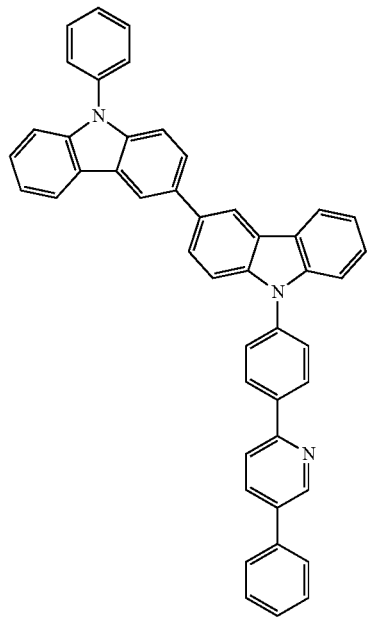
H2-27
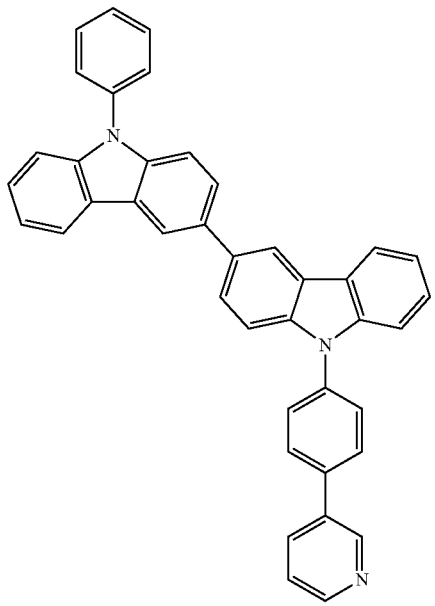
H2-26
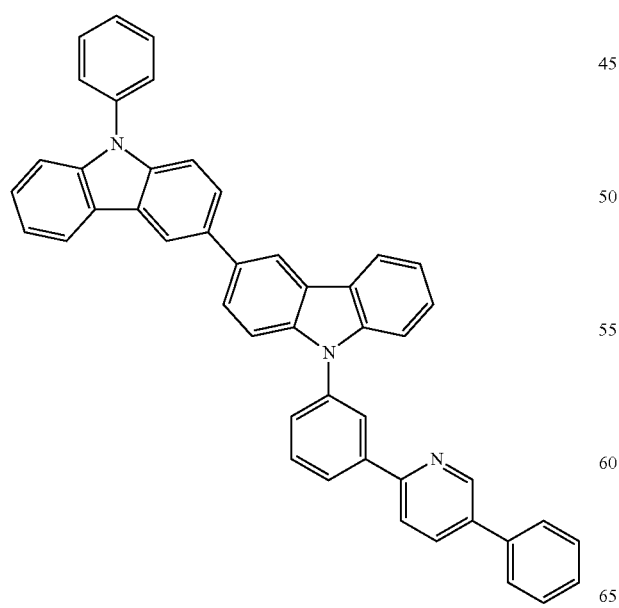
H2-28
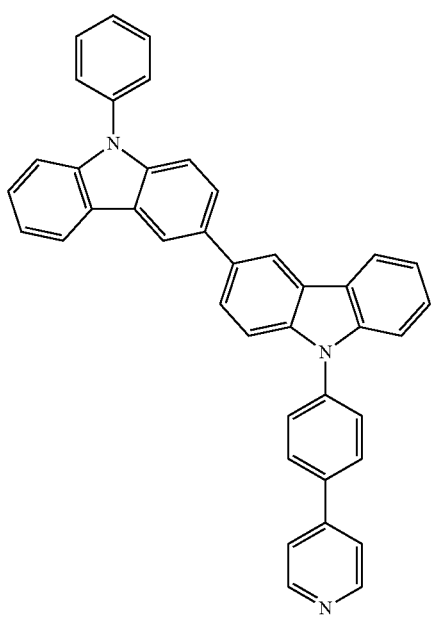

H2-29
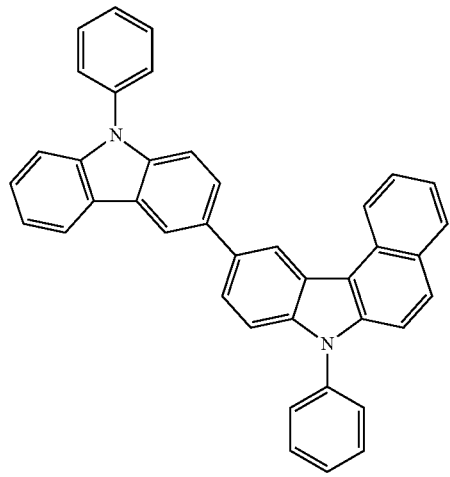
H2-32
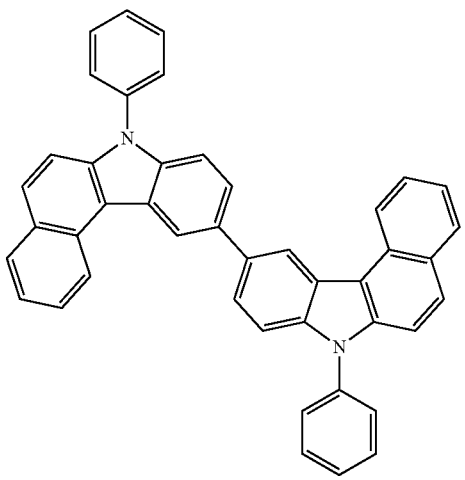
H2-30
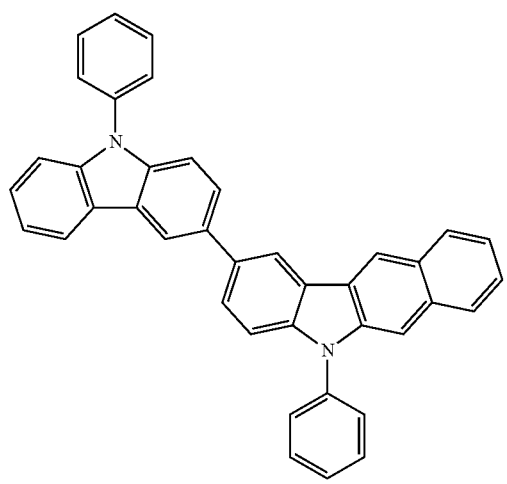
H2-33
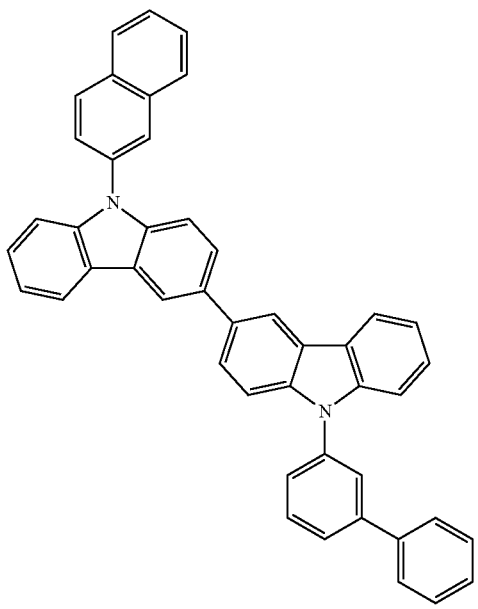
H2-31
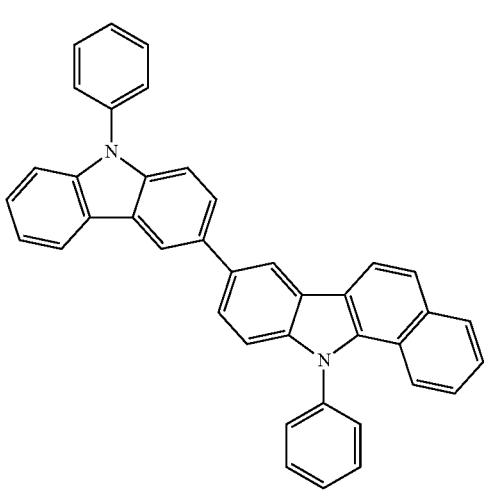

-continued

H2-34

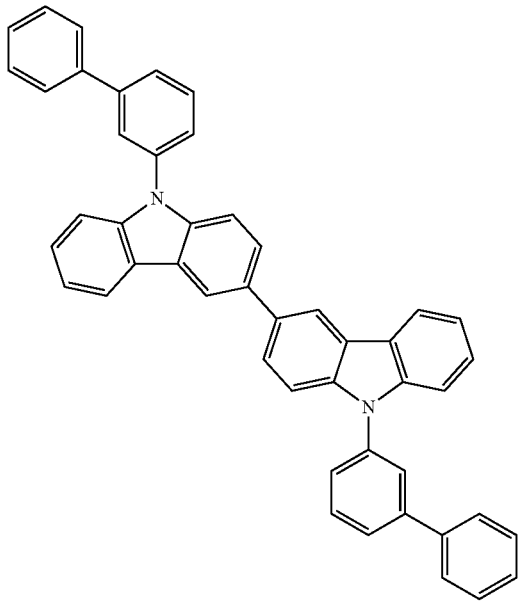

The compound of formula 11 according to the present disclosure may be prepared by a synthetic method known to one skilled in the art.

Hereinafter, the organic electroluminescent device to which the aforementioned organic electroluminescent compound and/or the organic electroluminescent material including the plurality of host materials are/is applied will be described.

The organic electroluminescent device according to one embodiment may comprise a first electrode; a second electrode; and at least one organic layer between the first and second electrodes. The organic layer comprises includes a light-emitting layer. The light-emitting layer may include a plurality of host materials comprising at least one first host material represented by formula 1 and at least one second host material represented by formula 11.

According to one embodiment, the organic electroluminescent material of the present disclosure includes at least one of compounds H1-1 to H1-144 as the first host material represented by formula 1 and at least one of compounds H2-1 to H2-34 as the second host material represented by formula 11. The plurality of host materials may be included in the same organic layer, for example a light-emitting layer or may be included in different light-emitting layers, respectively. The organic layer may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer, in addition to a light-emitting layer.

According to another embodiment, at least one of organic electroluminescent compounds H1-1 to H1-144 represented by formula 1 may be included in an electron transport zone. For example, the organic electroluminescent compound represented by formula 1 according to the present disclosure may be included in a hole blocking layer.

The organic layer may further comprise an amine-based compound and/or an azine-based compound, in addition to the light-emitting material of the present disclosure. Specifically, the hole injection layer, the hole transport layer, the hole auxiliary layer, the light-emitting layer, the light-emitting auxiliary layer, or the electron blocking layer may comprise an amine-based compound, for example, arylamine-based compound, a styrylarylamine-based compound, etc., as a hole injection material, a hole transport material, a hole auxiliary material, a light-emitting material, a light-emitting auxiliary material, or an electron blocking material. In addition, the electron transport layer, the electron injection layer, the electron buffer layer, and the hole blocking layer may comprise an azine-based compound as an electron transport material, an electron injection material, an electron buffer material, and a hole blocking material.

In addition, the organic layer further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising such a metal.

An organic electroluminescent material according to one embodiment may be used as light-emitting materials for a white organic light-emitting device. The white organic light-emitting device has suggested various structures such as a parallel side-by-side arrangement method, a stacking arrangement method, or color conversion material (CCM) method, etc., according to the arrangement of R (Red), G (Green), YG (yellowish green), or B (Blue) light-emitting units. In addition, the organic electroluminescent material according to one embodiment may also be applied to the organic electroluminescent device comprising a QD (quantum dot).

One of the first electrode and the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. In addition, the hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer may be placed between the electron transport layer (or electron injection layer) and the light-emitting layer, and blocks the arrival of holes to the cathode, thereby improving the probability of recombination of electrons and holes in the light-emitting layer. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_X(1 \leq X \leq 2)$, $AlO_X(1 \leq X \leq 1.5)$, SiON, SiAlON, etc.; the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

Further, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent device according to one embodiment may further include at least one dopant in the light-emitting layer.

The dopant comprised in the organic electroluminescent device of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), as necessary; more preferably an ortho-metallated complex compound(s) of a metal atom(s) selected from iridium (Ir), osmium (Os), copper (Cu), and platinum (Pt), as necessary; and even more preferably ortho-metallated iridium complex compound(s), as necessary.

The dopant comprised in the organic electroluminescent device of the present disclosure may use the compound represented by the following formula 101, but is not limited thereto:

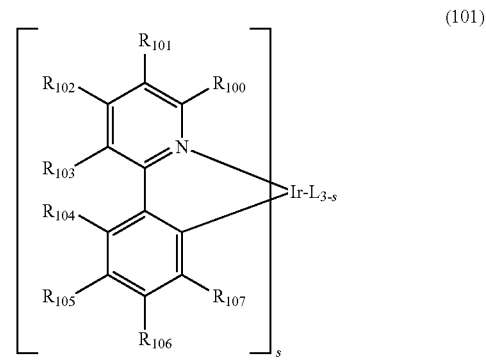

(101)

In formula 101,

L is selected from the following structures 1 to 3;

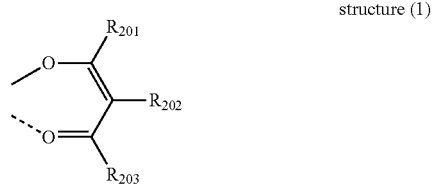

structure (1)

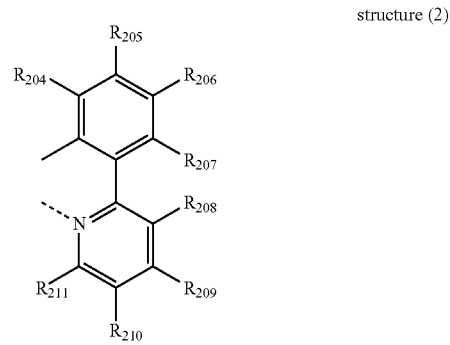

structure (2)

-continued structure (3)

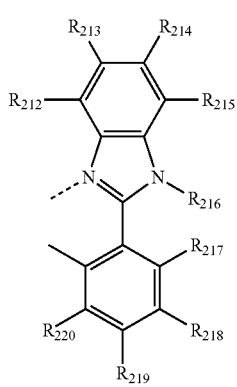

in structures 1 to 3, $R_{100}$ to $R_{103}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, cyano, a substituted or unsubstituted (3- to 30-membered) heteroaryl, or a substituted or unsubstituted (C1-C30)alkoxy; or adjacent substituent(s) may be linked to each other to form a ring(s), for example, to form a ring(s) with a pyridine, e.g., a substituted or unsubstituted quinoline, a substituted or unsubstituted isoquinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy; or adjacent substituent(s) may be linked to each other to form a ring(s), for example, to form a ring(s) with a benzene, e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{220}$ each independently represent hydrogen, deuterium, halogen, (C1-C30)alkyl unsubstituted or substituted with deuterium and/or halogen, a substituted or unsubstituted (C3-C30)cycloalkyl, or a substituted or unsubstituted (C6-C30)aryl; or adjacent substituent(s) may be linked to each other to form a substituted or unsubstituted ring(s); and s represents an integer of 1 to 3.

Specifically, the specific examples of the dopant compound include the following, but are not limited thereto:

D-1

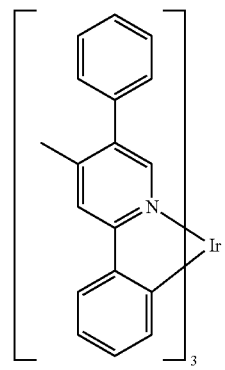

D-2

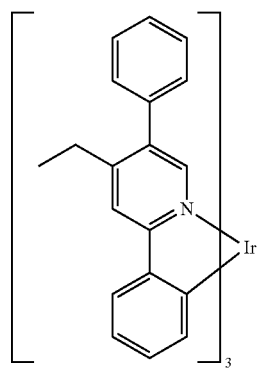

D-3

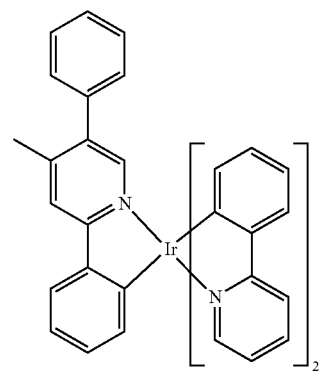

D-4

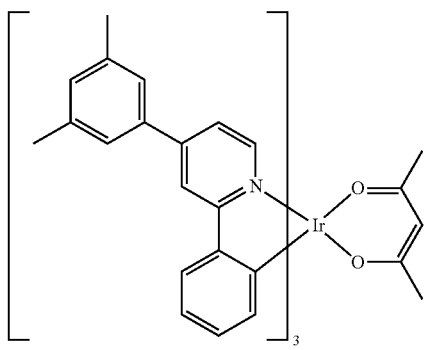

D-5 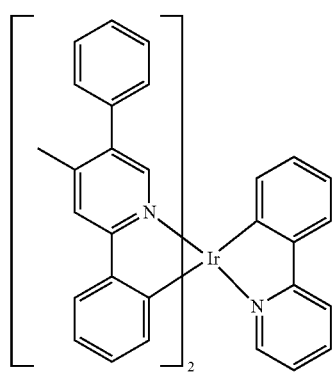
D-6 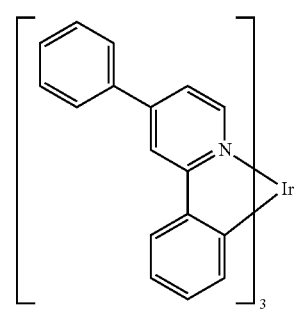
D-7 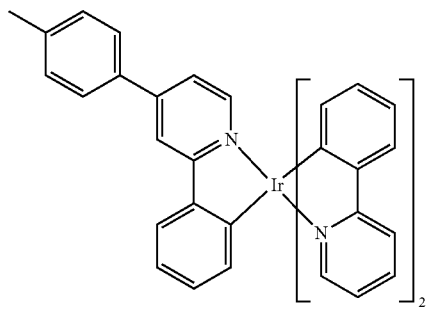
D-8 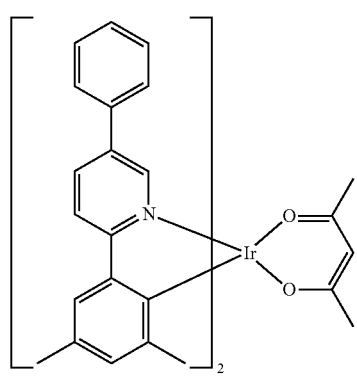
D-9 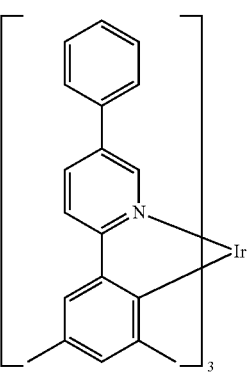
D-10 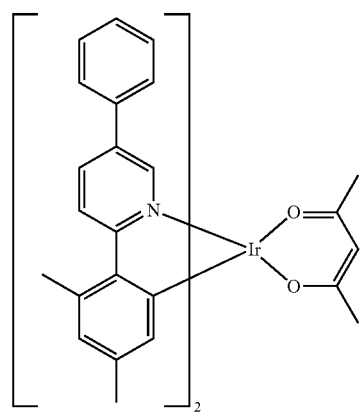
D-11 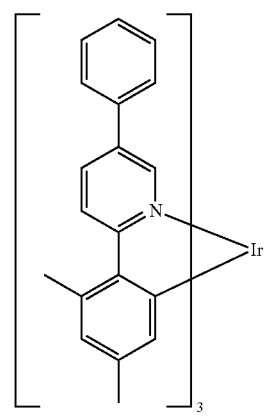
D-12 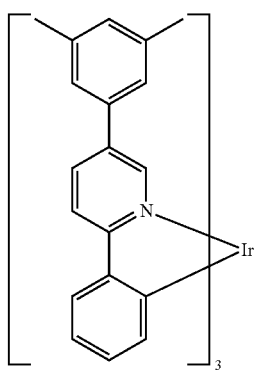

D-13
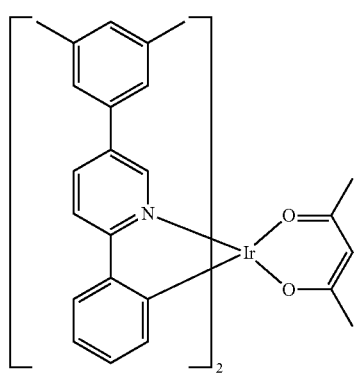
D-14
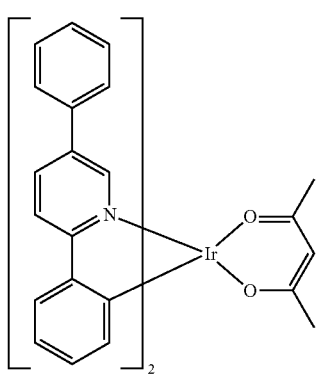
D-15
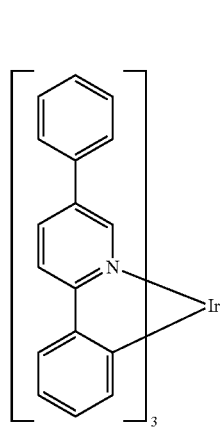
D-16
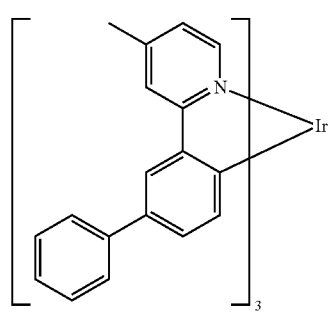
D-17
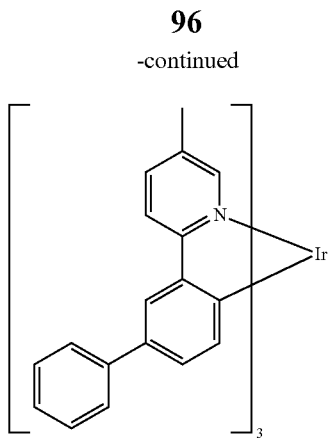
D-18
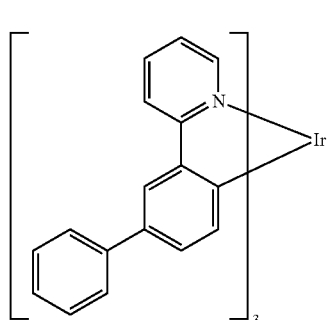
D-19
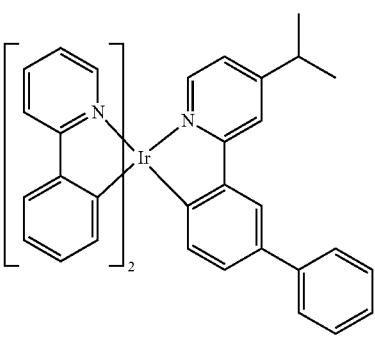
D-20
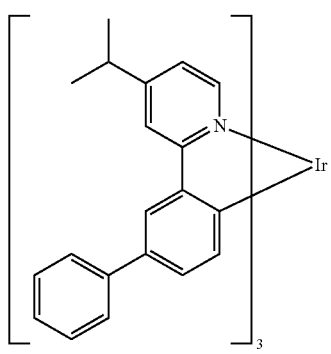

D-21
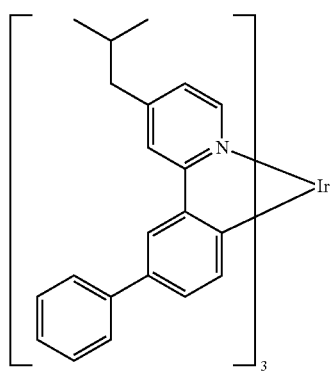
D-22
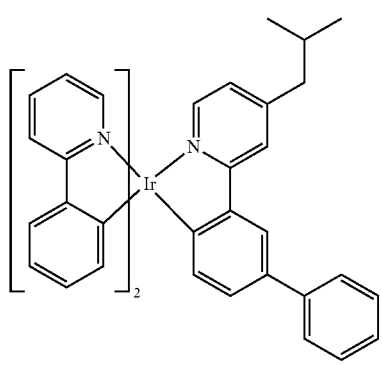
D-23
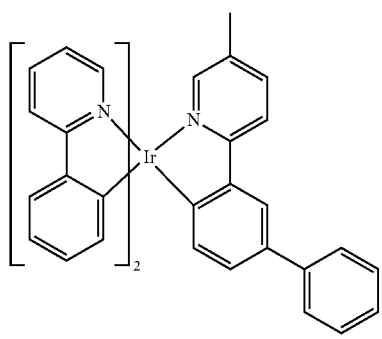
D-24
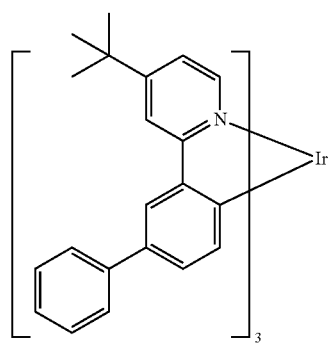
D-25
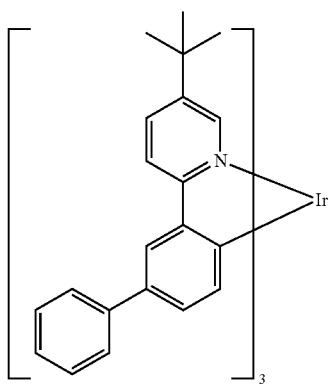
D-26
D-27
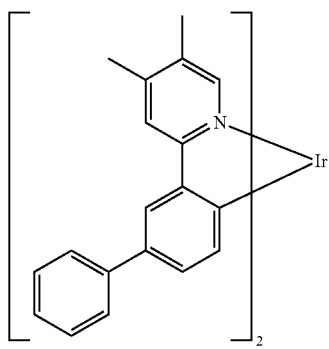
D-28
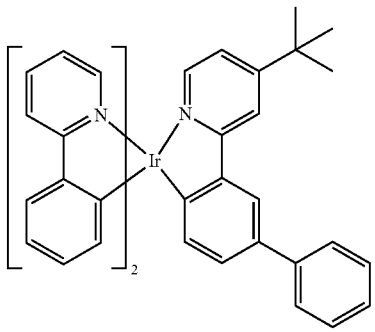

D-29 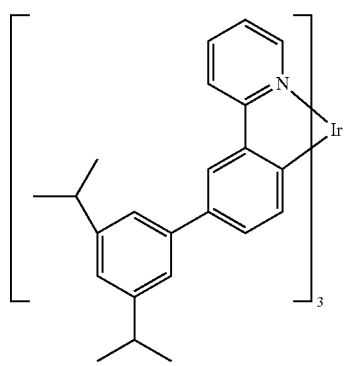
D-30 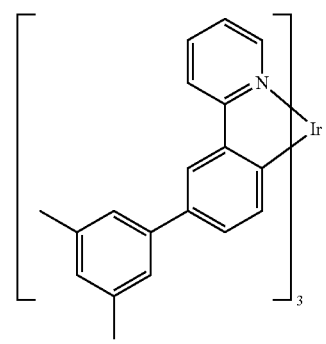
D-31 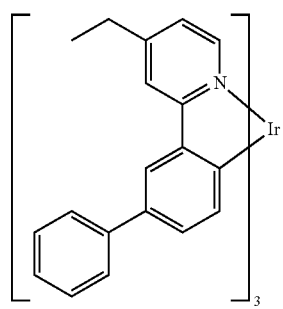
D-32 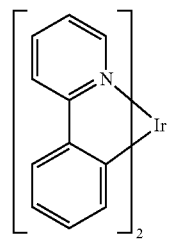
D-33 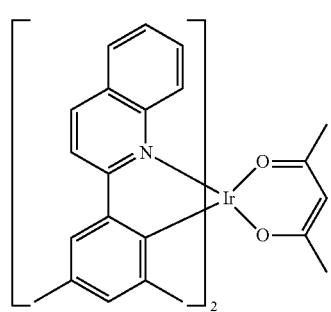
D-34 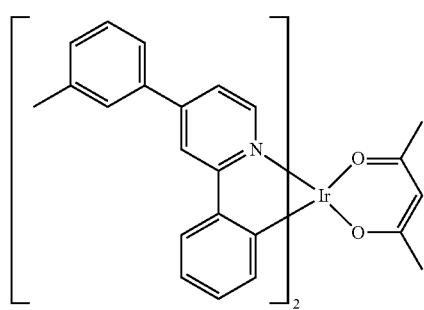
D-35 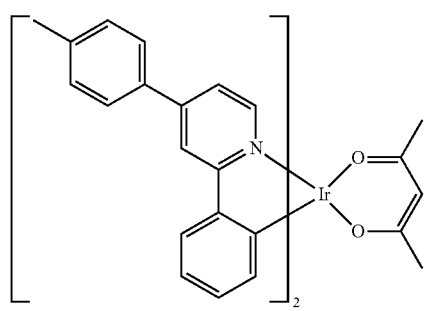
D-36 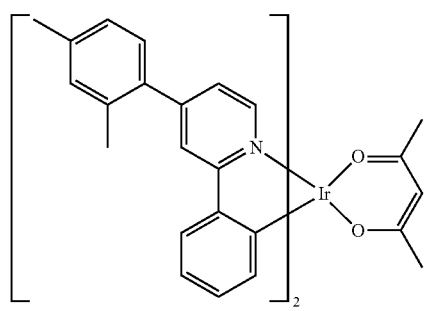
D-37 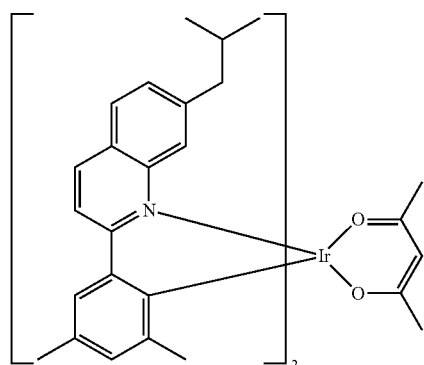
D-38 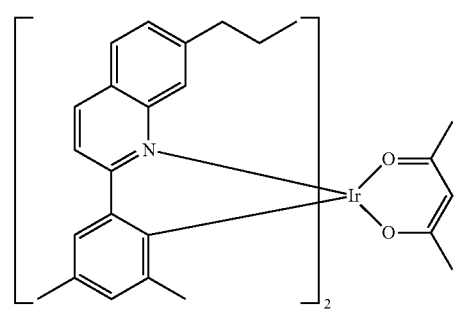

-continued
D-39
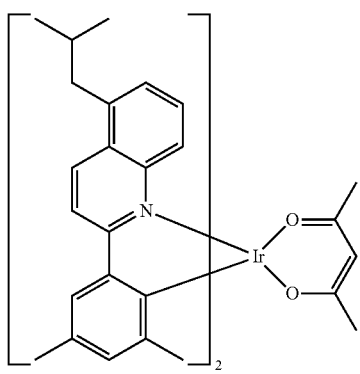
D-40
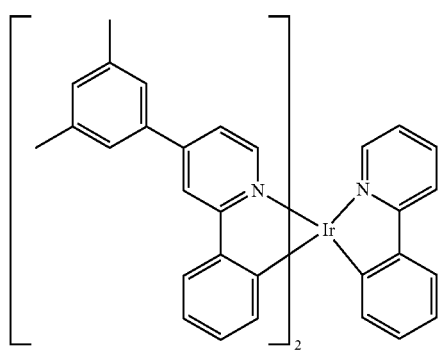
D-41
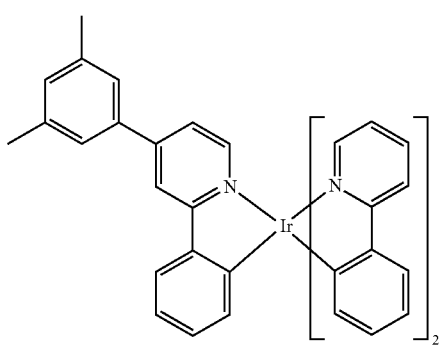
D-42
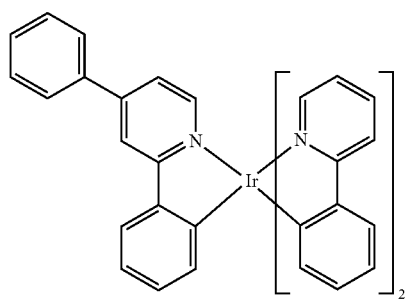
-continued
D-43
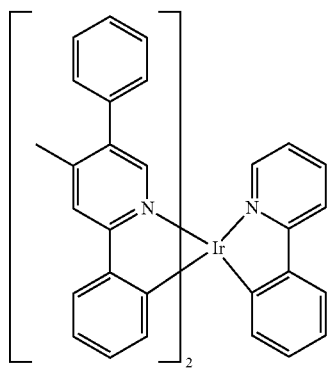
D-44
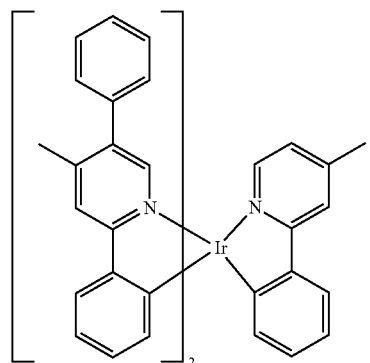
D-45
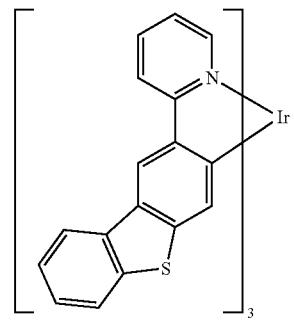
D-46
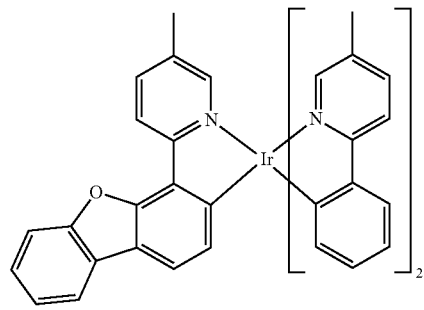

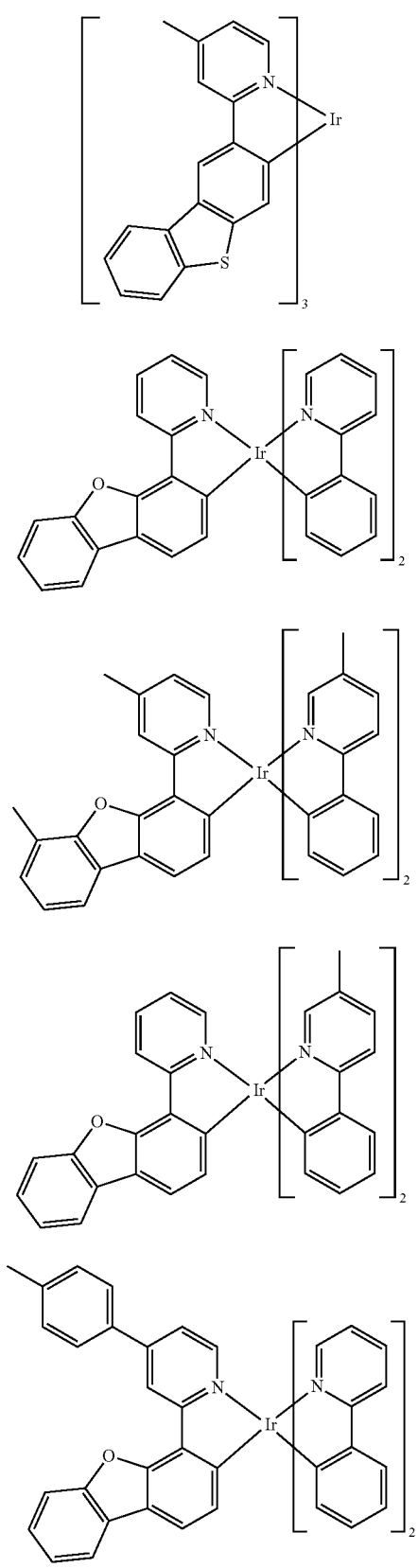
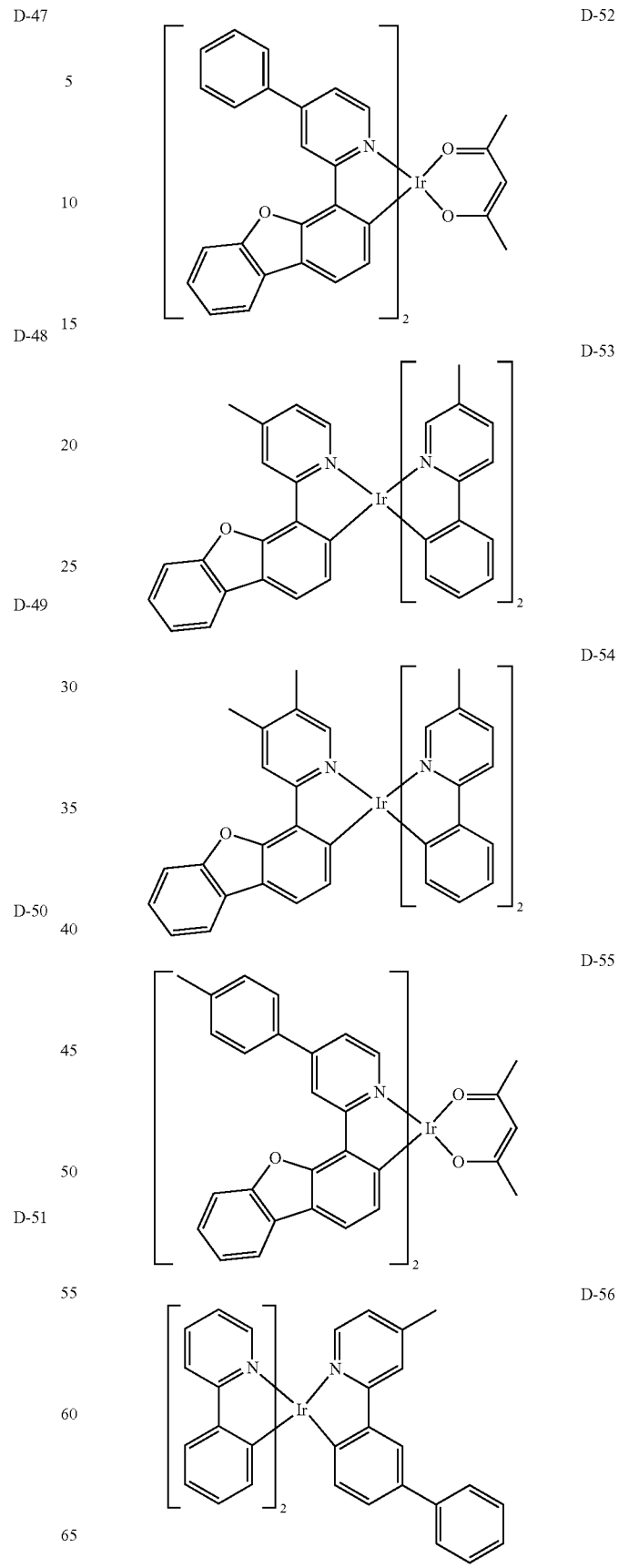

D-57
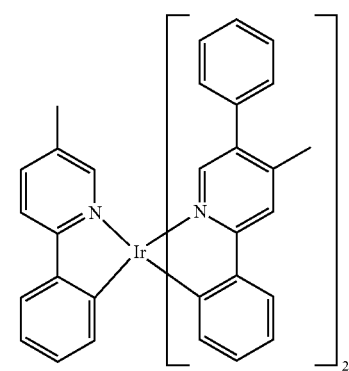
D-58
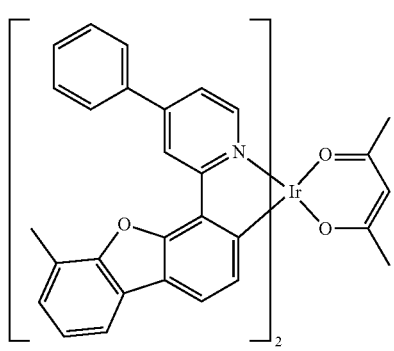
D-59
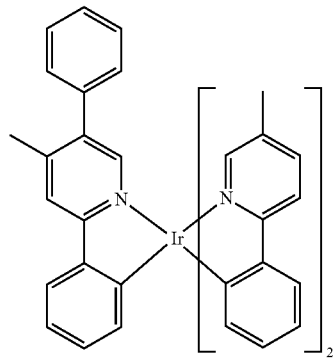
D-60
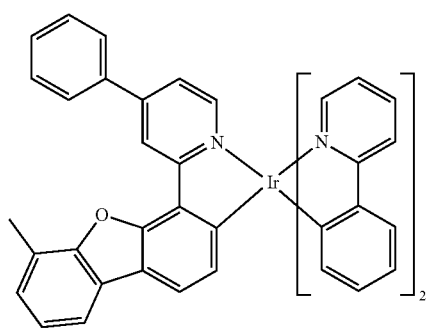
D-61
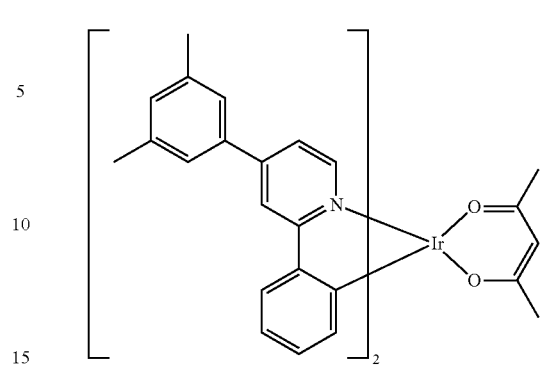
D-62
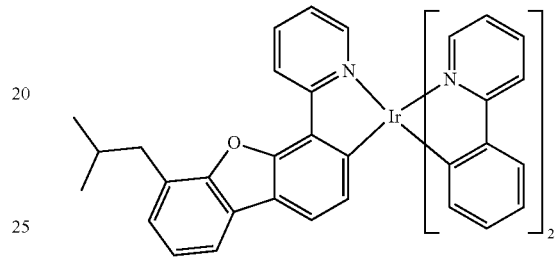
D-63
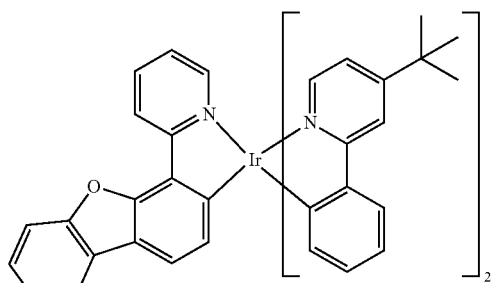
D-64
D-65
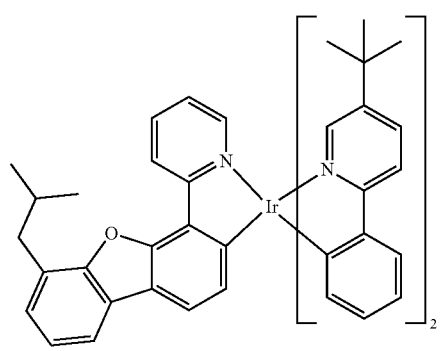

D-66
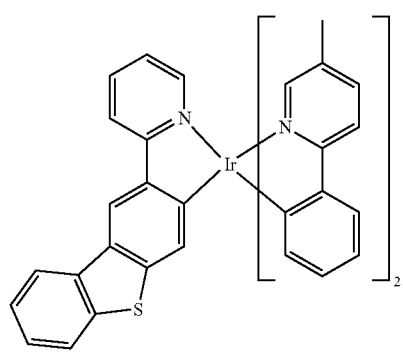
D-67
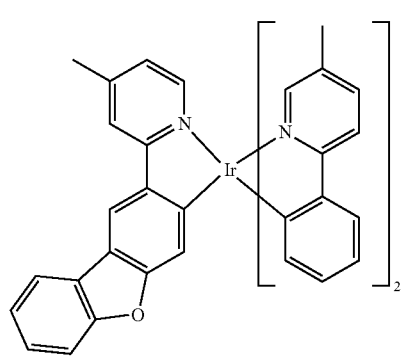
D-68
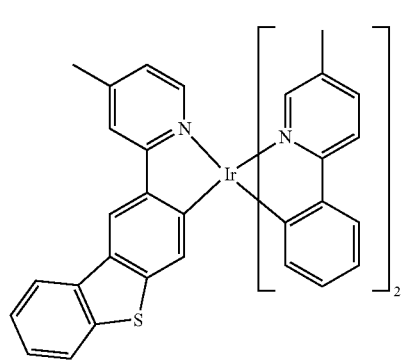
D-69
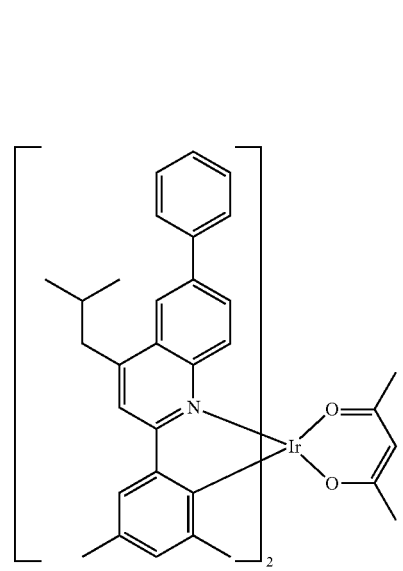
D-70
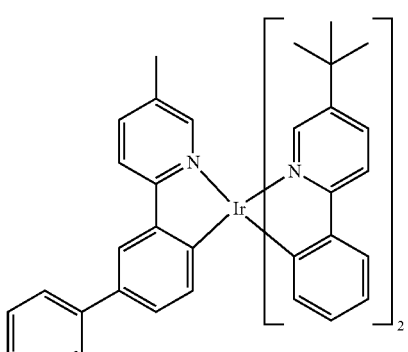
D-71
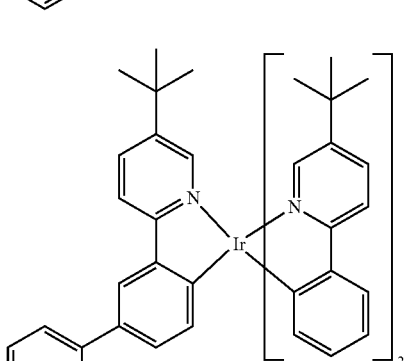
D-72
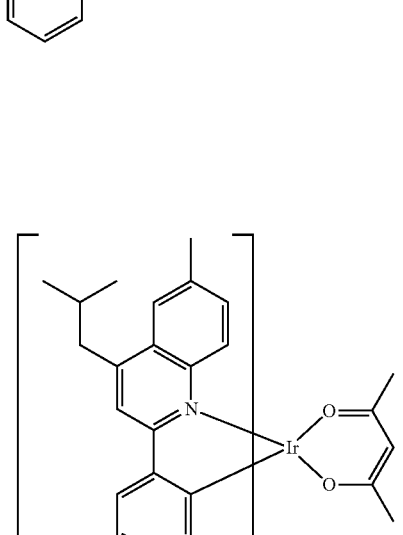
D-73
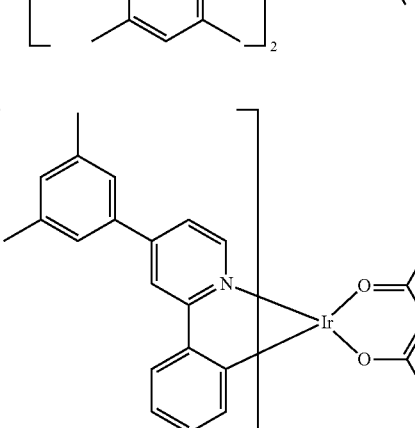

D-74
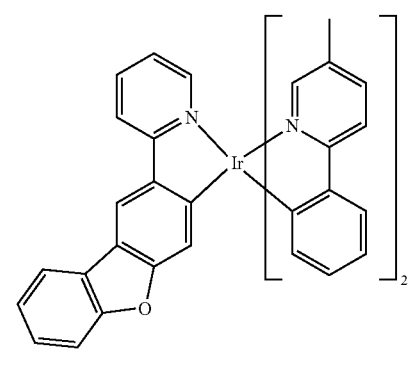
D-75
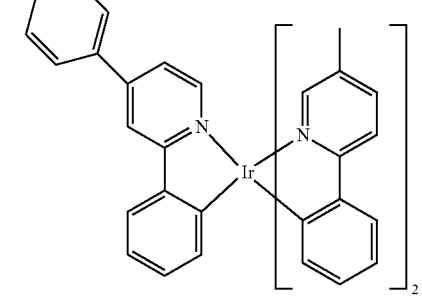
D-76
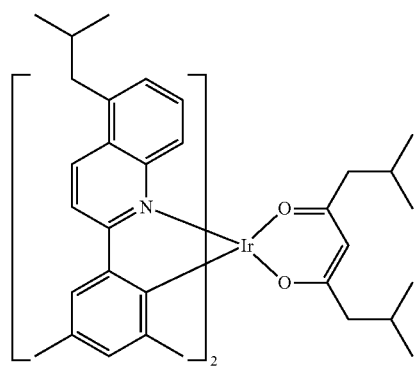
D-77
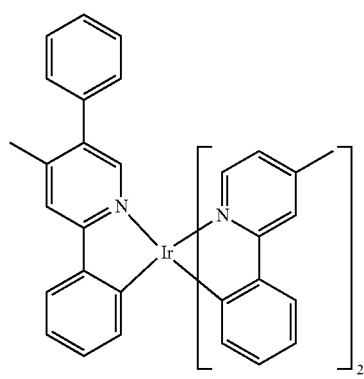
D-78
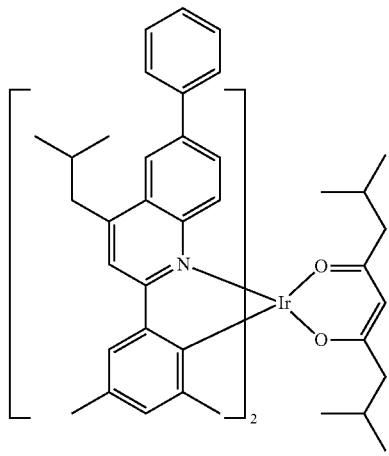
D-79
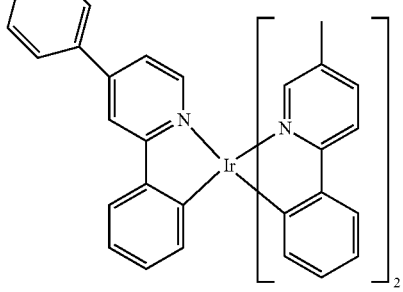
D-80
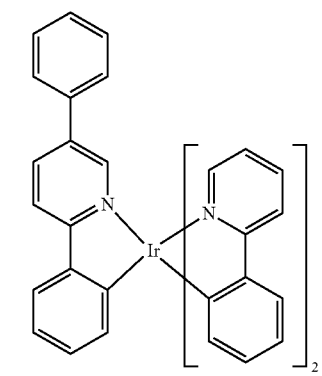

D-81
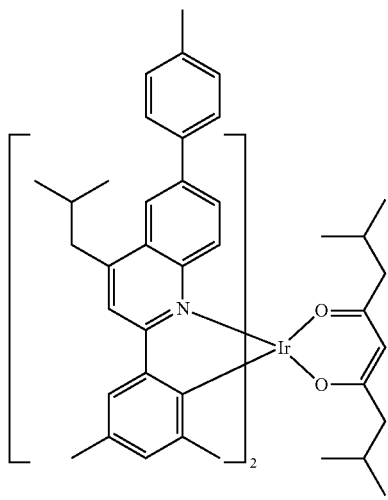
D-82
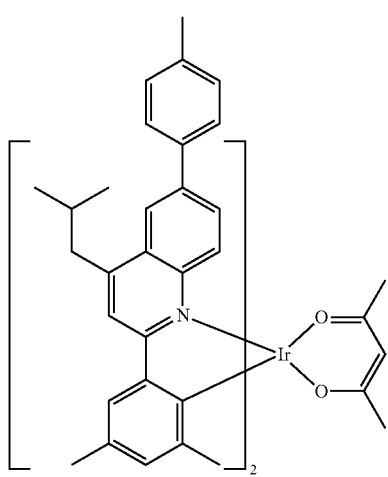
D-83
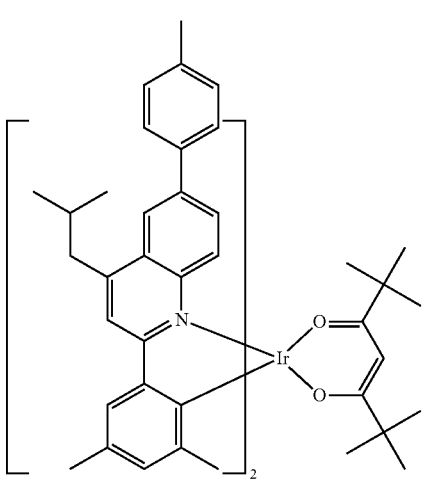
D-84
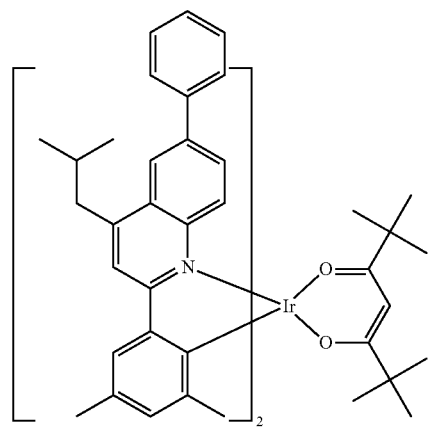
D-85
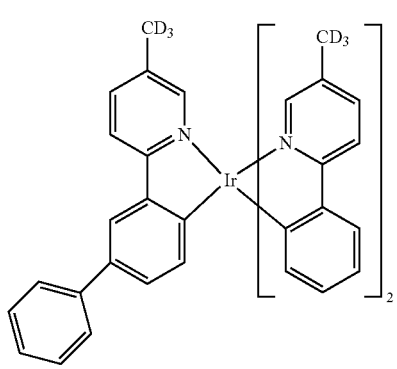
D-86
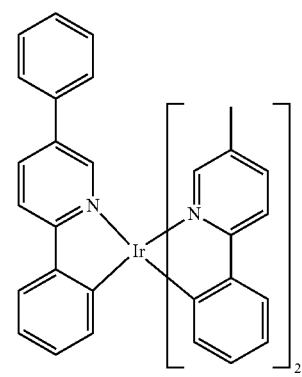
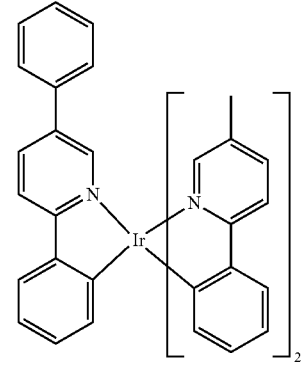
D-87
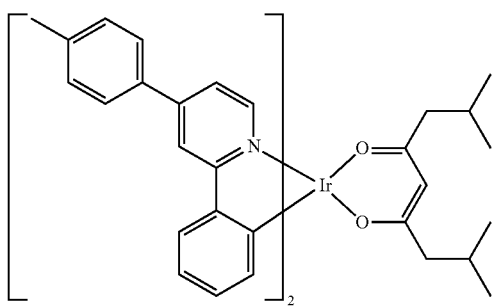

D-88
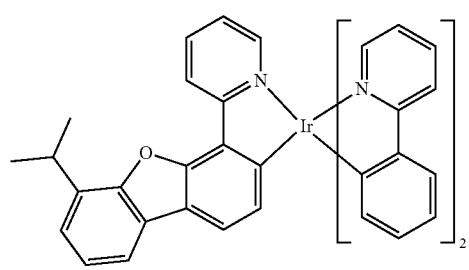
D-89
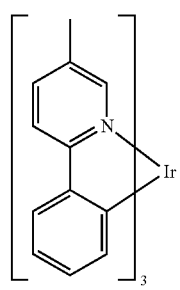
D-90
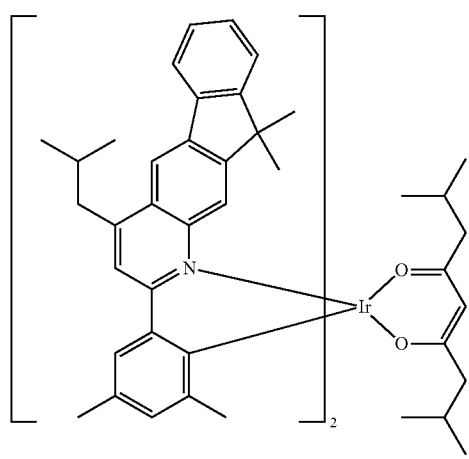
D-91
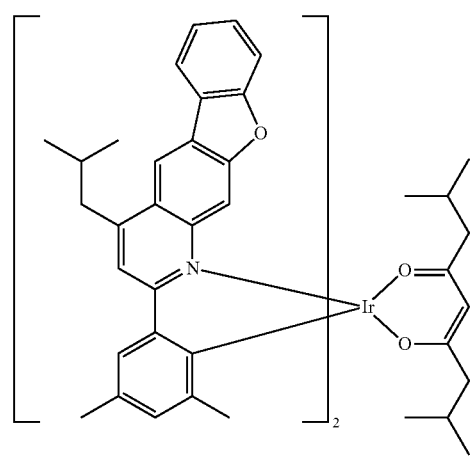
D-92
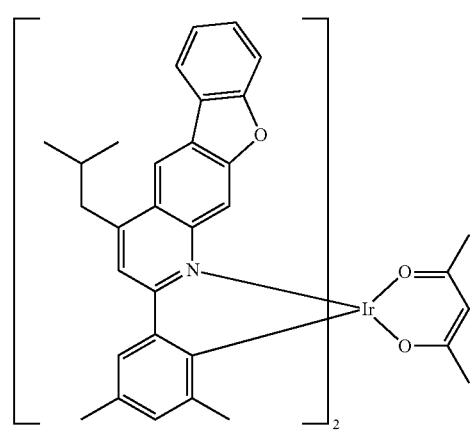
D-93
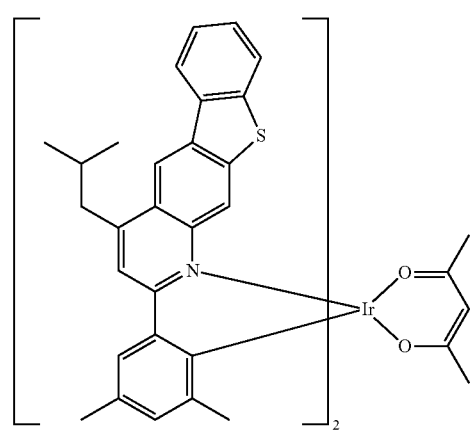
D-94

D-95
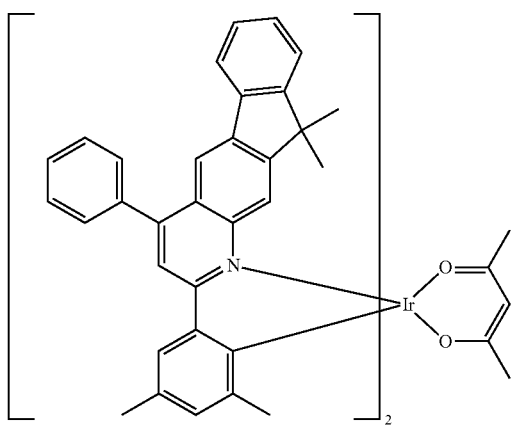
D-96
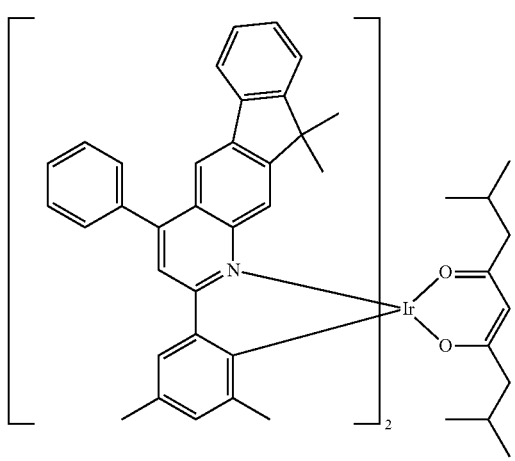
D-97
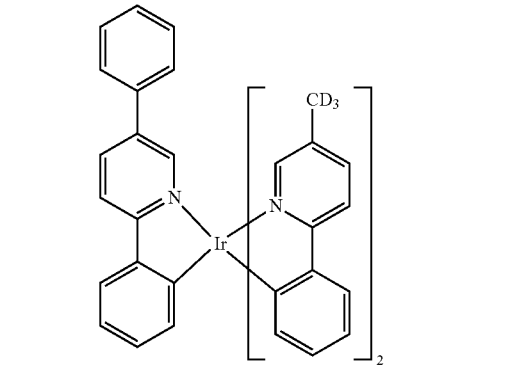
D-98
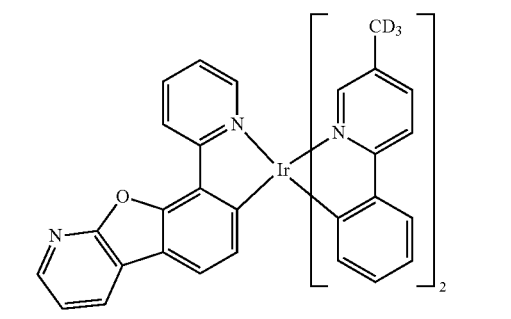
D-99
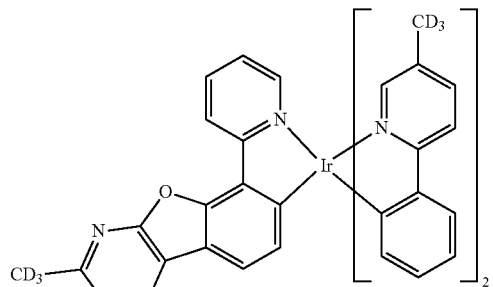
D-100
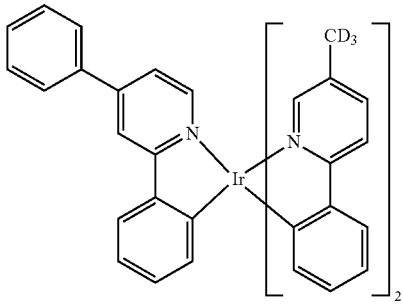
D-101
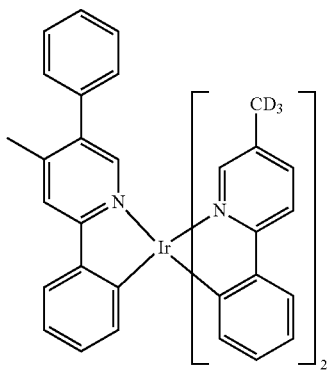
D-102
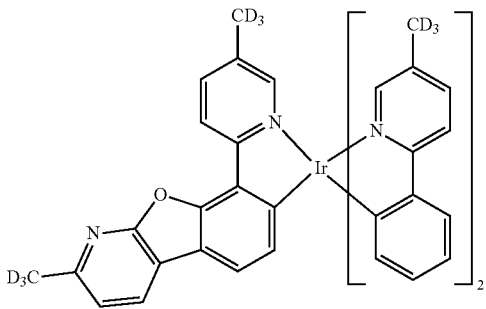
D-103
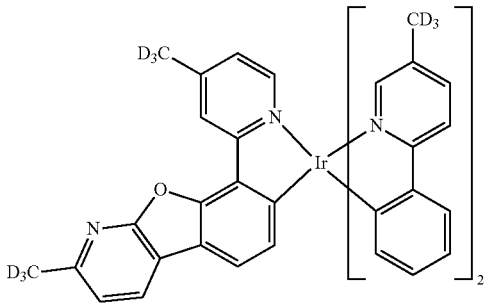

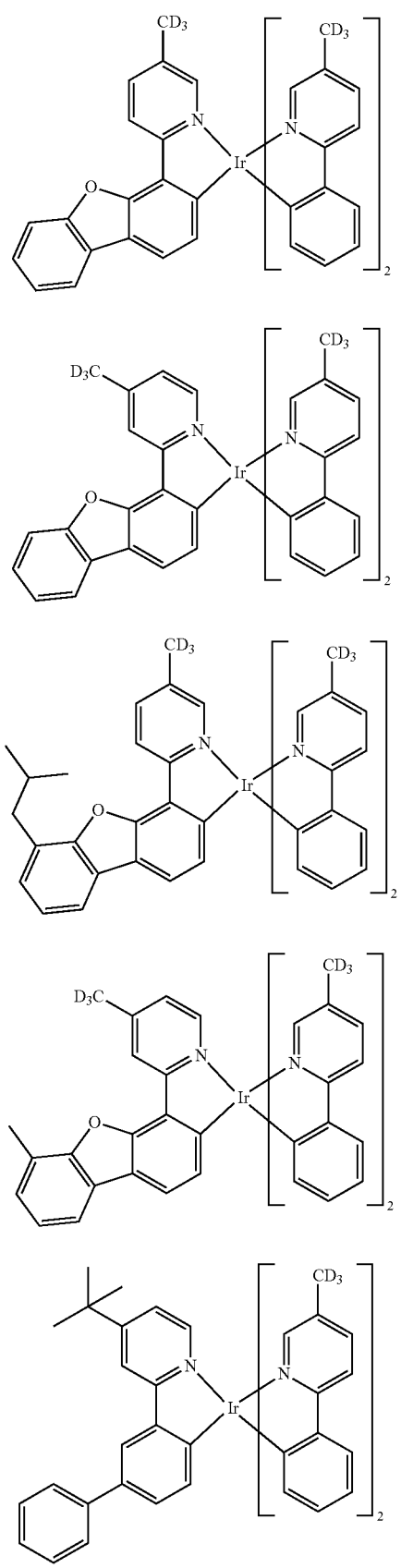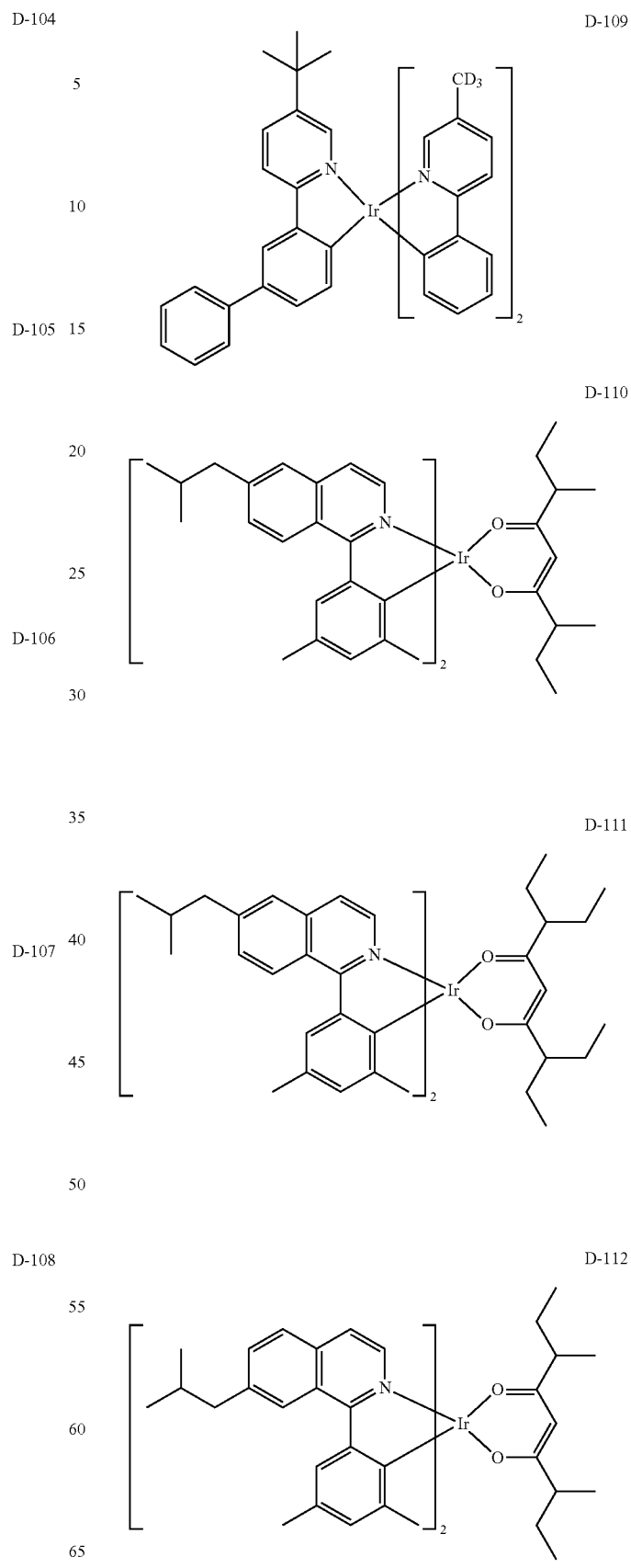

D-113
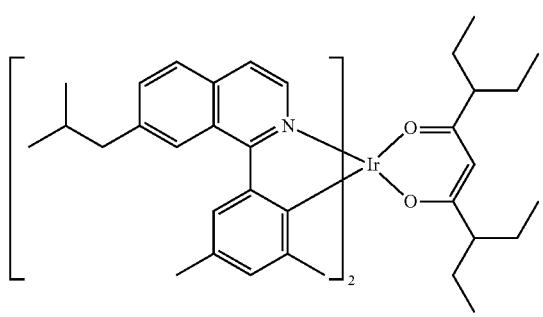
D-114
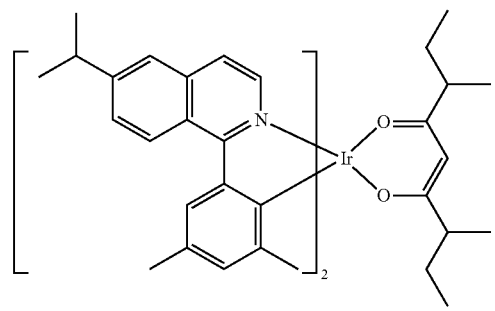
D-115
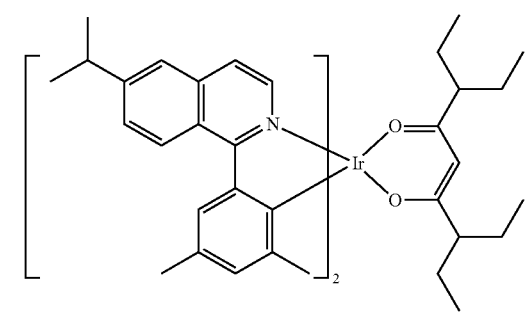
D-116
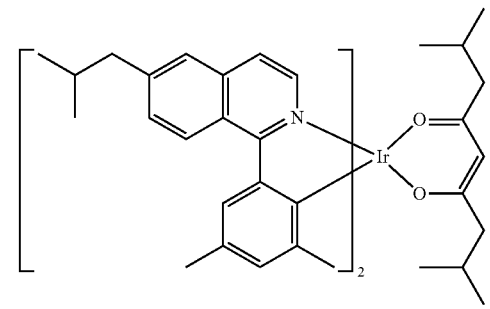
D-117
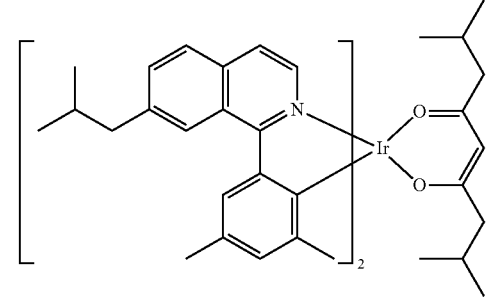
D-118
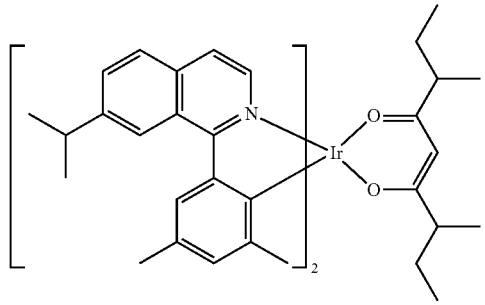
D-119
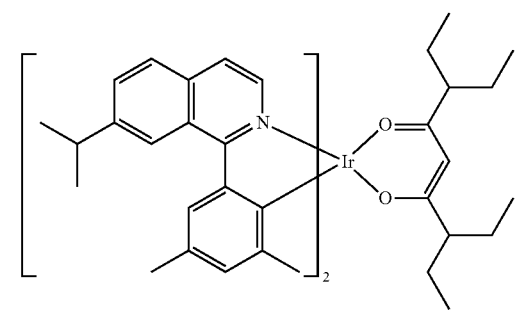
D-120
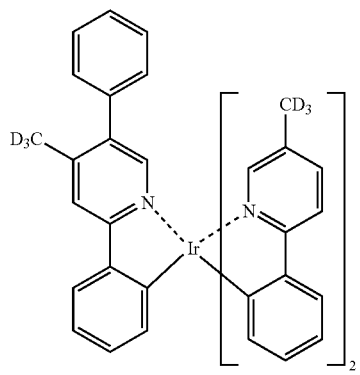
D-121
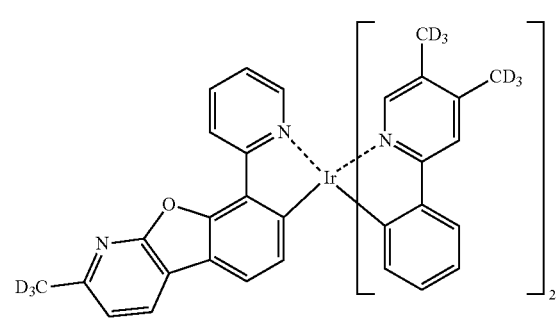

-continued
D-122
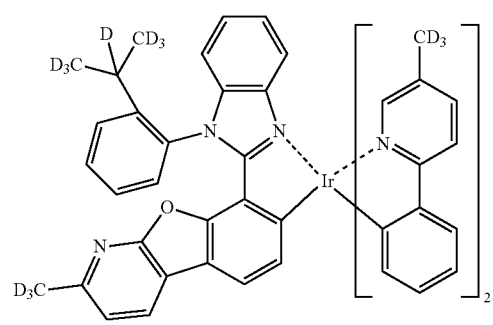
D-123
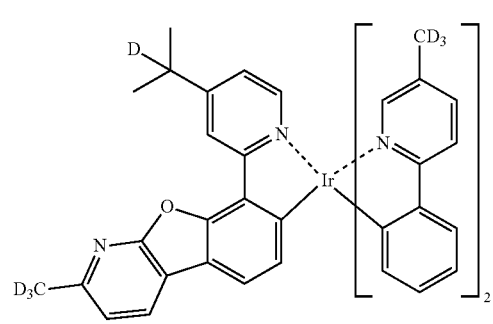
D-124
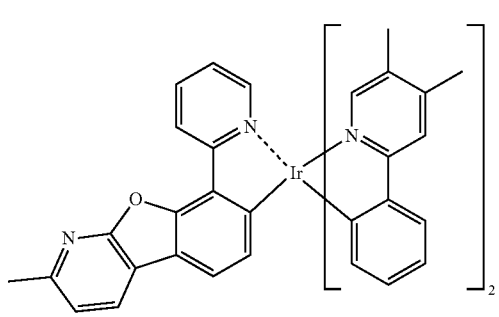
D-125
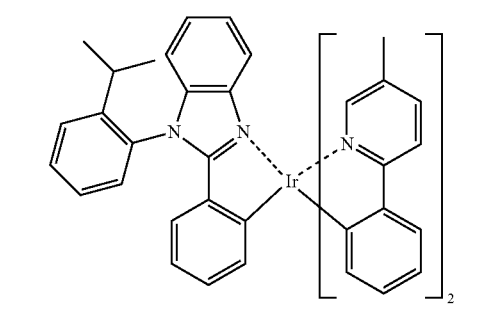
D-126
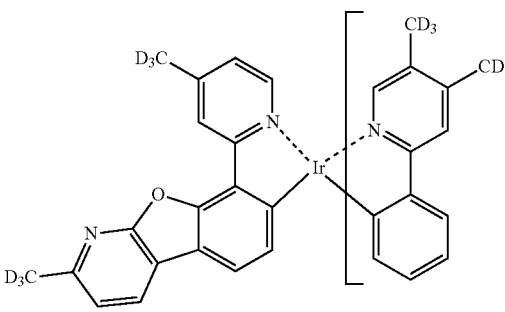
-continued
D-127
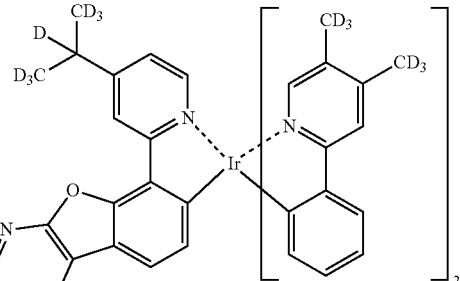
D-128
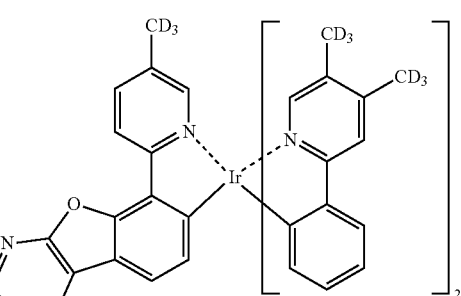
D-129
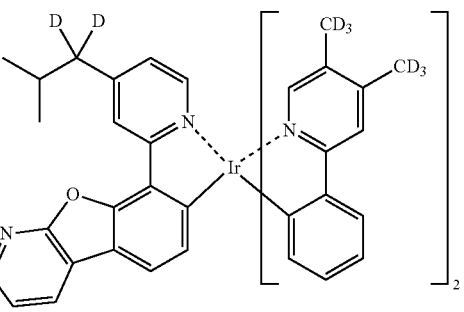
D-130
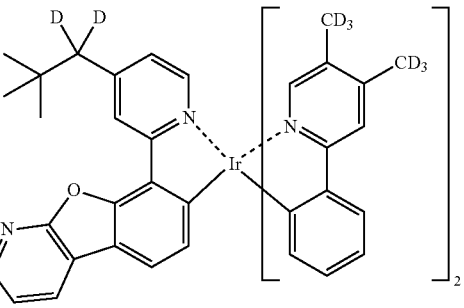

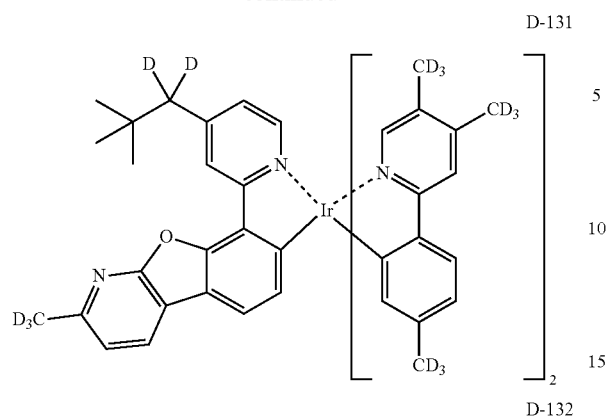
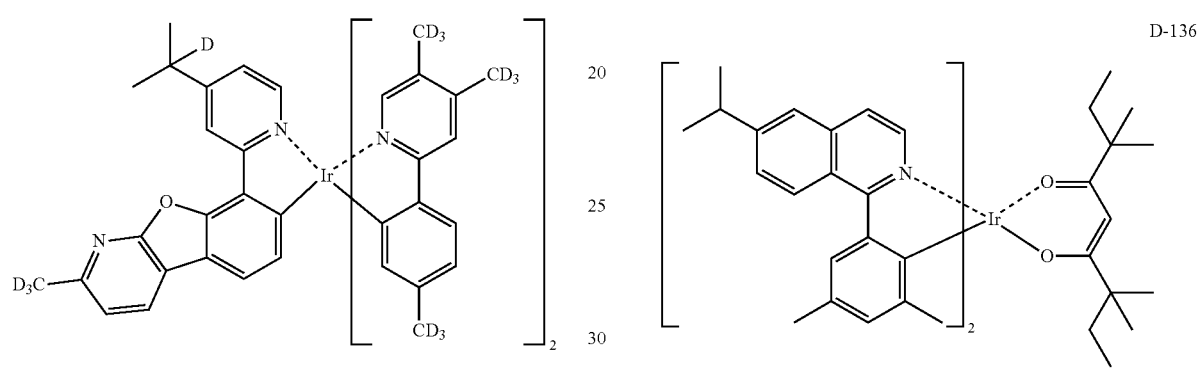
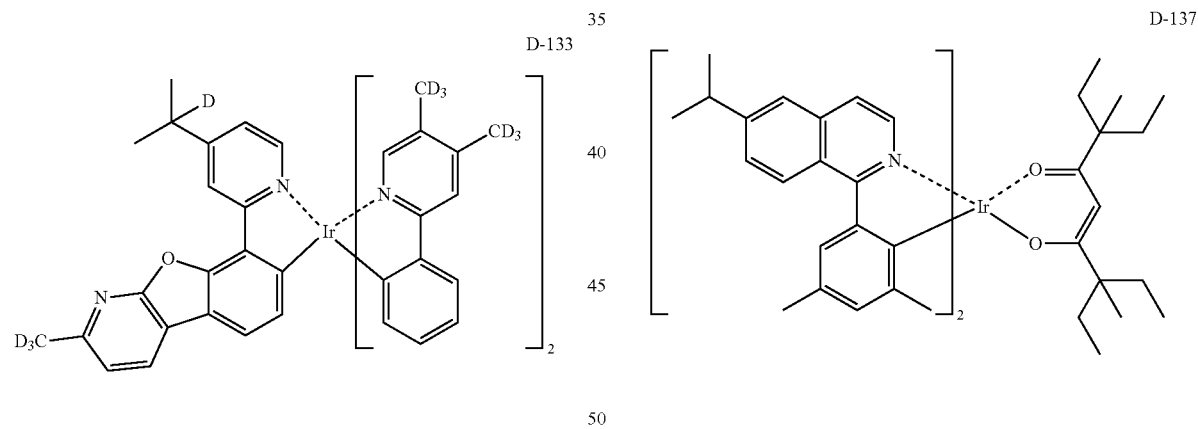
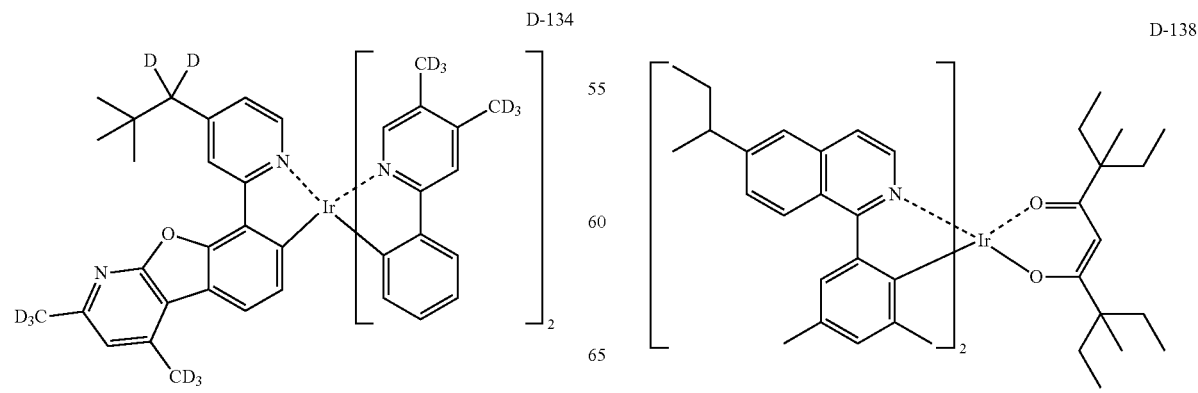

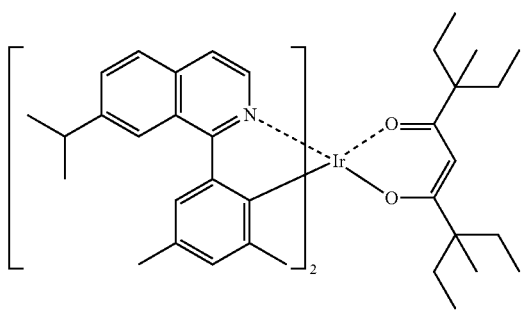

D-139

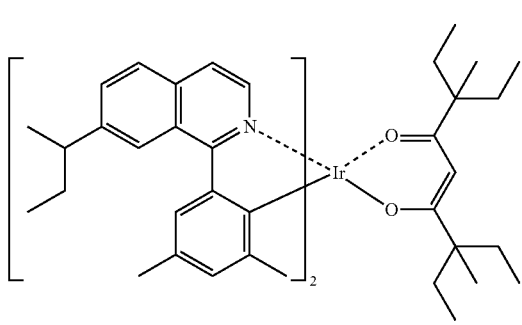

D-140

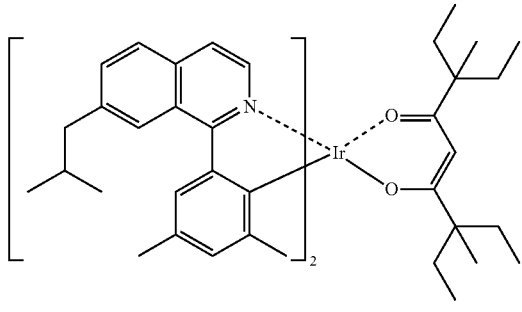

D-141

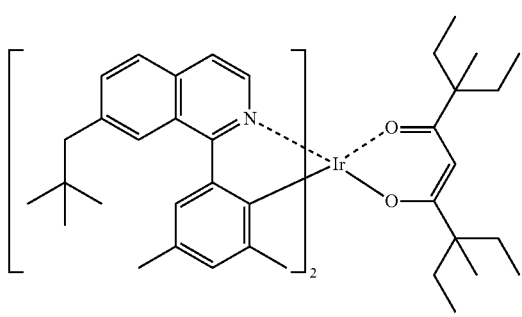

D-142

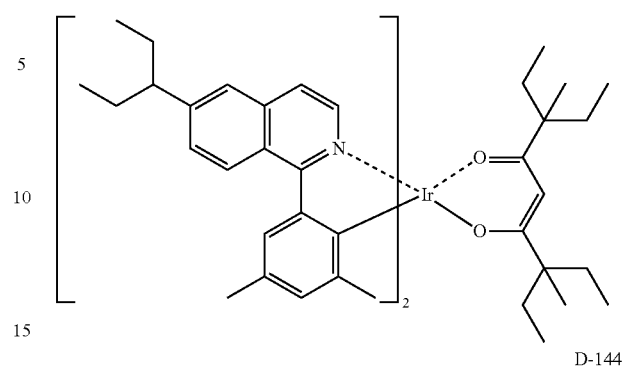

D-143

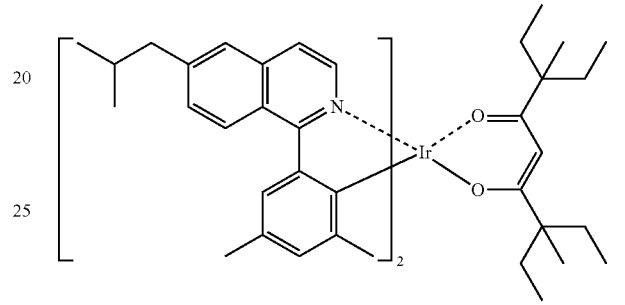

D-144

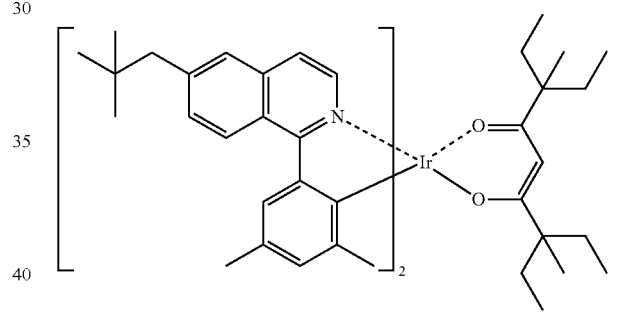

D-145

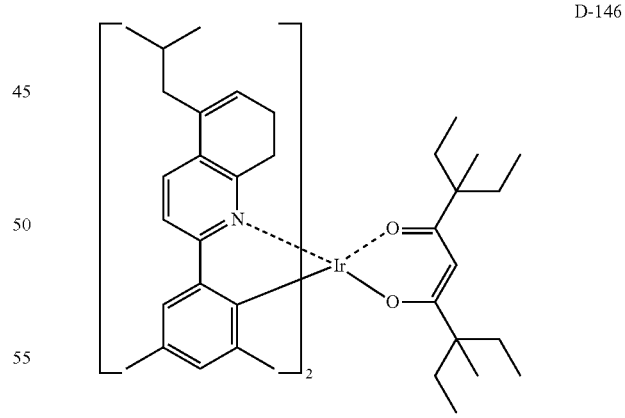

D-146

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the first host material and the second host material according to one embodiment, the layer can be formed by the above-listed methods, and can often be formed by co-deposition or mixture-deposition. The co-deposition is a mixed deposition method in which two or more isomer materials are put into respective individual crucible sources and a current is applied to both cells simultaneously to evaporate the materials and to perform mixed deposition; and the mixed deposition is a mixed deposition method in which two or more isomer materials are mixed in one crucible source before deposition, and then a current is applied to one cell to evaporate the materials.

According to one embodiment, when the first host material and the second host material exist in the same layer or different layers in the organic electroluminescent device, the layers by the two host compounds may be separately formed. For example, after depositing the first host material, a second host material may be deposited.

According to one embodiment, the present disclosure can provide display devices comprising a plurality of host materials including a first host material represented by formula 1 and a second host material represented by formula 11. In addition, by using the organic electroluminescent device of the present disclosure, it can be used for the manufacture of display devices such as smartphones, tablets, notebooks, PCs, TVs, or display devices for vehicles, or lighting devices such as outdoor or indoor lighting.

Hereinafter, the preparation method of compounds according to the present disclosure, and the properties thereof will be explained with reference to the synthesis method of a representative compound in order to understand the present disclosure in detail.

[Example 1] Preparation of Compound H1-1

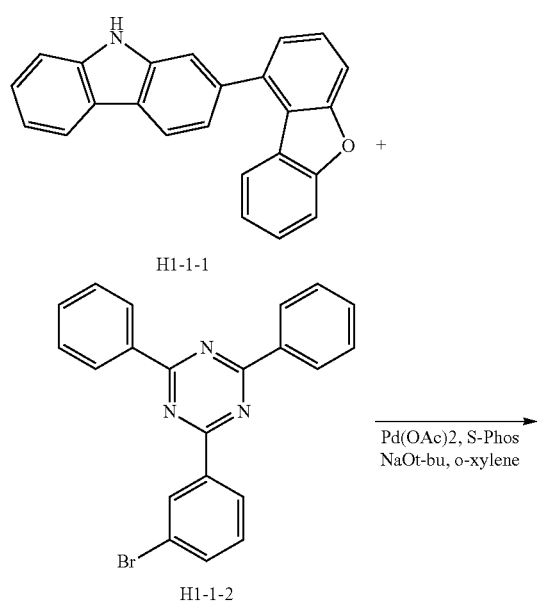

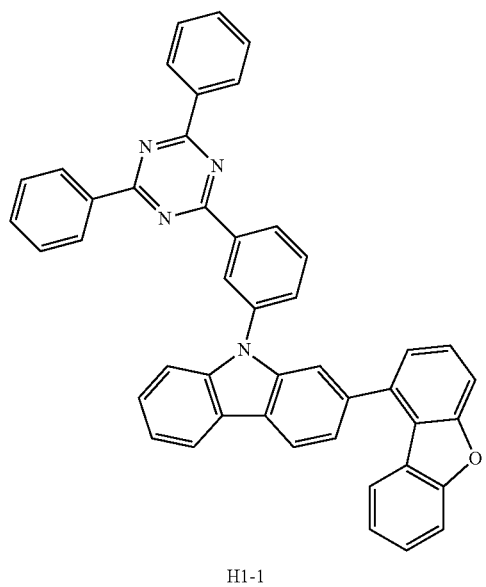

Compound H1-1-1 (4.0 g, 11.99 mmol), compound H1-1-2 (6.05 g, 15.59 mmol), Pd(OAc)$_2$ (0.13 g, 0.59 mmol), S-Phos (0.49 g, 1.19 mmol), NaOt-Bu (2.88 g, 29.99 mmol), and 150 mL of o-xylene were introduced into a flask and stirred at 160° C. for 3 hours. After completion of the reaction, the reaction mixture was cooled to room temperature, and the organic layer was extracted with ethyl acetate and dried with magnesium sulfate after removing residual moisture, and then separated by column chromatography to obtain compound H1-1 (5.2 g, yield: 67.70%).

|      | MW    | M.P      |
| ---- | ----- | -------- |
| H1-1 | 640.7 | 254.8° C. |

[Example 2] Preparation of Compound H1-16

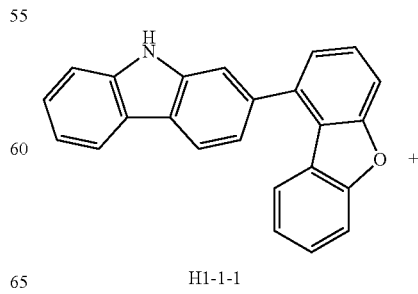

-continued

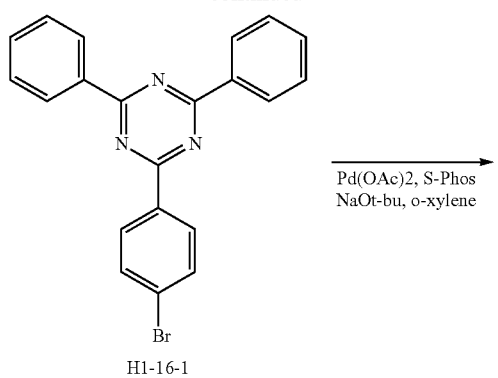

H1-16-1

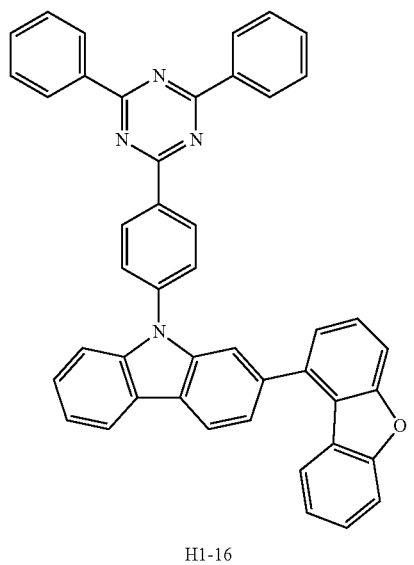

H1-16

Compound H1-1-1 (4.0 g, 11.99 mmol), compound H1-16-1 (5.6 g, 14.39 mmol), Pd(OAc)₂ (0.13 g, 0.59 mmol), S-Phos (0.49 g, 1.19 mmol), NaOt-Bu (2.88 g, 29.99 mmol), and 150 mL of o-xylene were introduced into a flask and stirred at 160° C. for 4 hours. After completion of the reaction, the reaction mixture was cooled to room temperature, and the organic layer was extracted with ethyl acetate and dried with magnesium sulfate after removing residual moisture, and then separated by column chromatography to obtain compound H1-16 (3.5 g, yield: 45.57%).

|  | MW | M.P |
|---|---|---|
| H1-16 | 640.7 | 233.5° C. |

[Example 3] Preparation of Compound H1-81

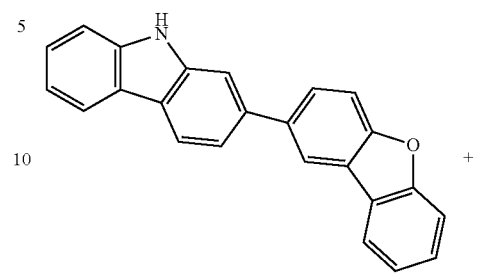

H1-81-1

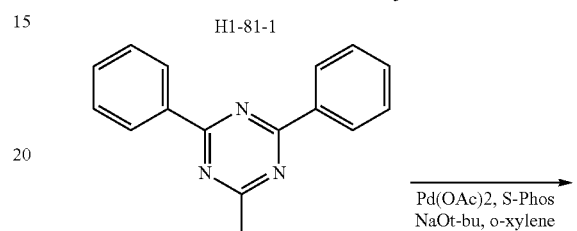

H1-1-2

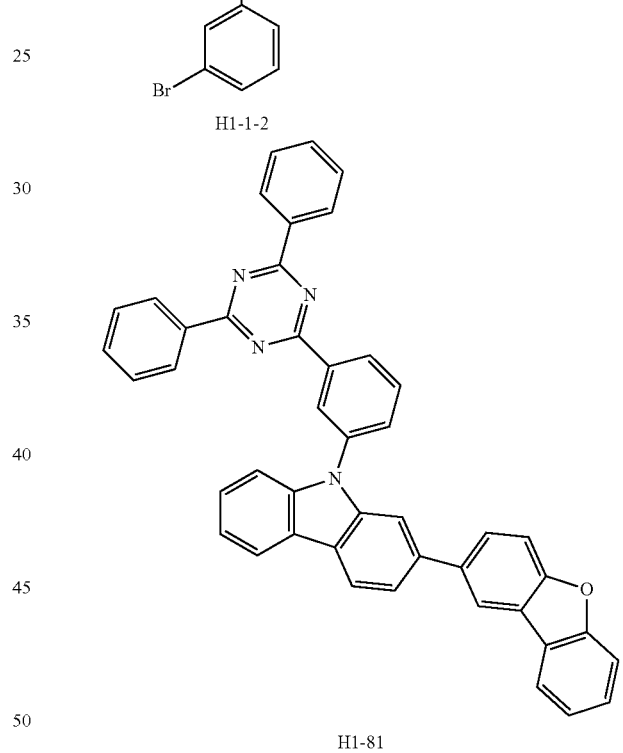

H1-81

Compound H1-81-1 (3.0 g, 9.0 mmol), compound H1-1-2 (4.2 g, 10.8 mmol), Pd(OAc)₂ (0.1 g, 0.45 mmol), S-Phos (0.37 g, 0.9 mmol), NaOt-Bu (1.73 g, 18.0 mmol), and 45 mL of o-xylene were introduced into a flask and stirred at 180° C. for 4.5 hours. After completion of the reaction, the reaction mixture was cooled to room temperature, and then the solid produced by adding methanol was filtered under reduced pressure. After dissolving the solid in chloroform, the mixture was separated by column chromatography to obtain compound H1-81 (2.3 g, yield: 40.35%).

|       | MW    | M.P     |
|-------|-------|---------|
| H1-81 | 640.7 | 239° C. |

[Device Examples 1 and 2] Preparation of OLEDs Comprising the Compound According to the Present Disclosure as a Host A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and thereafter was stored in isopropanol and then used. Thereafter, the ITO substrate was mounted on a substrate holder of a vacuum vapor deposition apparatus. Then, compound HI-1 as a first hole injection compound was introduced into a cell of the vacuum vapor deposition apparatus, and compound HT-1 as a first hole transport compound was introduced into another cell of the vacuum vapor deposition apparatus. The two materials were evaporated at different rates and the first hole injection compound was deposited in a doping amount of 3 wt % based on the total amount of the first hole injection compound and the first hole transport compound to form a first hole injection layer having a thickness of 10 nm. Next, compound HT-1 was deposited as a first hole transport layer having a thickness of 80 nm on the first hole injection layer. Compound HT-2 was then introduced into another cell of the vacuum vapor deposition apparatus and was evaporated by applying an electric current to the cell, thereby forming a second hole transport layer having a thickness of 30 nm on the first hole transport layer. After forming the hole injection layers and the hole transport layers, a light-emitting layer was formed thereon as follows: The respective hosts shown in Table 1 below were introduced into two cells of the vacuum vapor deposition apparatus as a host, and compound D-50 was introduced into another cell as a dopant. The two host materials were evaporated at different rates of 2:1 and the dopant material was evaporated at a different rate, simultaneously, and was deposited in a doping amount of 10 wt % based on the total amount of the host and dopant to form a light-emitting layer having a thickness of 40 nm on the hole transport layer. Next, compound ET-1 and compound EI-1 as an electron transport material were deposited at a weight ratio of 40:60 to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus.

Thus, OLEDs were produced. Each compound used for all the materials was purified by vacuum sublimation under $10^{-8}$ torr.

[Device Example 3] Preparation of an OLED Comprising the Compound According to the Present Disclosure as a Host An OLED was produced in the same manner as in Device Example 1, except that compound HT-3 was used as the second hole transport material, and compound H1-2 was used as the first host of the light-emitting layer.

[Device Example 4] Preparation of an OLED Comprising the Compound According to the Present Disclosure as a Host An OLED was produced in the same manner as in Device Example 1, except that compound HT-3 was used as the second hole transport material, and compound H1-31 was used as the first host of the light-emitting layer.

[Comparative Example 1] Preparation of an OLED Comprising a Conventional Compound as a Host An OLED was produced in the same manner as in Device Example 1, except that compound C-1 was used as the first host of the light-emitting layer.

[Comparative Example 2] Preparation of an OLED Comprising a Conventional Compound as a Host An OLED was produced in the same manner as in Comparative Example 1, except that compound HT-3 was used as the second hole transport material.

The driving voltage, the luminous efficiency, and the light-emitting color at a luminance of 1,000 nits, and the time taken for luminance to decrease from 100% to 95% at a luminance of 20,000 nits (lifespan; T95) of the organic eletroluminescent devices according to Device Examples 1 to 4 and Comparative Examples 1 and 2 produced as described above, are measured and the results thereof are shown in Table 1 below:

TABLE 1

|                       | second hole transport layer | First host | Second host | Driving Voltage (V) | Luminous Efficiency (cd/A) | Light-Emitting Color | Lifespan (T95) (hr) |
|-----------------------|-----------------------------|------------|-------------|---------------------|----------------------------|----------------------|---------------------|
| Device Example 1      | HT-2                        | H1-1       | H2-6        | 3.1                 | 85.3                       | Green                | 141                 |
| Device Example 2      | HT-2                        | H1-16      | H2-6        | 3.0                 | 84.8                       | Green                | 116                 |
| Device Example 3      | HT-3                        | H1-2       | H2-6        | 3.2                 | 92.0                       | Green                | 121                 |
| Device Example 4      | HT-3                        | H1-31      | H2-6        | 3.2                 | 91.9                       | Green                | 114                 |
| Comparative Example 1 | HT-2                        | C-1        | H2-6        | 3.1                 | 84.1                       | Green                | 106                 |
| Comparative Example 2 | HT-3                        | C-1        | H2-6        | 3.2                 | 90.0                       | Green                | 79.1                |

From Table 1 above, it can be confirmed that the organic electroluminescent device comprising the organic electroluminescent compounds according to the present disclosure as a host material not only has excellent luminous efficiency, but also, in particular, significantly improves lifespan characteristics, compared to the organic electroluminescent device comprising a conventional host material.

The compounds used in Device Examples 1 to 4 and Comparative Examples 1 and 2 above are shown in the following Table 2:

TABLE 2

| Hole Injection Layer/ Hole Transport Layer | [chemical structure] | HI-1 |
| | [chemical structure] | HT-1 |
| | [chemical structure] | HT-2 |

TABLE 2-continued
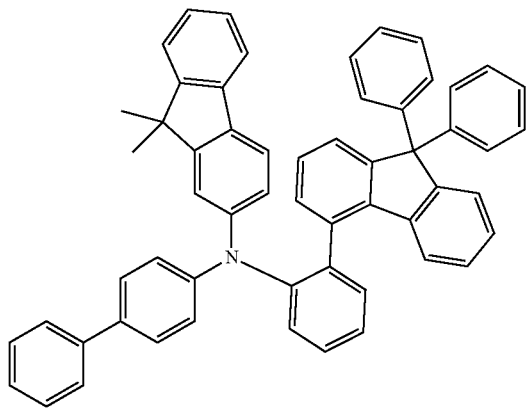 [SMILES: CC1(C)c2ccccc2-c2ccc(N(c3ccc(-c4ccccc4)cc3)c3ccccc3-c3cccc4c3-c3ccccc3C4(c3ccccc3)c3ccccc3)cc21]
HT-3
Light-Emitting Layer
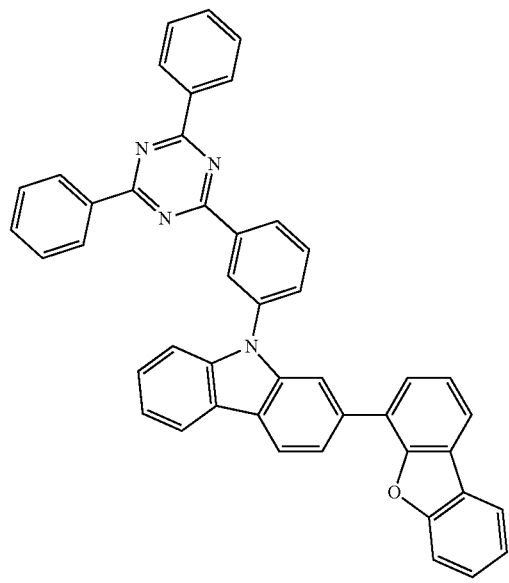 [SMILES: c1ccc(-c2nc(-c3ccccc3)nc(-c3cccc(-n4c5ccccc5c5ccc(-c6cccc7c6oc6ccccc67)cc54)c3)n2)cc1]
C-1
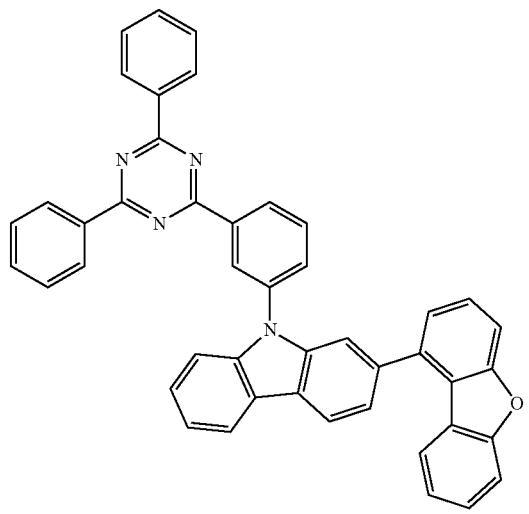 [SMILES: c1ccc(-c2nc(-c3ccccc3)nc(-c3cccc(-n4c5ccccc5c5ccc(-c6cccc7oc8ccccc8c67)cc54)c3)n2)cc1]
H1-1

TABLE 2-continued
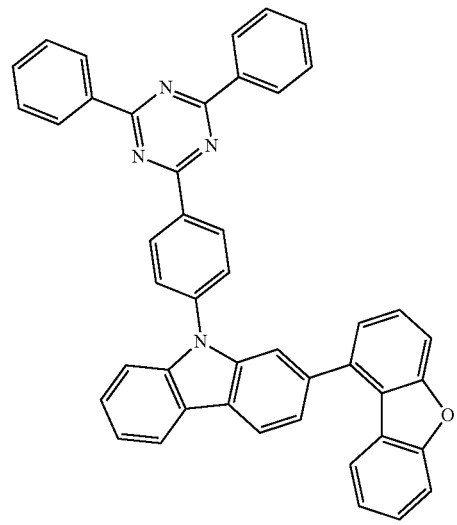 [SMILES: c1ccc(-c2nc(-c3ccccc3)nc(-c3ccc(-n4c5ccccc5c5ccc(-c6cccc7oc8ccccc8c67)cc54)cc3)n2)cc1]
H1-16
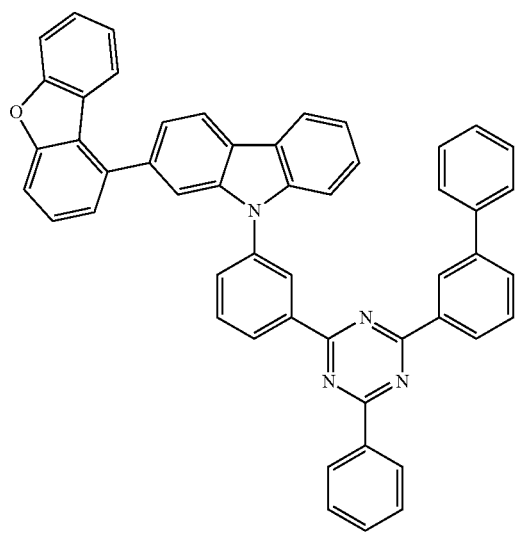 [SMILES: c1ccc(-c2cccc(-c3nc(-c4ccccc4)nc(-c4cccc(-n5c6ccccc6c6ccc(-c7cccc8oc9ccccc9c78)cc65)c4)n3)c2)cc1]
H1-2
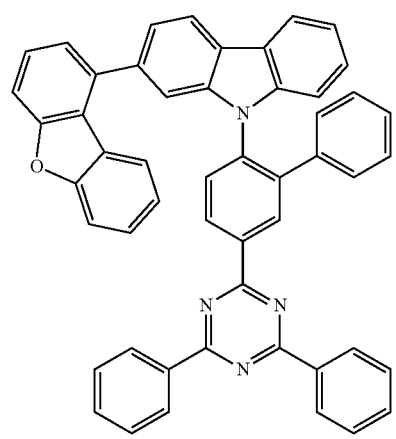 [SMILES: c1ccc(-c2nc(-c3ccccc3)nc(-c3ccc(-n4c5ccccc5c5ccc(-c6cccc7oc8ccccc8c67)cc54)c(-c4ccccc4)c3)n2)cc1]
H1-31

TABLE 2-continued
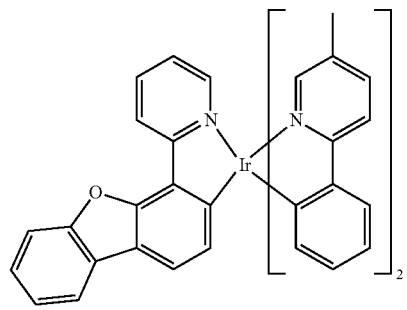
D-50
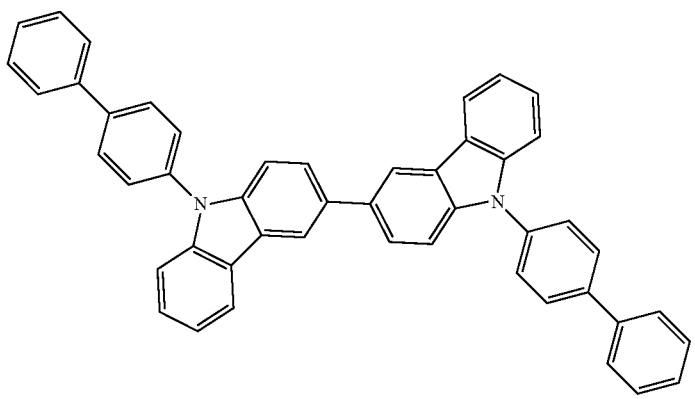 [SMILES: c1ccc(-c2ccc(-n3c4ccccc4c4cc(-c5ccc6c(c5)c5ccccc5n6-c5ccc(-c6ccccc6)cc5)ccc43)cc2)cc1]
H2-6
Electron
transport
Layer/
Electron
Injection Layer
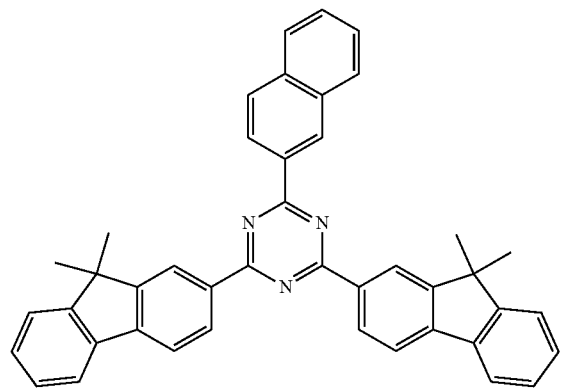 [SMILES: CC1(C)c2ccccc2-c2ccc(-c3nc(-c4ccc5c(c4)C(C)(C)c4ccccc4-5)nc(-c4ccc5ccccc5c4)n3)cc21]
ET-1
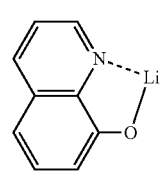
EI-1

[Device Example 5] Preparation of an OLED Comprising the Organic Electroluminescent Compound According to the Present Disclosure OLED was produced by using the organic electroluminescent compound according to the present disclosure. First, a transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and thereafter was stored in isopropanol and then used. Next, the ITO substrate was mounted on a substrate holder of a vacuum vapor deposition apparatus. Compound HT-1 was introduced into one cell of the vacuum vapor deposition apparatus, and compound HI-1 was introduced into another cell of the vacuum vapor deposition apparatus. The pressure in the chamber of the apparatus was then controlled to $10^{-8}$ torr. Thereafter, the two materials were evaporated and compound HI-1 was deposited in a doping amount of 3 wt % based on the total amount of compounds HT-1 and HI-1 to form a hole injection layer having a thickness of 10 nm on the ITO substrate. Compound HT-1 was then introduced into a cell of the vacuum vapor deposition apparatus, and an electric current was applied to the cell to evaporate the introduced material, thereby forming a first hole transport layer having a thickness of 75 nm on the hole injection layer. Next, compound HT-4 was introduced into another cell of the vacuum vapor deposition apparatus. Thereafter, an electric current was applied to the cell to evaporate the introduced material, thereby forming a second hole transport layer having a thickness of 5 nm on the first hole transport layer. After forming the hole injection layers and the hole transport layers, a light-emitting layer was then deposited thereon as follows: Compound BH-1 as a host was introduced into a cell of the vacuum vapor deposition apparatus and the compound BD-1 was introduced into another cell as a dopant. Simultaneously, the dopant material was evaporated at a different rate. The dopant was doped in a doping amount of 2 wt % with respect to the total amount of the host and dopant, to form a light-emitting layer having a thickness of 20 nm on the second hole transport layer. Next, compound H1-1 as a hole blocking layer was deposited in a thickness of 5 nm. Compounds ET-1 and EI-1 were introduced into another two cells, were evaporated at a rate of 4:6, respectively, and were deposited to form an electron transport layer having a thickness of 30 nm on the hole blocking layer. Thereafter, compound EI-1 having a thickness of 2 nm was deposited as an electron injection layer, and an Al cathode having a thickness of 80 nm was deposited by another vacuum vapor deposition apparatus. Thus, OLED was produced.

[Device Example 6] Preparation of an OLED Comprising the Organic Electroluminescent Compound According to the Present Disclosure An OLED was produced in the same manner as in Device Example 5, except that compound H1-16 was used as a hole blocking material.

[Device Example 7] Preparation of an OLED Comprising the Organic Electroluminescent Compound According to the Present Disclosure An OLED was produced in the same manner as in Device Example 5, except that compound H1-81 was used as a hole blocking material.

[Comparative Example 3] Preparation of OLED Comprising the Conventional Organic Electroluminescent Compound An OLED was produced in the same manner as in Device Example 5, except that compound C-1 was used as a hole blocking material.

The driving voltage, the luminous efficiency, and the light-emitting color at a luminance of 1,000 nits of the organic electroluminescent devices according to Device Examples 5 to 7 and Comparative Example 3 produced as described above are measured, and further, the time taken for luminance to decrease from 100% to 95% at a luminance of 2,500 nits (lifespan; T95) of the organic electroluminescent devices according to Device Example 7 and Comparative Example 3 are measured. The results thereof are shown in Tables 3 and 4 below, respectively:

TABLE 3

|  | Hole Blocking Material | Driving Voltage (V) | Luminous Efficiency (cd/A) | Light-emitting Color |
| --- | --- | --- | --- | --- |
| Device Example 5 | H1-1 | 4.1 | 7.7 | Blue |
| Device Example 6 | H1-16 | 4.2 | 7.5 | Blue |
| Comparative Example 3 | C-1 | 4.3 | 7.1 | Blue |

From Table 3 above, it can be confirmed that the organic electroluminescent device comprising the organic electroluminescent compounds according to the present disclosure as a hole blocking material has low driving voltage and high luminous efficiency, compared to the organic electroluminescent device comprising the conventional hole blocking material.

TABLE 4

|  | Hole Blocking Material | Driving Voltage (V) | Luminous Efficiency (cd/A) | Light-emitting Color | Lifespan (T95) (hr) |
| --- | --- | --- | --- | --- | --- |
| Device Example 7 | H1-81 | 4.3 | 7.0 | Blue | 38.1 |
| Comparative Example 3 | C-1 | 4.3 | 7.1 | Blue | 34.0 |

From Table 4 above, it can be confirmed that the organic electroluminescent device comprising the organic electroluminescent compounds according to the present disclosure as a hole blocking material exhibits a luminous efficiency equal to or higher than that of an organic electroluminescent device comprising the conventional hole blocking material, and in particular, significantly improves lifespan characteristics, compared to the organic electroluminescent device comprising the conventional hole blocking material. Moreover, the organic electroluminescent device according to the present disclosure can manufacture a blue organic electroluminescent device having a long life, and thus a lifespan balance between the organic electroluminescent device according to the present disclosure and the red or green organic electroluminescent device can be maintained.

The compounds used in Device Examples 5 to 7 and Comparative Example 3 above are shown in the following Table 5:

TABLE 5
Hole Injection Layer/ Hole Transport Layer
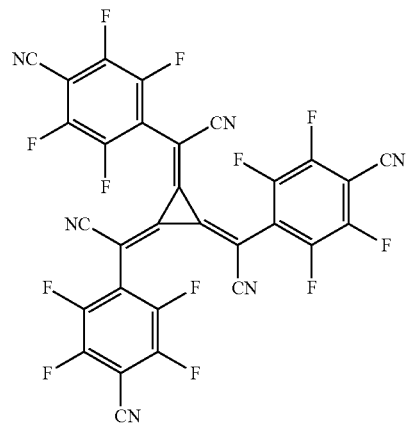 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F]
HI-1
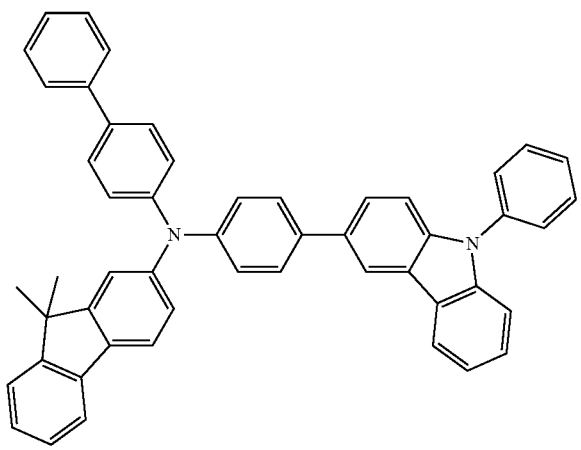 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT-1
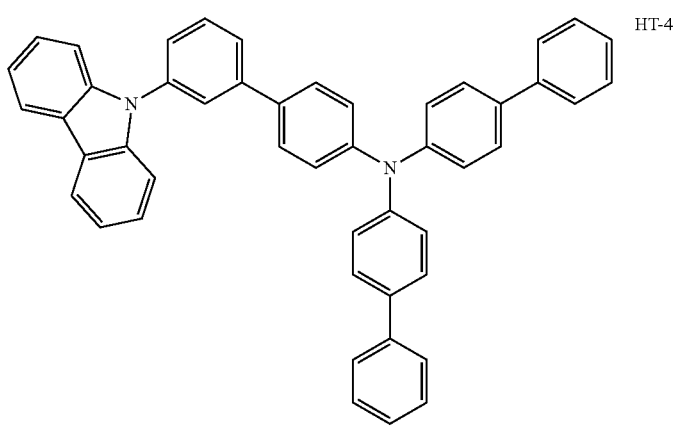
HT-4
Light-Emitting Layer
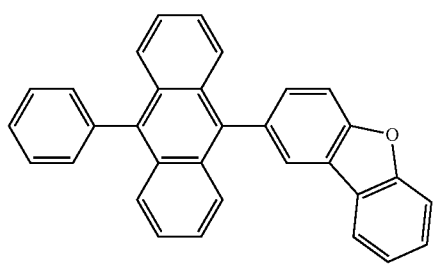 [SMILES: c1ccc(-c2c3ccccc3c(-c3ccc4oc5ccccc5c4c3)c3ccccc23)cc1]
BH-1

TABLE 5-continued
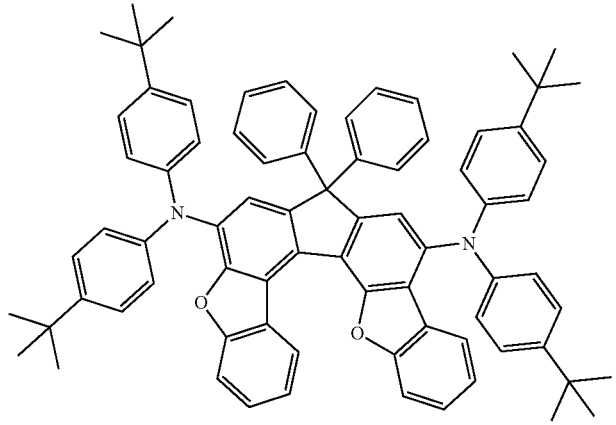 [SMILES: CC(C)(C)c1ccc(N(c2ccc(C(C)(C)C)cc2)c2cc3c(c4c2oc2ccccc24)-c2c(cc(N(c4ccc(C(C)(C)C)cc4)c4ccc(C(C)(C)C)cc4)c4c2oc2ccccc24)C3(c2ccccc2)c2ccccc2)cc1]
BD-1
Hole Blocking Layer
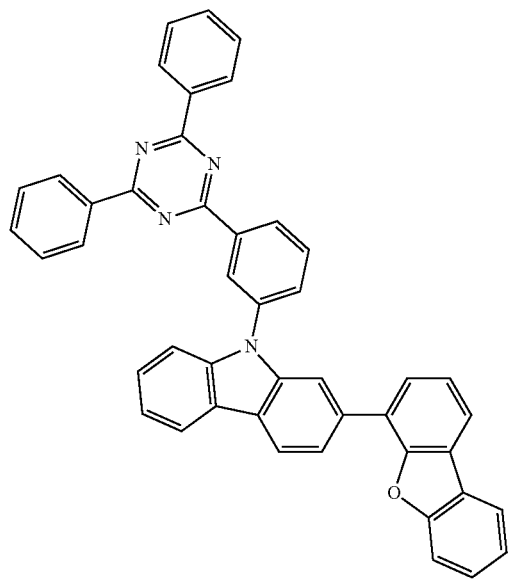 [SMILES: c1ccc(-c2nc(-c3ccccc3)nc(-c3cccc(-n4c5ccccc5c5ccc(-c6cccc7c6oc6ccccc67)cc54)c3)n2)cc1]
C-1
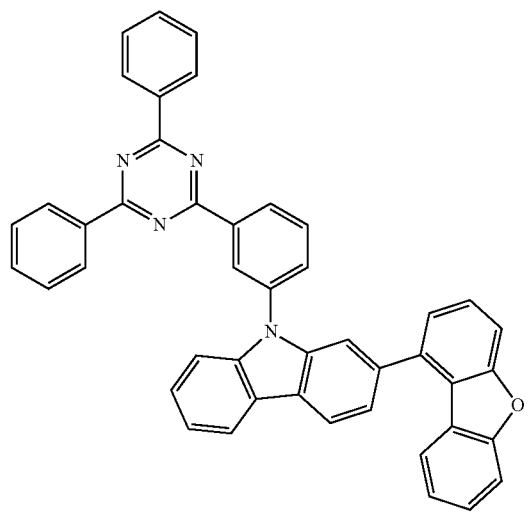 [SMILES: c1ccc(-c2nc(-c3ccccc3)nc(-c3cccc(-n4c5ccccc5c5ccc(-c6cccc7oc8ccccc8c67)cc54)c3)n2)cc1]
H1-1

TABLE 5-continued
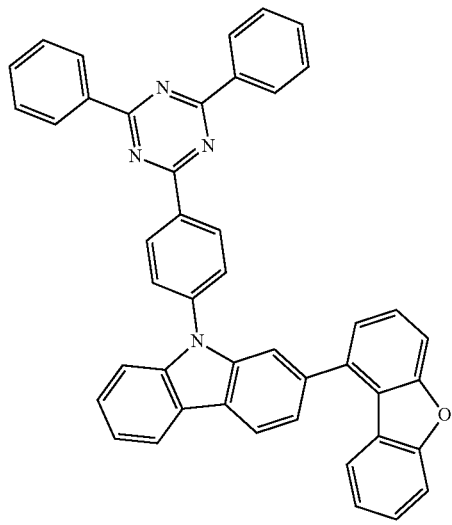 [SMILES: c1ccc(-c2nc(-c3ccccc3)nc(-c3ccc(-n4c5ccccc5c5ccc(-c6cccc7oc8ccccc8c67)cc54)cc3)n2)cc1]
H1-16
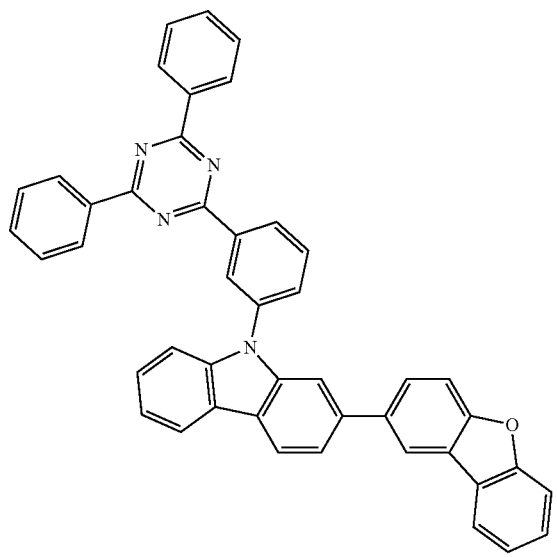 [SMILES: c1ccc(-c2nc(-c3ccccc3)nc(-c3cccc(-n4c5ccccc5c5ccc(-c6ccc7oc8ccccc8c7c6)cc54)c3)n2)cc1]
H1-81
Electron Transport Layer/ Electron Injection Layer
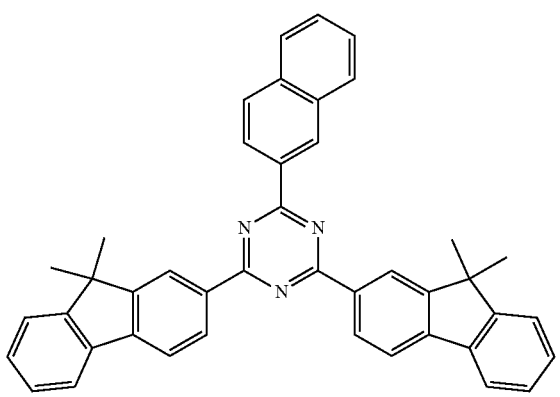 [SMILES: CC1(C)c2ccccc2-c2ccc(-c3nc(-c4ccc5c(c4)C(C)(C)c4ccccc4-5)nc(-c4ccc5ccccc5c4)n3)cc21]
ET-1
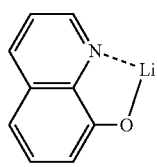
EI-1

The invention claimed is:

1. An organic electroluminescent compound represented by the following formula 1-1 or 1-2:

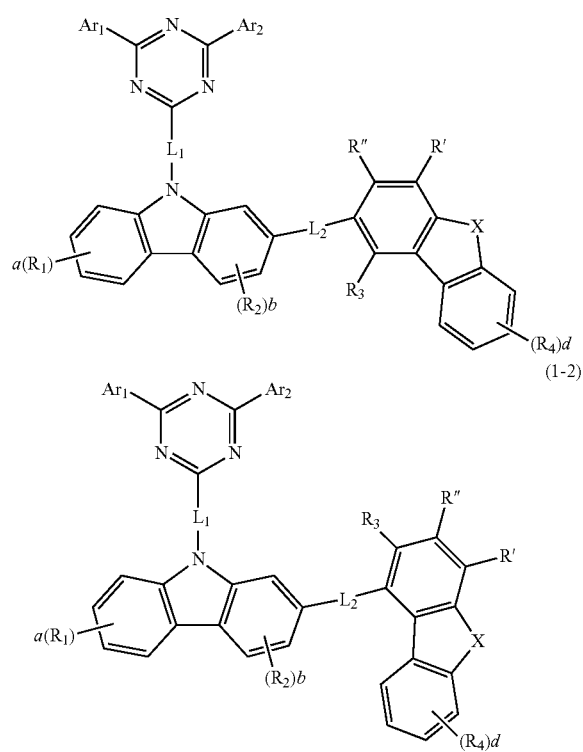

wherein
X represents O or S;
Ar$_1$ and Ar$_2$ each independently represent a substituted or unsubstituted phenyl, a substituted or unsubstituted biphenyl, a substituted or unsubstituted naphthyl, a substituted or unsubstituted terphenyl, a substituted or unsubstituted 9,9-dimethylfluorenyl, a substituted or unsubstituted 9,9-diphenylfluorenyl, a substituted or unsubstituted 9,9'-spirobifluorenyl, a substituted or unsubstituted dibenzofuranyl, a substituted or unsubstituted dibenzothiophenyl, a substituted or unsubstituted 9-phenyl-carbazolyl, a substituted or unsubstituted 2-phenylbenzoxazolyl, or a substituted or unsubstituted 2-phenylbenzothiazolyl;
L$_1$ and L$_2$ each independently represent a single bond, a substituted or unsubstituted phenylene, a substituted or unsubstituted biphenylene, a substituted or unsubstituted naphthylene, a substituted or unsubstituted terphenylene, a substituted or unsubstituted dibenzothiophenylene, a substituted or unsubstituted 9-phenyl-carbazolylene, a substituted or unsubstituted 9,9-dimethylfluorenylene, a substituted or unsubstituted 9,9-diphenylfluorenylene, or a substituted or unsubstituted 9,9'-spirobifluorenylene;
R$_1$ to R$_4$, R', and R'' each independently represent hydrogen or deuterium; and
a and d each independently represent an integer of 1 to 4, b represents an integer of 1 to 3; and
when a, b, and d are an integer of 2 or more, each of R$_1$, R$_2$, and R$_4$ may be the same or different.

2. The organic electroluminescent compound according to claim 1, wherein the substituents of the substituted phenyl (ene), the substituted biphenyl(ene), the substituted naphthyl (ene), the substituted terphenyl(ene), the substituted 9,9-dimethylfluorenyl(ene), the substituted 9,9-diphenylfluorenyl(ene), the substituted 9,9'-spirobifluorenyl (ene), the substituted dibenzofuranyl, the substituted dibenzothiophenyl(ene), the substituted 9-phenyl-carbazolyl (ene), the substituted 2-phenylbenzoxazolyl, and the substituted 2-phenylbenzothiazolyl in the Ar$_1$, Ar$_2$, L$_1$, and L$_2$ each independently represent at least one selected from the group consisting of deuterium, cyano, (C1-05)alkyl, (C6-C12)aryl, and (5- to 15-membered)heteroaryl.

3. The organic electroluminescent compound according to claim 1, wherein the Ar$_1$ and Ar$_2$ each independently are selected from any one of the substituents listed in the following group 1:

[Group 1]

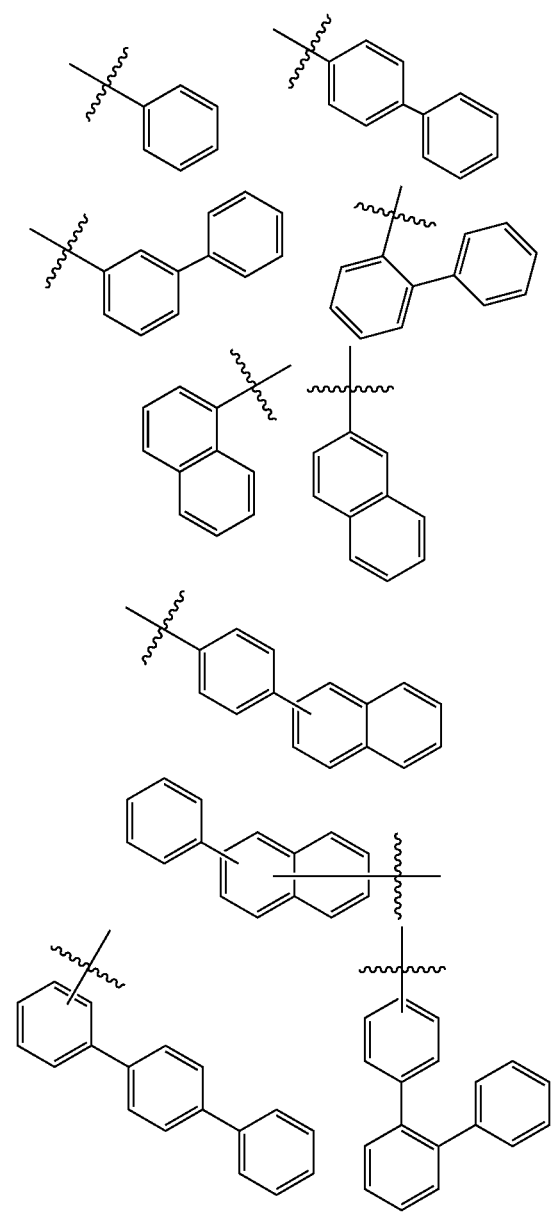

151
-continued
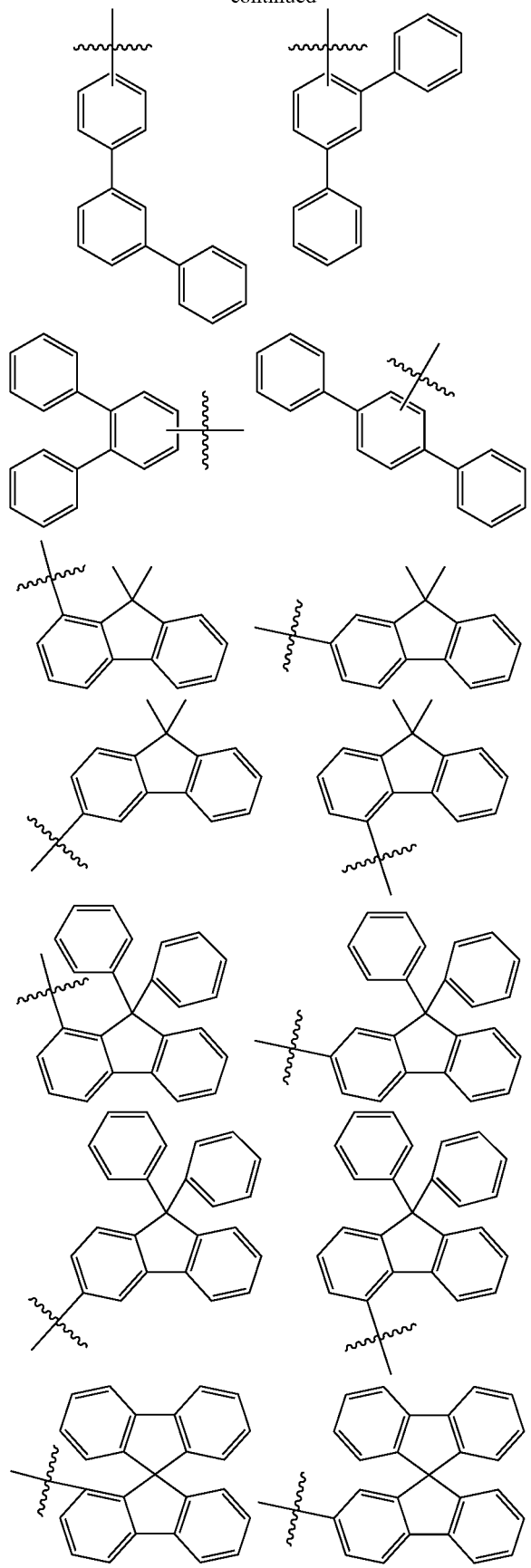
152
-continued
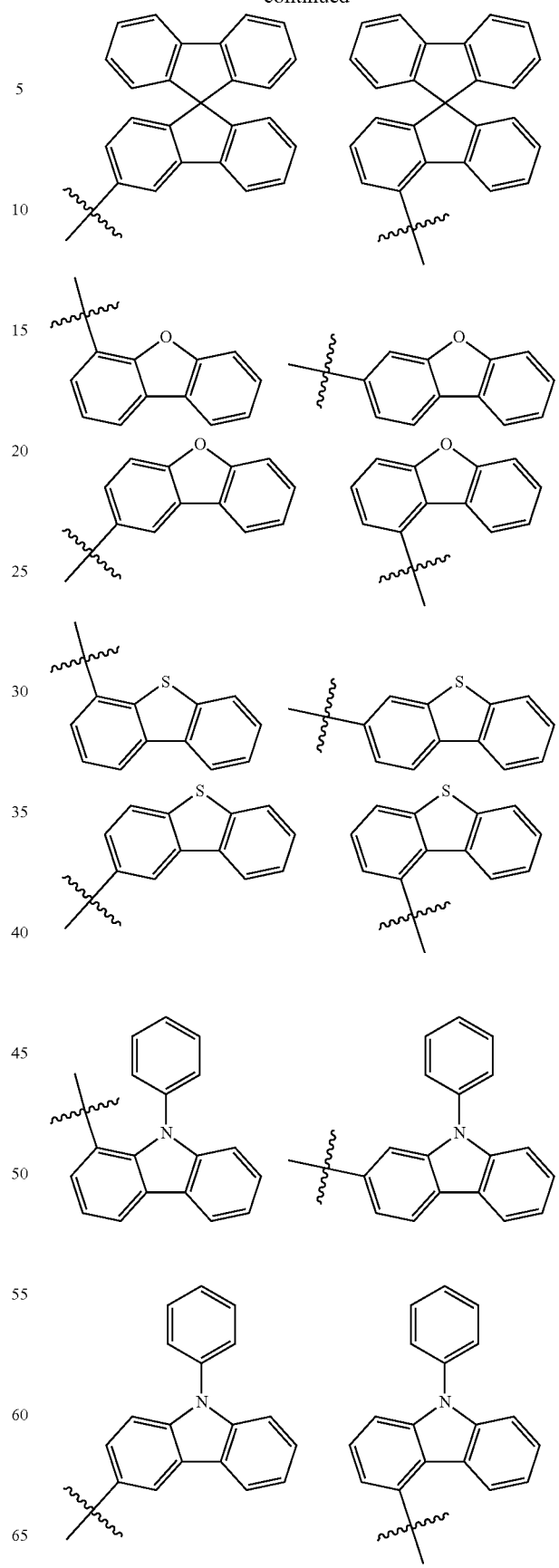

153
-continued
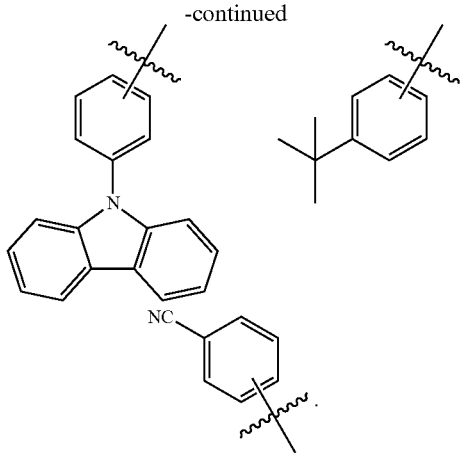
4. The organic electroluminescent compound according to claim 1, wherein the compound represented by formula 1 is selected from the following compounds:
H1-1
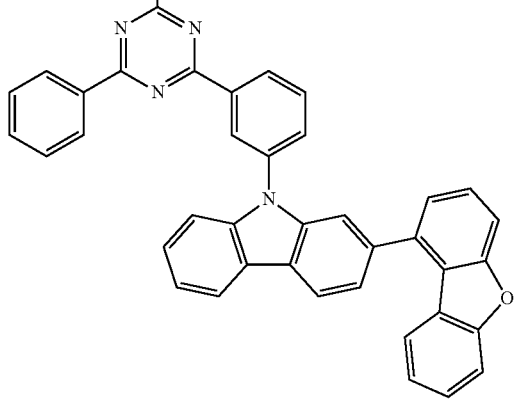
H1-2
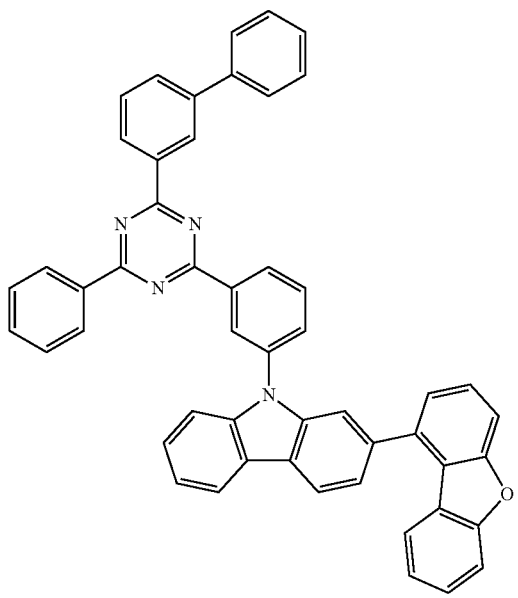
154
-continued
H1-3
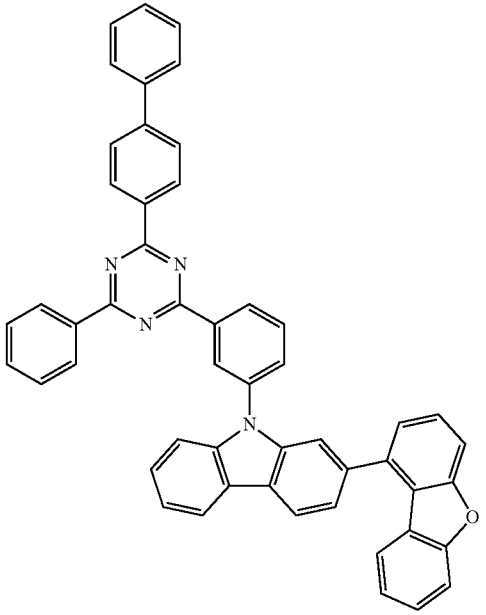
H1-4
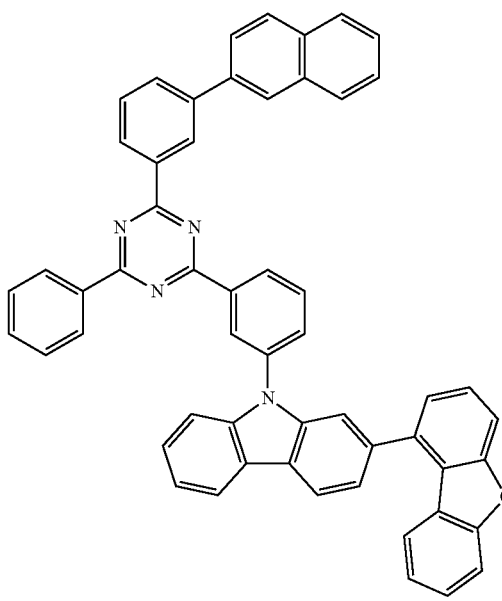

H1-5
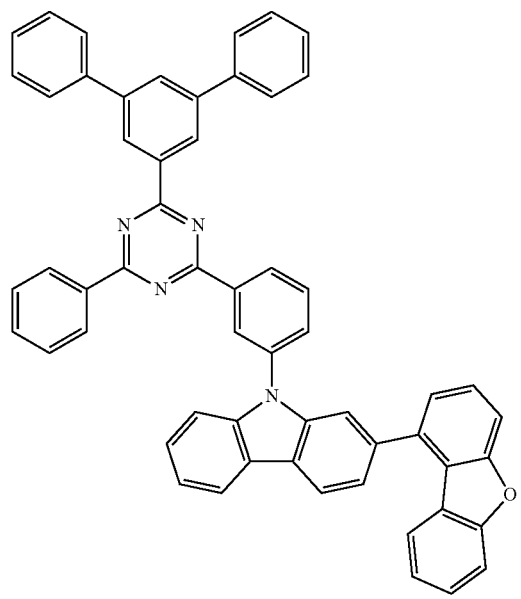
H1-6
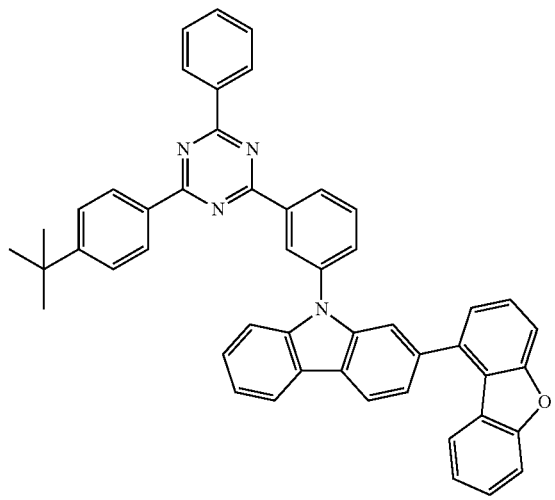
H1-7
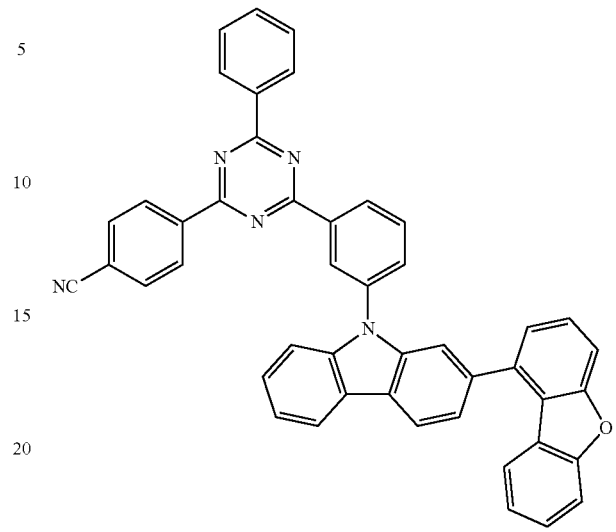
H1-8
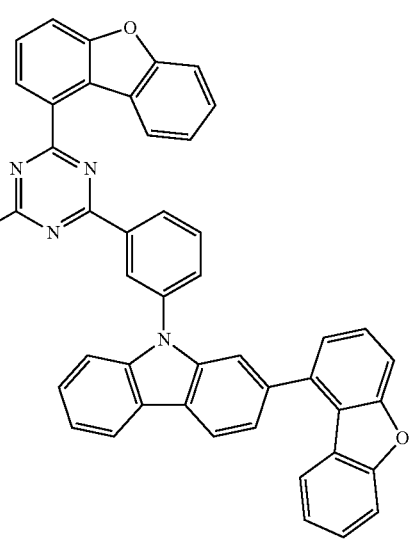
H1-9

H1-10
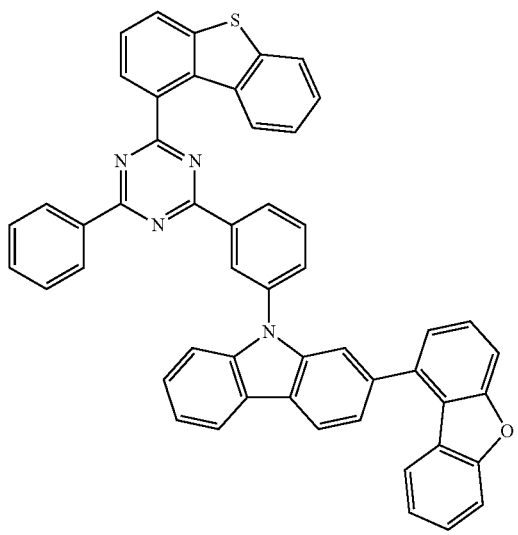
H1-11
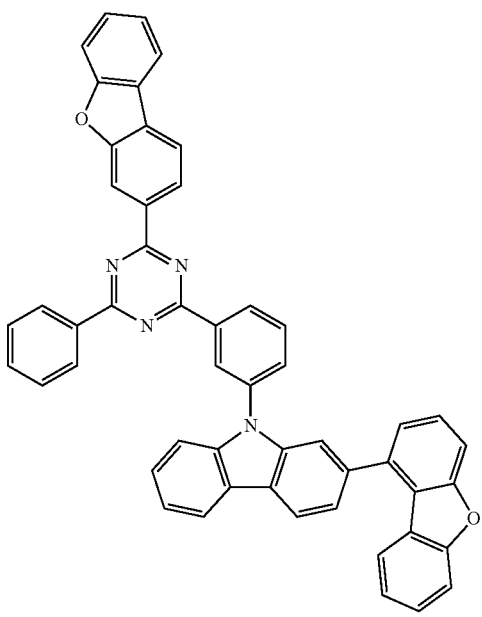
H1-12
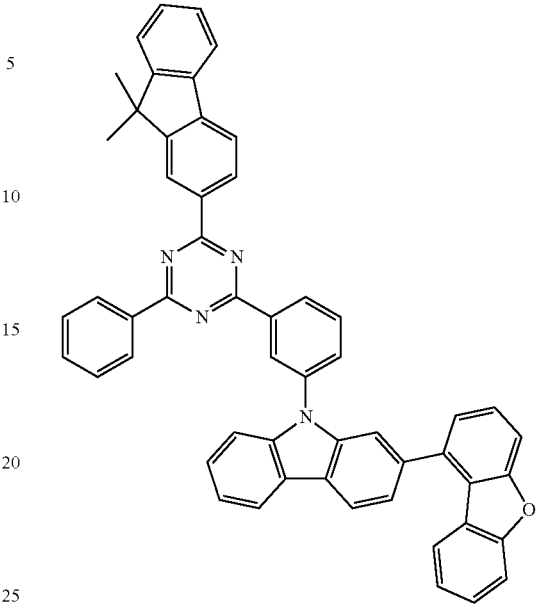
H1-13
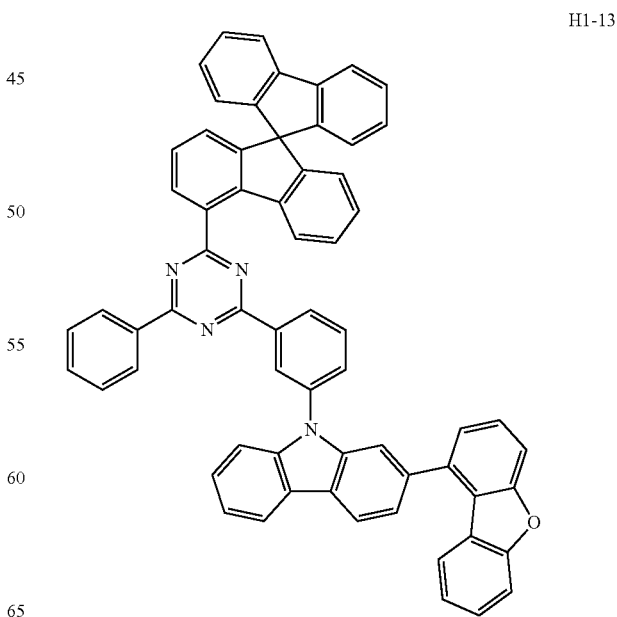

H1-14
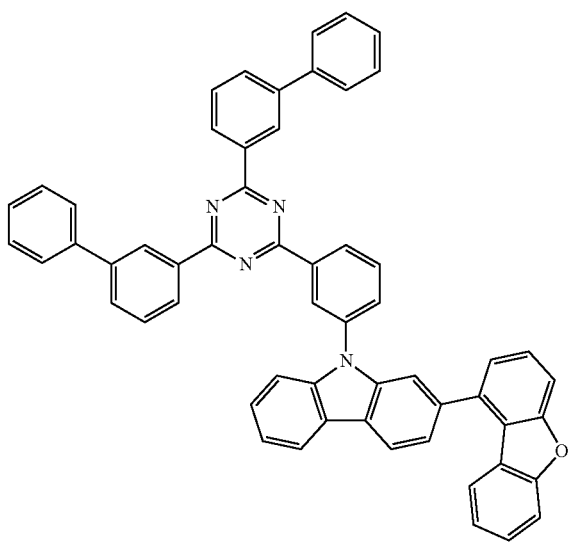
H1-15
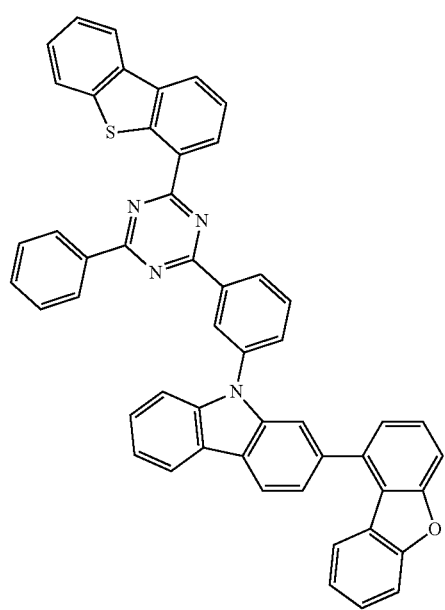
H1-16
H1-17
H1-18
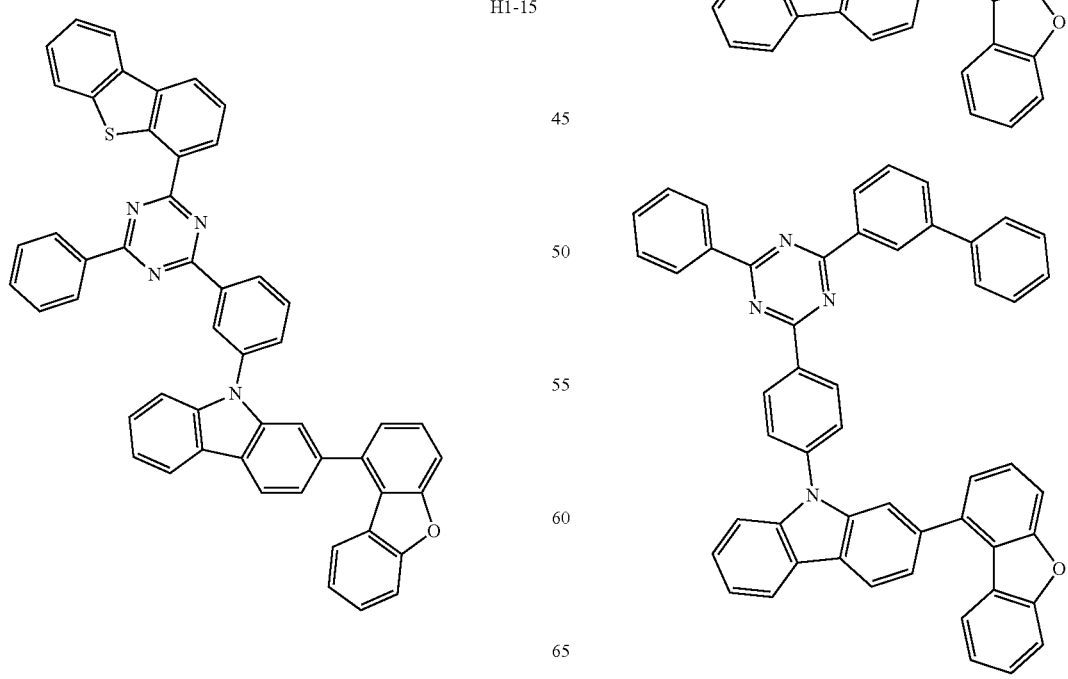

H1-19
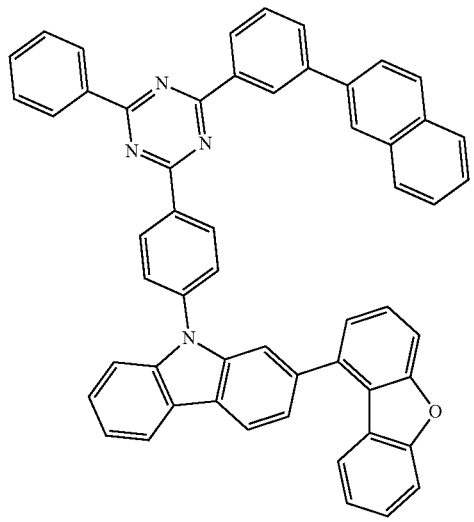
H1-20
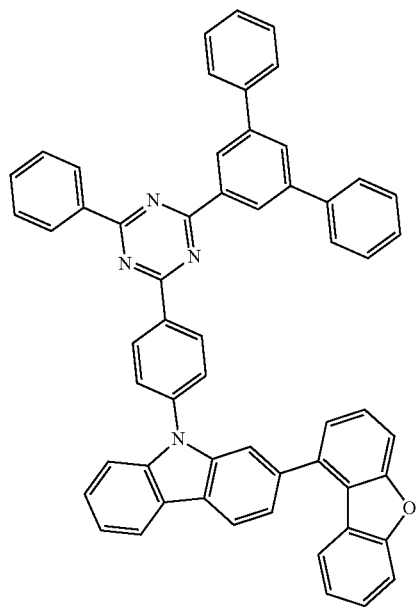
H1-21
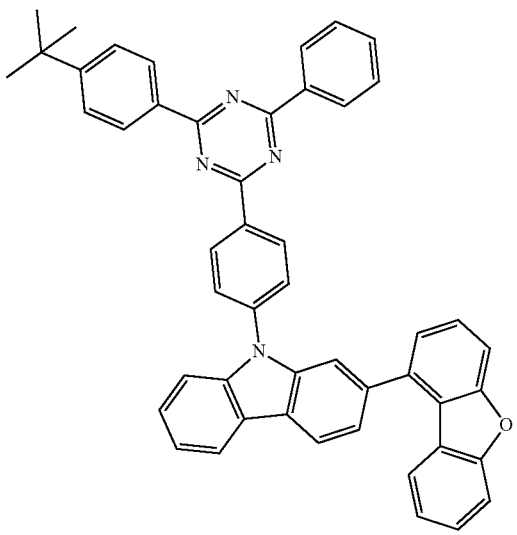
H1-22
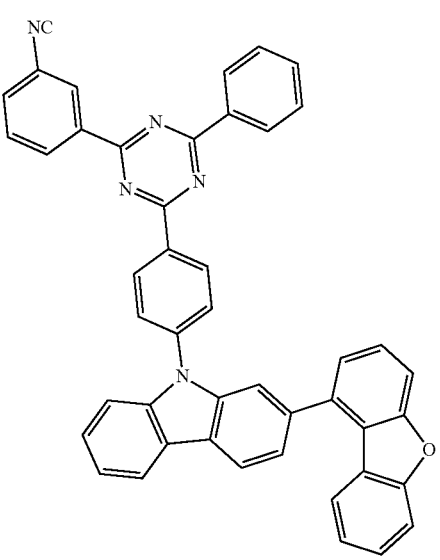
H1-23
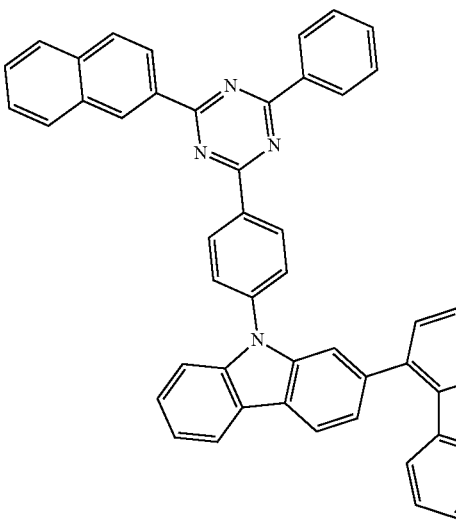

H1-24
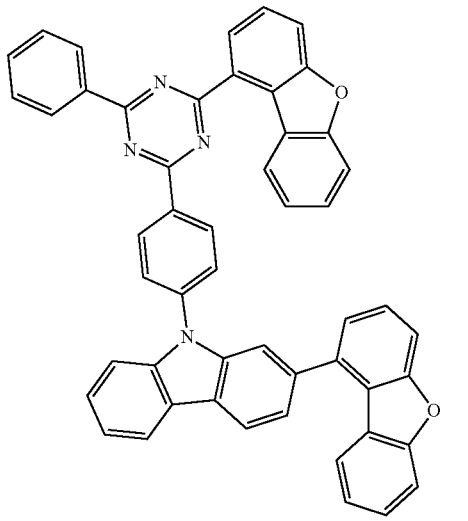
H1-25
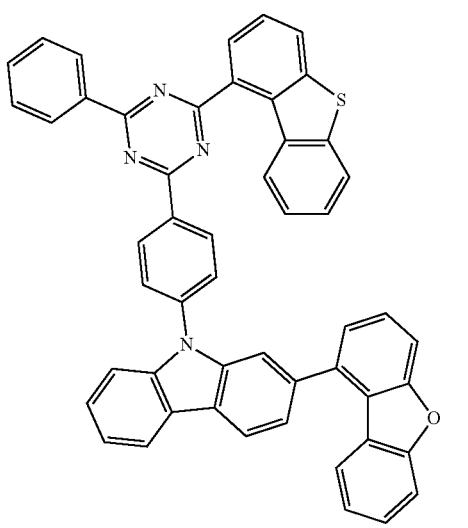
H1-26
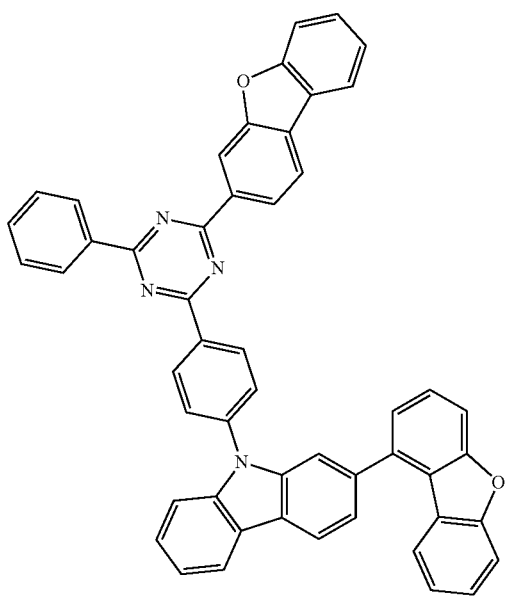
H1-27
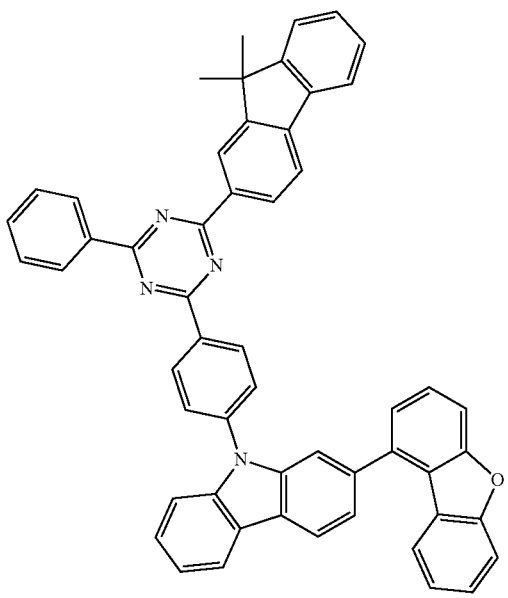
H1-28
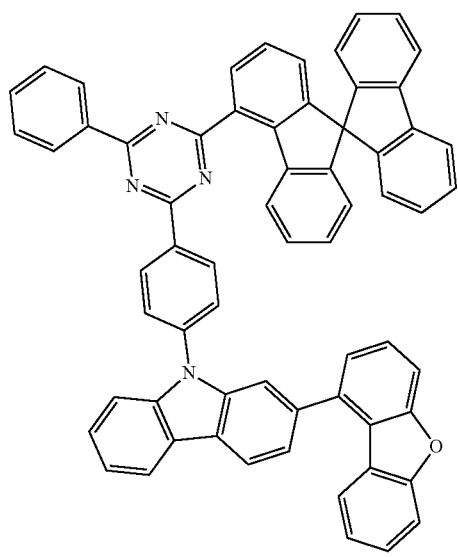

H1-29
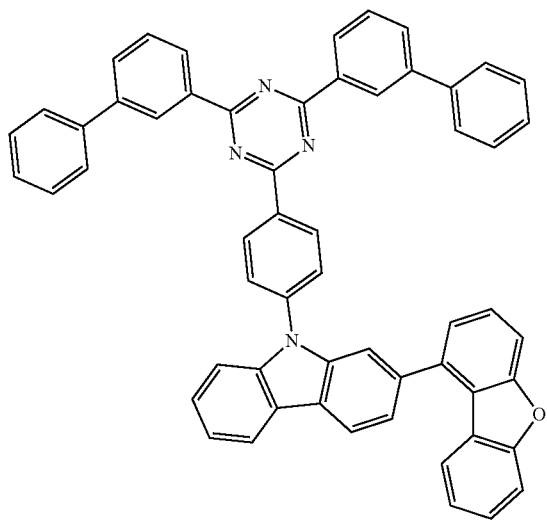
H1-30
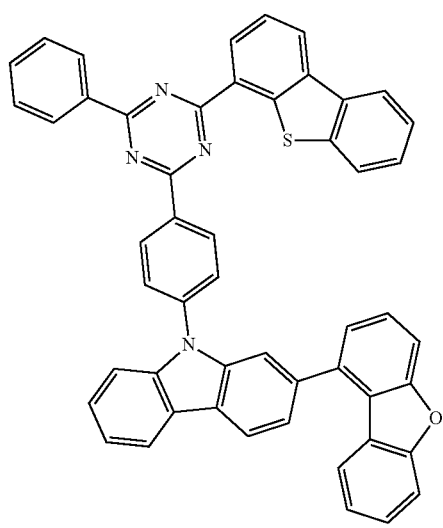
H1-31
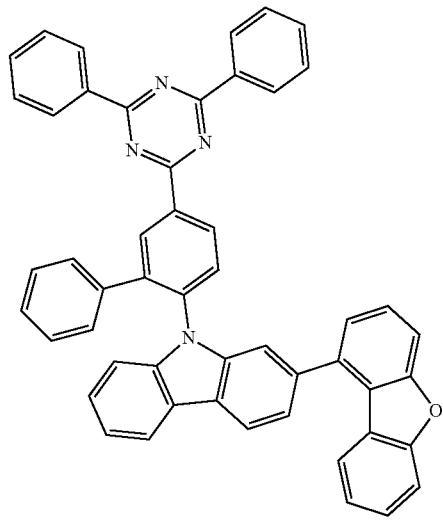
H1-32
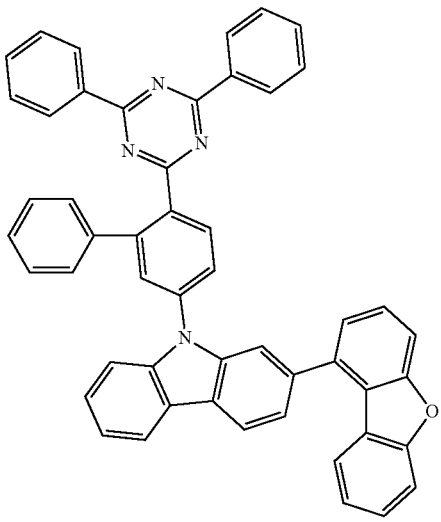
H1-33
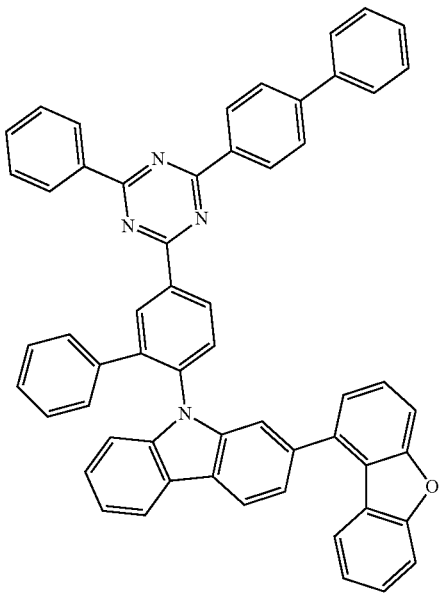
H1-34
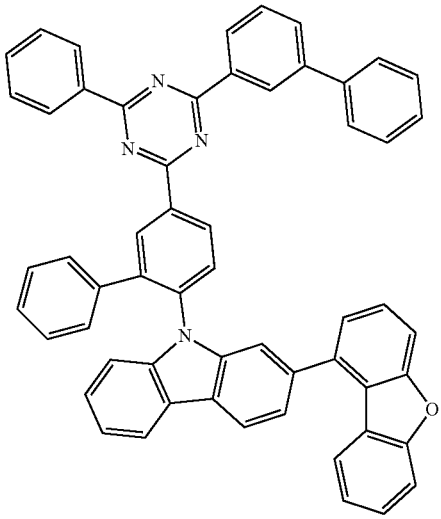

H1-35
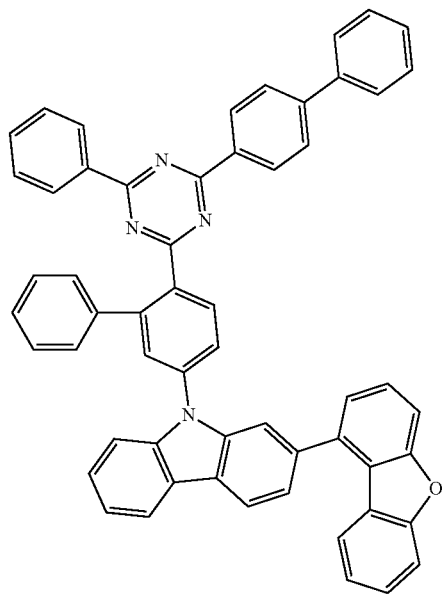
H1-36
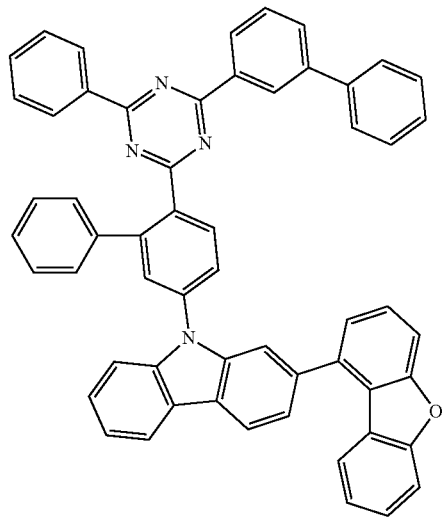
H1-37
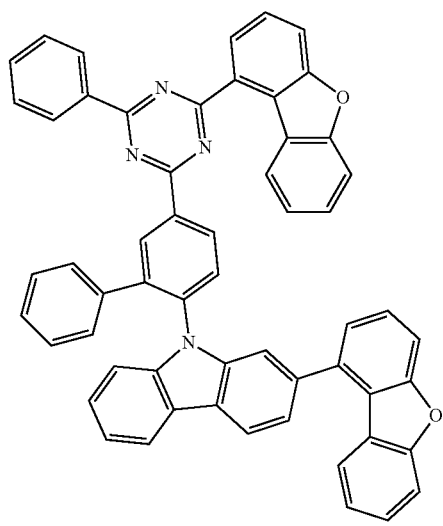
H1-38
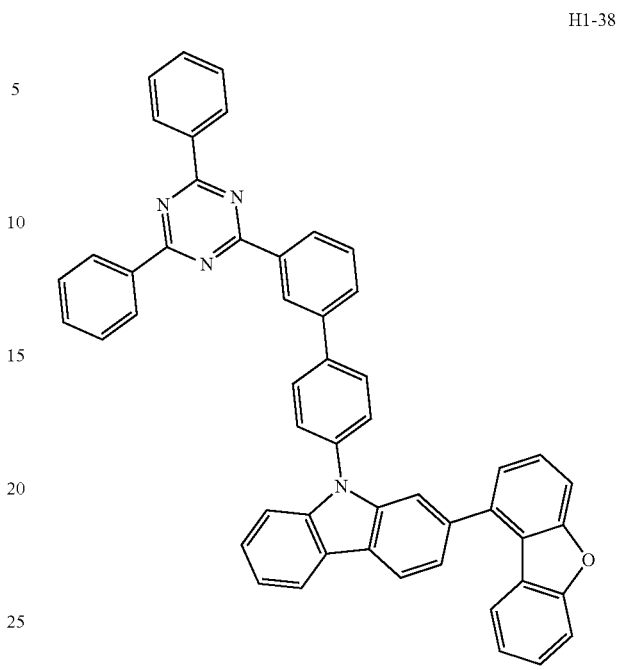
H1-39
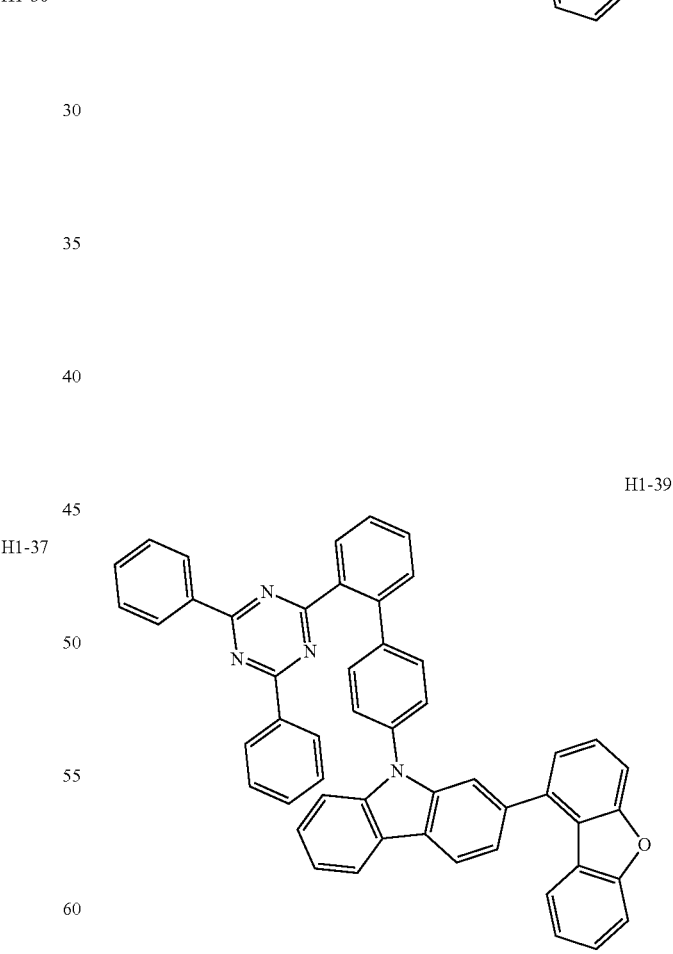

H1-40
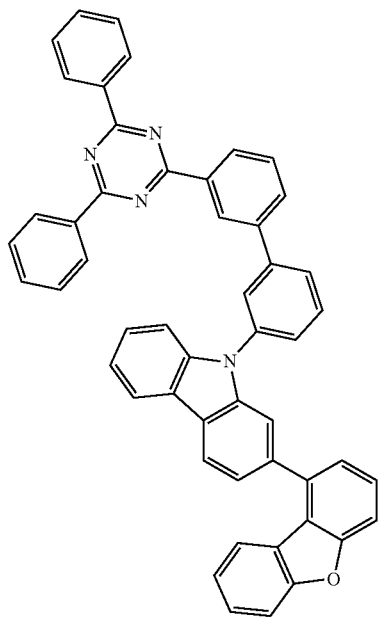
H1-42
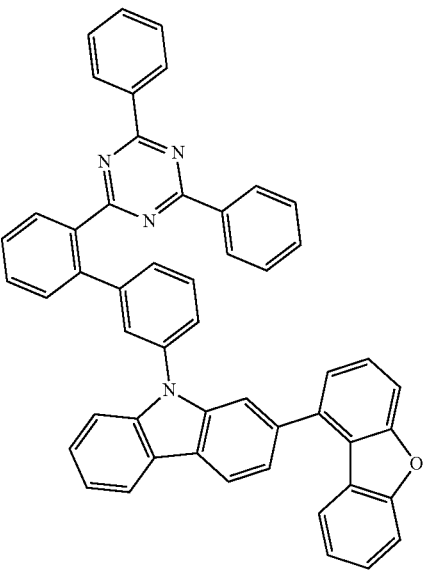
H1-41
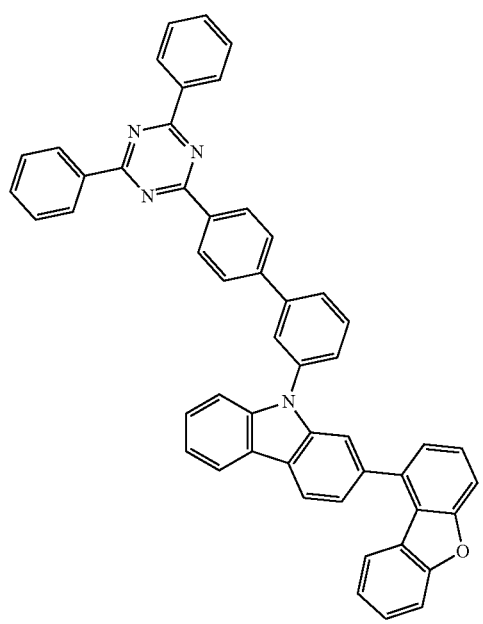
H1-43
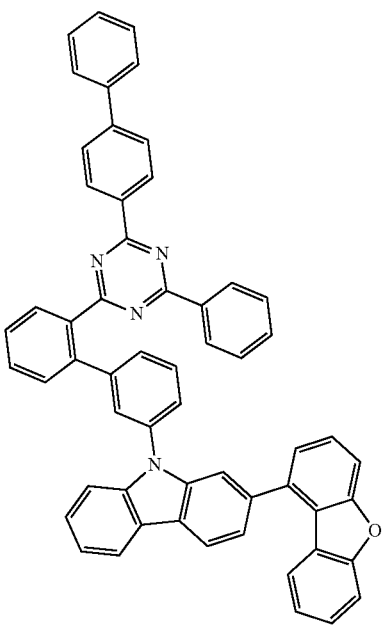

H1-44
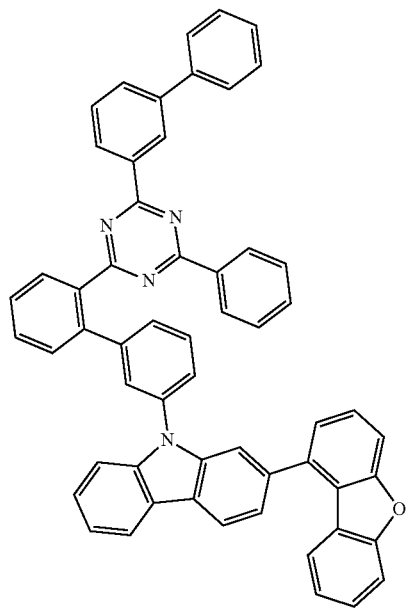
H1-45
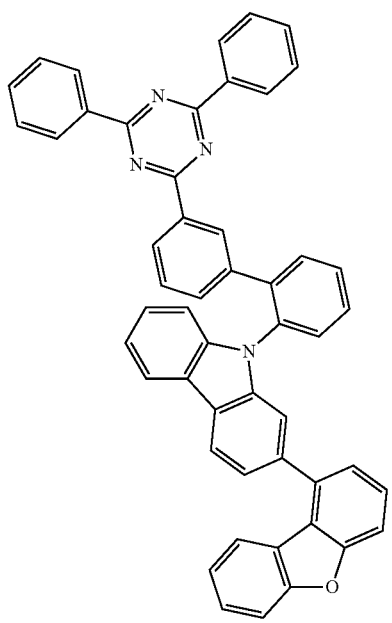
H1-46
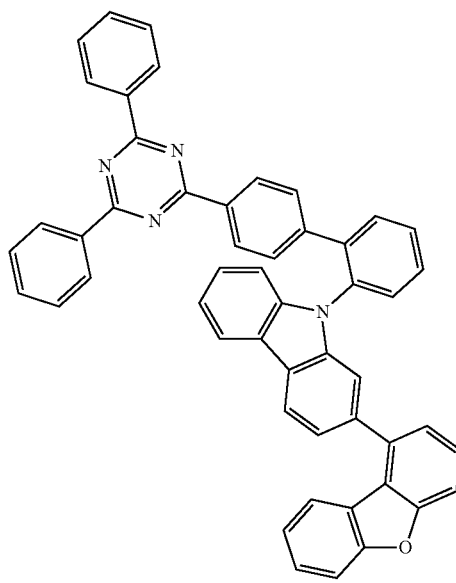
H1-47
H1-48

H1-49
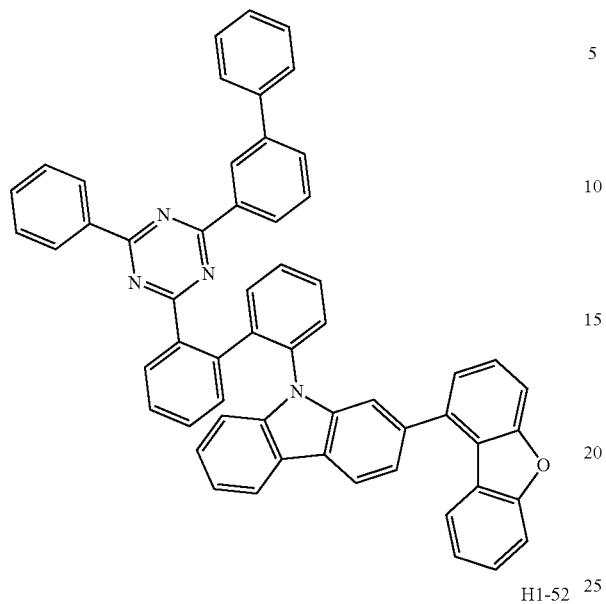
H1-54
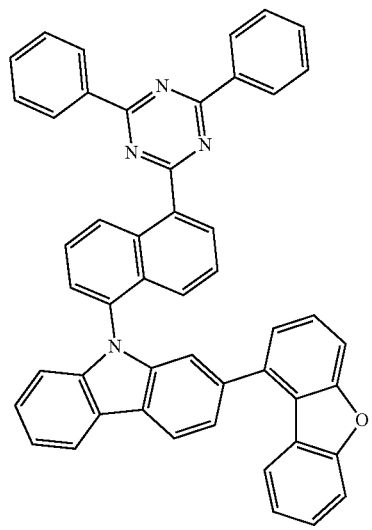
H1-52
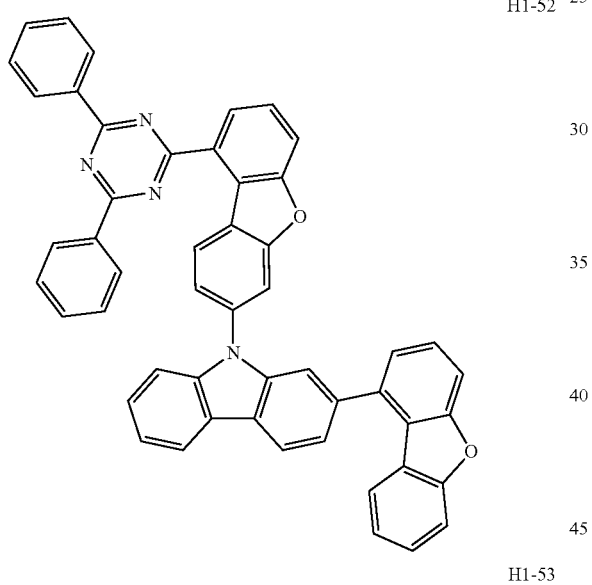
H1-55
H1-53
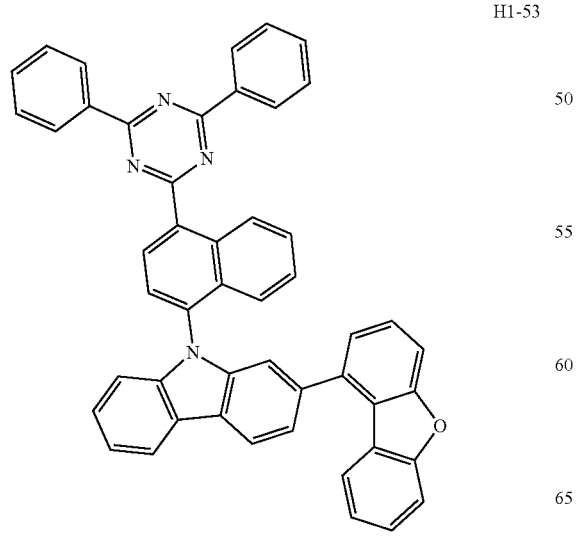
H1-56

H1-57
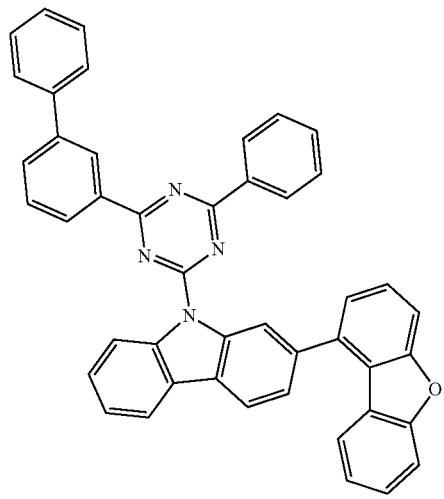
H1-58
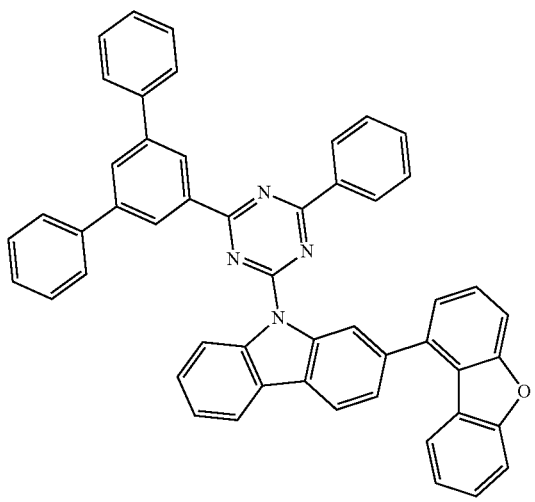
H1-59
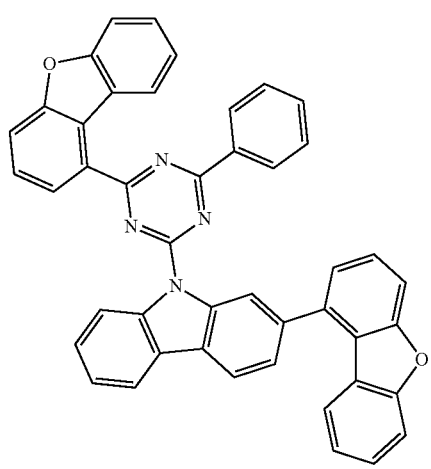
H1-60
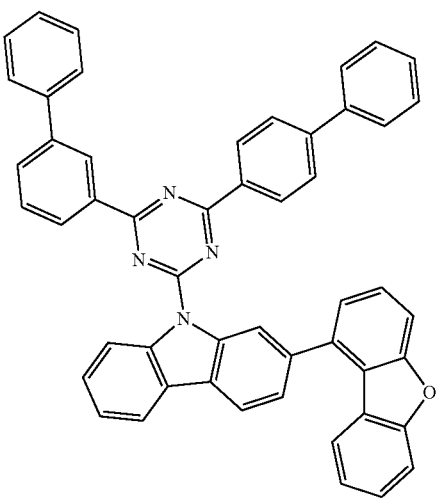
H1-61
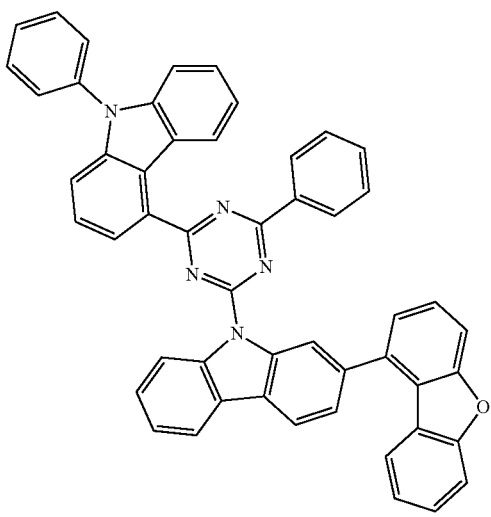
H1-62
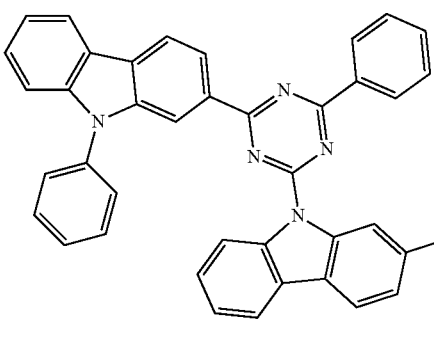

H1-63
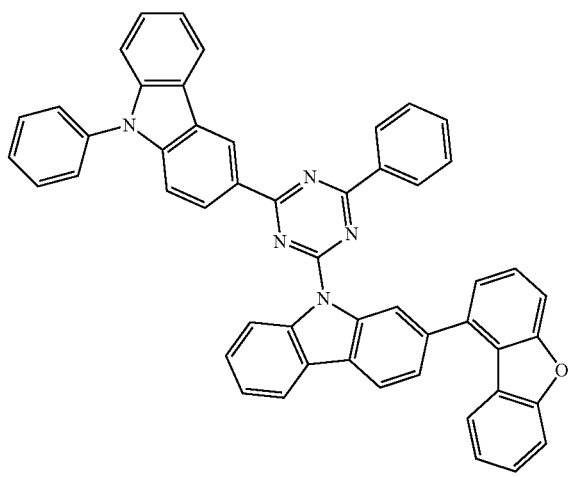
H1-64
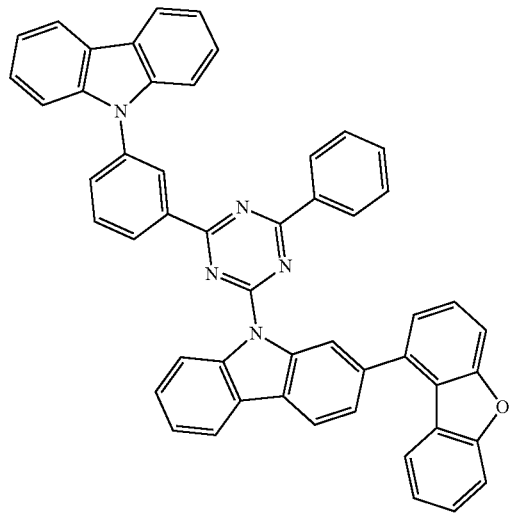
H1-65
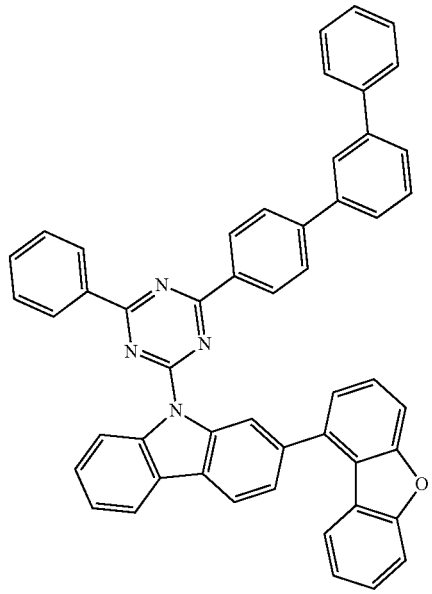
H1-66
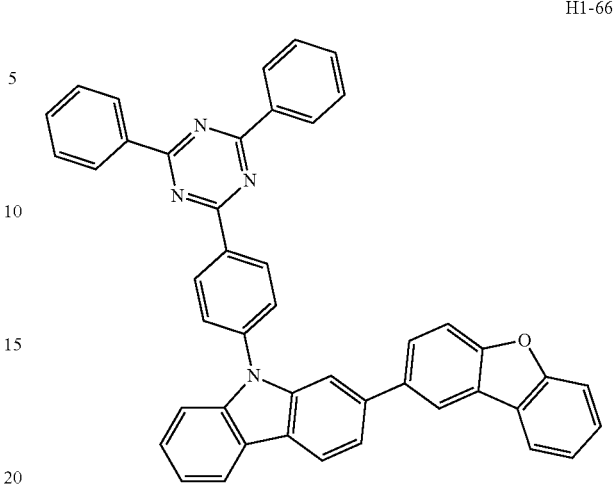
H1-67
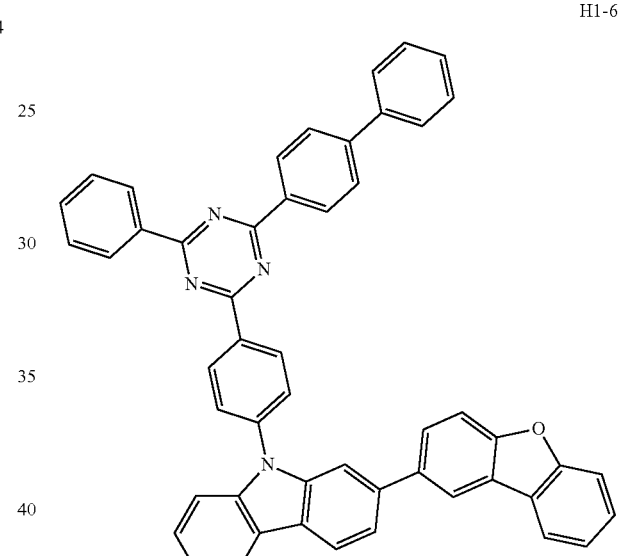
H1-68
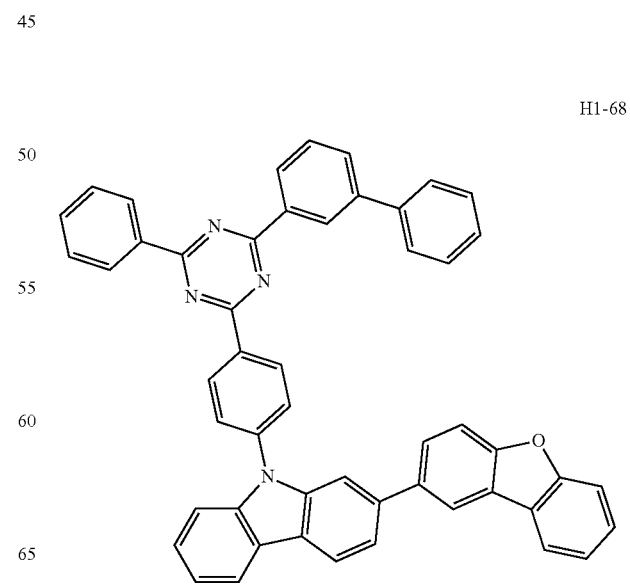

H1-69
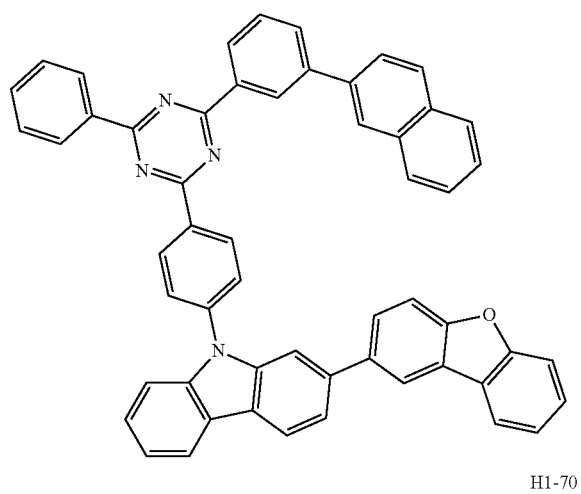
H1-70
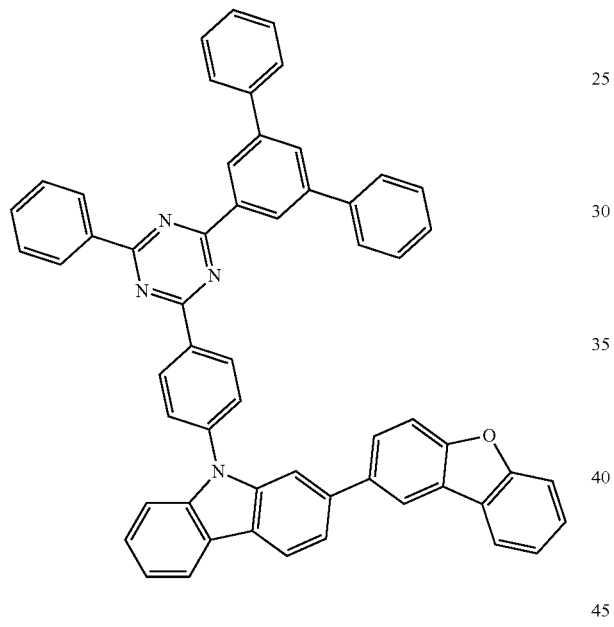
H1-71
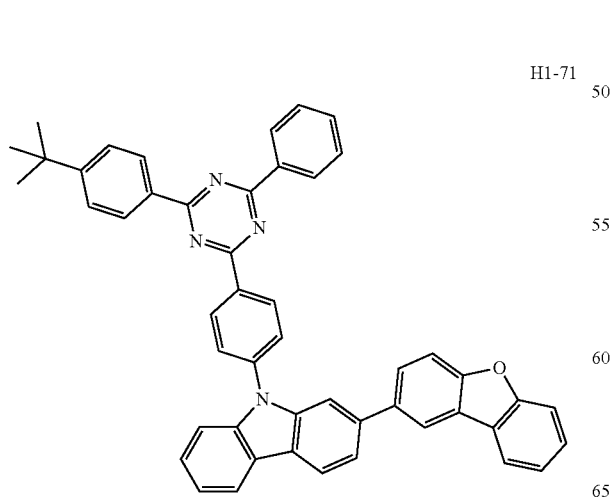
H1-72
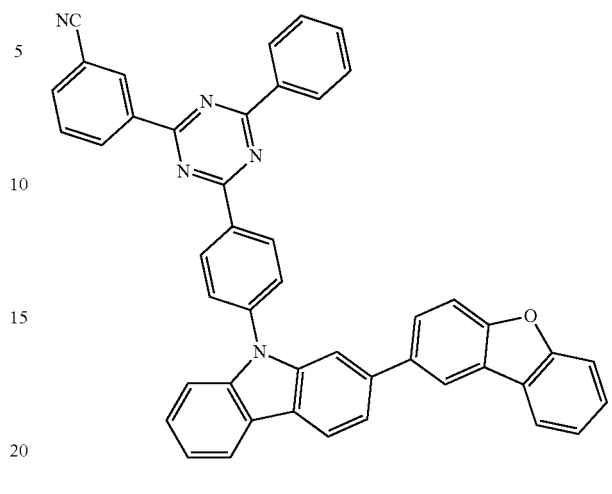
H1-73
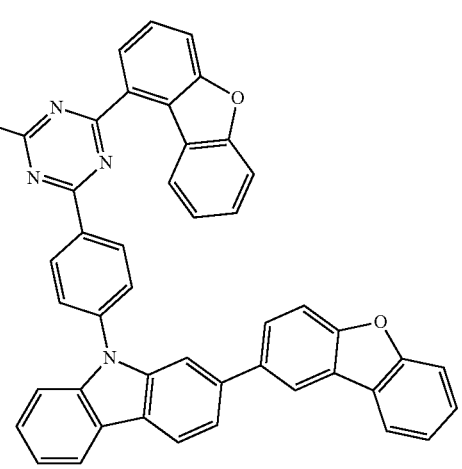
H1-74

-continued
H1-75
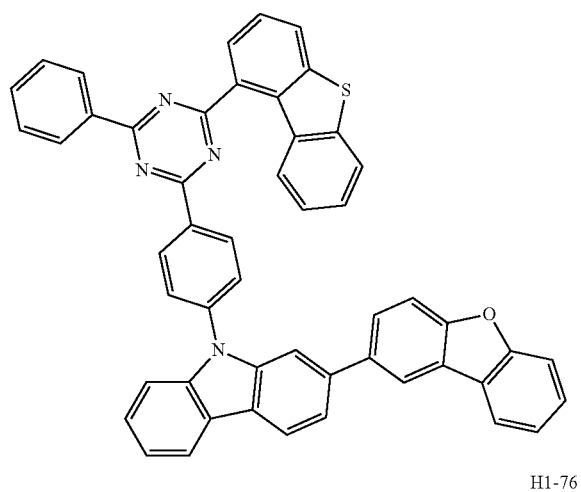
H1-76
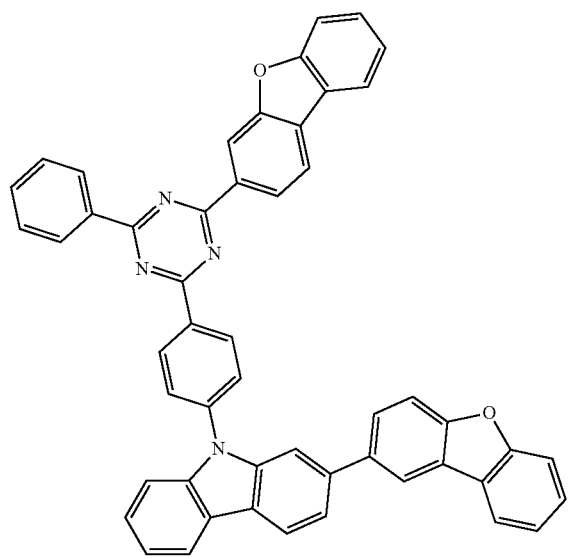
H1-77
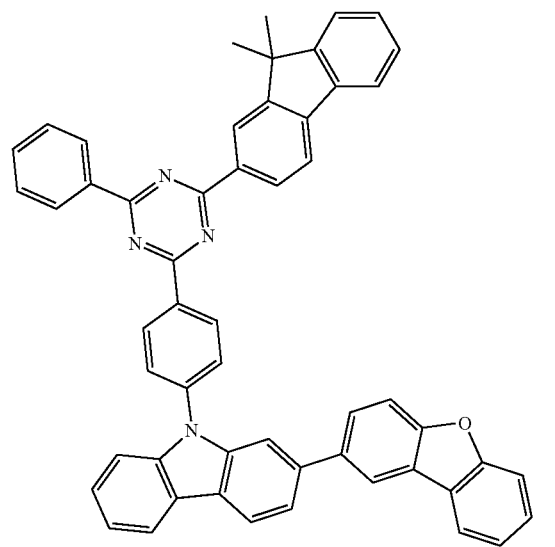
-continued
H1-78
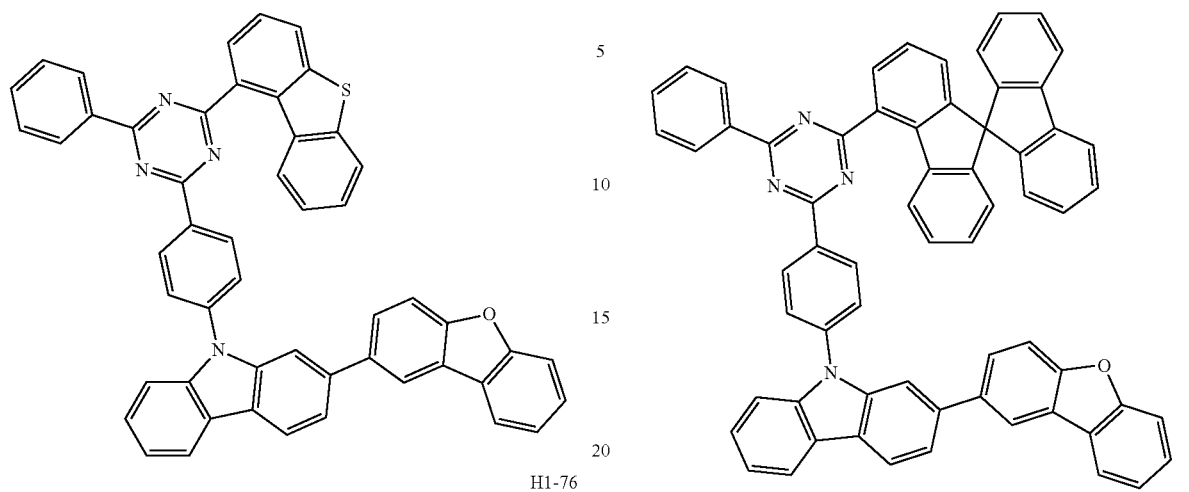
H1-79
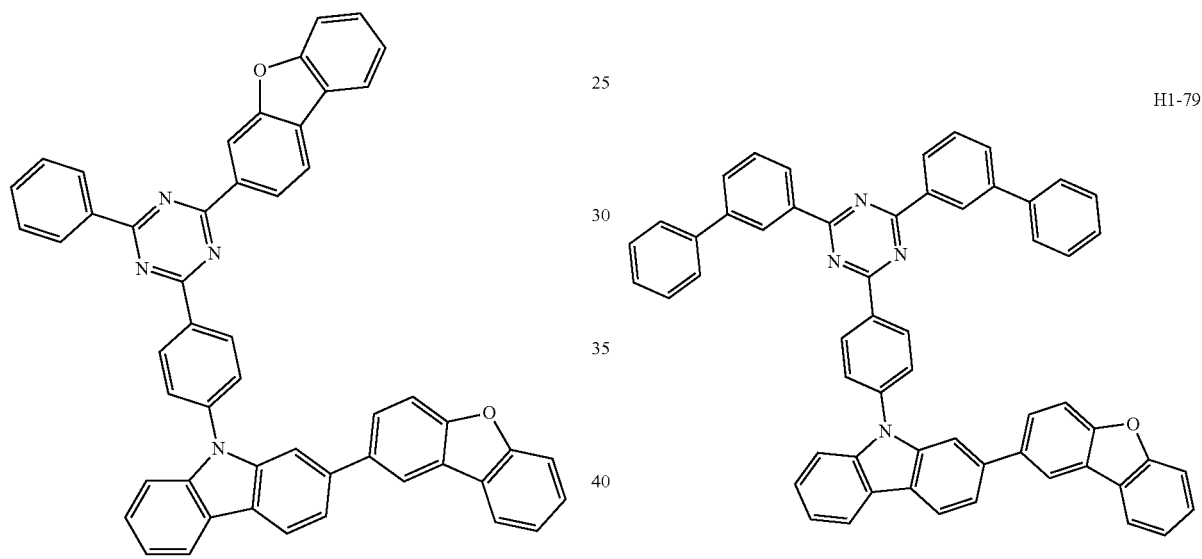
H1-80
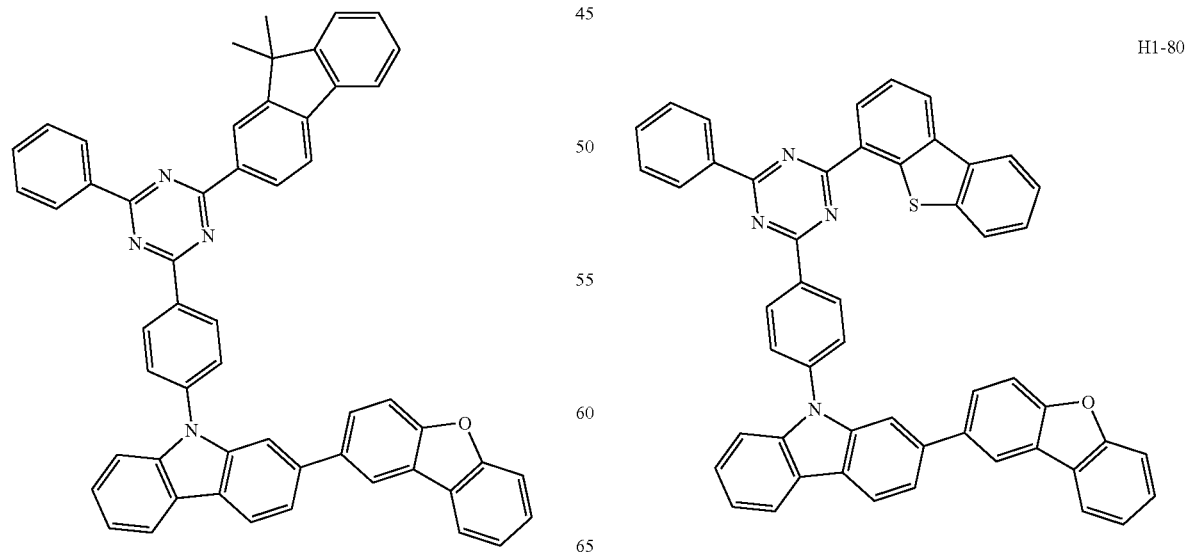

H1-81
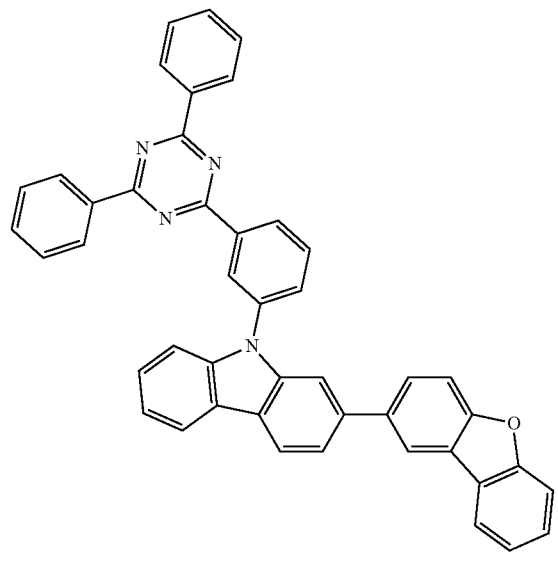
H1-83
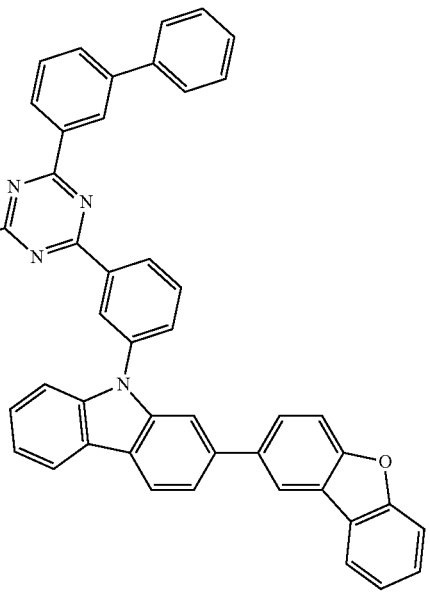
H1-82
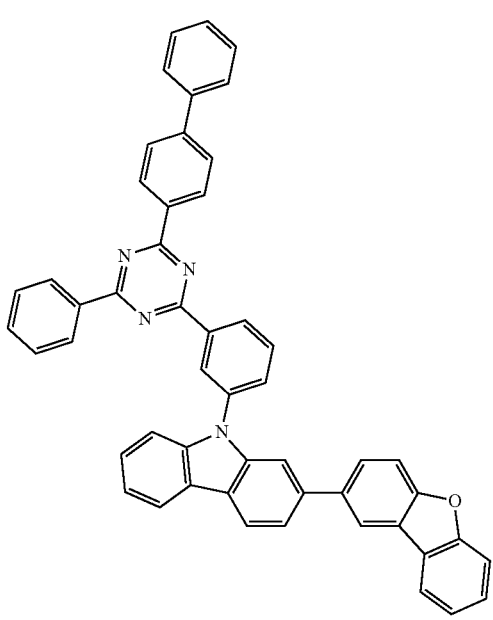
H1-84
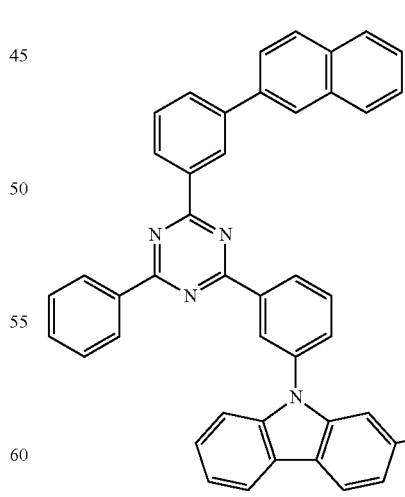

H1-85
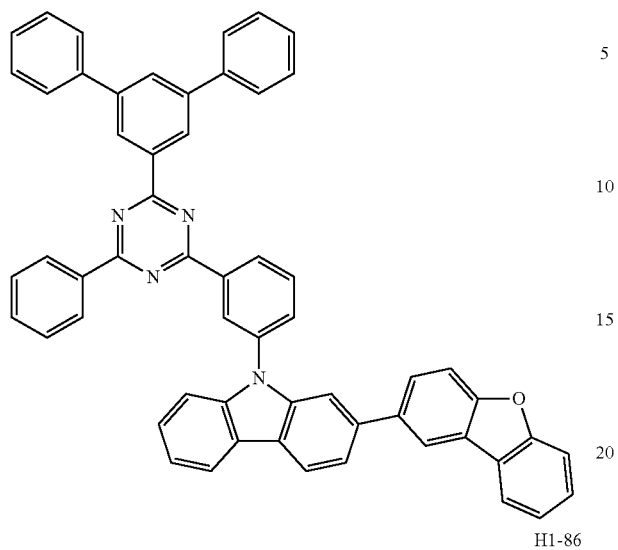
H1-86
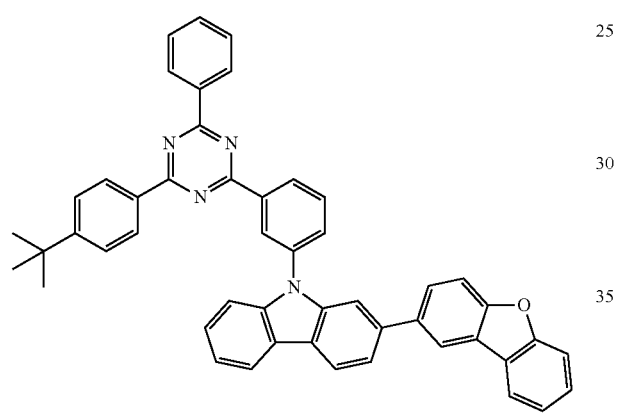
H1-87
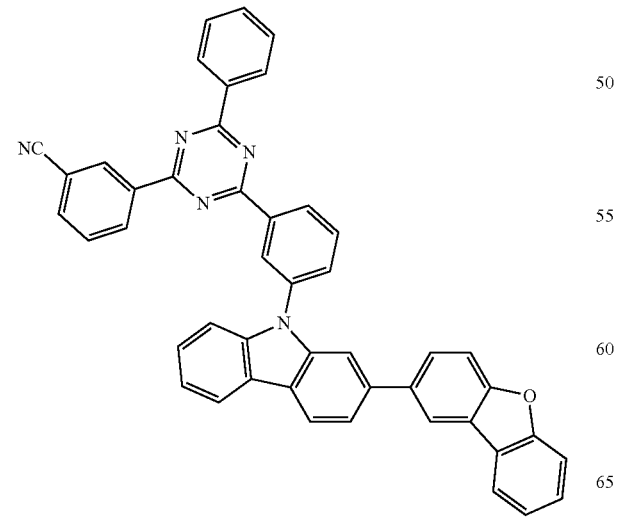
H1-88
H1-89
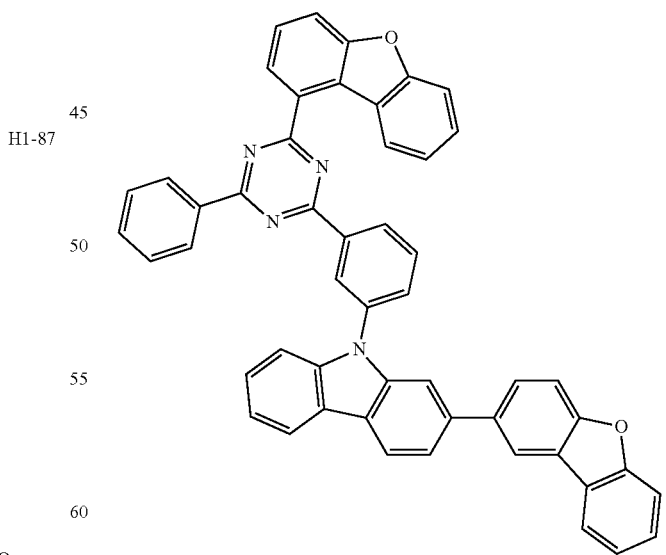

H1-90
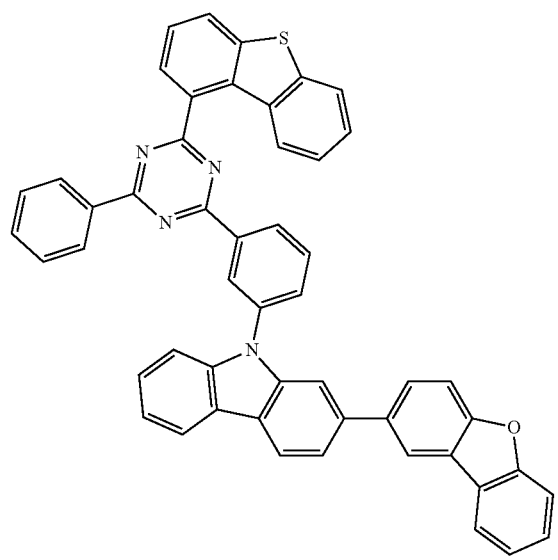
H1-91
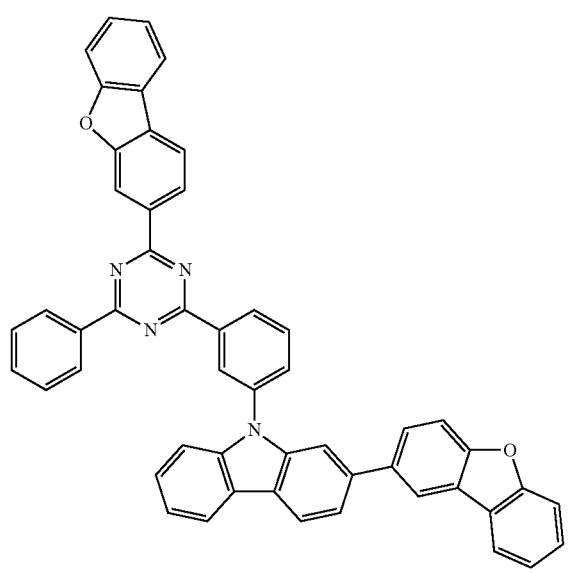
H1-92
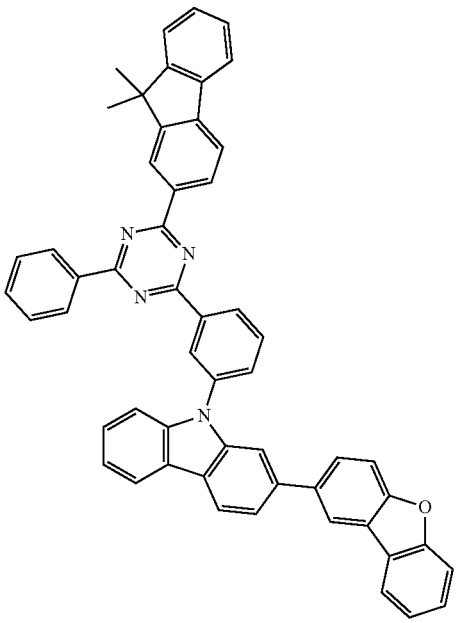
H1-93
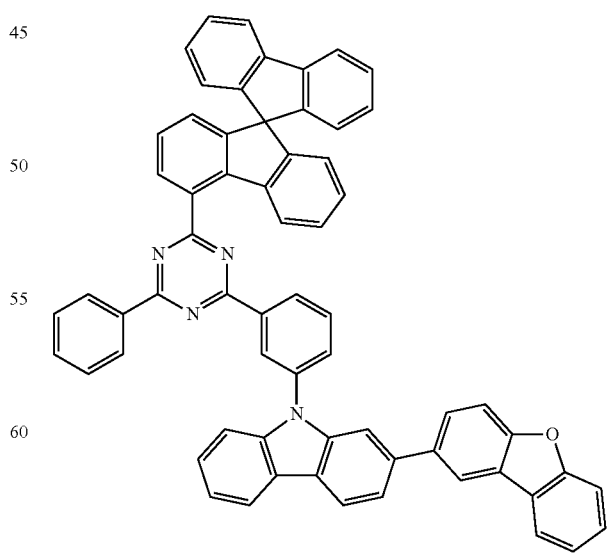

H1-94
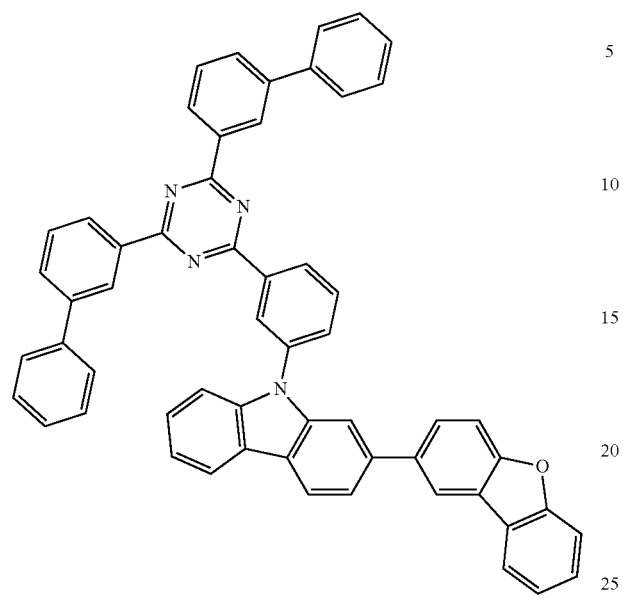
H1-95
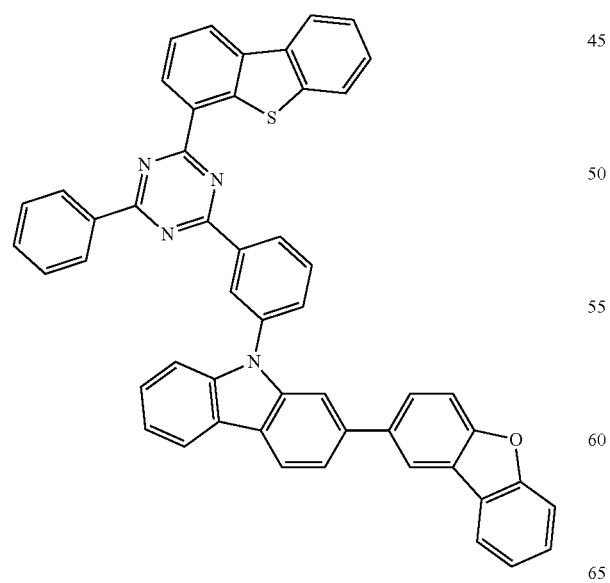
H1-96
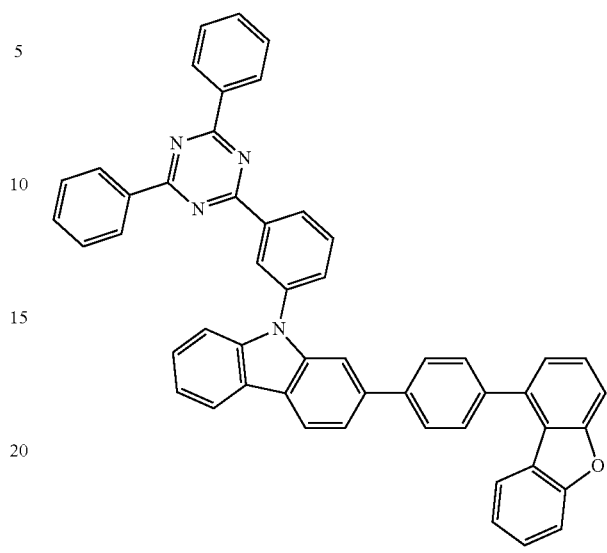
H1-97
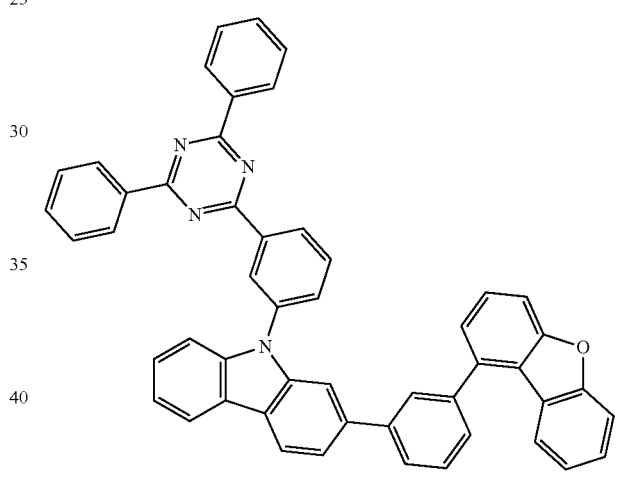
H1-98
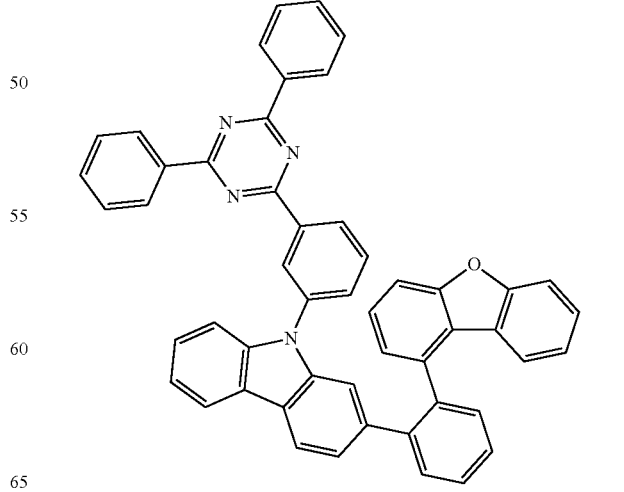

H1-99
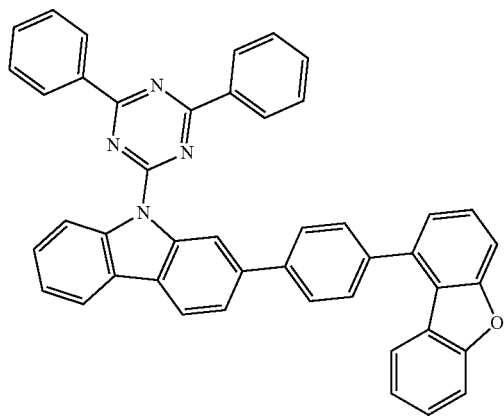
H1-100
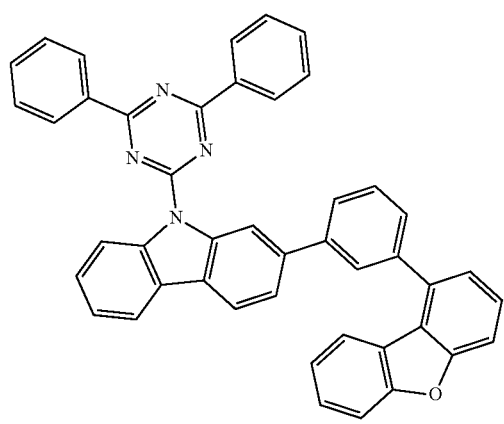
H1-101
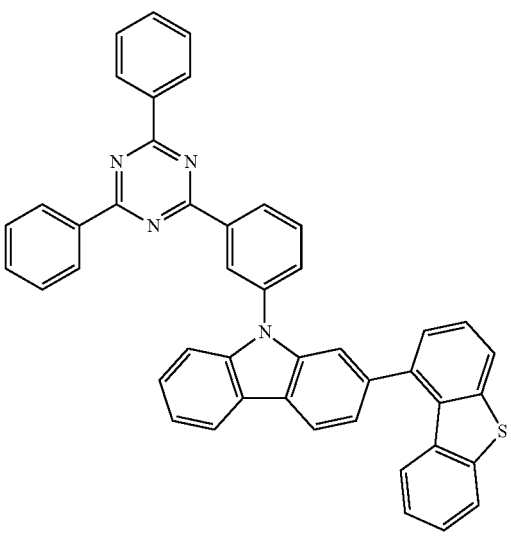
H1-102
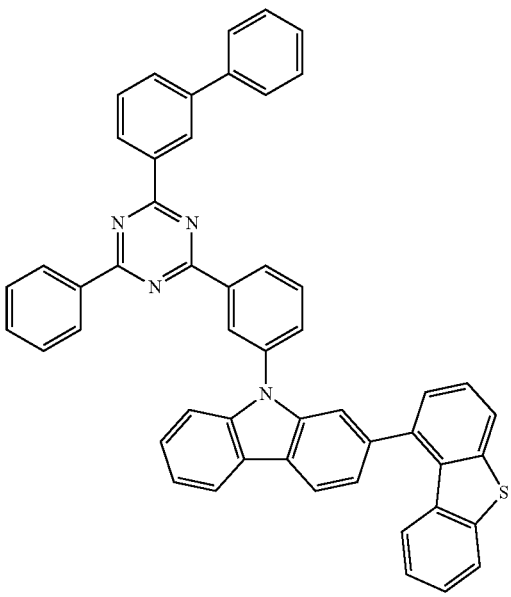
H1-103
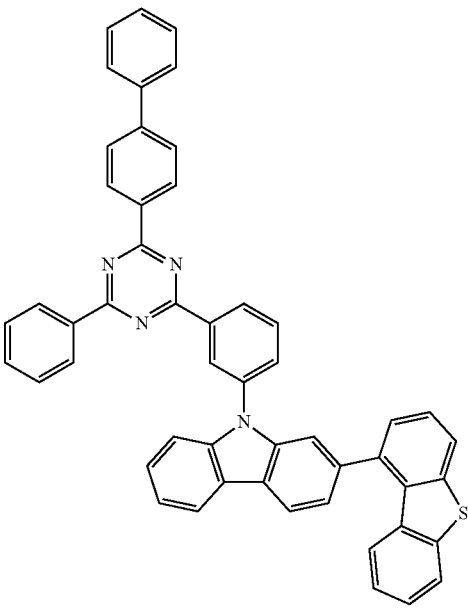

H1-104
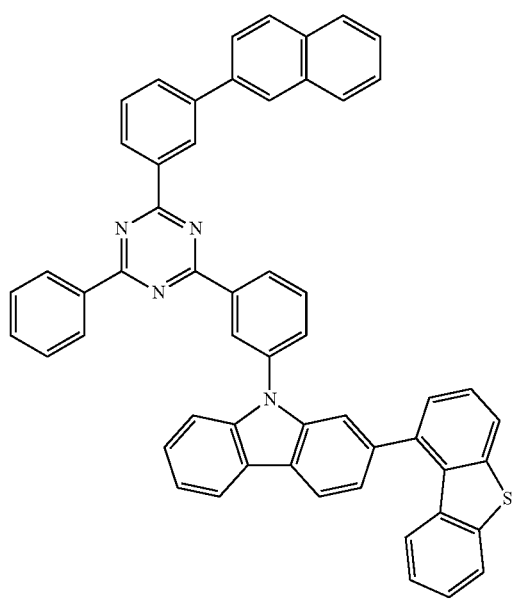
H1-105
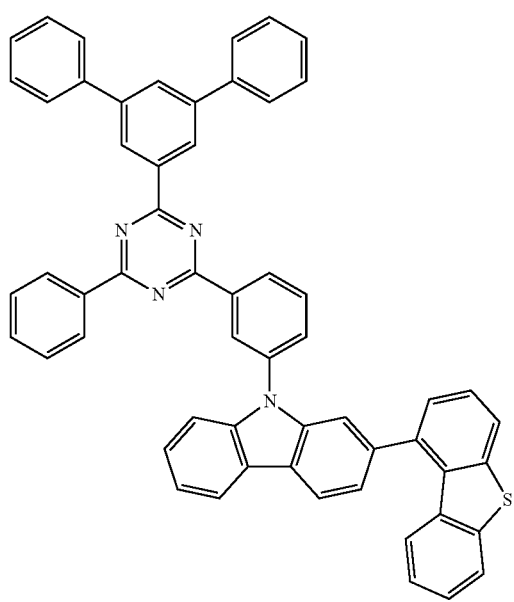
H1-106
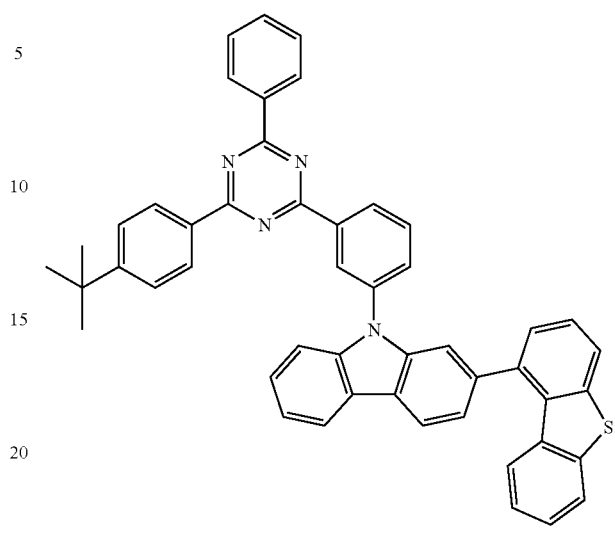
H1-107
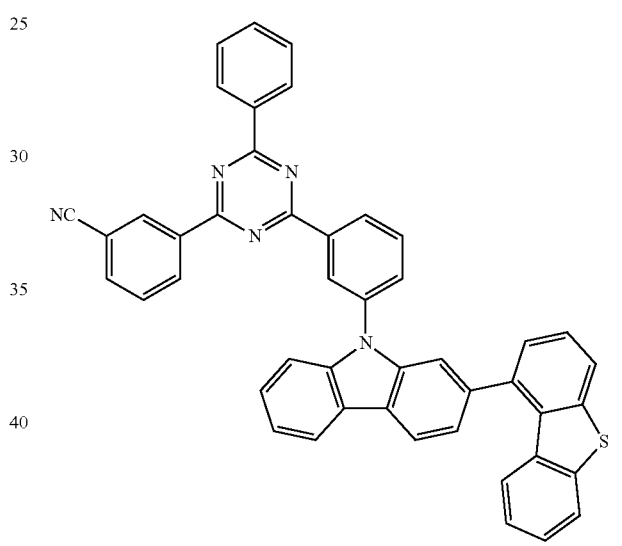
H1-108
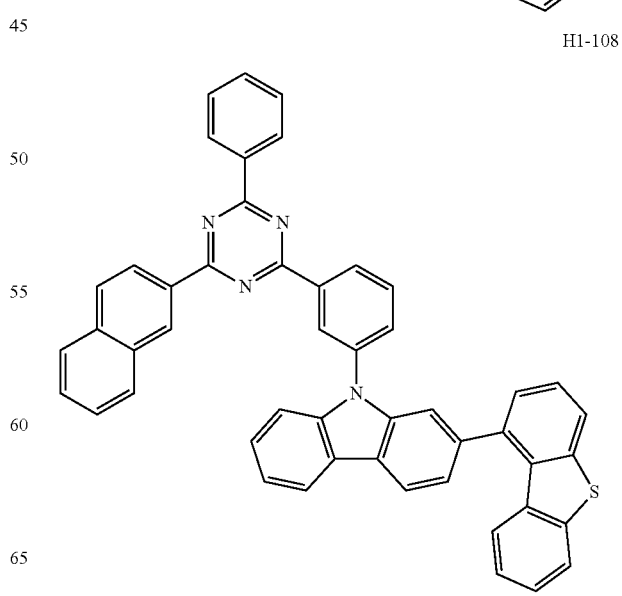

H1-109
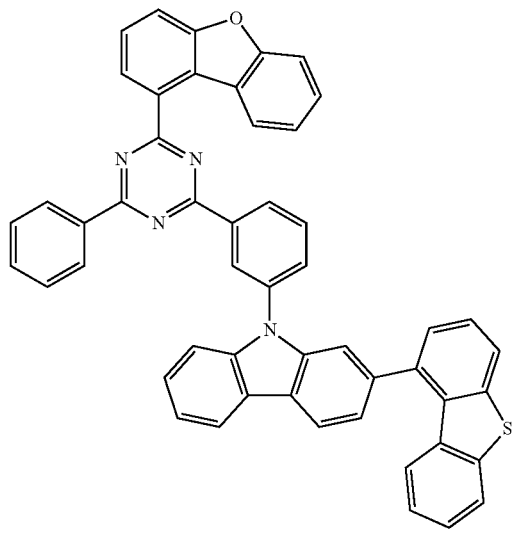
H1-110
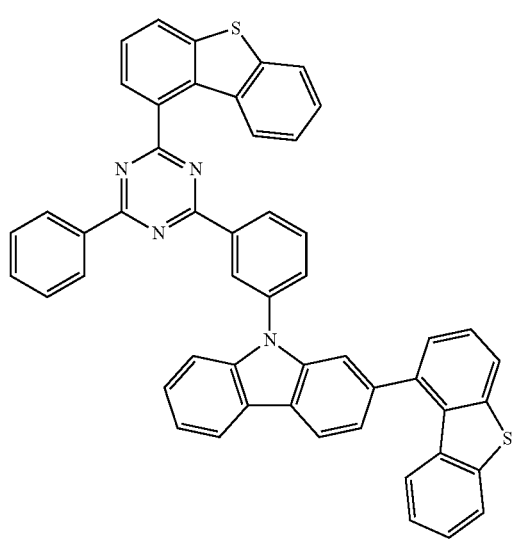
H1-111
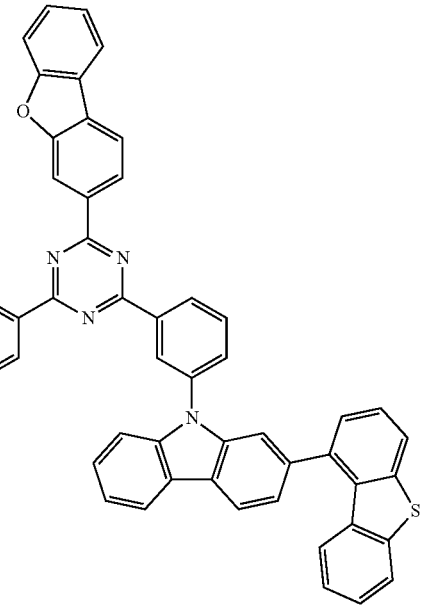
H1-112
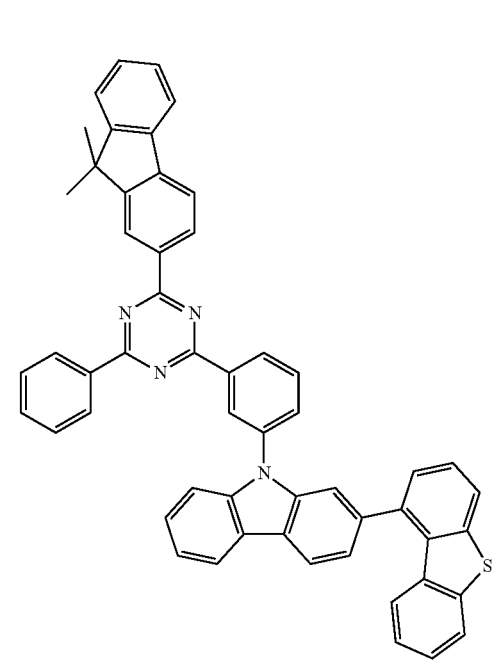

H1-113
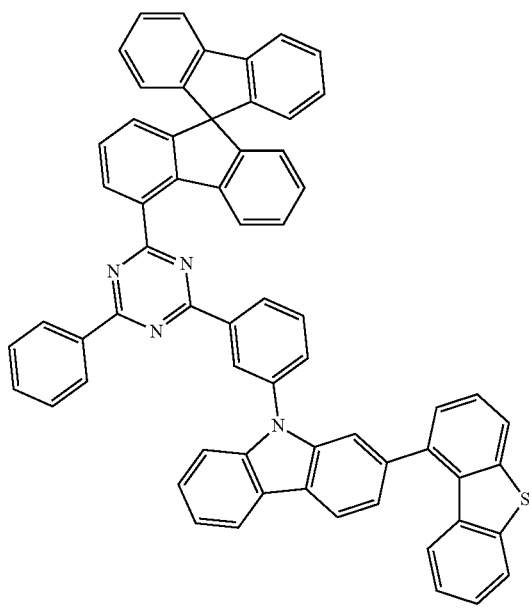
H1-114
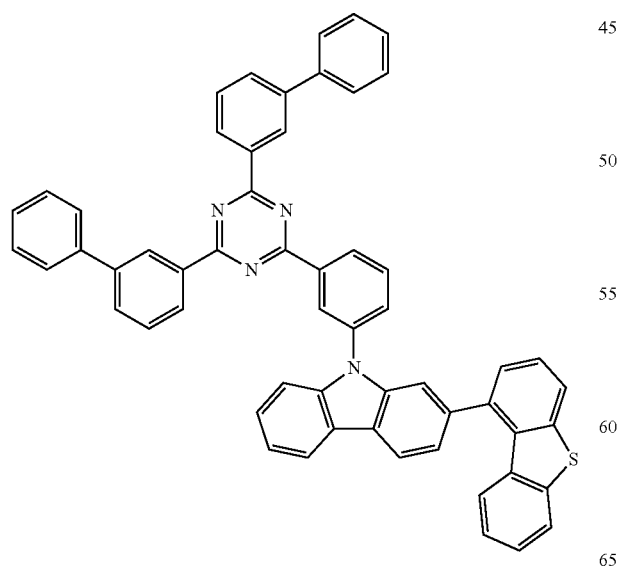
H1-115
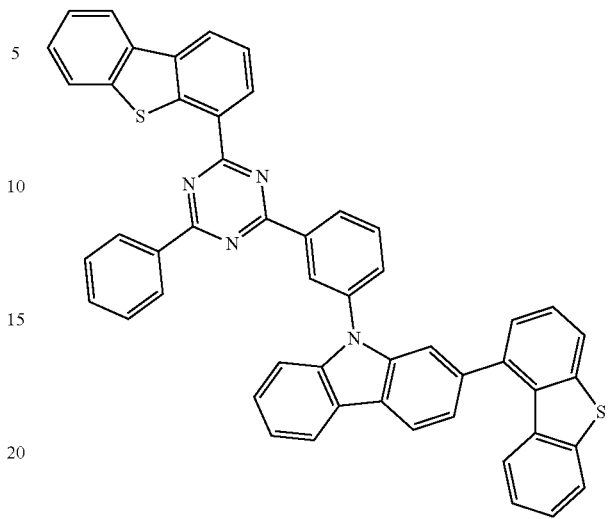
H1-116
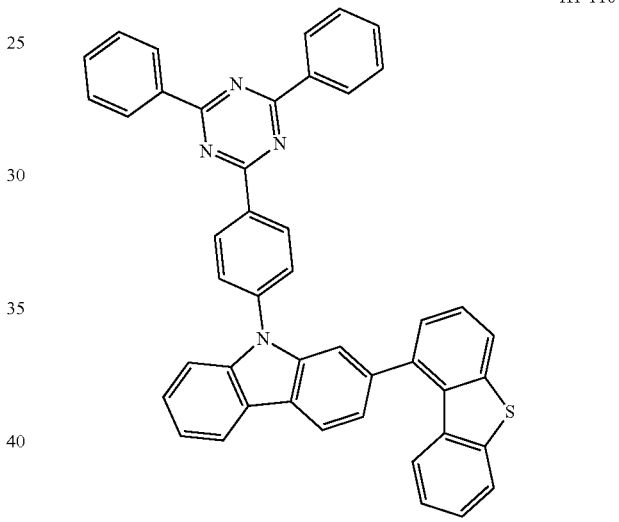
H1-117
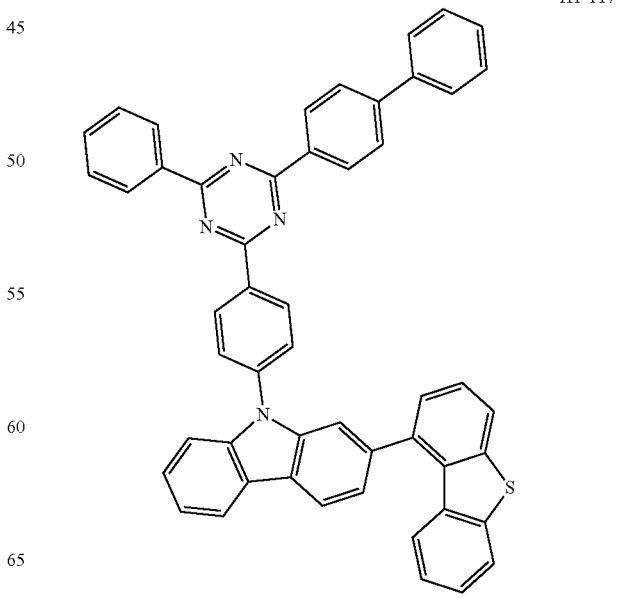

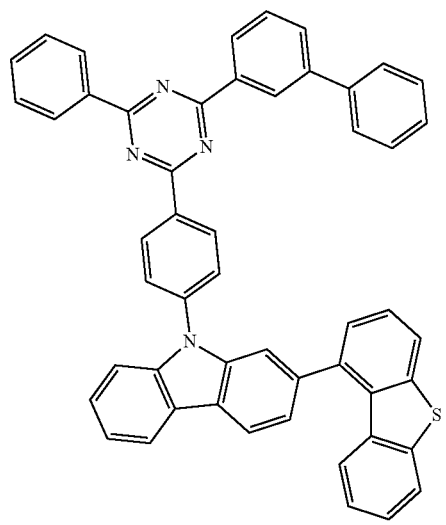
H1-118
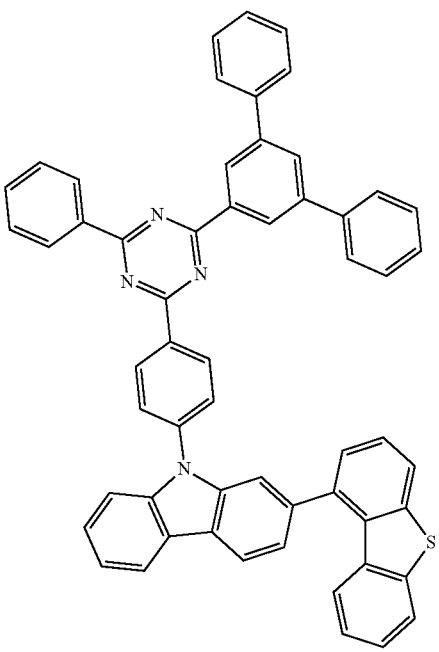
H1-120
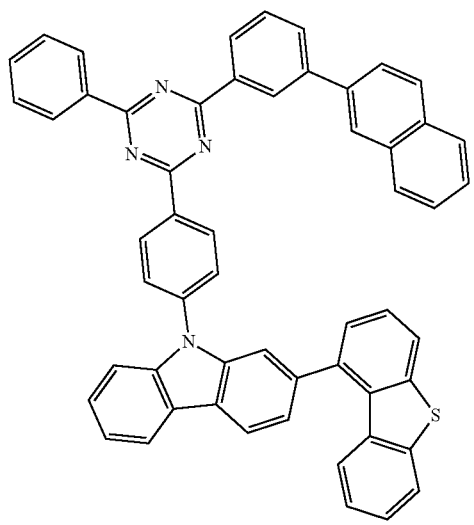
H1-119
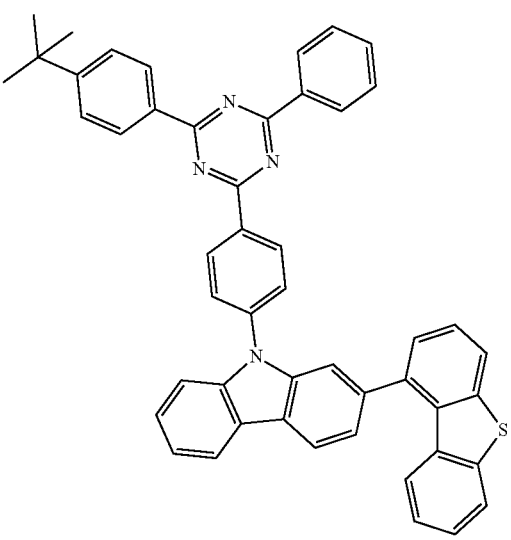
H1-121

H1-122
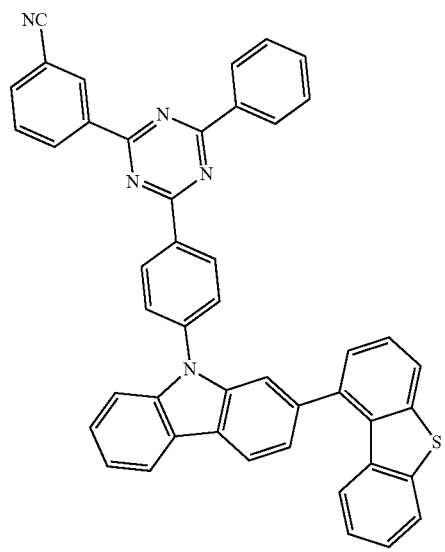
H1-123
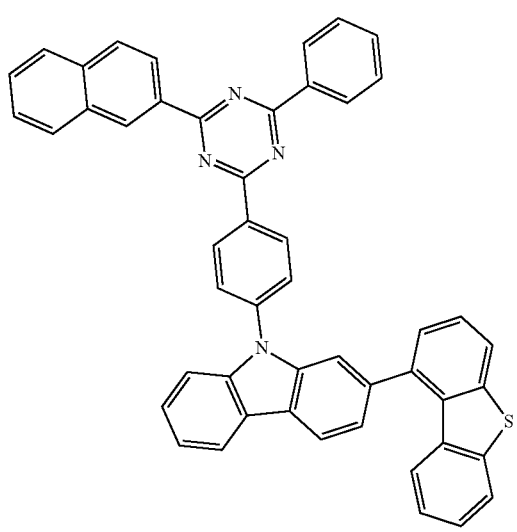
H1-124
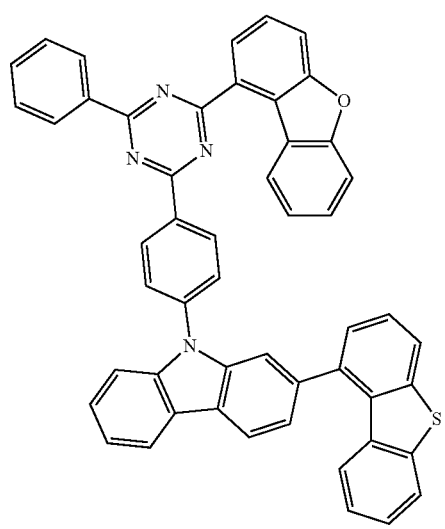
H1-125
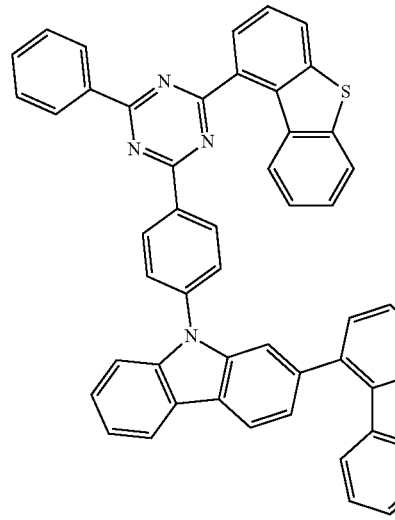
H1-126
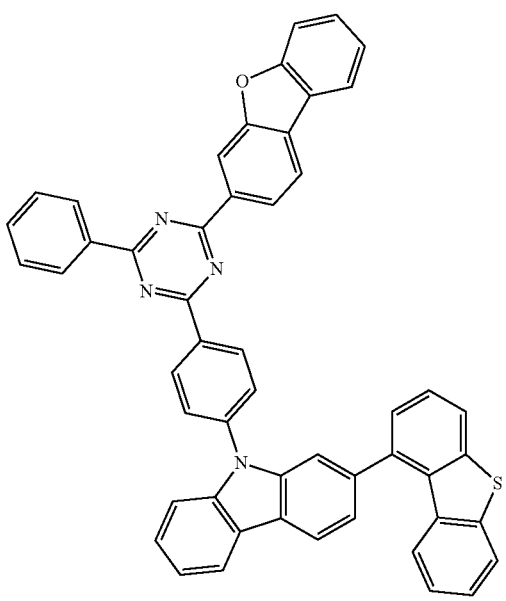

-continued
H1-127
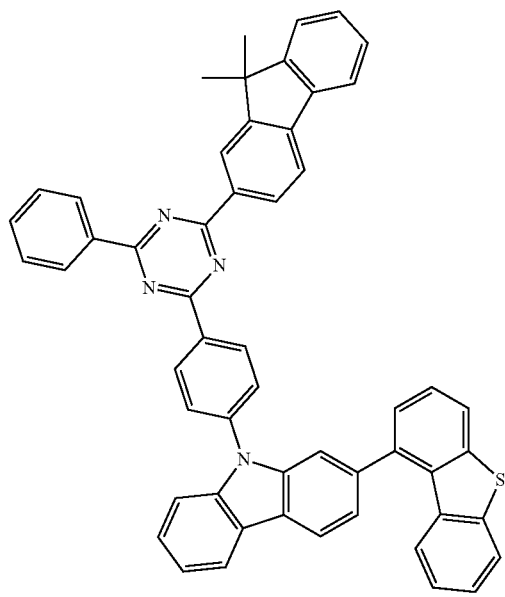
H1-128
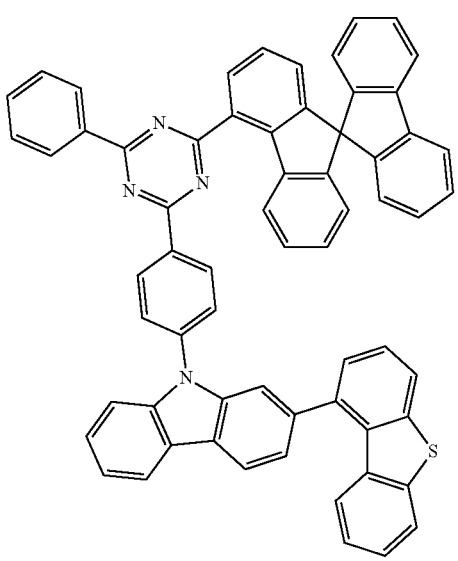
H1-129
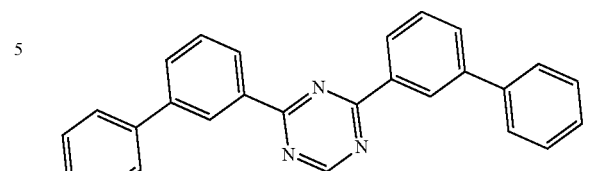
H1-130
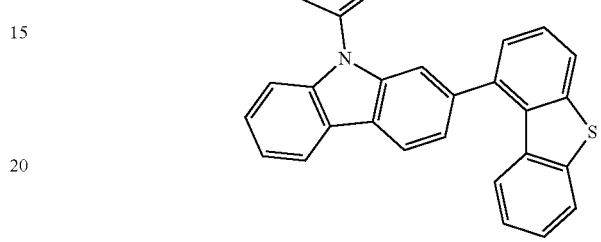
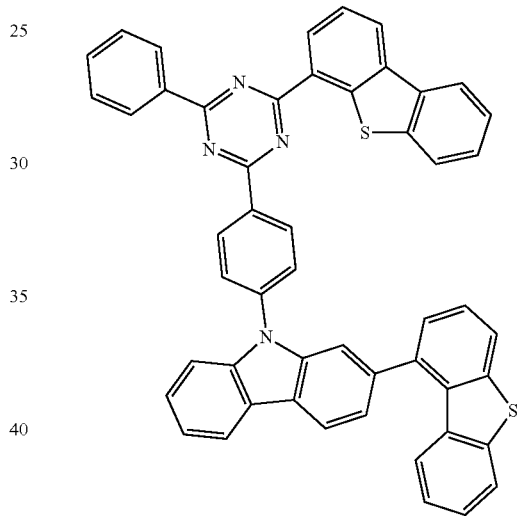
H1-131
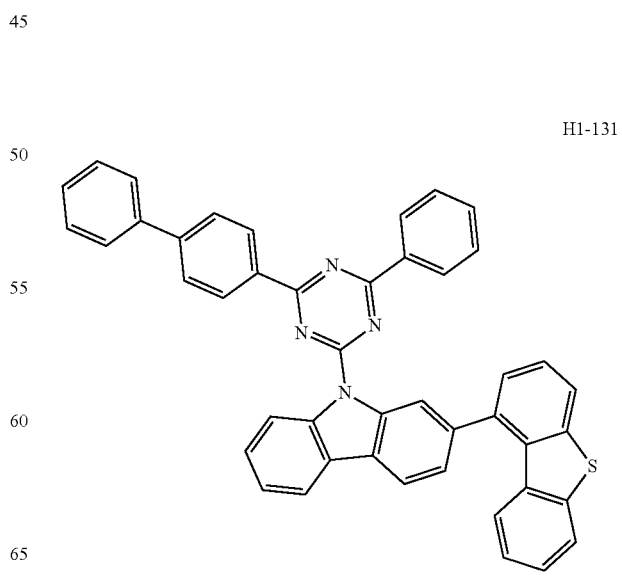

205
-continued
H1-132
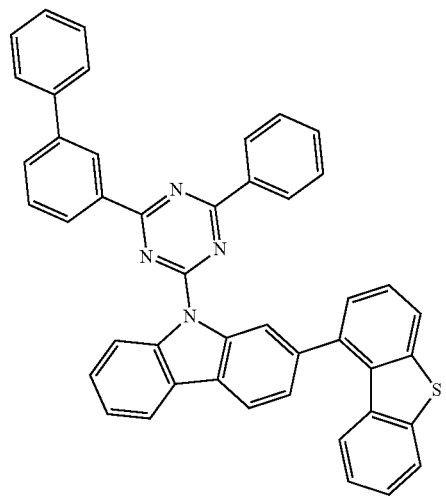
H1-133
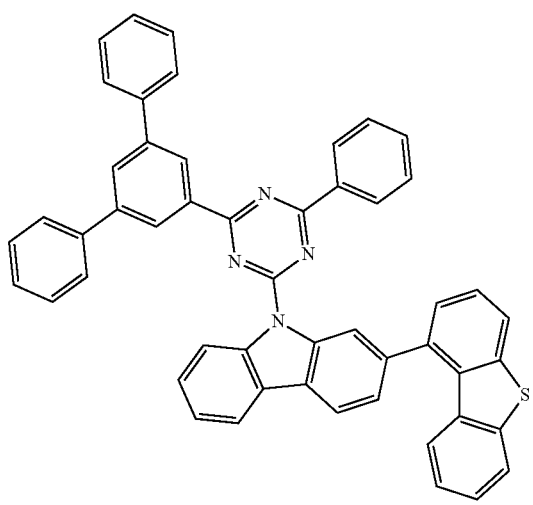
H1-134
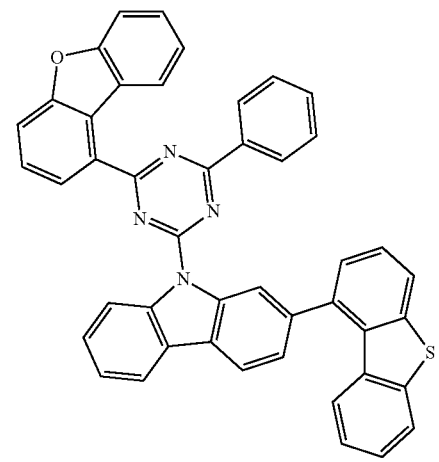
206
-continued
H1-135
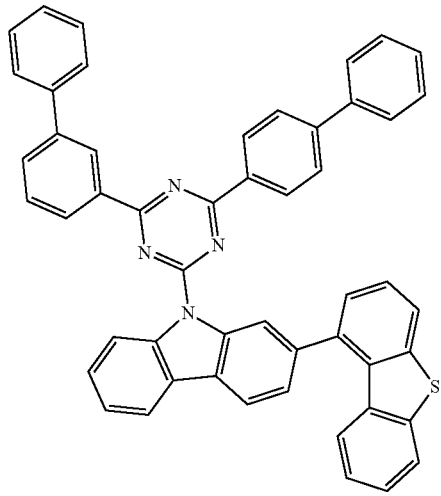
H1-136
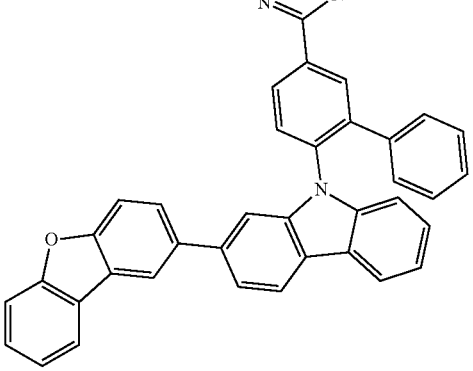
H1-137
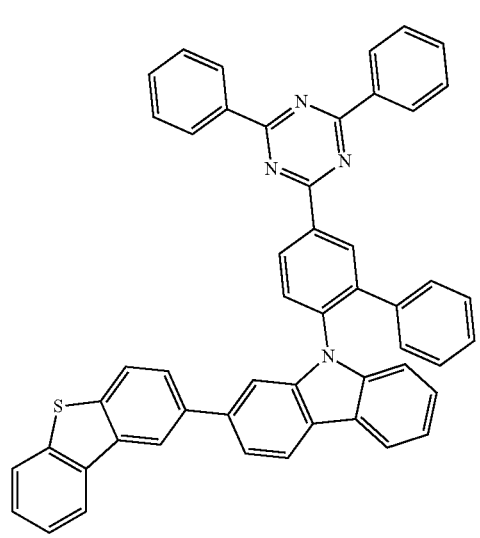

H1-138
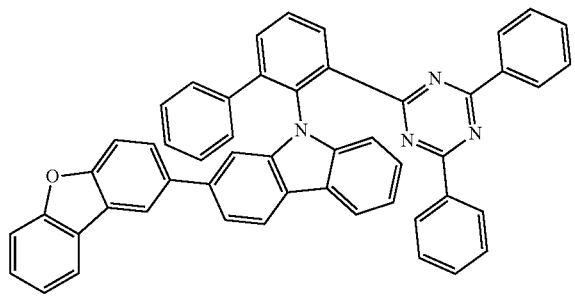

H1-139
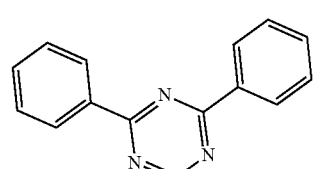

H1-140
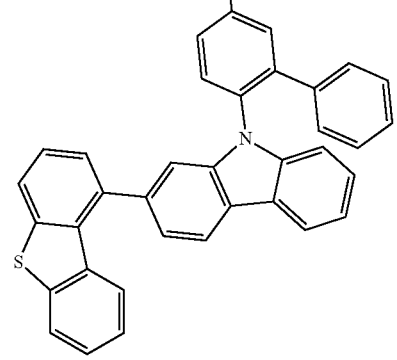

H1-141
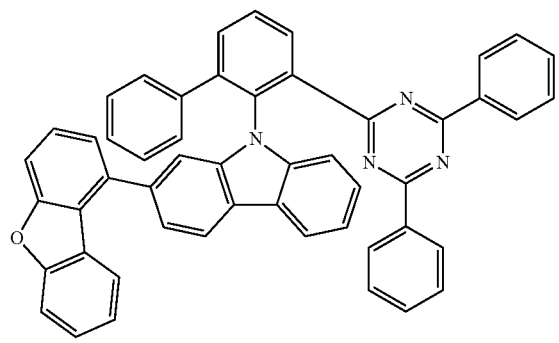

H1-142
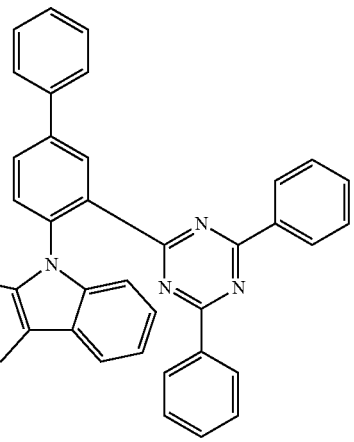

H1-143
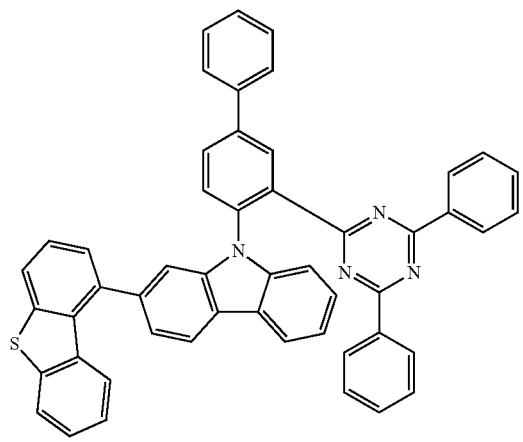

and

H1-144
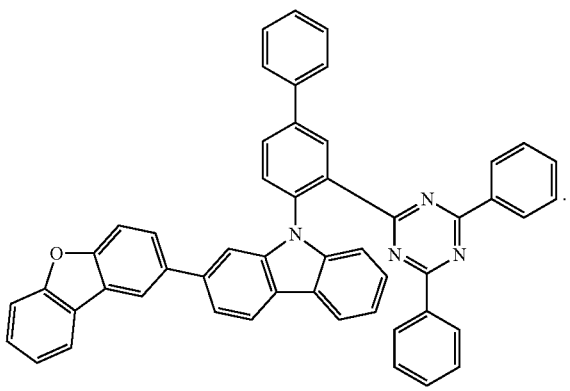

5. An organic electroluminescent material comprising the organic electroluminescent compound according to claim 1.

6. A plurality of host materials comprising at least one of the organic electroluminescent material according to claim 5 as a first host material, and at least one of a second host material which is different from the first host material.

7. The plurality of host materials according to claim 6, wherein the second host material comprises a compound represented by the following formula 11:

(11)

[Structural formula 11 showing two carbazole units connected via L₁₁ linker, with substituents X₁₁–X₁₄ on one carbazole, X₂₃–X₂₆ on the other, N-substituents A₁ and A₂, and (X')ₘ, (X")ₙ substituents on the linker-adjacent rings]

wherein

A₁ and A₂ each independently represent a substituted or unsubstituted (C6-C30)aryl;

L₁₁ represents a single bond or a substituted or unsubstituted (C6-C30)arylene;

X', X", $X_{11}$ to $X_{14}$, and $X_{23}$ to $X_{26}$ each independently represent hydrogen, deuterium, halogen, cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino; or adjacent substituent(s) may be linked to each other to form a ring(s);

m and n each independently represent an integer of 1 to 3; and when m and n are an integer of 2 or more, each of X' and X" may be the same or different.

8. The plurality of host materials according to claim 7, wherein the compound represented by formula 11 is selected from the following compounds:

H2-1

[Chemical structure of compound H2-1]

H2-2

[Chemical structure of compound H2-2]

H2-3

[Chemical structure of compound H2-3]

-continued
H2-4
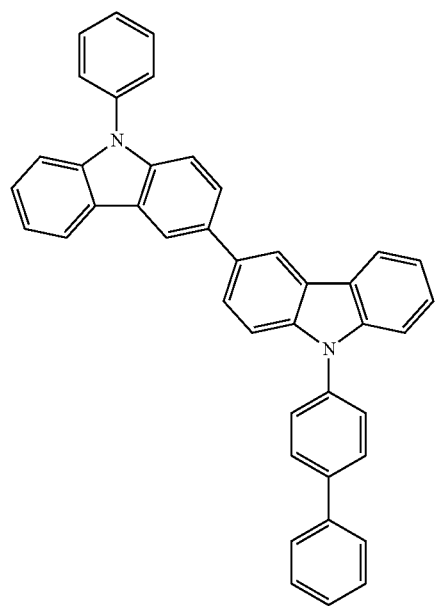
H2-5
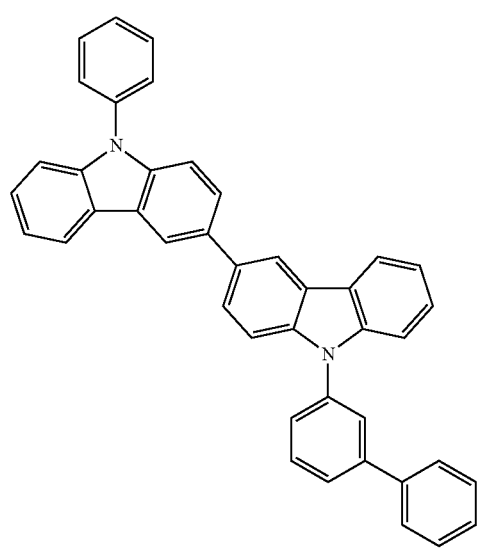
H2-6
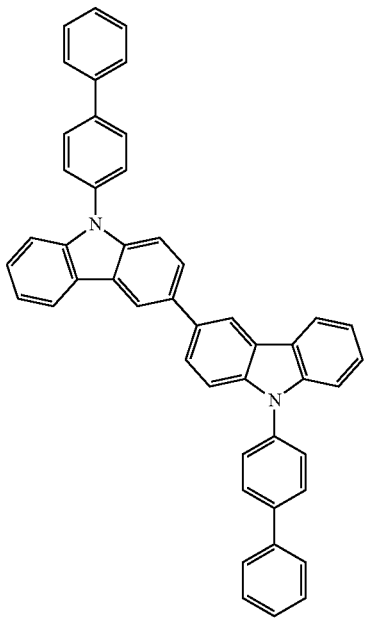
H2-7
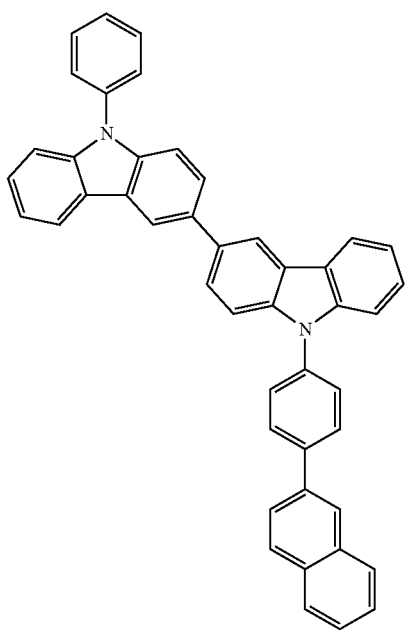

H2-8
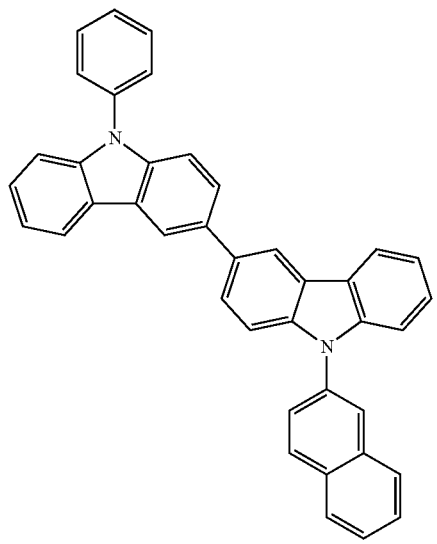
H2-9
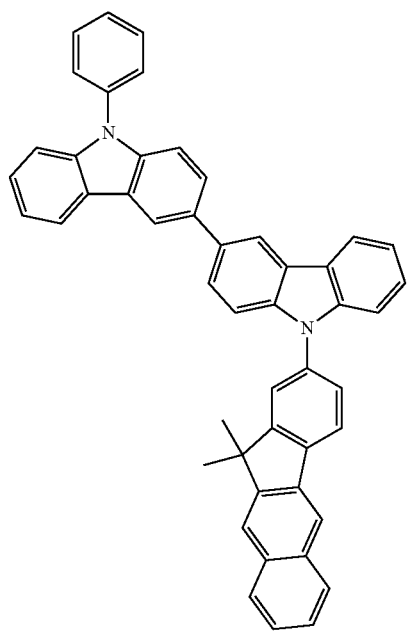
H2-10
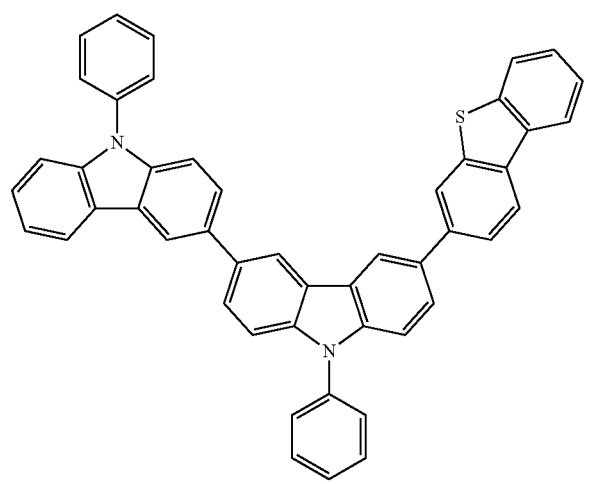
H2-11
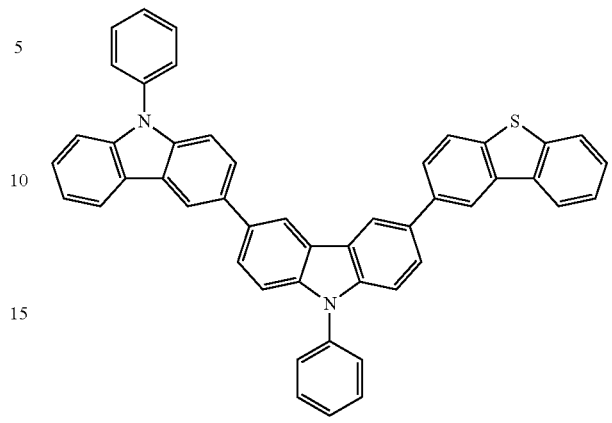
H2-12
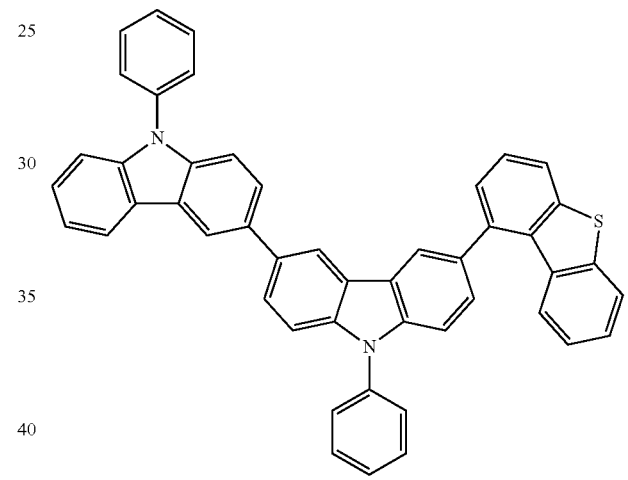
H2-13
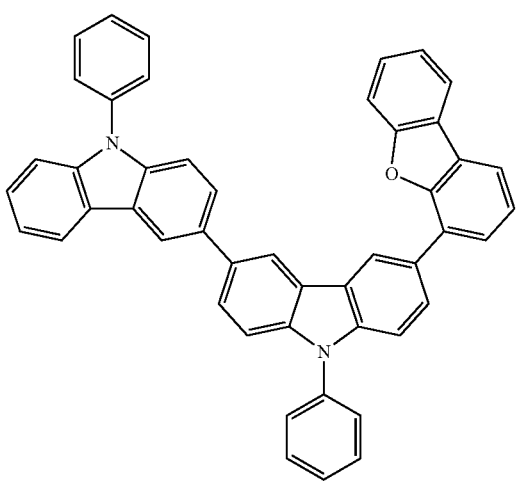

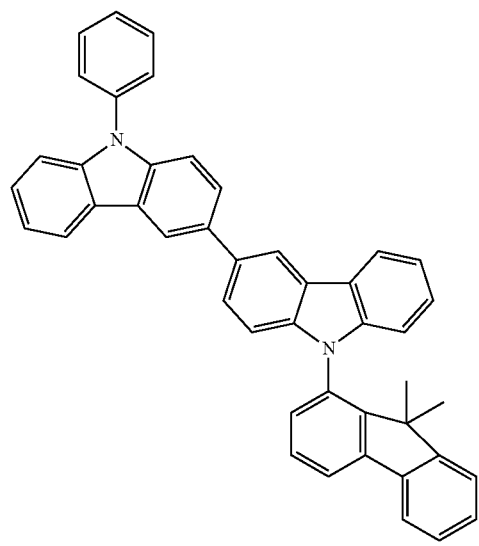
H2-14
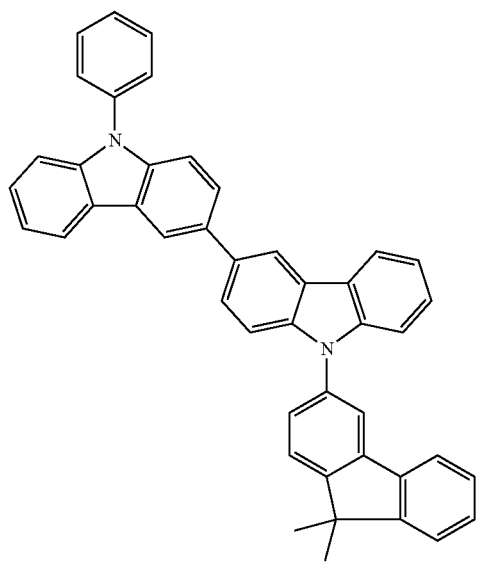
H2-16
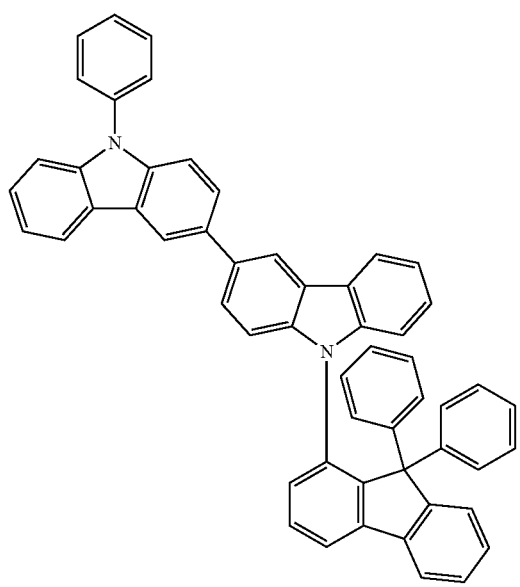
H2-15
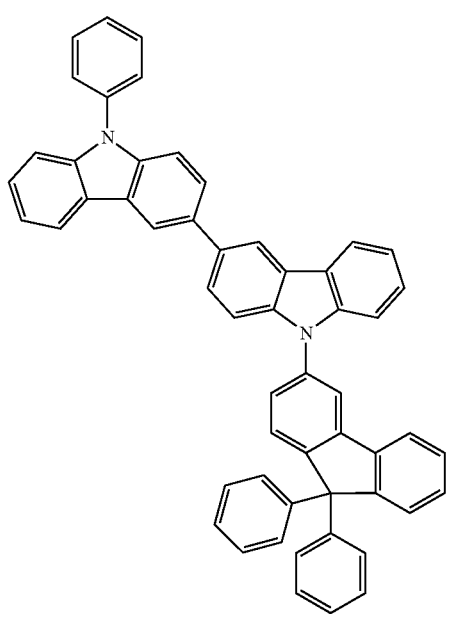
H2-17

H2-18
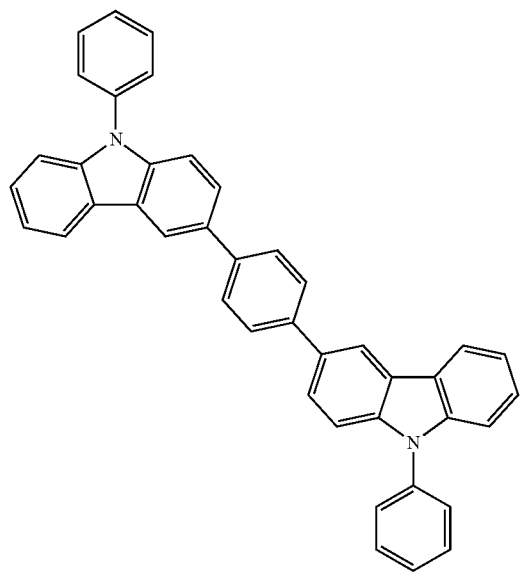
H2-20
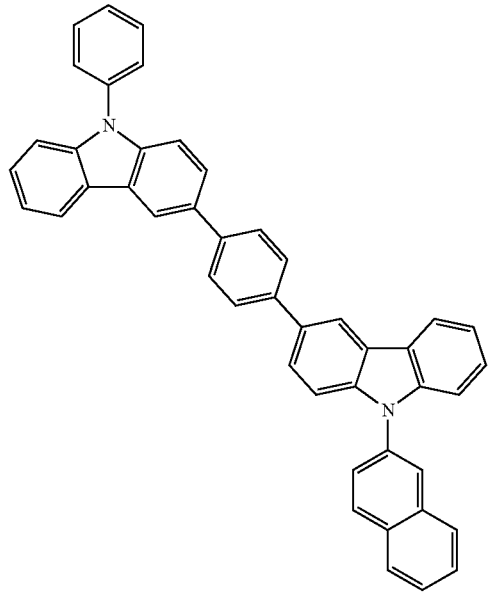
H2-19
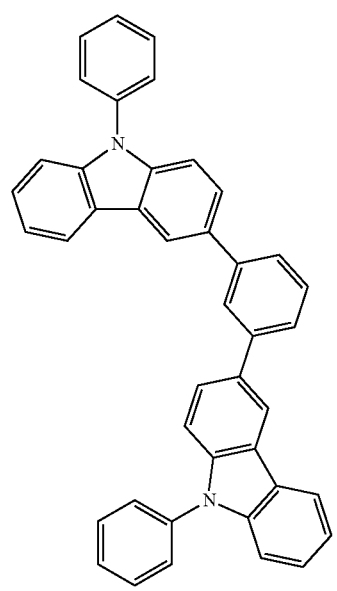
H2-21
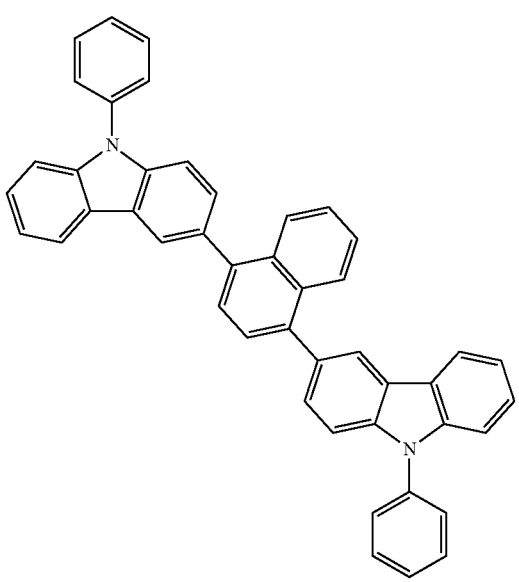

H2-22
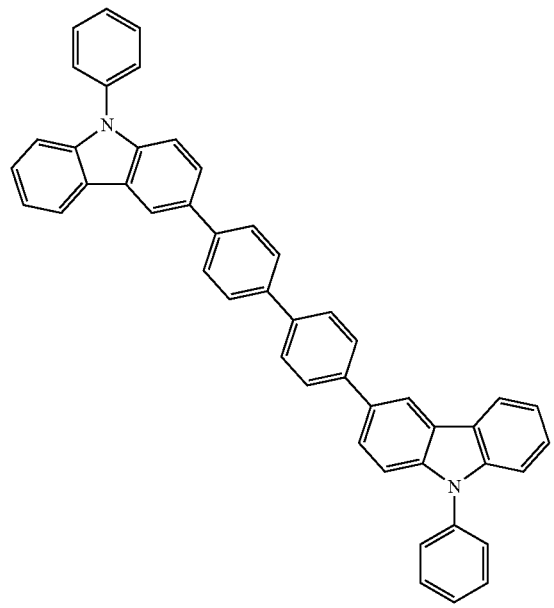
H2-23
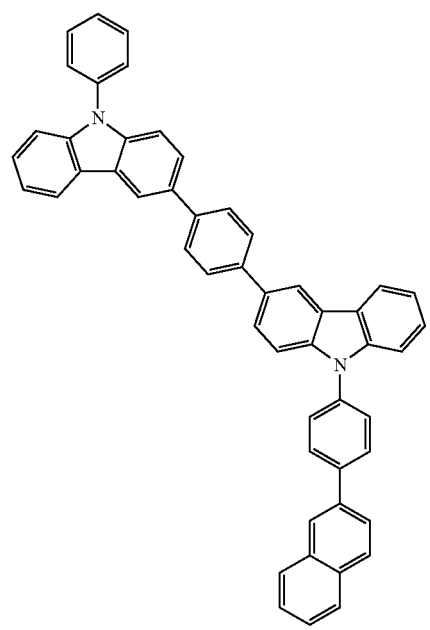
H2-24
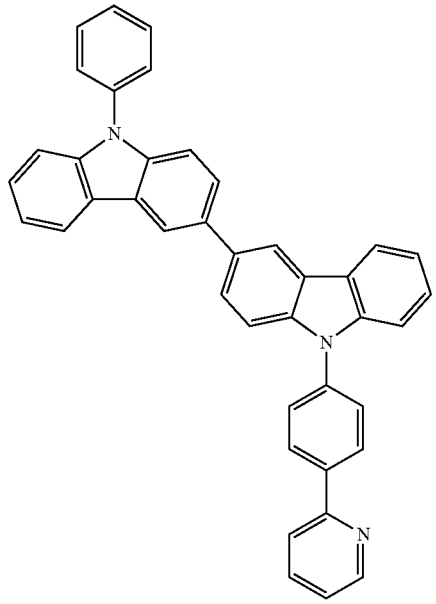
H2-25
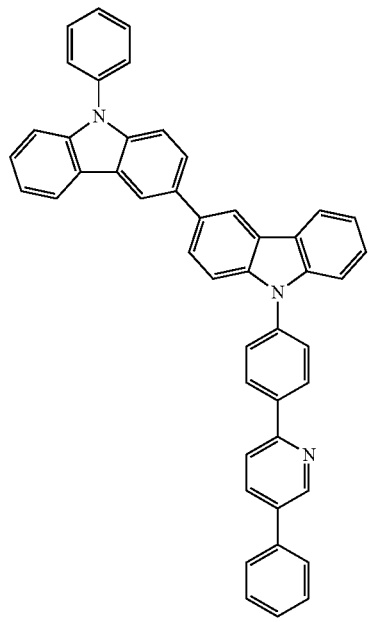

H2-26
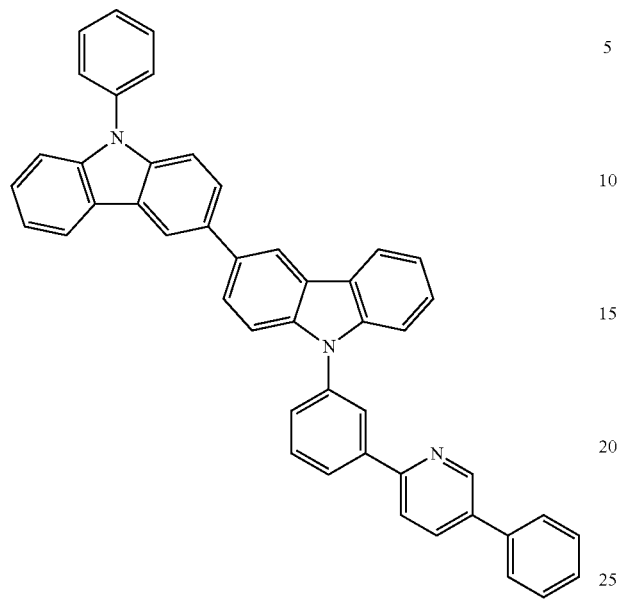
H2-28
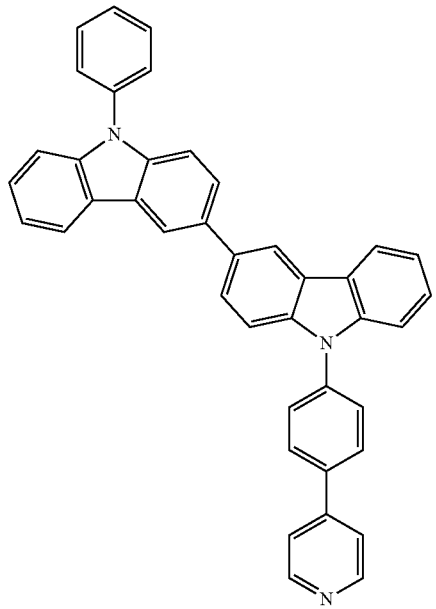
H2-29
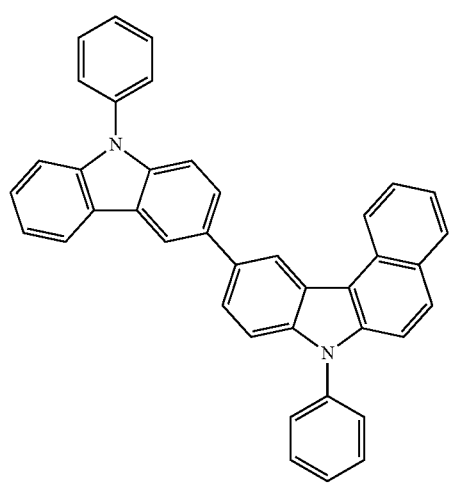
H2-27
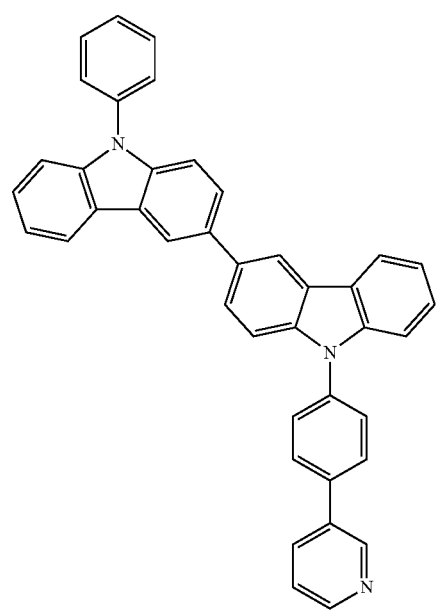
H2-30
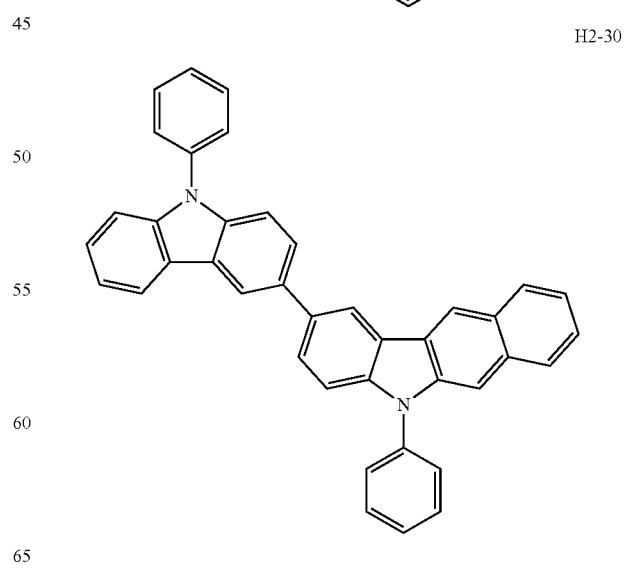

H2-31

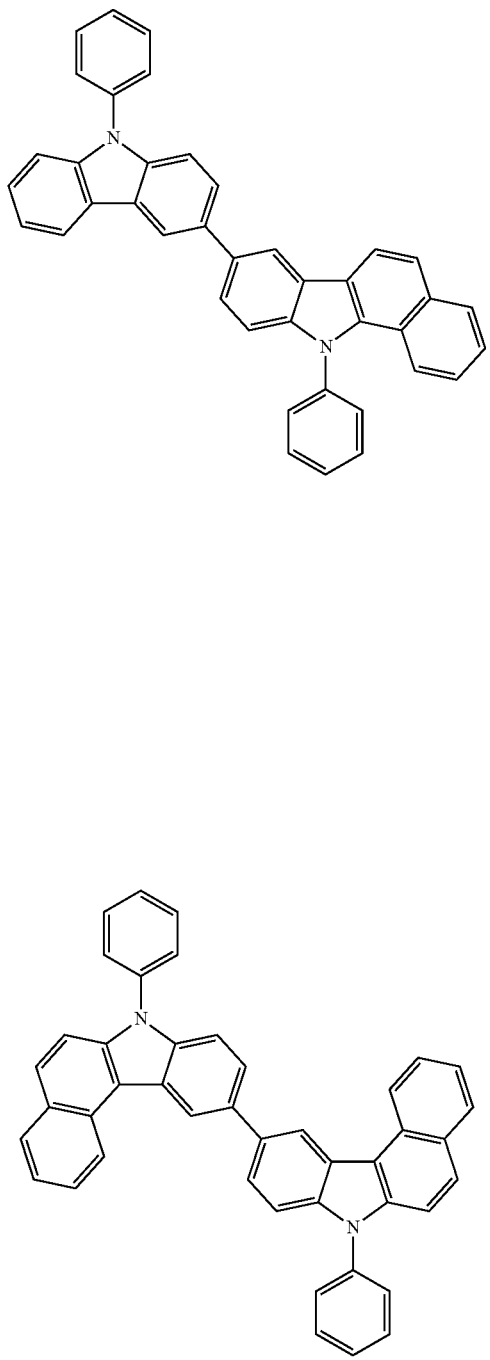

H2-32

H2-33

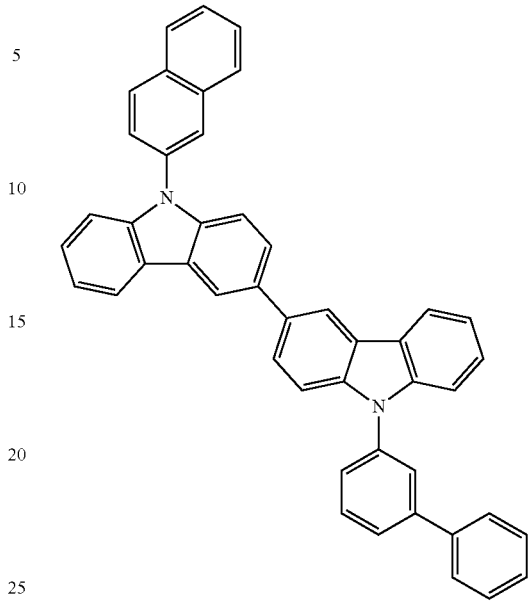

and

H2-34

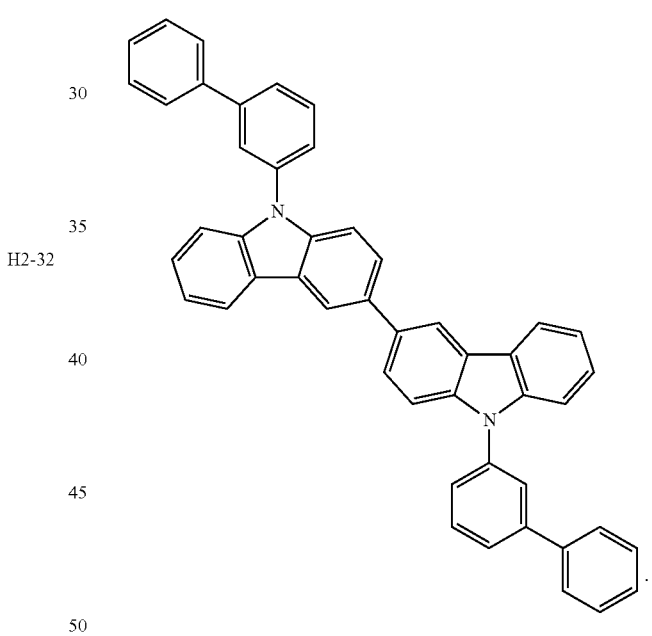

9. An organic electroluminescent device comprising the organic electroluminescent compound according to claim 1.

10. The organic electroluminescent device according to claim 9, wherein the organic electroluminescent compound is included in a light-emitting layer and/or an electron transport zone.

11. An organic electroluminescent device comprising an anode; a cathode; and at least one light-emitting layer between the anode and the cathode, wherein the at least one light-emitting layer comprise a plurality of host materials according to claim 6.

* * * * *